US008614229B2

(12) United States Patent
Anilkumar et al.

(10) Patent No.: US 8,614,229 B2
(45) Date of Patent: Dec. 24, 2013

(54) SUBSTITUTED INDOLE DERIVATIVES AND METHODS OF USE THEREOF

(75) Inventors: Gopinadhan N. Anilkumar, Edison, NJ (US); Frank Bennett, Cranford, NJ (US); Tin-Yau Chan, Edison, NJ (US); Kevin X. Chen, Edison, NJ (US); Mousumi Sannigrahi, Summit, NJ (US); Francisco Velazquez, Clinton, NJ (US); Srikanth Venkatraman, Edison, NJ (US); Qingbei Zeng, Edison, NJ (US); Jose S. Duca, Cranford, NJ (US); Charles A. Lesburg, Short Hills, NJ (US); Joseph A. Kozlowski, Princeton, NJ (US); F. George Njoroge, Warren, NJ (US); Stuart B. Rosenblum, West Orange, NJ (US); Neng-Yang Shih, Lexington, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 227 days.

(21) Appl. No.: 12/675,891

(22) PCT Filed: Aug. 27, 2008

(86) PCT No.: PCT/US2008/010148
§ 371 (c)(1),
(2), (4) Date: Nov. 23, 2010

(87) PCT Pub. No.: WO2009/032124
PCT Pub. Date: Mar. 12, 2009

(65) Prior Publication Data
US 2011/0104110 A1    May 5, 2011

Related U.S. Application Data

(60) Provisional application No. 60/968,698, filed on Aug. 29, 2007.

(51) Int. Cl.
| | |
|---|---|
| *A61K 31/47* | (2006.01) |
| *A61K 31/4402* | (2006.01) |
| *A61K 31/426* | (2006.01) |
| *A61K 31/428* | (2006.01) |
| *A61K 31/4184* | (2006.01) |
| *A61K 31/404* | (2006.01) |
| *C07D 239/96* | (2006.01) |
| *C07D 239/88* | (2006.01) |
| *C07D 241/44* | (2006.01) |
| *C07D 471/04* | (2006.01) |
| *C07D 215/18* | (2006.01) |
| *C07D 401/04* | (2006.01) |
| *C07D 211/88* | (2006.01) |
| *C07D 277/18* | (2006.01) |
| *C07D 487/04* | (2006.01) |
| *C07D 275/04* | (2006.01) |
| *C07D 249/18* | (2006.01) |

(52) U.S. Cl.
USPC .......... 514/311; 514/352; 514/369; 514/373; 514/395; 514/419; 544/285; 544/286; 544/287; 544/356; 546/122; 546/152; 546/256; 546/278.1; 546/290; 546/300; 548/190; 548/212; 548/257; 548/306.1; 548/364.7

(58) Field of Classification Search
None
See application file for complete search history.

(56) References Cited

U.S. PATENT DOCUMENTS

| | | | |
|---|---|---|---|
| 3,632,805 | A | 1/1972 | Yamamoto et al. |
| 3,759,897 | A | 9/1973 | Yamamoto et al. |
| 3,867,372 | A | 2/1975 | Yamamoto et al. |
| 3,910,889 | A | 10/1975 | Akatsu et al. |
| 4,634,697 | A | 1/1987 | Hamashima |
| 4,812,561 | A | 3/1989 | Hamashima et al. |
| 4,933,443 | A | 6/1990 | Hamashima et al. |
| 5,017,380 | A | 5/1991 | Hamashima et al. |
| 6,800,434 | B2 | 10/2004 | Saksena et al. |
| 6,838,475 | B2 | 1/2005 | Arasappan et al. |
| 6,846,802 | B2 | 1/2005 | Chen et al. |
| 6,911,428 | B2 | 6/2005 | Zhu et al. |
| 6,914,122 | B2 | 7/2005 | Venkatraman et al. |
| 7,012,066 | B2 | 3/2006 | Saksena et al. |
| 2002/0160962 | A1 | 10/2002 | Saksena et al. |
| 2004/0077704 | A1 | 4/2004 | Beight et al. |
| 2005/0075331 | A1 | 4/2005 | Pratt et al. |
| 2005/0101770 | A1 | 5/2005 | Presta |

(Continued)

FOREIGN PATENT DOCUMENTS

| | | |
|---|---|---|
| AU | 2002313410 B2 | 7/2002 |
| DE | 648639 C | 8/1937 |

(Continued)

OTHER PUBLICATIONS

Lohani, S. (2006) Understanding nucleation process in the crystallization of polymorphs. (Doctoral dissertataion). Retrieved from ProQuest Dissertataions and Thesis. (Assession Order No. AAT3234930).*

(Continued)

*Primary Examiner* — Jason M Nolan
*Assistant Examiner* — Po-Chih Chen
(74) *Attorney, Agent, or Firm* — Henry P. Wu; Sheldon O. Heber

(57) ABSTRACT

The present invention relates to Substituted Indole Derivatives, compositions comprising at least one Substituted Indole Derivative, and methods of using these Substituted Indole Derivatives for treating or preventing a viral infection or a virus-related disorder in a patient.

12 Claims, No Drawings

(56) References Cited

U.S. PATENT DOCUMENTS

| | | | |
|---|---|---|---|
| 2005/0176648 | A1 | 8/2005 | Saksena et al. |
| 2005/0249702 | A1 | 11/2005 | Njoroge et al. |
| 2006/0089345 | A1 | 4/2006 | Barth et al. |
| 2007/0274951 | A1 | 11/2007 | Tong et al. |
| 2010/0098661 | A1 | 4/2010 | Chen et al. |
| 2010/0196319 | A1 | 8/2010 | Anilkumar et al. |
| 2010/0239527 | A1 | 9/2010 | Anilkumar et al. |
| 2010/0260711 | A1 | 10/2010 | Chen et al. |
| 2010/0322901 | A1* | 12/2010 | Bennett et al. ............... 424/85.4 |
| 2011/0033417 | A1 | 2/2011 | Anilkumar et al. |
| 2011/0104109 | A1 | 5/2011 | Bennett et al. |
| 2011/0104110 | A1 | 5/2011 | Anikumar et al. |
| 2011/0165118 | A1 | 7/2011 | Chan et al. |

FOREIGN PATENT DOCUMENTS

| | | | |
|---|---|---|---|
| EP | 0449196 | A2 | 10/1991 |
| FR | 2768146 | A1 | 3/1999 |
| JP | 47-37166 | B | 9/1972 |
| JP | 49-4461 | B | 2/1974 |
| JP | 49-45876 | B | 12/1974 |
| JP | 4-149429 | | 5/2004 |
| JP | 2004149429 | | 5/2004 |
| WO | 96/37619 | A1 | 11/1996 |
| WO | 98/14181 | A1 | 4/1998 |
| WO | 98/17679 | A1 | 4/1998 |
| WO | 98/22496 | A2 | 5/1998 |
| WO | 99/07734 | A2 | 2/1999 |
| WO | 02/30895 | A1 | 4/2002 |
| WO | 02/068412 | A1 | 9/2002 |
| WO | 2003-010140 | A2 | 2/2003 |
| WO | 2003-010141 | A2 | 2/2003 |
| WO | 2004/035571 | A1 | 4/2004 |
| WO | 2004/106328 | A1 | 12/2004 |
| WO | 2005/034941 | A1 | 4/2005 |
| WO | WO 2005/034941 | A1 | 4/2005 |
| WO | 2005/084315 | A2 | 9/2005 |
| WO | 2005/087731 | A1 | 9/2005 |
| WO | 2005/111018 | A1 | 11/2005 |
| WO | WO 2005/111018 | A1 | 11/2005 |
| WO | 2006/020082 | A1 | 2/2006 |
| WO | 2006/032541 | A1 | 3/2006 |
| WO | 2006/034337 | A2 | 3/2006 |
| WO | WO 2006/032541 | A1 | 3/2006 |
| WO | 2006/046030 | A2 | 5/2006 |
| WO | 2006/076529 | A1 | 7/2006 |
| WO | 2007/029029 | A2 | 3/2007 |
| WO | 2007/038209 | A2 | 4/2007 |
| WO | 2007/084413 | A2 | 7/2007 |
| WO | 2007/084435 | A2 | 7/2007 |
| WO | WO 2007/084413 | A1 | 7/2007 |
| WO | 2008/082484 | A1 | 7/2008 |

OTHER PUBLICATIONS

Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Morissette, S. L., Almarsson, O., Peterson, M. L., Remenar, J. F., Read, M. J., Lemmo, A. V., Ellis, S., Cima, M. J., Gardner, C. R. High-throughput crystallization: polymorphs, salts, co-crystals, and solvates of pharmaceutical solids. Advanced Drug Delivery Reviews. Feb. 2004, 56, 275-300.*
Hamdi, N., Feutelais, Y., Yagoubi, N., de Girolamo, D., Legendre, B. Solvates of indomethacin. Journal of thermal analysis and calorimetry. Nov. 2004, 76, 985-1001.*
Tan et al., "Hepatitis C Therapeutics: Current Status and Emerging Strategies", Nature Reviews, 2002, vol. 1, pp. 867-881.
Written Opinion for PCT/US2008/083358, filed Nov. 13, 2008 (5 pages).
International Search Report for International Application No. PCT/US2008/010148, mailed Dec. 9, 2008, (3 pages).
Written Opinion for PCT1US20081010148, filed Aug. 27, 2008 (7 pages).
International Search Report for International Application No. PCT/US2009/046822, mailed Oct. 7, 2009, (5 pages).
Written Opinion for PCT1US20091046822, filed Jun. 10, 2009 (8 pages).
Ingallinella et al., "Potent Peptide Inhibitors of Human Hepatitis C Virus NS3 Protease are Obtained by Optimizing the Cleavage Products", Biochemistry, 1998, vol. 37, pp. 8906-8914.
Landro et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 1997, vol. 36, pp. 9340-9348.
Lindsay et al., "Sml2-Promoted Radical Addition Reactions with N-(2-Indolylacyl)oxazolidinones: Synthesis of Bisindole Compounds", Journal of Organic Chemistry, 2007, vol. 72, pp. 4181-4188, No. 11.
Llinas-Brunet et al., "Peptide-Based Inhibitors of the Hepatitis C Virus Serine Protease", Bioorganic & Medicinal Chemistry Letters, 1998, vol. 8, pp. 1713-1718.
Malcolm et al., "SCH 503034, a Mechanism-Based Inhibitor of Hepatitis C Virus NS3 Protease, Suppresses Polyprotein Maturation and Enhances the Antiviral Activity of Alpha Interferon in Replicon Cells", Antimicrobial Agents and Chemotherapy, 2006, vol. 50, pp. 1013-1020, No. 3.
Martin, et al., "Affinity selection of a camelized VH domain antibody inhibitor of hepatitis C virus NS3 protease", Protein Engineering, 1997, vol. 10, pp. 607-614, No. 5.
Martin et al., "Design of Selective Eglin Inhibitors of HCV NS3 Proteinase", Biochemistry, 1998, vol. 37, pp. 11459-11468.
Muratake et al., "Synthesis of Duocarmycin SA by Way of Methyl 4-(Methoxycarbonyl)oxy-3H-pyrrolo[3,2-f] quinoline-2-carboxylate as a Tricyclic Heteroaromatic Intermediate", Chem. Pharm. Bulletin, 1998, vol. 46, pp. 400-412, No. 3.
Ni et al., "Progress and development of small molecule HCV antivirals", Current Opinion in Drug Discovery & Development, 2004, vol. 7, pp. 446-459, No. 4.
Rawal et al., "Photocyclization of Pyrrole Analogues of Stilbene: an Expedient Approach to Anti-tumour Agent CC-1065", Journal Chem. Soc., Chem. Commun., 1984, pp. 1526-1527.
Sechi et al., "Design and Synthesis of Novel Indole β-Diketo Acid Derivatives as HIV-1 Integrase Inhibitors", J. Med. Chem., 2004, vol. 47, pp. 5298-5310, No. 21.
Silvestri et al., "Synthesis and biological evaluation of 5H-indolo [3,2-b][1,5]benzothiazepine derivatives, designed as conformationally constrained analogues of the human immunodeficiency virus type 1 reverse transcriptase inhibitor L-737,126", Antiviral Chemistry & Chemotherapy, 1998, vol. 9, pp. 139-148.
Beaulieu et al., "Inhibitors of the HCV NS5B polymerase: New hope for the treatment of hepatitis C infections", Current Opinion in Investigational Drugs, 2004, vol. 5, pp. 838-850, No. 8.
Behrens et al., "Identification and properties of the RNA-dependent RNA polymerase of hepatitis C virus", The EMBO Journal, 1996, vol. 15, pp. 12-22, No. 1.
Bioworld Today, 9 (217):4 Nov. 10, 1998, pp. 1-5.
Birnbock et al., "Sulfate Derivatives of 2-Phenylindols as Novel Steroid Sulfatase Inhibitors", Biochemical Pharmacology, 1990, vol. 39, pp. 1709-1713, No. 11.
Bunker et al., "1,3-Diaryl-2-Carboxyindoles as Potent Non-Peptide Endothelin Antagonists", Bioorganic & Medicinal Chemistry Letters, 1996, vol. 6, pp. 1061-1066, No. 9.
Denmark et al., "Palladium-Catalyzed Cross-Coupling Reactions of Silanolates: A Paradigm Shift in Silicon-Based Cross-Coupling Reactions", Chem. Eur. J., 2006, vol. 12, pp. 4954-4963.
Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 1997, vol. 71, pp. 7461-7469, No. 10.
Elzouki et al., "Serine protease inhibitors in patients with chronic viral hepatitis", Journal of Hepatology, 1997, vol. 27, pp. 42-48.

(56) References Cited

OTHER PUBLICATIONS

Ferrari et al., "Characterization of Soluble Hepatitis C Virus RNA-Dependent RNA Polymerase Expressed in *Escherichia coli*", Journal of Virology, 1999, vol. 73, pp. 1649-1654, No. 2.

Fonseca et al., "Synthesis and antiviral evaluation of benzimidazoles, quinoxalines and indoles from dehydroabietic acid", Bioorganic & Medicinal Chemistry, 2004, vol. 12, pp. 103-112.

Forbes et al., "Synthesis, Biological Activity, and Molecular Modeling Studies of Selective 5-HT2C/2B Receptor Antagonists", J. Med. Chem., 1996, vol. 39, pp. 4966-4977, No. 25.

Goldsmith et al., "Studies in the Benzindole Series", J. Org. Chem, 1952, vol. 18, pp. 507-514.

Gopalsamy et al., "Design and synthesis of 2,3,4,9-tetrahydro-1H-carbazole and 1,2,3,4-tetrahydro-cyclopenta[b] indole derivatives as non-nucleoside inhibitors of hepatitis C virus NS5B RNA-dependent RNA polymerase", Bioorganic & Medicinal Chemistry Letters, 2006, vol. 16, pp. 2532-2534.

Humphrey et al., "Practical Methodologies for the Synthesis of Indoles", Chem. Rev., 2006, vol. 106, pp. 2875-2911.

International Search Report for International Application No. PCT/US2007/025754, mailed May 13, 2008, (4 pages).

Written Opinion for PCT/US2007/025754, filed Dec. 17, 2007, (7 pages).

International Search Report for International Application No. PCT/US2007/025765, mailed May 13, 2008, (6 pages).

Written Opinion for PCT/US2007/025765, filed Dec. 17, 2007, (8 pages).

International Search Report for International Application No. PCT/US2007/025757, mailed Mar. 6, 2009, (8 pages).

Written Opinion for PCT/US2007/025757, filed Dec. 17, 2007 (12 pages).

International Search Report for International Application No. PCT/US2008/010130, mailed Jan. 22, 2009, (5 pages).

Written Opinion for PCT1US20081010130, filed Aug. 27, 2008 (9 pages).

International Search Report for International Application No. PCT/US2008/010149, mailed Feb. 2, 2009, (5 pages).

Written Opinion for PCT/US2008/010149, filed Aug. 27, 2008 (6 pages).

International Search Report for International Application No. PCT/US2008/083351, mailed Feb. 27, 2009, (3 pages).

Written Opinion for PCT/US2008/083351, filed Nov. 13, 2008 (5 pages).

International Search Report for International Application No. PCT/US2008/010147, mailed May 4, 2009, (3 pages).

Written Opinion for PCT/US2008/010147, filed Aug. 27, 2008 (6 pages).

International Search Report for International Application No. PCT/US2008/083358, mailed Mar. 6, 2009, (2 pages).

PCT Written Opinion of the International Searching Authority for PCT/US2008/010148, (8 pages).

International Search Report for PCT/US2008/010148, mailed Dec. 9, 2008 (5 pages).

Hirai et al., "Peptidoanninobenzophenones, a novel class of ring-opened derivatives of 1,4-benzoidazepines", J Med Chem, 1980, pp. 764-73, vol. 23.

Inaba et al.,. "Benzodiazepines. IV. New synthesis of 1-diethylaminoethyl-substituted 1,4-benzodiazepin-2-ones", Chem Pharm Bull, 1971, pp. 263-272, vol. 19.

Sternbach et al., "Quinazolines and 1,4-Benzodiazepines. V. o-Aminobenzophenones", J Org Chem, 1962, pp. 3781-3788, vol. 27.

Walser et al., "Nucleophilic displacement of aromatic fluorine. III. Indoloquinolines and benzofuranoquinolines", J Heterocyclic Chemistry, 1975, pp. 351-358, vol. 12.

\* cited by examiner

SUBSTITUTED INDOLE DERIVATIVES AND METHODS OF USE THEREOF

REFERENCE TO SEQUENCE LISTING SUBMITTED ELECTRONICALLY

The sequence listing of the present application is submitted electronically via EFS-Web as an ASCII formatted sequence listing with a file name "IN106705US01_SEQLIST_23NOV2010.TXT," creation date of Nov. 23, 2010, and a size of 1.14 KB. This sequence listing submitted via EFS-Web is part of the specification and is herein incorporated by reference in its entirety.

FIELD OF THE INVENTION

The present invention relates to 2-Carboxy Substituted Indole Derivatives, compositions comprising at least one 2-Carboxy Substituted Indole Derivative, and methods of using the 2-Carboxy Substituted Indole Derivatives for treating or preventing a viral infection or a virus-related disorder in a patient.

BACKGROUND OF THE INVENTION

HCV is a (+)-sense single-stranded RNA virus that has been implicated as the major causative agent in non-A, non-B hepatitis (NANBH). NANBH is distinguished from other types of viral-induced liver disease, such as hepatitis A virus (HAV), hepatitis B virus (HBV), hepatitis delta virus (HDV), as well as from other forms of liver disease such as alcoholism and primary biliary cirrhosis.

Hepatitis C virus is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1-5% of patients). The World Health Organization estimates that 170 million people are chronically infected with HCV, with an estimated 4 million living in the United States.

HCV has been implicated in cirrhosis of the liver and in induction of hepatocellular carcinoma. The prognosis for patients suffering from HCV infection remains poor as HCV infection is more difficult to treat than other forms of hepatitis. Current data indicates a four-year survival rate of below 50% for patients suffering from cirrhosis and a five-year survival rate of below 30% for patients diagnosed with localized resectable hepatocellular carcinoma. Patients diagnosed with localized unresectable hepatocellular carcinoma fare even worse, having a five-year survival rate of less than 1%.

HCV is an enveloped RNA virus containing a single-stranded positive-sense RNA genome approximately 9.5 kb in length. The RNA genome contains a 5'-nontranslated region (5' NTR) of 341 nucleotides, a large open reading frame (ORF) encoding a single polypeptide of 3,010 to 3,040 amino acids, and a 3'-nontranslated region (3'-NTR) of variable length of about 230 nucleotides. HCV is similar in amino acid sequence and genome organization to flaviviruses and pestiviruses, and therefore HCV has been classified as a third genus of the family Flaviviridae.

The 5' NTR, one of the most conserved regions of the viral genome, contains an internal ribosome entry site (IRES) which plays a pivotal role in the initiation of translation of the viral polyprotein. A single long open reading frame encodes a polyprotein, which is co- or post-translationally processed into structural (core, E1, E2 and p7) and nonstructural (NS2, NS3, NS4A, NS4B, NS5A, and NS5B) viral proteins by either cellular or viral proteinases. The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. By analogy to other plus-strand RNA viruses, the 3'-NTR is thought to play an important role in viral RNA synthesis. The order of the genes within the genome is: $NH_2$—C-E1-E2-p7-NS2-NS3-NS4A-NS4B—NS5A-NS5B—COOH.

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2. The NS2-3 proteinase, which is a metalloprotease, then cleaves at the NS2/NS3 junction. The NS3/4A proteinase complex (NS3 being a serine protease and NS4A acting as a cofactor of the NS3 protease), is then responsible for processing all the remaining cleavage junctions. RNA helicase and NTPase activities have also been identified in the NS3 protein. One-third of the NS3 protein functions as a protease, and the remaining two-thirds of the molecule acts as the helicase/ATPase that is thought to be involved in HCV replication. NS5A may be phosphorylated and acts as a putative cofactor of NS5B. The fourth viral enzyme, NS5B, is a membrane-associated RNA-dependent RNA polymerase (RdRp) and a key component responsible for replication of the viral RNA genome. NS5B contains the "GDD" sequence motif, which is highly conserved among all RdRps characterized to date.

Replication of HCV is thought to occur in membrane-associated replication complexes. Within these, the genomic plus-strand RNA is transcribed into minus-strand RNA, which in turn can be used as a template for synthesis of progeny genomic plus-strands. At least two viral enzymes appear to be involved in this reaction: the NS3 helicase/NTPase, and the NS5B RNA-dependent RNA polymerase. While the role of NS3 in RNA replication is less clear, NS5B is the key enzyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently confirmed and further characterized through the use of the HCV RNA genome as a substrate. Other studies have shown that NS5B with a C-terminal 21 amino-acid truncation expressed in *Escherichia coli* is also active for in vitro RNA synthesis. On certain RNA templates, NS5B has been shown to catalyze RNA synthesis via a de novo initiation mechanism, which has been postulated to be the mode of viral replication in vivo. Templates with single-stranded 3' termini, especially those containing a 3'-terminal cytidylate moiety, have been found to direct de novo synthesis efficiently. There has also been evidence for NS5B to utilize di- or tri-nucleotides as short primers to initiate replication.

It is well-established that persistent infection of HCV is related to chronic hepatitis, and as such, inhibition of HCV replication is a viable strategy for the prevention of hepatocellular carcinoma. Present treatment approaches for HCV infection suffer from poor efficacy and unfavorable side-effects and there is currently a strong effort directed to the discovery of HCV replication inhibitors that are useful for the treatment and prevention of HCV related disorders. New approaches currently under investigation include the development of prophylactic and therapeutic vaccines, the identification of interferons with improved pharmacokinetic characteristics, and the discovery of agents designed to inhibit the function of three major viral proteins: protease, helicase and polymerase. In addition, the HCV RNA genome itself, particularly the IRES element, is being actively exploited as an antiviral target using antisense molecules and catalytic ribozymes.

Particular therapies for HCV infection include α-interferon monotherapy and combination therapy comprising α-interferon and ribavirin. These therapies have been shown to be effective in some patients with chronic HCV infection. The use of antisense oligonucleotides for treatment of HCV infection has also been proposed as has the use of free bile acids, such as ursodeoxycholic acid and chenodeoxycholic acid, and conjugated bile acids, such as tauroursodeoxycholic acid. Phosphonoformic acid esters have also been proposed as potentially for the treatment of various viral infections including HCV. Vaccine development, however, has been hampered by the high degree of viral strain heterogeneity and immune evasion and the lack of protection against reinfection, even with the same inoculum.

The development of small-molecule inhibitors directed against specific viral targets has become a major focus of anti-HCV research. The determination of crystal structures for NS3 protease, NS3 RNA helicase, and NS5B polymerase has provided important structural insights that should assist in the rational design of specific inhibitors.

NS5B, the RNA-dependent RNA polymerase, is an important and attractive target for small-molecule inhibitors. Studies with pestiviruses have shown that the small molecule compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene. Inhibition of RdRp activity by (−)β-L-2',3'-dideoxy-3'-thiacytidine 5'-triphosphate (3TC; lamivudine triphosphate) and phosphonoacetic acid also has been observed.

Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders.

SUMMARY OF THE INVENTION

In one aspect, the present invention provides compounds of formula (I):

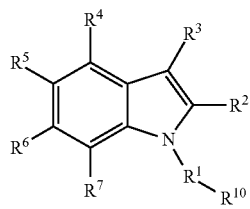

(I)

and pharmaceutically acceptable salts, solvates, esters and prodrugs thereof, wherein:

$R^1$ is a bond, —[C($R^{12}$)$_2$]$_r$—, —[C($R^{12}$)$_2$]$_r$—O—[C($R^{12}$)$_2$]$_q$—, —[C($R^{12}$)$_2$]$_r$—N($R^9$)—[C($R^{12}$)$_2$]$_q$—, —[C($R^{12}$)$_2$]$_q$—CH═CH—[C($R^{12}$)$_2$]$_q$—, —[C($R^{12}$)$_2$]$_q$—C≡C—[C($R^{12}$)$_2$]$_q$— or —[C($R^{12}$)$_2$]$_q$—SO$_2$—[C($R^{12}$)$_2$]$_q$—;

$R^2$ is —C(O)$R^9$, —C(O)O$R^9$, —C(O)OCH$_2$O$R^9$, —C(O)N($R^9$)$_2$, —[C($R^{12}$)$_2$]$_q$—C(O)O$R^9$, —[C($R^{12}$)$_2$]$_q$—C(O)N($R^9$)$_2$, —[C($R^{12}$)$_2$]$_q$—C(O)N($R^9$)C(═N$R^9$)N$R^9$, -alkyl, —[C($R^{12}$)$_2$]$_q$-aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heteroaryl or —[C($R^{12}$)$_2$]$_q$-heterocycloalkenyl, wherein an aryl, cycloalkyl, cycloalkenyl, heterocycloalkyl, heterocycloalkenyl or heteroaryl, group can be optionally substituted with up to 4 substituents, which are the same or different, and are selected from alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, —OH, —O$R^9$, —CN, —[C($R^{12}$)$_2$]$_q$—C(O)$R^8$, —[C($R^{12}$)$_2$]$_q$—C(O)O$R^9$, —[C($R^{12}$)$_2$]$_q$—C(O)N($R^9$)$_2$, —[C($R^{12}$)$_2$]$_q$—O$R^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—N$R^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ and —SO$_2$N($R^9$)C(O)N($R^9$)$_2$;

$R^3$ is:

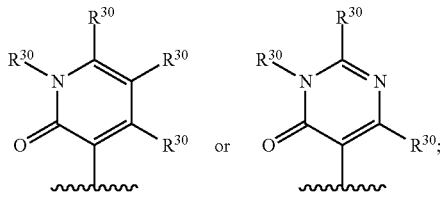

$R^4$, $R^5$, $R^6$ and $R^7$ are each, independently, H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, —OH, —O$R^9$, —CN, —[C($R^{12}$)$_2$]$_q$—C(O)$R^8$, —[C($R^{12}$)$_2$]$_q$—C(O)O$R^9$, —[C($R^{12}$)$_2$]$_q$—C(O)N($R^9$)$_2$, —[C($R^{12}$)$_2$]$_q$—O$R^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—N$R^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ or —SO$_2$N($R^9$)C(O)N($R^9$)$_2$;

each occurrence of $R^8$ is independently H, alkyl, alkenyl, alkynyl, —[C($R^{12}$)$_2$]$_q$-aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, haloalkyl or hydroxyalkyl;

each occurrence of $R^9$ is independently H, alkyl, alkenyl, alkynyl, —[C($R^{12}$)$_2$]$_q$—O-alkyl, —[C($R^{12}$)$_2$]$_q$—N(alkyl)$_2$, —[C($R^{12}$)$_2$]$_q$-aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, haloalkyl or hydroxyalkyl;

$R^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkenyl, aryl or heteroaryl group can be optionally and independently substituted with up to 4 substituents, which are each independently selected from H, alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$- heteroaryl, —[C(R$^{12}$)$_2$]$_q$-haloalkyl, —[C(R$^{12}$)$_2$]$_q$-hydroxyalkyl, halo, —OH, —OR$^9$, —CN, —NO$_2$, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$, such that when R$^1$ is a bond, R$^{10}$ is not H;

each occurrence of R$^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkenyl, aryl or heteroaryl group can be optionally and independently substituted with up to 4 substituents, which are each independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$alkyl, —[C(R$^{12}$)$_2$]$_q$—NHSO$_2$cycloalkyl, —[C(R$^{12}$)$_2$]$_q$—NHSO$_2$aryl, —[C(R$^{12}$)$_2$]$_q$—SO$_2$N(R$^9$)$_2$ and —SO$_2$N(R$^9$)C(O)N(R$^9$)$_2$;

each occurrence of R$^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, —OH, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C═O group;

each occurrence of R$^{20}$ is independently alkyl, aryl, cycloalkyl, heterocycloalkyl or heteroaryl, or both R$^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be substituted with up to 4 groups, which are each independently selected from alkyl, alkenyl, alkynyl, halo, —OH, —OR$^9$, —CN, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-haloalkyl, —[C(R$^{12}$)$_2$]$_q$-hydroxyalkyl, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

each occurrence of R$^{30}$ is independently H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ or —SO$_2$N(R$^9$)C(O)N(R$^9$)$_2$, or two adjacent R$^{30}$ groups, together with the carbon atoms to which they are attached, join to form a –3- to 7-membered ring selected from aryl, cycloalkyl, heteroaryl and heterocycloalkyl;

each occurrence of p is independently 0, 1 or 2;

each occurrence of q is independently an integer ranging from 0 to 4; and each occurrence of r is independently an integer ranging from 1 to 4.

In another aspect, the present invention provides compounds of formula (II):

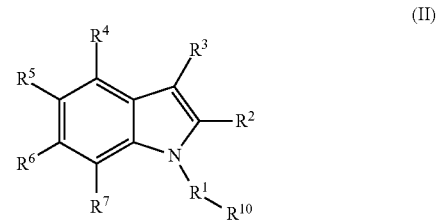

(II)

and pharmaceutically acceptable salts, solvates, esters and prodrugs thereof, wherein:

R$^1$ is a bond, —[C(R$^{12}$)$_2$]$_r$—, —[C(R$^{12}$)$_2$]$_r$—O—[C(R$^{12}$)$_2$]$_q$—, —[C(R$^{12}$)$_2$]$_r$—N(R$^9$)—[C(R$^{12}$)$_2$]$_q$—, —[C(R$^{12}$)$_2$]$_q$—CH═CH—[C(R$^{12}$)$_2$]$_q$—, —[C(R$^{12}$)$_2$]$_q$—C≡C—[C(R$^{12}$)$_2$]$_q$— or —[C(R$^{12}$)$_2$]$_q$—SO$_2$—[C(R$^{12}$)$_2$]$_q$—;

R$^2$ is —C(O)R$^9$, —C(O)OR$^9$, —C(O)OCH$_2$OR$^9$, —C(O)N(R$^9$)$_2$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—C(O)N(R$^9$)C(═NR$^9$)NR$^9$, -alkyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heteroaryl or —[C(R$^{12}$)$_2$]$_q$-heterocycloalkenyl, wherein an aryl, cycloalkyl, cycloalkenyl, heterocycloalkyl, heterocycloalkenyl or heteroaryl, group can be optionally substituted with up to 4 substituents, which are the same or different, and are selected from alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

R$^3$ is

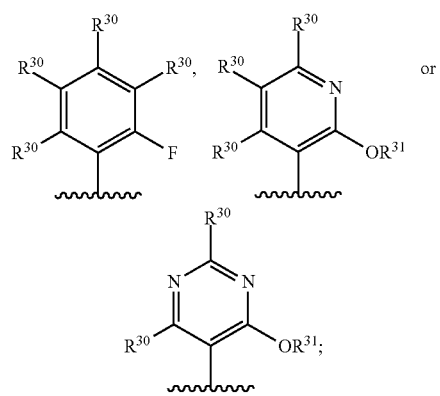

$R^4$, $R^5$, $R^6$ and $R^7$ are each, independently, H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ or —SO$_2$N(R$^9$)C(O)N(R$^9$)$_2$;

each occurrence of R$^8$ is independently H, alkyl, alkenyl, alkynyl, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, haloalkyl or hydroxyalkyl;

each occurrence of R$^9$ is independently H, alkyl, alkenyl, alkynyl, —[C(R$^{12}$)$_2$]$_q$—O-alkyl, —[C(R$^{12}$)$_2$]$_q$—N(alkyl)$_2$, —[C(R$^{12}$)$_2$]$_q$-aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, haloalkyl or hydroxyalkyl;

R$^{10}$ is H, cycloalkyl, cycloalkenyl, heterocycloalkyl, heterocycloalkenyl, aryl, heteroaryl, wherein a cycloalkyl, cycloalkenyl, heterocycloalkyl, heterocycloalkyl, aryl or heteroaryl group can be optionally and independently substituted with up to 4 substituents, which are each independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —NO$_2$, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$, such that when R$^1$ is a bond, R$^{10}$ is not H;

each occurrence of R$^{11}$ is independently alkyl, aryl, cycloalkyl, cycloalkenyl, heterocycloalkyl, heterocycloalkenyl, heteroaryl, haloalkyl, hydroxy or hydroxyalkyl, wherein a cycloalkyl, cycloalkenyl, heterocycloalkyl, heterocycloalkyl, aryl or heteroaryl group can be optionally and independently substituted with up to 4 substituents, which are each independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$alkyl, —[C(R$^{12}$)$_2$]$_q$—NHSO$_2$-cycloalkyl, —[C(R$^{12}$)$_2$]$_q$—NHSO$_2$aryl, —[C(R$^{12}$)$_2$]$_q$—SO$_2$N(R$^9$)$_2$ and —SO$_2$N(R$^9$)C(O)N(R$^9$)$_2$;

each occurrence of R$^{12}$ is independently H, halo, —N(R$^9$)$_2$, —OR$^9$, alkyl, cycloalkyl, cycloalkenyl, heterocycloalkyl or heterocycloalkenyl, wherein a cycloalkyl, cycloalkenyl, heterocycloalkyl or heterocycloalkenyl group can be optionally and independently substituted with up to 4 substituents, which are each independently selected from alkyl, halo, haloalkyl, hydroxyalkyl, —OH, —CN, —C(O)alkyl, —C(O)Oalkyl, —C(O)NHalkyl, —C(O)N(alkyl)$_2$, —O-alkyl, —NH$_2$, —NH(alkyl), —N(alkyl)$_2$, —NHC(O)alkyl, —NHSO$_2$alkyl, —SO$_2$alkyl or —SO$_2$NH-alkyl, or two R$^{12}$ groups, together with the carbon atoms to which they are attached, join to form a cycloalkyl, heterocycloalkyl or C=O group;

each occurrence of R$^{20}$ is independently alkyl, aryl, cycloalkyl, heterocycloalkyl or heteroaryl, or both R$^{20}$ groups and the carbon atoms to which they are attached, join to form a cycloalkyl, cycloheteroalkyl, aryl or heteroaryl group wherein a cycloalkyl, cycloheteroalkyl, aryl or heteroaryl group can be substituted with up to 4 groups, which are each independently selected from alkyl, alkenyl, alkynyl, halo, —OH, —OR$^9$, —CN, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-haloalkyl, —[C(R$^{12}$)$_2$]$_q$-hydroxyalkyl, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$;

each occurrence of R$^{30}$ is independently selected from —H, alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl, —[C(R$^{12}$)$_2$]$_q$-hydroxyalkyl, halo, —OH, —OR$^9$, —CN, —[C(R$^{12}$)$_2$]$_q$—C(O)R$^8$, —[C(R$^{12}$)$_2$]$_q$—C(O)OR$^9$, —[C(R$^{12}$)$_2$]$_q$—C(O)N(R$^9$)$_2$, —[C(R$^{12}$)$_2$]$_q$—OR$^9$, —[C(R$^{12}$)$_2$]$_q$—N(R$^9$)$_2$, —[C(R$^{12}$)$_2$]$_q$—NHC(O)R$^8$, —[C(R$^{12}$)$_2$]$_q$—NR$^8$C(O)N(R$^9$)$_2$, —[C(R$^{12}$)$_2$]$_q$—NHSO$_2$R$^{11}$, —[C(R$^{12}$)$_2$]$_q$—S(O)$_p$R$^{11}$, —[C(R$^{12}$)$_2$]$_q$—SO$_2$N(R$^9$)$_2$ and —SO$_2$N(R$^9$)C(O)N(R$^9$)$_2$, or two adjacent R$^{30}$ groups, together with the carbon atoms to which they are attached, join to form a –3- to 7-membered ring selected from aryl, cycloalkyl, heteroaryl and heterocycloalkyl;

R$^{31}$ is alkyl, alkenyl, alkynyl, aryl, —[C(R$^{12}$)$_2$]$_q$-cycloalkyl, —[C(R$^{12}$)$_2$]$_q$-cycloalkenyl, —[C(R$^{12}$)$_2$]$_q$-heterocycloalkyl, —[C(R$^{12}$)$_2$]$_q$-heterocycloalkenyl, —[C(R$^{12}$)$_2$]$_q$-heteroaryl, —[C(R$^{12}$)$_2$]$_q$-haloalkyl or —[C(R$^{12}$)$_2$]$_q$-hydroxyalkyl;

each occurrence of p is independently 0, 1 or 2;

each occurrence of q is independently an integer ranging from 0 to 4; and each occurrence of r is independently an integer ranging from 1 to 4.

The compounds of formulas (I) and (II) (herein referred to collectively as the "2-Carboxy Substituted Indole Derivatives") and pharmaceutically acceptable salts, solvates, esters and prodrugs thereof can be useful for treating or preventing a viral infection or a virus-related disorder in a patient.

Also provided by the invention are methods for treating or preventing a viral infection or a virus-related disorder in a patient, comprising administering to the patient an effective amount of at least one 2-Carboxy Substituted Indole Derivative.

The present invention further provides pharmaceutical compositions comprising an effective amount of at least one 2-Carboxy Substituted Indole Derivative or a pharmaceutically acceptable salt, solvate thereof, and a pharmaceutically acceptable carrier. The compositions can be useful for treating or preventing a viral infection or a virus-related disorder in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

In an embodiment, the present invention provides 2-Carboxy Substituted Indole Derivatives, pharmaceutical compositions comprising at least one 2-Carboxy Substituted Indole Derivative, and methods of using the 2-Carboxy Substituted Indole Derivatives for treating or preventing a viral infection or in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "alkyl" as used herein, refers to an aliphatic hydrocarbon group, wherein one of the aliphatic hydrocarbon group's hydrogen atoms is replaced with a single bond. An alkyl group can be straight or branched and can contain from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or optionally substituted by one or more substituents which may be the same or different, each substituent being independently selected from the group consisting of halo, alkenyl, alkynyl, —O-aryl, aryl, heteroaryl, cycloalkyl, cycloalkenyl, cyano, —OH, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkyl group is unsubstituted. In another embodiment, an alkyl group is a straight chain alkyl group. In another embodiment, an alkyl group is a branched alkyl group.

The term "alkenyl" as used herein, refers to an aliphatic hydrocarbon group having at least one carbon-carbon double bond, wherein one of the aliphatic hydrocarbon group's hydrogen atoms is replaced with a single bond. An alkenyl group can be straight or branched and can contain from about 2 to about 15 carbon atoms. In one embodiment, an alkenyl group contains from about 2 to about 10 carbon atoms. In another embodiment, an alkenyl group contains from about 2 to about 6 carbon atoms. Non-limiting examples of illustrative alkenyl groups include ethenyl, propenyl, n-butenyl, 3-methylbut-2-enyl, n-pentenyl, octenyl and decenyl. An alkenyl group may be unsubstituted or optionally substituted by one or more substituents which may be the same or different, each substituent being independently selected from the group consisting of halo, alkyl, alkynyl, —O-aryl, aryl, cycloalkyl, cycloalkenyl, cyano, —OH, —O-alkyl, —O-haloalkyl, -alkylene-O-alkyl, alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkenyl group is unsubstituted. In another embodiment, an alkenyl group is a straight chain alkenyl group. In another embodiment, an alkenyl group is a branched alkenyl group.

The term "alkynyl" as used herein, refers to an aliphatic hydrocarbon group having at least one carbon-carbon triple bond, wherein one of the aliphatic hydrocarbon group's hydrogen atoms is replaced with a single bond. An alkynyl group can be straight or branched and can contain from about 2 to about 15 carbon atoms. In one embodiment, an alkynyl group contains from about 2 to about 10 carbon atoms. In another embodiment, an alkynyl group contains from about 2 to about 6 carbon atoms. Non-limiting examples of illustrative alkynyl groups include ethynyl, propynyl, 2-butynyl and 3-methylbutynyl. An alkynyl group may be unsubstituted or optionally substituted by one or more substituents which may be the same or different, each substituent being independently selected from the group consisting of halo, alkyl, alkenyl, —O-aryl, aryl, cycloalkyl, cycloalkenyl, cyano, —OH, —O-alkyl, -alkylene-O-alkyl, —O-haloalkyl, -alkylthio, —NH$_2$, —NH(alkyl), —N(alkyl)$_2$, —NH-aryl, —NH-heteroaryl, —NHC(O)-alkyl, —NHC(O)NH-alkyl, —NHSO$_2$-alkyl, —NHSO$_2$-aryl, —NHSO$_2$-heteroaryl, —NH(cycloalkyl), —OC(O)-alkyl, —OC(O)-aryl, —OC(O)-cycloalkyl, —C(O)alkyl, —C(O)NH$_2$, —C(O)NH-alkyl, —C(O)OH and —C(O)O-alkyl. In one embodiment, an alkynyl group is unsubstituted. In another embodiment, an alkynyl group is a straight chain alkynyl group. In another embodiment, an alkynyl group is a branched alkynyl group.

The term "alkylene" as used herein, refers to an alkyl group, as defined above, wherein one of the alkyl group's hydrogen atoms is replaced with a bond. Illustrative examples of alkylene include, but are not limited to, —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH$_2$CH(CH$_3$)CH$_2$— and —CH$_2$CH$_2$CH(CH$_3$)—. In one embodiment, an alkylene group is a straight chain alkylene group. In another embodiment, an alkylene group is a branched alkylene group.

"Aryl" means an aromatic monocyclic or multicyclic ring system having from about 6 to about 14 ring carbon atoms. In one embodiment, an aryl group has from about 6 to about 10 ring carbon atoms. An aryl group can be optionally substituted with one or more "ring system substituents" which may be the same or different, and are as defined herein below. Non-limiting examples of illustrative aryl groups include phenyl and naphthyl. In one embodiment, an aryl group is unsubstituted. In another embodiment, an aryl group is a phenyl group.

The term "cycloalkyl" as used herein, refers to a non-aromatic mono- or multicyclic ring system having from about 3 to about 10 ring carbon atoms. In one embodiment, a cycloalkyl has from about 5 to about 10 ring carbon atoms. In another embodiment, a cycloalkyl has from about 5 to about 7 ring carbon atoms. Non-limiting examples of illustrative monocyclic cycloalkyls include cyclopropyl, cyclopentyl, cyclohexyl, cycloheptyl and the like. Non-limiting examples of illustrative multicyclic cycloalkyls include 1-decalinyl, norbornyl, adamantyl and the like. A cycloalkyl group can be optionally substituted with one or more "ring system substituents" which may be the same or different, and are as defined herein below. In one embodiment, a cycloalkyl group is unsubstituted.

The term "cycloalkenyl" as used herein, refers to a non-aromatic mono- or multicyclic ring system comprising from about 3 to about 10 ring carbon atoms and containing at least one endocyclic double bond. In one embodiment, a cycloalkenyl contains from about 5 to about 10 ring carbon atoms. In another embodiment, a cycloalkenyl contains 5 or 6 ring carbon atoms. Non-limiting examples of illustrative monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. In one embodiment, a cycloalkenyl group is unsubstituted.

The term "halo" as used herein, means —F, —Cl, —Br or —I. In one embodiment, halo refers to —Cl or —F.

The term "haloalkyl" as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of illustrative haloalkyl groups include —CH$_2$F, —CHF$_2$, —CF$_3$, —CH$_2$Cl and —CCl$_3$.

The term "hydroxyalkyl" as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of illustrative hydroxyalkyl groups include hydroxymethyl, 2-hydroxyethyl, 3-hydroxypropyl, 4-hydroxybutyl and —CH(OH)CH$_2$CH$_3$.

The term "heteroaryl" as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is monocyclic and has 5 or 6 ring atoms and at least one nitrogen ring atom. A heteroaryl group can be optionally substituted by one or more "ring system substituents" which may be the same or different, and are as defined herein below. A heteroaryl group is joined via a ring carbon atom and any nitrogen atom of a heteroaryl can be optionally oxidized to the corresponding N-oxide. The term "heteroaryl" also encompasses a heteroaryl group, as defined above, which has been fused to a benzene ring. Non-limiting examples of illustrative heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is a 6-membered heteroaryl group. In another embodiment, a heteroaryl group is a 5-membered heteroaryl group.

Unless otherwise indicated, the group:

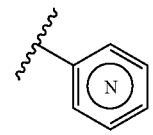

represents a 6-membered heteroaryl group containing 1 or 2 ring nitrogen atoms and no other ring heteroatoms. Examples of such a group include, but are not limited to pyridyl, pyrimidinyl, pyridazinyl and pyrazinyl. In one embodiment, this group has 1 ring nitrogen atom. In another embodiment, this group has 2 ring nitrogen atoms.

The term "heterocycloalkyl" as used herein, refers to a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocycloalkyl group has from about 5 to about 10 ring atoms. In another embodiment, a heterocycloalkyl group has 5 or 6 ring atoms. There are no adjacent oxygen and/or sulfur atoms present in the ring system. Any —NH group in a heterocycloalkyl ring may exist protected such as, for example, as an —N(Boc), —N(CBz), —N(Tos) group and the like; such protected heterocycloalkyl groups are considered part of this invention. A heterocycloalkyl group can be optionally substituted by one or more "ring system substituents" which may be the same or different, and are as defined herein below. The nitrogen or sulfur atom of the heterocyclyl can be optionally oxidized to the corresponding N-oxide, S-oxide or S,S-dioxide. Non-limiting examples of illustrative monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocycloalkyl group may be functionalized as a carbonyl group. An illustrative example of such a heterocycloalkyl group is pyrrolidonyl:

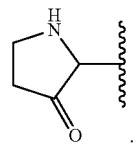

In one embodiment, a heterocycloalkyl group is a 6-membered heterocycloalkyl group. In another embodiment, a heterocycloalkyl group is a 5-membered heterocycloalkyl group.

The term "heterocycloalkenyl" as used herein, refers to a heterocycloalkyl group, as defined above, wherein the heterocycloalkyl group contains from 3 to 10 ring atoms, and at least one endocyclic carbon-carbon or carbon-nitrogen double bond. In one embodiment, a heterocycloalkenyl group has from 5 to 10 ring atoms. In another embodiment, a heterocycloalkenyl group is monocyclic and has 5 or 6 ring atoms. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of illustrative heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. A ring carbon atom of a heterocyclenyl group may be functionalized as a carbonyl group. An illustrative example of such a heterocyclenyl group is:

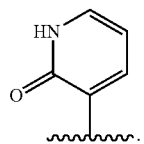

In one embodiment, a heterocycloalkenyl group is a 6-membered heterocycloalkenyl group. In another embodiment, a heterocycloalkenyl group is a 5-membered heterocycloalkenyl group.

The term "ring system substituent" as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, —OH, hydroxyalkyl, —O-alkyl, -alkylene-O-alkyl, —O-aryl, aralkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —OC(O)-alkyl, —OC(O)-aryl, —OC(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkylene-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

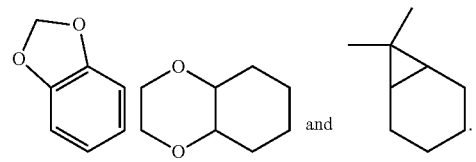

The term "substituted," as used herein, means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" as used herein, means optional substitution with the specified groups, radicals or moieties.

The terms "purified", "in purified form" or "in isolated and purified form" as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, R[11], etc.) occurs more than one time in any constituent or in Formula (I) or (II), its definition on each occurrence is independent of its definition at every other occurrence, unless otherwise noted.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" as used herein, refers to a compound (e.g, a drug precursor) that is transformed in vivo to yield a 2,3-Substituted Indole Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a 2,3-Substituted Indole Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a 2,3-Substituted Indole Derivative contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate), and the like.

If a 2,3-Substituted Indole Derivative incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$)cycloalkyl, benzyl, or R-carbonyl is a natural α-aminoacyl or natural α-aminoacyl, —C(OH)C(O)$OY^1$ wherein $Y^1$ is H, ($C_1$-$C_6$)alkyl or benzyl, —C($OY^2$)$Y^3$ wherein $Y^2$ is ($C_1$-$C_4$)alkyl and $Y^3$ is ($C_1$-$C_6$)alkyl, carboxy ($C_1$-$C_6$)alkyl, amino($C_1$-$C_4$)alkyl or mono-N- or di-N,N—($C_1$-$C_6$)alkylaminoalkyl, —C($Y^4$)$Y^5$ wherein $Y^4$ is H or methyl and $Y^5$ is mono-N- or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "effective amount" or "therapeutically effective amount" is meant to describe an amount of compound or a composition of the present invention that is effective to treat or prevent a viral infection or a virus-related disorder.

Metabolic conjugates, such as glucuronides and sulfates which can undergo reversible conversion to the 2,3-Substituted Indole Derivatives are contemplated in the present invention.

The 2,3-Substituted Indole Derivatives may form salts, and all such salts are contemplated within the scope of this invention. Reference to a 2,3-Substituted Indole Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a 2,3-Substituted Indole Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a 2,3-Substituted Indole Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, choline, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

The 2,3-Substituted Indole Derivatives may contain asymmetric or chiral centers, and, therefore, exist in different stereoisomeric forms. It is intended that all stereoisomeric forms of the 2,3-Substituted Indole Derivatives as well as mixtures thereof, including racemic mixtures, form part of the present invention. In addition, the present invention embraces all geometric and positional isomers. For example, if a 2,3-Substituted Indole Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the 2,3-Substituted Indole Derivatives may be atropisomers (e.g., substituted biaryls) and are considered as part of this invention. Enantiomers can also be separated by use of chiral HPLC column.

The straight line — as a bond generally indicates a mixture of, or either of, the possible isomers, non-limiting example(s) include, containing (R)- and (S)-stereochemistry. For example,

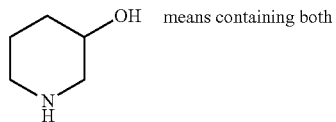 means containing both 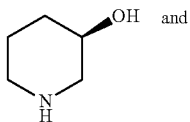 and

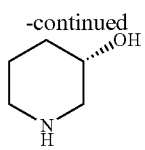

A dashed line ( - - - ) represents an optional bond.
Lines drawn into the ring systems, such as, for example:

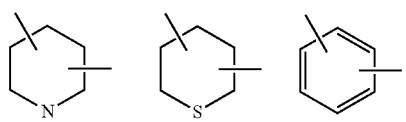

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

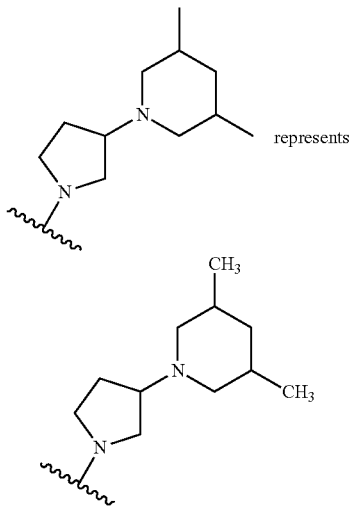

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a 2,3-Substituted Indole Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Such compounds are useful as therapeutic, diagnostic or research reagents. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled 2,3-Substituted Indole Derivatives (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled 2,3-Substituted Indole Derivatives can generally be prepared by following procedures analogous to those disclosed in the Schemes and/or in the Examples herein below, by substituting an appropriate isotopically labelled reagent for a non-isotopically labelled reagent.

Polymorphic forms of the 2,3-Substituted Indole Derivatives, and of the salts, solvates, hydrates, esters and prodrugs of the 2,3-Substituted Indole Derivatives, are intended to be included in the present invention.

The following abbreviations are used below and have the following meanings: CDI is N,N'-Carbonyldiimidazole; DABCO is 1,4-Diazabicyclo[2.2.2]octane; dba is dibenzylideneacetone; DBU is 1,8-Diazabicyclo[5.4.0]undec-7-ene; DCM is dichloromethane; DIEA is diethylamine; DIPEA is diisopropylethylamine; DMF is dimethylformamide; dppf is 1,1'-bis(diphenylphosphino)ferrocene; EDCI is 1-(3-dimethylaminopropyl)-3-ethylcarbodiimide; Et is ethyl; Et$_3$N is triethylamine; EtOAc is ethyl acetate; HATU is N-(diethylamino)-1H-1,2,3-triazolo[4,5-b]pyridine-1-yl-methylene]-N-methylmethanaminium hexafluorophosphate N-oxide; HPLC is high performance liquid chromatography; MeOH is methanol; MS is mass spectrometry; NBS is N-bromosuccinimide; MS is N-iodosuccinimide; PPA is polyphosphoric acid; TBAF is tetra-n-butylammonium fluoride; THF is tetrahydrofuran; TLC is thin layer chromatography and TMS is trimethylsilyl.

The 2-Carboxy Substituted Indole Derivatives of Formula (I)

The present invention provides 2-Carboxy Substituted Indole Derivatives having the formula:

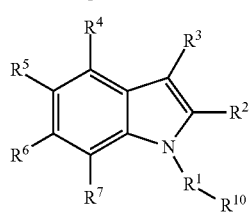
(I)

and pharmaceutically acceptable salts, solvates, esters and prodrugs thereof, wherein $R^1$, $R^2$, $R^3$, $R^4$, $R^5$, $R^6$, $R^7$ and $R^{10}$ are defined above for the compounds of formula (I).

In one embodiment, $R^1$ is bond.

In another embodiment, $R^1$ is —[C(R$^{12}$)$_2$]$_r$—.

In another embodiment, $R^1$ is —[C(R$^{12}$)$_2$]$_r$—O—[C(R$^{12}$)$_2$]$_q$—.

In still another embodiment, $R^1$ is —[C(R$^{12}$)$_2$]$_r$—N(R$^9$)—[C(R$^{12}$)$_2$]$_q$—.

In yet another embodiment, $R^1$ is —[C(R$^{12}$)$_2$]$_q$—CH=CH—[C(R$^{12}$)$_2$]$_q$—.

In another embodiment, $R^1$ is —[C(R$^{12}$)$_2$]$_q$—C≡C—[C(R$^{12}$)$_2$]$_q$—.

In a further embodiment, $R^1$ is —[C(R$^{12}$)$_2$]$_q$—SO$_2$—[C(R$^{12}$)$_2$]$_q$—.

In one embodiment, $R^1$ is —CH$_2$—, —CH$_2$CH$_2$—, —CH(CH$_3$)— or

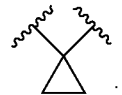 [SMILES: *C1(*)CC1]

In another embodiment, $R^1$ is —CH$_2$—.

In another embodiment, $R^1$ is

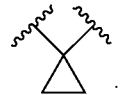 [SMILES: *C1(*)CC1]

In one embodiment, $R^{10}$ is aryl.

In another embodiment, $R^{10}$ is H.

In another embodiment, $R^{10}$ is cycloalkyl.

In another embodiment, $R^{10}$ is cycloalkenyl.

In still another embodiment, $R^{10}$ is heterocycloalkenyl.

In another embodiment, $R^{10}$ is heteroaryl.

In another embodiment, $R^{10}$ is heterocycloalkyl.

In another embodiment, $R^{10}$ is phenyl.

In another embodiment, $R^{10}$ is phenyl, which is substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$.

In yet another embodiment, $R^{10}$ is pyridyl.

In a further embodiment, $R^{10}$ is

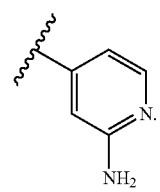

In another embodiment, —$R^{10}$ is:

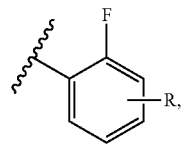

wherein R represents up to 2 optional and additional phenyl substituents, each independently selected from halo, —O-alkyl, alkyl, —$CF_3$, —CN, —$NHSO_2$-alkyl, —$NO_2$, —C(O)$NH_2$, —C(O)OH, —$NH_2$, —$SO_2$-alkyl, —$SO_2$NH-alkyl, —S-alkyl, —$CH_2NH_2$, —$SO_2NH_2$, —NHC(O)-alkyl, —C(O)O-alkyl, —C(O)-heterocycloalkyl and heteroaryl.

In another embodiment, $R^{10}$ is

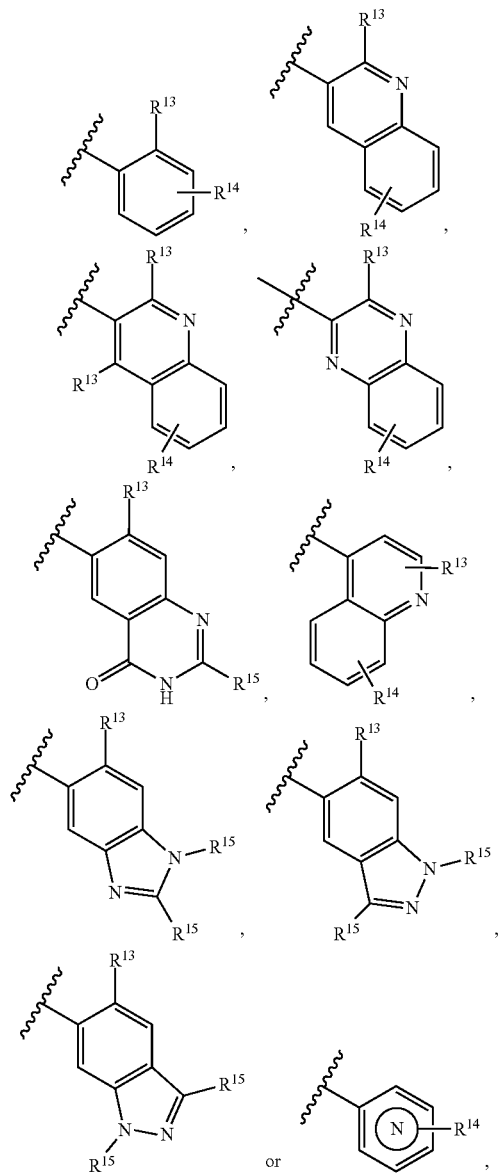

wherein $R^{13}$ is F or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In another embodiment, $R^{10}$ is:

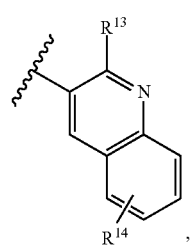

wherein $R^{13}$ is Cl and $R^{14}$ represents up to 4 optional and additional substituents, each independently selected from alkyl, cycloalkyl or halo.

In one embodiment, $R^{10}$ is:

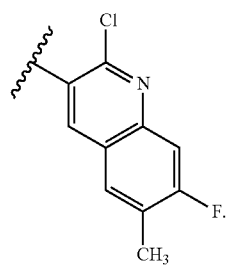 [SMILES: *c1cc2cc(C)c(F)cc2nc1Cl]

In still another embodiment, $R^1$ is —$CH_2$— or

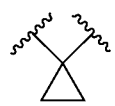

and $R^{10}$ is

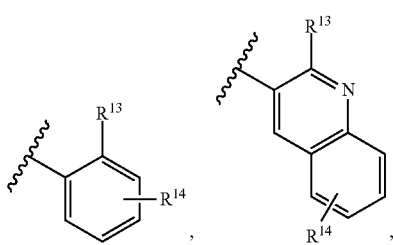

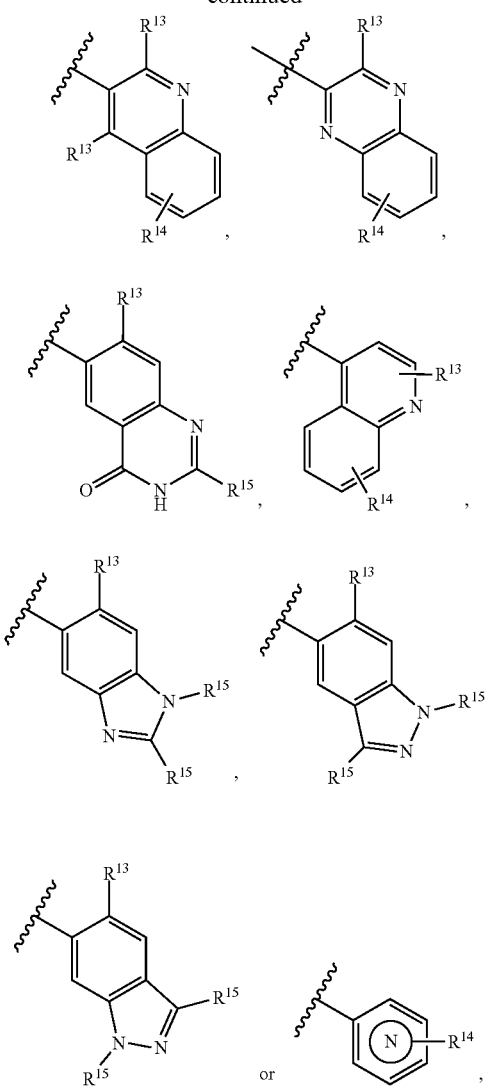

wherein R[13] is F or Cl; R[14] represents up to 4 optional and additional substituents, each independently selected from alkyl, cycloalkyl, CF₃, —CN, halo, —O-alkyl, —NHSO₂-alkyl, —NO₂, —C(O)NH₂, —C(O)NH-alkyl, —C(O)OH, —OH, —NH₂, —SO₂-alkyl, —SO₂NH-alkyl, —S-alkyl, —CH₂NH₂, —CH₂OH, —SO₂NH₂, —NHC(O)-alkyl, —C(O)O-alkyl, —C(O)-heterocycloalkyl and heteroaryl; and each occurrence of R[15] is independently alkyl, cycloalkyl, CF₃, —CN, halo, —O-alkyl, —NHSO₂-alkyl, —NO₂, —C(O)NH₂, —C(O)NH-alkyl, —C(O)OH, —OH, —NH₂, —SO₂-alkyl, —SO₂NH-alkyl, —S-alkyl, —CH₂NH₂, —CH₂OH, —SO₂NH₂, —NHC(O)-alkyl, —C(O)O-alkyl, —C(O)-heterocycloalkyl or heteroaryl.

In one embodiment, —R¹-R¹⁰ is benzyl.

In another embodiment, —R¹-R¹⁰ is benzyl, wherein the phenyl moiety of the benzyl group is substituted with from 1-4 groups independently selected from: halo, —NH₂, —NHSO₂-alkyl, haloalkyl, methoxy, —O-haloalkyl, —[C(R¹²)₂]_q—NHC(O)NH-alkyl, alkyl, —OH, —CN, —C(O)NH₂ or —[C(R¹²)₂]_q—NH₂.

In still another embodiment, —R¹-R¹⁰ is

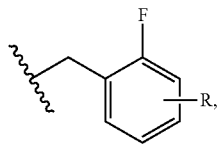

wherein R represents up to 2 optional and additional phenyl substituents, each independently selected from halo, —O-alkyl, alkyl, —CF₃, —CN, —NHSO₂-alkyl, —NO₂, —C(O)NH₂, —C(O)OH, —NH₂, —SO₂-alkyl, —SO₂NH-alkyl, —S-alkyl, —CH₂NH₂, —SO₂NH₂, —NHC(O)-alkyl, —C(O)O-alkyl, —C(O)-heterocycloalkyl and heteroaryl.

In another embodiment, —R¹-R¹⁰ is

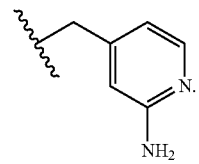

In another embodiment, —R¹-R¹⁰ is

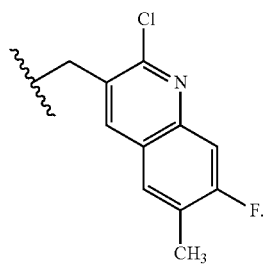 [SMILES: *Cc1cc2cc(C)c(F)cc2nc1Cl]

In still another embodiment, —R¹-R¹⁰ is alkyl.

In yet another embodiment, —R¹-R¹⁰ is —R¹-R¹⁰ is benzyl, wherein the phenyl moiety of the benzyl group is substituted with 1 or 2 fluorine atoms.

In yet another embodiment, —R¹-R¹⁰ is R¹-R¹⁰ is benzyl, wherein the phenyl moiety of the benzyl group is substituted with 1 or 2 methyl groups.

In yet another embodiment, —R¹-R¹⁰ is —R¹-R¹⁰ is benzyl, wherein the phenyl moiety of the benzyl group is substituted with one fluorine atom and one methyl group.

In another embodiment, —R¹-R¹⁰ is haloalkyl.

In a further embodiment, —R¹-R¹⁰ is —CH₂-cycloalkyl.

In one embodiment, R² is —C(O)R⁹.

In another embodiment, R² is —C(O)OR⁹.

In another embodiment, R² is —C(O)OCH₂OR⁹.

In still another embodiment, R² is —C(O)N(R⁹)₂.

In yet another embodiment, R² is —[C(R¹²)₂]_q—C(O)OR⁹.

In another embodiment, R² is —[C(R¹²)₂]_q—C(O)N(R⁹)₂.

In a further embodiment, R² is -alkyl.

In another embodiment, R² is —[C(R¹²)₂]_q-aryl.

In another embodiment, R² is —[C(R¹²)₂]_q-cycloalkyl.

In still another embodiment, R² is [—C(R¹²)₂]_q-cycloalkenyl.

In still another embodiment, R² is —[C(R¹²)₂]_q-heterocycloalkyl.

In yet another embodiment, R² is —[C(R¹²)₂]_q-heteroaryl.

In another embodiment, $R^2$ is —[C($R^{12}$)$_2$]$_q$-heterocycloalkenyl.

In a further embodiment, $R^2$ is —C(O)O$R^9$ or —C(O)OCH$_2$O$R^9$.

In another embodiment, $R^2$ is —C(O)O$R^9$ or —C(O)N($R^9$)$_2$.

In another embodiment, $R^2$ is $R^2$ is —C(O)O$R^9$ or —C(O)N($R^9$)$_2$, wherein $R^9$ is H, alkyl, aryl, cycloalkyl, heteroaryl or heterocycloalkyl.

In another embodiment, $R^2$ is —C(O)OH, —C(O)NH$_2$, —C(O)O-alkyl, —C(O)O-cycloalkyl, —C(O)NH-alkyl or —C(O)NH-cycloalkyl.

In another embodiment, $R^2$ is —C(O)OH.

In another embodiment, $R^2$ is —C(O)NH$R^9$.

In another embodiment, $R^2$ is —C(O)NH$_2$.

In still another embodiment, $R^2$ is —C(O)$R^9$, —C(O)O$R^9$, —C(O)OCH$_2$O$R^9$, —C(O)N($R^9$)$_2$, —[C($R^{12}$)$_2$]$_q$—C(O)O$R^9$, —[C($R^{12}$)$_2$]$_q$—C(O)N($R^9$)$_2$ or —[C($R^{12}$)$_2$]$_q$-heteroaryl wherein a heteroaryl group can be optionally substituted with up to 4 substituents, which are the same or different, and are selected from alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, —OH, —O$R^9$, —CN, —[C($R^{12}$)$_2$]$_q$—C(O)$R^8$, —[C($R^{12}$)$_2$]$_q$—C(O)O$R^9$, —[C($R^{12}$)$_2$]$_q$—C(O)N($R^9$)$_2$, —[C($R^{12}$)$_2$]$_q$—O$R^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—N$R^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ and —SO$_2$N($R^9$)C(O)N($R^9$)$_2$.

In one embodiment, $R^3$ is

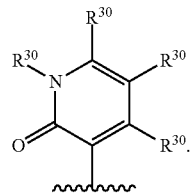

In another embodiment, $R^3$ is

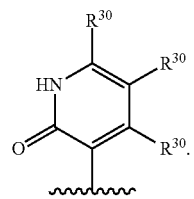

In another embodiment, $R^3$ is

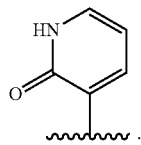

In still another embodiment, $R^3$ is

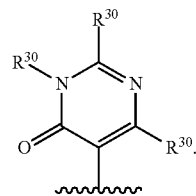

In another embodiment, $R^3$ is

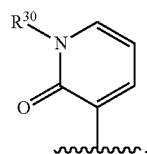

In another embodiment, $R^3$ is

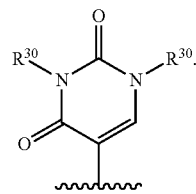

In one embodiment, $R^4$ is H.
In another embodiment, $R^4$ is H or F.
In another embodiment, $R^4$ is F.
In another embodiment, $R^5$ is H.
In another embodiment, $R^6$ is H.
In another embodiment, $R^6$ is H or F.
In another embodiment, $R^6$ is F.
In still another embodiment, $R^7$ is H.
In another embodiment, $R^4$ and $R^7$ are each H.
In another embodiment, $R^5$ and $R^6$ are each other than H.
In yet another embodiment, $R^4$, $R^6$ and $R^7$ are each H.
In another embodiment, $R^4$, $R^5$, $R^6$ and $R^7$ are each H.
In a further embodiment, $R^4$, $R^6$ and $R^7$ are each H and $R^5$ is other than H.
In another embodiment, $R^4$, $R^6$ and $R^7$ are each H and $R^5$ is alkyl.
In another embodiment, $R^4$, $R^6$ and $R^7$ are each H and $R^5$ is halo.
In another embodiment, $R^4$, $R^6$ and $R^7$ are each H and $R^5$ is methyl.
In a further embodiment, $R^4$, $R^6$ and $R^7$ are each H and $R^5$ is Cl.
In another embodiment, $R^4$ and $R^7$ are each H and $R^5$ and $R^6$ are each other than H.
In another embodiment, $R^4$ and $R^7$ are each H and $R^5$ and $R^6$ are each independently selected from alkyl, halo and haloalkyl.
In yet another embodiment, $R^4$ and $R^7$ are each H and $R^5$ and $R^6$ are each independently selected from alkyl and halo.
In another embodiment, $R^5$ is other than H.
In still another embodiment, $R^5$ is alkyl.
In yet another embodiment, $R^5$ is halo.
In still another embodiment, $R^5$ is methyl.
In another embodiment, $R^5$ is ethyl.
In another embodiment, $R^6$ is H.

In another embodiment, $R^6$ is other than H.
In a further embodiment, $R^6$ is alkyl.
In yet another embodiment, $R^6$ is halo.
In still another embodiment, $R^6$ is methyl.
In another embodiment, $R^6$ is F.
In another embodiment, $R^4$ is H or F; $R^5$ is methyl or ethyl; $R^6$ is H or F; and $R^7$ is H.
In a further embodiment, $R^4$ and $R^7$ are each independently H, alkyl, halo or —OH, $R^5$ is H, alkyl, —O-alkyl, —O-haloalkyl, cycloalkyl, halo, haloalkyl, —OH, hydroxyalkyl, —$NH_2$ or —CN, and $R^6$ is H, alkyl, —O-alkyl, —O-haloalkyl, cycloalkyl, halo, haloalkyl, —OH, hydroxyalkyl, —$NH_2$ or —CN.

In one embodiment, $R^2$ is —$C(O)OR^9$ or —$C(O)N(R^9)_2$, and $R^3$ is:

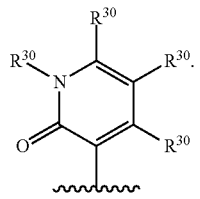

In one embodiment, $R^2$ is —C(O)O-alkyl or —$C(O)NHR^9$, $R^3$ is:

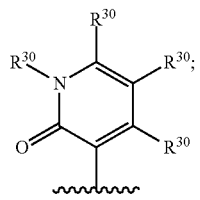

and two adjacent $R^{30}$ groups and the carbon atoms to which they are attached, join to form a benzene ring.

In one embodiment, $R^2$ is —C(O)OH, and $R^3$ is

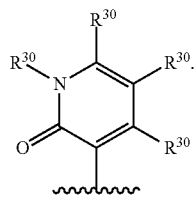

In still another embodiment, $R^2$ is —$C(O)R^9$, —$C(O)OR^9$, —$C(O)OCH_2OR^9$, —$C(O)N(R^9)_2$, —$[C(R^{12})_2]_q$—$C(O)OR^9$, —$[C(R^{12})_2]_q$—$C(O)N(R^9)_2$ or —$[C(R^{12})_2]_q$-heteroaryl wherein a heteroaryl group can be optionally substituted with up to 4 substituents, which are the same or different, and are selected from alkyl, alkenyl, alkynyl, aryl, —$[C(R^{12})_2]_q$-cycloalkyl, —$[C(R^{12})_2]_q$-cycloalkenyl, —$[C(R^{12})_2]_q$-heterocycloalkyl, —$[C(R^{12})_2]_q$-heterocycloalkenyl, —$[C(R^{12})_2]_q$-heteroaryl, —$[C(R^{12})_2]_q$-haloalkyl, —$[C(R^{12})_2]_q$-hydroxyalkyl, halo, —OH, —$OR^9$, —CN, —$[C(R^{12})_2]_q$—$C(O)R^8$, —$[C(R^{12})_2]_q$—$C(O)OR^9$, —$[C(R^{12})_2]_q$—$C(O)N(R^9)_2$, —$[C(R^{12})_2]_q$—$OR^9$, —$[C(R^{12})_2]_q$—$N(R^9)_2$, —$[C(R^{12})_2]_q$—$NHC(O)R^8$, —$[C(R^{12})_2]_q$—$NR^8C(O)N(R^9)_2$, —$[C(R^{12})_2]_q$—$NHSO_2R^{11}$, —$[C(R^{12})_2]_q$—$S(O)_pR^{11}$, —$[C(R^{12})_2]_q$—$SO_2N(R^9)_2$ and —$SO_2N(R^9)C(O)N(R^9)_2$, and $R^3$ is

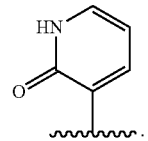

In one embodiment, $R^2$ is —$C(O)OR^9$ and $R^3$ is

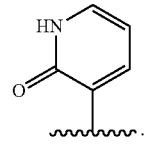

In one embodiment, $R^2$ is —C(O)OH, and $R^3$ is

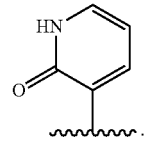

In one embodiment, $R^2$ is —$C(O)N(R^9)2$, where $R^9$ is H, alkyl, cycloalkyl, or heterocycloalkyl; and $R^3$ is

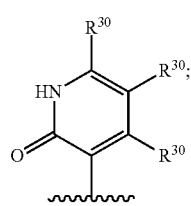

In another embodiment, $R^2$ is —$C(O)OR^9$ or —$C(O)N(R^9)_2$;
$R^3$ is:

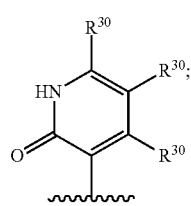

and $R^4$ and $R^7$ are each independently H, halo or hydroxy.

In another embodiment, $R^2$ is —C(O)OR$^9$ or —C(O)N(R$^9$)$_2$;
$R^3$ is:

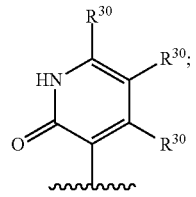

and $R^5$ is H, alkyl, —O-alkyl, cycloalkyl, halo, haloalkyl, —OH, hydroxyalkyl, —NH$_2$ or —CN.

In another embodiment, $R^2$ is —C(O)OR$^9$ or —C(O)N(R$^9$)$_2$;
$R^3$ is

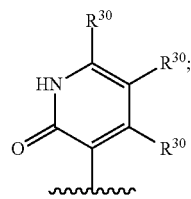

and $R^5$ is alkyl, cycloalkyl, halo or hydroxy.

In another embodiment, $R^2$ is —C(O)OR$^9$ or —C(O)N(R$^9$)$_2$;
$R^3$ is:

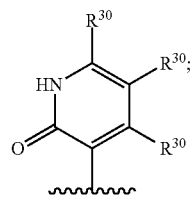

and $R^6$ is H, alkyl, —O-alkyl, cycloalkyl, halo, haloalkyl, —OH, hydroxyalkyl, —NH$_2$ or —CN.

In another embodiment, $R^2$ is —C(O)OR$^9$ or —C(O)N(R$^9$)$_2$;
$R^3$ is

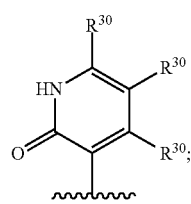

and $R^6$ is alkyl, cycloalkyl, halo or hydroxy.

In still another embodiment, $R^1$ is —[C(R$^{12}$)$_2$]$_r$—; $R^2$ is —C(O)OR$^9$ or —C(O)N(R$^9$)$_2$;
$R^3$ is:

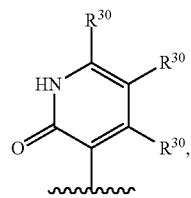

and $R^{10}$ is aryl or heteroaryl;

In one embodiment, $R^1$ is —[C(R$^{12}$)$_2$]$_r$—; $R^2$ $R^2$ is —C(O)OR$^9$ or —C(O)N(R$^9$)$_2$;
and $R^3$ is:

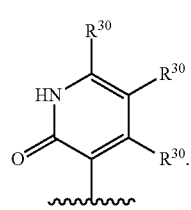

In another embodiment, $R^1$ is —[C(R$^{12}$)$_2$]$_r$—; $R^2$ is —C(O)OR$^9$ or —C(O)N(R$^9$)$_2$;
$R^3$ is:

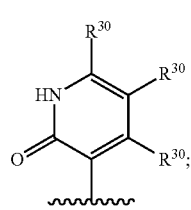

and $R^{10}$ is phenyl, naphthyl, pyridyl, quinolinyl or quinoxalinyl, each of which can be optionally substituted as set forth in claim 1;

In yet another embodiment, $R^1$ is —[C(R$^{12}$)$_2$]$_r$—; $R^2$ is —C(O)OR$^9$ or —C(O)N(R$^9$)$_2$;
$R^3$ is:

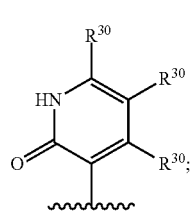

and R$^{10}$ is:

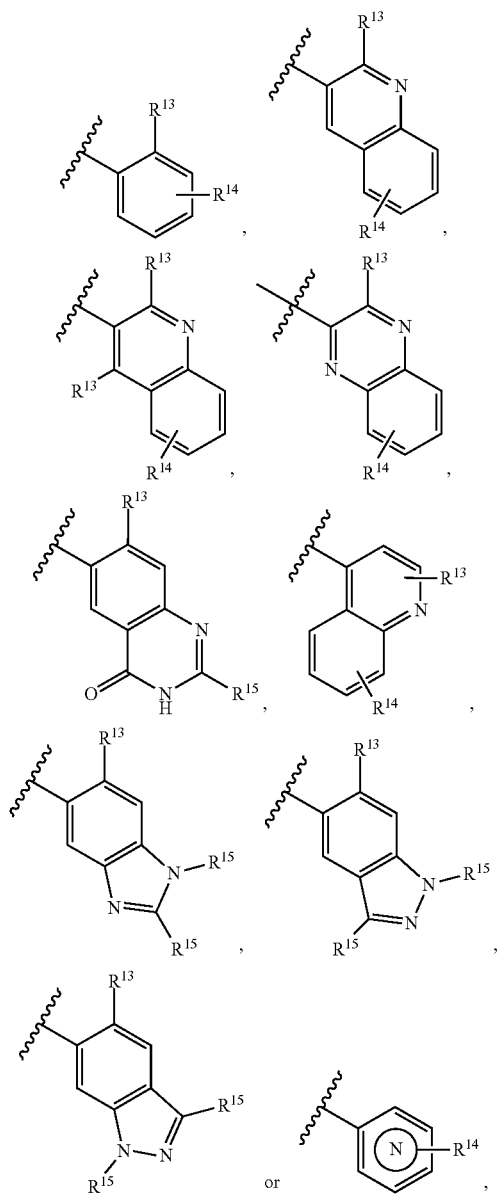

wherein R$^{13}$ is F or Cl; R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of R$^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, R$^1$ is —[C(R$^{12}$)$_2$]$_r$—; R$^2$ is —C(O)OR$^9$ or —C(O)N(R$^9$)$_2$;

R$^3$ is:

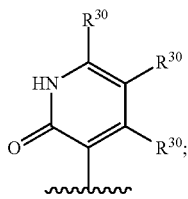

R$^5$ is H, alkyl, —O-alkyl, cycloalkyl, halo, haloalkyl, —OH, hydroxyalkyl, —NH$_2$ or —CN; R$^6$ is H, alkyl, —O-alkyl, cycloalkyl, halo, haloalkyl, —OH, hydroxyalkyl, —NH$_2$ or —CN; and R$^{10}$ is phenyl, naphthyl, pyridyl, quinolinyl or quinoxalinyl, each of which can be optionally substituted as set forth in claim 1.

In a further embodiment, R$^1$ is —[C(R$^{12}$)$_2$]$_r$—; R$^2$ is —C(O)OR$^9$ or —C(O)N(R$^9$)$_2$;

R$^3$ is:

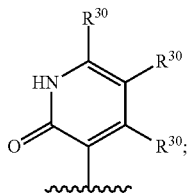

R$^5$ is H, methyl, ethyl or cyclopropyl; R$^6$ is H, F or hydroxy; and R$^{10}$ is phenyl, naphthyl, pyridyl, quinolinyl or quinoxalinyl, each of which can be optionally substituted as set forth in claim 1.

In another embodiment, R$^1$ is —[C(R$^{12}$)$_2$]$_r$—; R$^2$ is —C(O)OR$^9$ or —C(O)N(R$^9$)$_2$;

R$^3$ is:

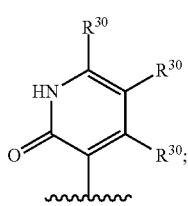

R$^9$ is H, methyl or ethyl; R$^{10}$ is phenyl, naphthyl, pyridyl, quinolinyl or quinoxalinyl, each of which can be optionally substituted as set forth in claim 1; and R$^{11}$ is methyl, ethyl, cyclopropyl or phenyl.

In one embodiment, R$^1$ is —[C(R$^{12}$)$_2$]$_r$—; R$^2$ is —C(O)OR$^9$ or —C(O)N(R$^9$)$_2$;

R$^3$ is:

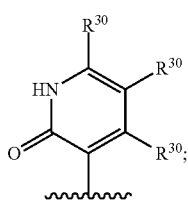

$R^9$ is H, methyl or ethyl; $R^{10}$ is phenyl, naphthyl, pyridyl, quinolinyl or quinoxalinyl, each of which can be optionally substituted as set forth in claim 1; and $R^{11}$ is methyl, cyclopropyl or phenyl.

In another embodiment, $R^1$ is $-[C(R^{12})_2]_r-$; $R^2$ is $-C(O)OR^9$ or $-C(O)N(R^9)_2$;

and $R^3$ is

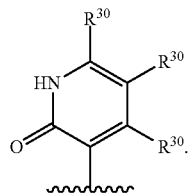

In another embodiment, $R^1$ is $-CH_2-$, $-CH_2CH_2-$, $-CH(CH_3)-$ or

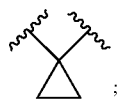

$R^2$ is $-C(O)OR^9$ or $-C(O)N(R^9)_2$; and $R^3$ is:

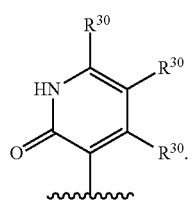

In another embodiment, $R^1$ is $-CH_2-$ or

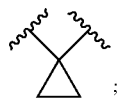

$R^2$ is $-C(O)OR^9$ or $-C(O)N(R^9)_2$; and $R^3$ is

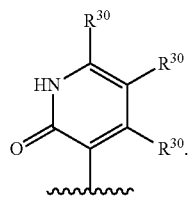

In one embodiment, $R^1$ is $-CH_2-$ or

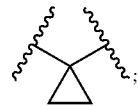

$R^2$ is $-C(O)OR^9$ or $-C(O)N(R^9)_2$;
$R^3$ is

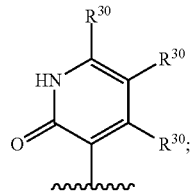

and $R^{10}$ is aryl or heteroaryl.

In one embodiment, $R^1$ is $-CH_2-$ or

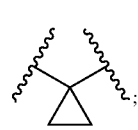

$R^2$ is $-C(O)OR^9$ or $-C(O)N(R^9)_2$;
$R^3$ is

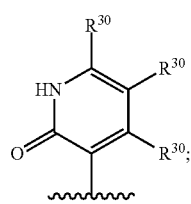

and $R^{10}$ is phenyl, naphthyl, pyridyl, quinolinyl or quinoxalinyl, each of which can be optionally substituted as set forth in formula (I).

In one embodiment, $R^1$ is $-CH_2-$ or

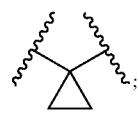

$R^2$ is $-C(O)OR^9$ or $-C(O)N(R^9)_2$;
$R^3$ is

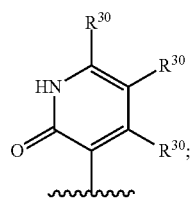

and $R^{10}$ is

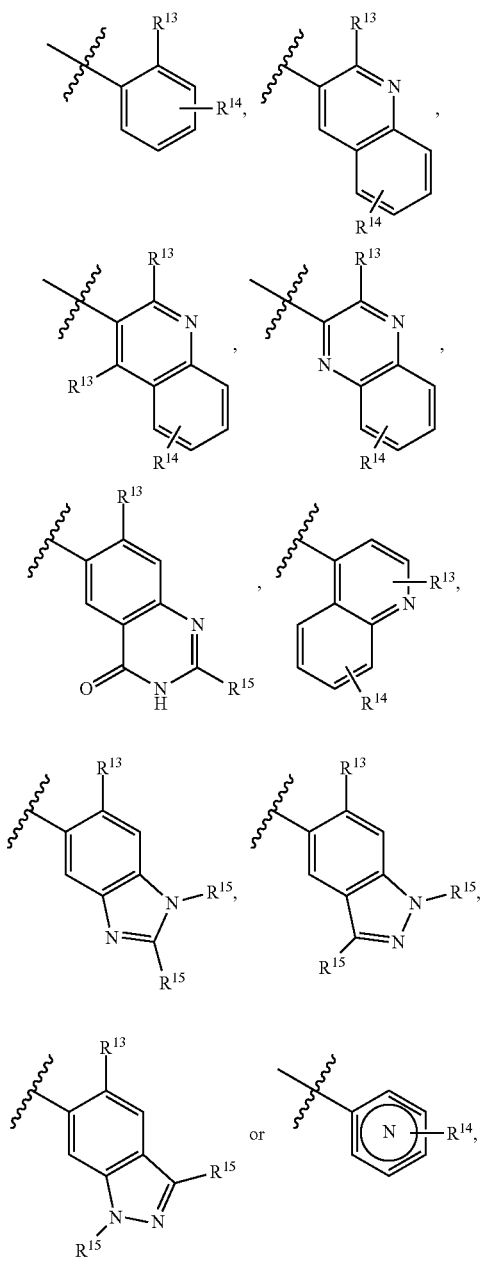

wherein $R^{13}$ is F or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In another embodiment, $R^1$ is —$CH_2$— or

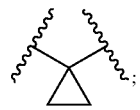 [SMILES: *C1(*)CC1]

$R^2$ is —C(O)$OR^9$ or —C(O)N($R^9$)$_2$; $R^3$ is

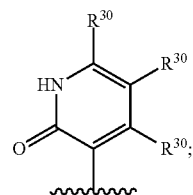

$R^5$ is alkyl, cycloalkyl, halo or hydroxy; $R^6$ is alkyl, cycloalkyl, halo or hydroxy; and $R^{10}$ is

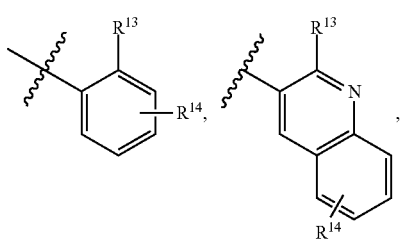

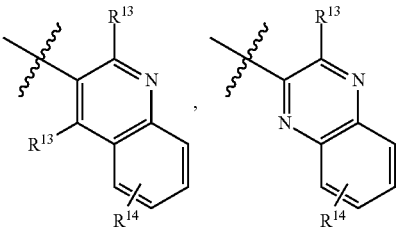

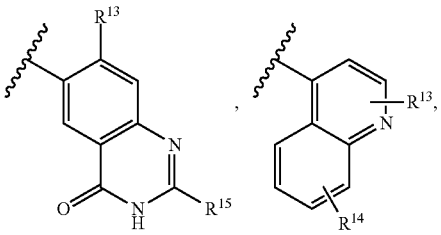

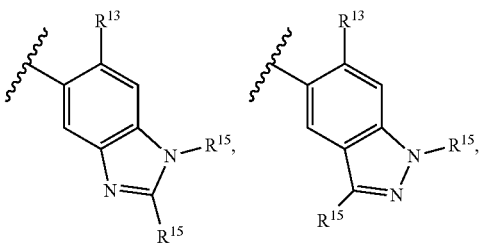

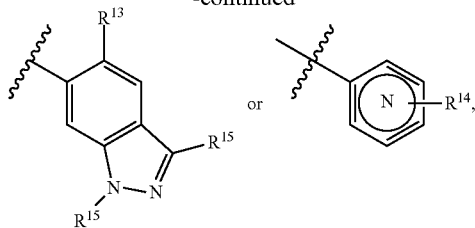 or 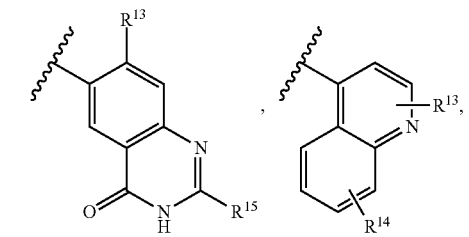

wherein $R^{13}$ is F or Cl; $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, $R^1$ is —CH$_2$— or

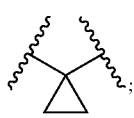 [SMILES: *C1(*)CC1]

$R^2$ is —C(O)OR$^9$ or —C(O)N(R$^9$)$_2$; $R^3$ is

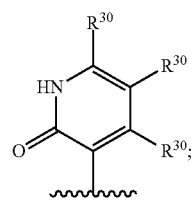

$R^5$ is methyl, ethyl or cyclopropyl; $R^6$ is H, F or hydroxy; and $R^{10}$ is

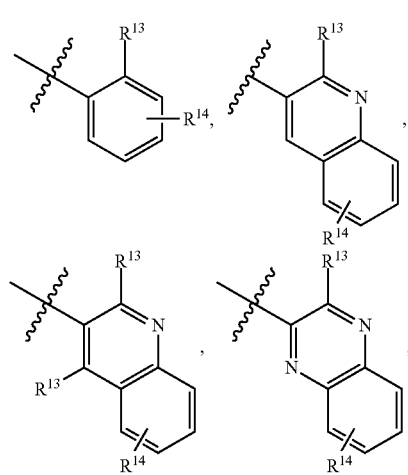

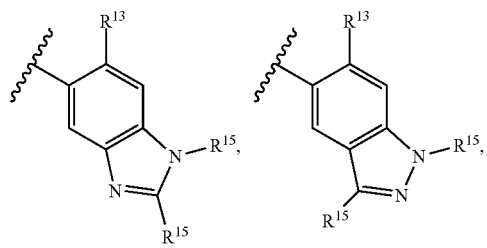

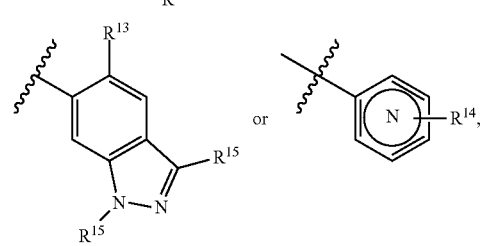

wherein $R^{13}$ is F or Cl; $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In still another embodiment, $R^1$ is —CH$_2$— or

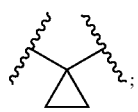 [SMILES: *C1(*)CC1]

$R^2$ is —C(O)OR$^9$ or —C(O)N(R$^9$)$_2$; $R^3$ is

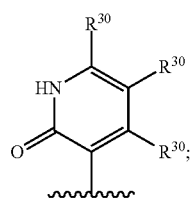

$R^9$ is H, methyl or ethyl; $R^{10}$ is

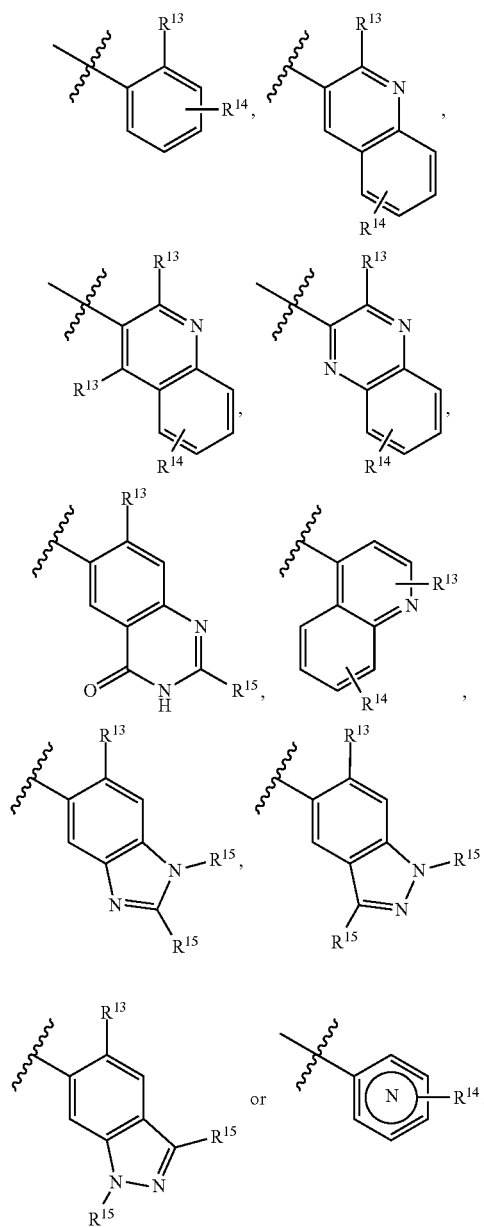

wherein $R^{13}$ is F or Cl; $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and $R^{11}$ is methyl, ethyl, cyclopropyl or phenyl.

In another embodiment, $R^1$ is —CH$_2$— or

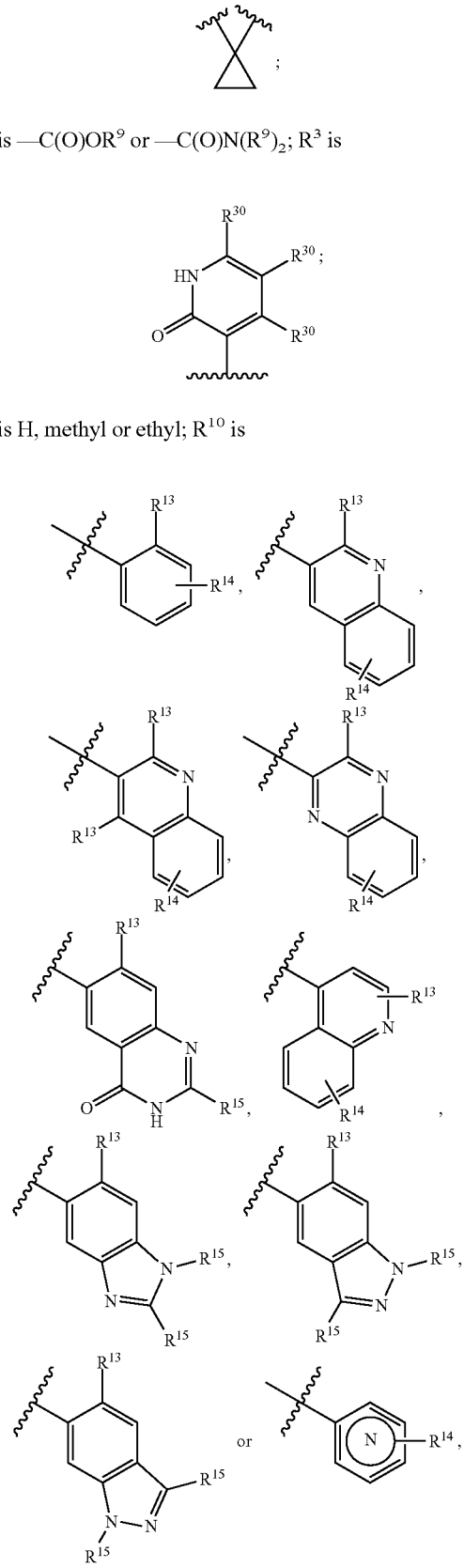

$R^2$ is —C(O)OR$^9$ or —C(O)N(R$^9$)$_2$; $R^3$ is $R^9$ is H, methyl or ethyl; $R^{10}$ is wherein R$^{13}$ is F or Cl; R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of R$^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and R$^{11}$ is methyl, ethyl or phenyl.

In one embodiment, R$^1$-R$^{10}$ is

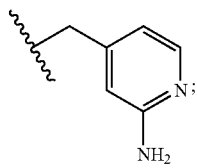 [SMILES: *Cc1ccnc(N)c1]

R$^2$ is —C(O)OH and R$^3$ is

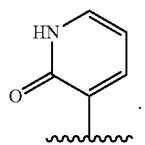

In one embodiment, R$^1$-R$^{10}$ is

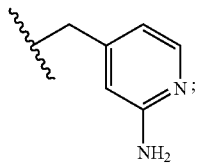 [SMILES: *Cc1ccnc(N)c1]

In one embodiment, R$^1$-R$^{10}$ is

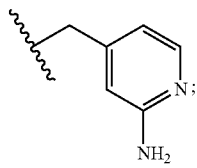 [SMILES: *Cc1ccnc(N)c1]

R$^2$ is —C(O)OH; and R$^3$ is

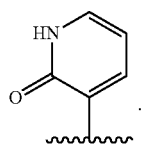

In one embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is —C(O)OR$^9$, and R$^3$ is

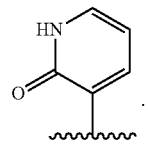

In one embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is —C(O)OH; and R$^3$ is

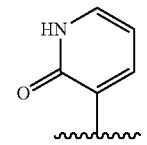 [SMILES: *c1ccc[nH]c1=O]

In one embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is —C(O)OR$^9$, and R$^3$ is

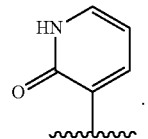 [SMILES: *c1ccc[nH]c1=O]

In one embodiment, R$^1$-R$^{10}$ is

R$^2$ is —C(O)OH; R$^3$ is

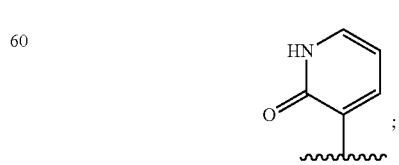

R$^4$, R$^6$ and R$^7$ are each H; and R$^5$ is other than H.

In another embodiment, $R^1$-$R^{10}$ is

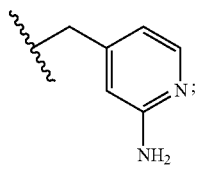

$R^2$ is —C(O)OH; $R^3$ is

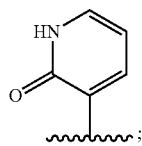

$R^4$, $R^6$ and $R^7$ are each H; and $R^5$ is other than H.

In another embodiment, $R^1$-$R^{10}$ is

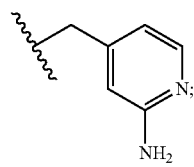 [SMILES: *Cc1ccnc(N)c1]

$R^2$ is —C(O)OH; $R^3$ is

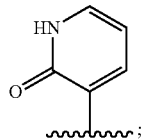

$R^4$, $R^6$ and $R^7$ are each H; and $R^5$ is other than H.

In one embodiment, $R^1$-$R^{10}$ is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, —OH, —CN, —C(O)$NH_2$ or —[C($R^{12}$)$_2$]$_q$—$NH_2$; $R^2$ is —C(O)$OR^9$; $R^3$ is

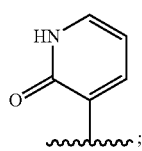

$R^4$, $R^6$ and $R^7$ are each H; and $R^5$ is other than H.

In another embodiment, $R^1$-$R^{10}$ is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, —OH, —CN, —C(O)$NH_2$ or —[C($R^{12}$)$_2$]$_q$—$NH_2$; $R^2$ is —C(O)OH; $R^3$ is

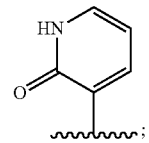 [SMILES: *c1ccc[nH]c1=O]

$R^4$, $R^6$ and $R^7$ are each H; and $R^5$ is other than H.

In another embodiment, $R^1$-$R^{10}$ is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, —OH, —CN, —C(O)$NH_2$ or —[C($R^{12}$)$_2$]$_q$—$NH_2$; $R^2$ is —C(O)$OR^9$, $R^9$ is H, alkyl, or cycloalkyl; $R^3$ is

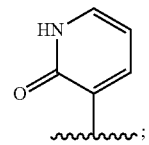 [SMILES: *c1ccc[nH]c1=O]

$R^4$, $R^6$ and $R^7$ are each H; and $R^5$ is other than H.

In one embodiment, $R^1$-$R^{10}$ is

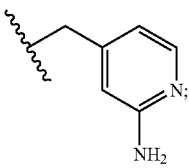

$R^2$ is —C(O)OH; $R^3$ is

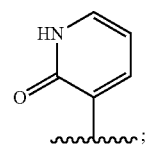

$R^4$ is H or F; $R^5$ is methyl or ethyl; $R^6$ is H or F; and $R^7$ is H.

In another embodiment, $R^1$-$R^{10}$ is

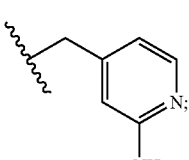

In another embodiment, $R^1$-$R^{10}$ is

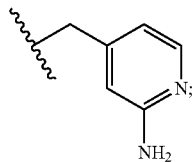 [SMILES: *Cc1ccnc(N)c1]

$R^2$ is —C(O)OH; $R^3$ is

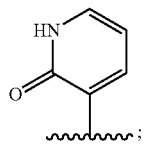

$R^4$ is H or F; $R^5$ is methyl or ethyl; $R^6$ is H or F; and $R^7$ is H.

In one embodiment, $R^1$-$R^{10}$ is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, —OH, —CN, —C(O)$NH_2$ or —[C($R^{12}$)$_2$]$_q$—$NH_2$; $R^2$ is —C(O)OH; $R^3$ is

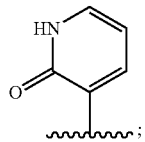

$R^4$ is H or F; $R^5$ is methyl or ethyl; $R^6$ is H or F; and $R^7$ is H.

In another embodiment, $R^1$-$R^{10}$ is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, —OH, —CN, —C(O)$NH_2$ or —[C($R^{12}$)$_2$]$_q$—$NH_2$; $R^2$ is —C(O)OH, $R^3$ is

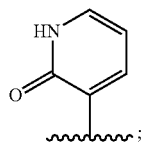

$R^4$ is H or F; $R^5$ is methyl or ethyl; $R^6$ is H or F; and $R^7$ is H.

In another embodiment, $R^1$-$R^{10}$ is benzyl, wherein the phenyl moiety of the benzyl group is optionally substituted with from 1-4 groups independently selected from: halo, —$NH_2$, —$NHSO_2$-alkyl, haloalkyl, methoxy, —O-haloalkyl, —[C($R^{12}$)$_2$]$_q$—NHC(O)NH-alkyl, alkyl, —OH, —CN, —C(O)$NH_2$ or —[C($R^{12}$)$_2$]$_q$—$NH_2$; $R^2$ is —C(O)O$R^9$, $R^9$ is H, alkyl or cycloalkyl; $R^3$ is

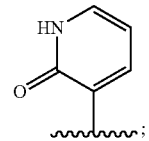 [SMILES: *c1ccc[nH]c1=O]

$R^4$ is H or F; $R^5$ is methyl or ethyl; $R^6$ is H or F; and $R^7$ is H.

In one embodiment, $R^1$ is —$CH_2$—; $R^2$ is —C(O)OH or —C(O)$NH_2$; $R^3$ is

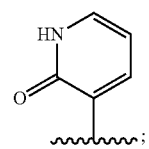

$R^4$ is H or F; $R^5$ is methyl or ethyl; $R^6$ is H or F; $R^7$ is H; and —$R^{10}$ is:

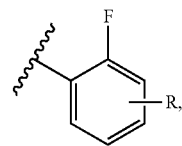

wherein R represents up to 2 optional and additional phenyl substituents, each independently selected from halo, —O-alkyl, alkyl, —$CF_3$, —CN, —$NHSO_2$-alkyl, —$NO_2$, —C(O)$NH_2$, —C(O)OH, —$NH_2$, —$SO_2$-alkyl, —$SO_2$NH-alkyl, —S-alkyl, —$CH_2NH_2$, —$SO_2NH_2$, —NHC(O)-alkyl, —C(O)O-alkyl, —C(O)-heterocycloalkyl and heteroaryl.

In another embodiment, $R^2$ is —C(O)O$R^9$ or —C(O)N($R^9$)$_2$, wherein $R^9$ is H, alkyl, aryl, cycloalkyl, heteroaryl or heterocycloalkyl; and $R^3$ is:

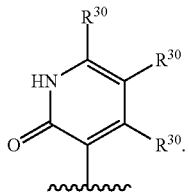

In another embodiment, $R^2$ is —C(O)O$R^9$ or —C(O)N($R^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and $R^1$ is —[C($R^{12}$)$_2$]$_r$—.

In still another embodiment, $R^2$ is —C(O)O$R^9$ or —C(O)N($R^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and $R^1$ is —$CH_2$—, —$CH_2CH_2$—, —CH($CH_3$)— or

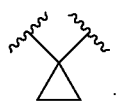

In another embodiment, $R^2$ is —C(O)OR$^9$ or —C(O)N(R$^9$)$_2$, wherein $R^9$ is H, alkyl, aryl, cycloalkyl, heteroaryl or heterocycloalkyl; and wherein $R^4$ and $R^7$ are each independently H, alkyl, halo or —OH, $R^5$ is H, alkyl, —O-alkyl, —O-haloalkyl, cycloalkyl, halo, haloalkyl, —OH, hydroxyalkyl, —NH$_2$ or —CN, and $R^6$ is H, alkyl, —O-alkyl, —O-haloalkyl, cycloalkyl, halo, haloalkyl, —OH, hydroxyalkyl, —NH$_2$ or —CN.

In yet another embodiment, $R^2$ is —C(O)OR$^9$ or —C(O)N(R$^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and $R^{10}$ is aryl or heteroaryl.

In yet another embodiment, $R^2$ is —C(O)OR$^9$ or —C(O)N(R$^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and $R^{10}$ is:

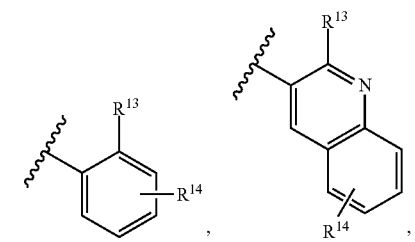

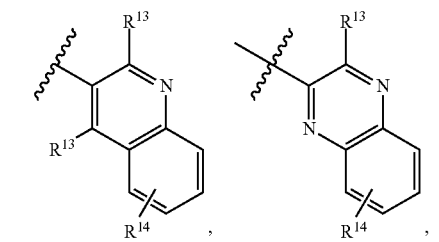

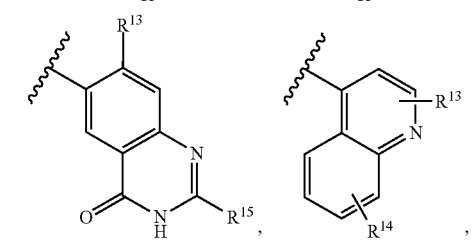

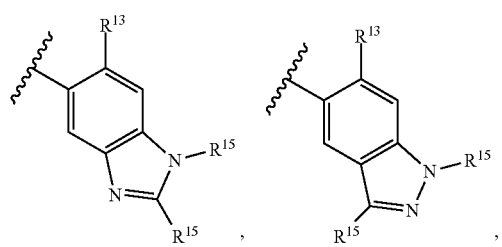

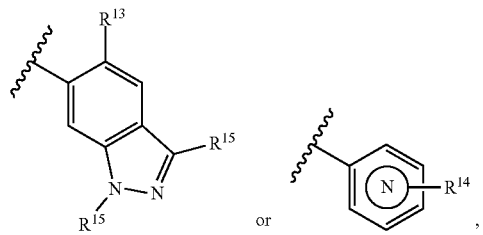

wherein $R^{13}$ is F or Cl; $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of $R^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and

represents a pyridyl group, wherein the ring nitrogen atom can be at any of the five unsubstituted ring atom positions.

In yet another embodiment, $R^2$ is —C(O)OR$^9$ or —C(O)N(R$^9$)$_2$, wherein $R^9$ is H, alkyl, aryl, cycloalkyl, heteroaryl or heterocycloalkyl; $R^{10}$ is:

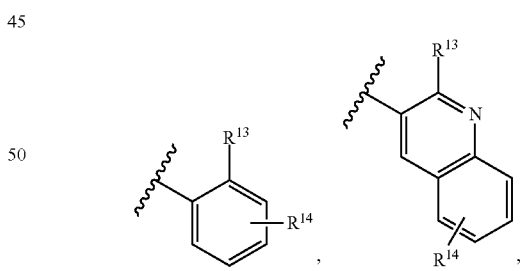

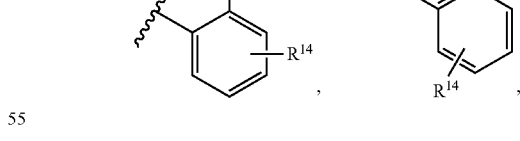

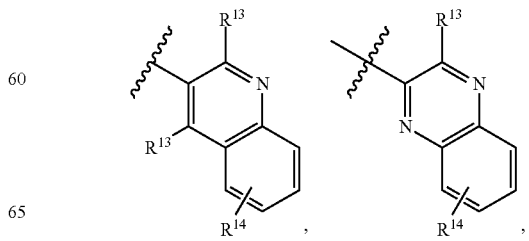

-continued

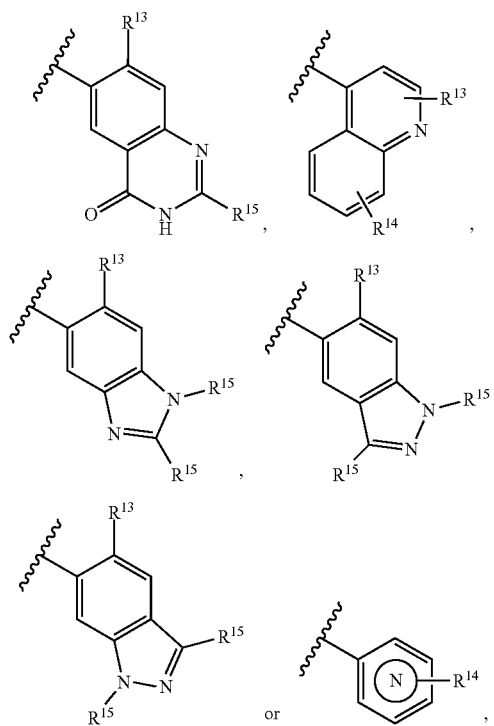

wherein R[13] is F or Cl; R[14] represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of R[15] is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and

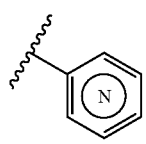

represents a pyridyl group, wherein the ring nitrogen atom can be at any of the five unsubstituted ring atom positions; and R[4] and R[7] are each independently H, halo or hydroxy; R[5] is H, alkyl, —O-alkyl, —O-haloalkyl, cycloalkyl, halo, haloalkyl, —OH, hydroxyalkyl, —NH$_2$ or —CN; and R[6] is H, alkyl, —O-alkyl, —O-haloalkyl, cycloalkyl, halo, haloalkyl, —OH, hydroxyalkyl, —NH$_2$ or —CN.

In one embodiment, R[2] is —C(O)OR[9] or —C(O)N(R[9])$_2$, and R[3] is:

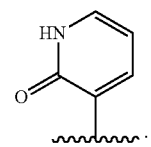

In another embodiment, R[2] is —C(O)OR[9] or —C(O)N(R[9])$_2$, and R[3] is:

In another embodiment, R[2] is —C(O)OR[9] or —C(O)N(R[9])$_2$, and R[1] is —[C(R[12])$_2$]$_r$—.

In still another embodiment, R[2] is —C(O)OR[9] or —C(O)N(R[9])$_2$, and R[1] is —CH$_2$—, —CH$_2$CH$_2$—, —CH(CH$_3$)— or

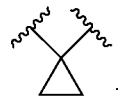

In another embodiment, R[2] is —C(O)OR[9] or —C(O)N(R[9])$_2$, R[4] and R[7] are each independently H, alkyl, halo or —OH; R[5] is H, alkyl, —O-alkyl, —O-haloalkyl, cycloalkyl, halo, haloalkyl, —OH, hydroxyalkyl, —NH$_2$ or —CN; and R[6] is H, alkyl, —O-alkyl, —O-haloalkyl, cycloalkyl, halo, haloalkyl, —OH, hydroxyalkyl, —NH$_2$ or —CN.

In another embodiment, R[2] is —C(O)OR[9] or —C(O)N(R[9])$_2$, R[4] and R[7] are each H; R[5] is H, alkyl, —O-alkyl, —O-haloalkyl, cycloalkyl, halo, haloalkyl, —OH, hydroxyalkyl, —NH$_2$ or —CN; and R[6] is H, alkyl, —O-alkyl, —O-haloalkyl, cycloalkyl, halo, haloalkyl, —OH, hydroxyalkyl, —NH$_2$ or —CN.

In a further embodiment, R[2] is —C(O)OR[9] or —C(O)N(R[9])$_2$, R[4] and R[7] are each H; and R[5] and R[6] are each other than H.

In one embodiment, R[2] is —C(O)OR[9] or —C(O)N(R[9])$_2$, R[4] and R[7] are each H; and R[5] and R[6] are each independently selected from alkyl, halo and haloalkyl.

In another embodiment, R[2] is —C(O)OR[9] or —C(O)N(R[9])$_2$, R[4] and R[7] are each H; and R[5] and R[6] are each independently selected from alkyl and halo.

In another embodiment, R[2] is —C(O)OR[9] or —C(O)N(R[9])$_2$, and R[10] is aryl or heteroaryl.

In still another embodiment, R[2] is —C(O)OR[9] or —C(O)N(R[9])$_2$, and R[10] is:

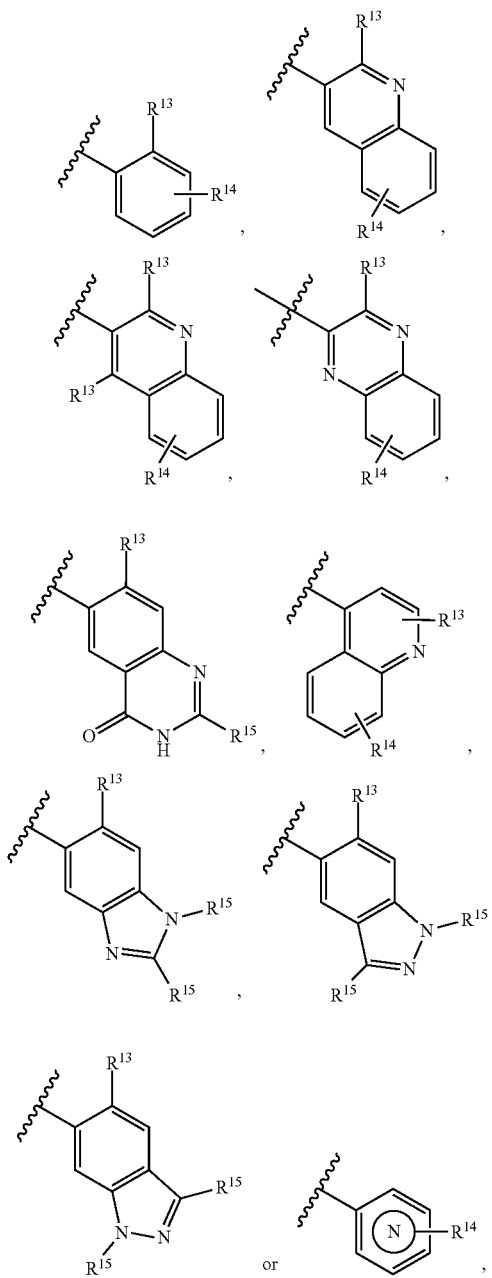

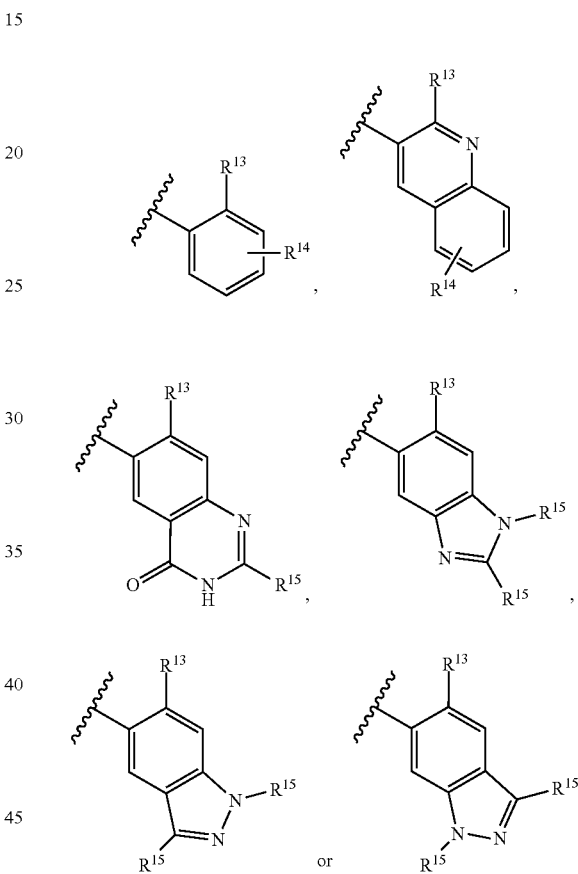

represents a pyridyl group, wherein the ring nitrogen atom can be at any of the five unsubstituted ring atom positions.

In another embodiment, $R^2$ is —C(O)OR$^9$ or —C(O)N(R$^9$)$_2$, and $R^{10}$ is:

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of $R^{15}$ is independently alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and wherein $R^{13}$ is H, F, Br or Cl; $R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of $R^{15}$ is independently alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, $R^2$ is —C(O)OR$^9$ or —C(O)N(R$^9$)$_2$, and $R^{10}$ is:

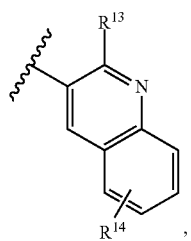

wherein $R^{13}$ is H, F, Br or Cl and $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2$OH, —$SO_2NH_2$, —NHC(O)-alkyl, —C(O)O-alkyl, —C(O)-heterocycloalkyl and heteroaryl.

In yet another embodiment, $R^2$ is —C(O)$OR^9$ or —C(O)N$(R^9)_2$, and $R^{10}$ is:

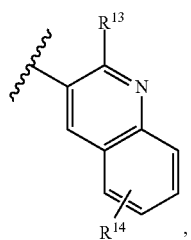

wherein $R^{13}$ is Cl and $R^{14}$ represents up to 4 optional and additional substituents, each independently selected from alkyl, cycloalkyl or halo.

In another embodiment, $R^2$ is —C(O)$OR^9$ or —C(O)N$(R^9)_2$, and $R^{10}$ is:

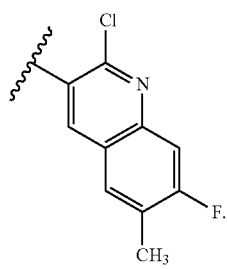

In another embodiment, $R^1$ is —$CH_2$—; $R^2$ is —C(O)$OR^9$ or —C(O)N$(R^9)_2$, $R^{10}$ is:

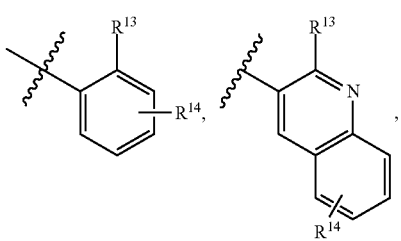

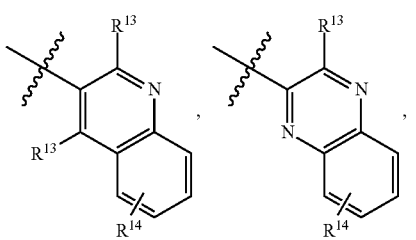

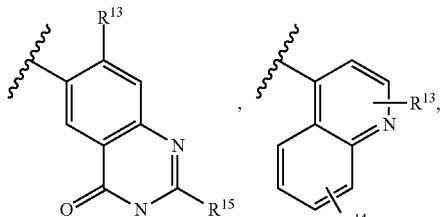

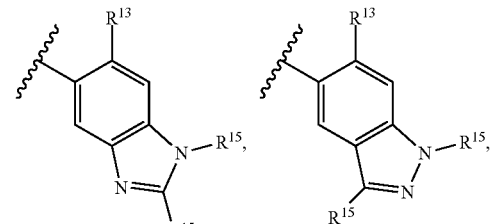

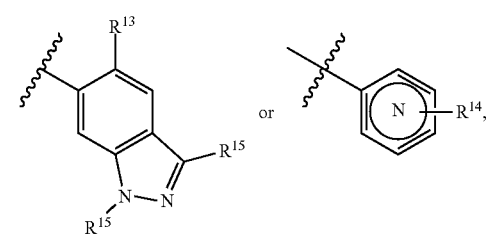

$R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2$OH, —$SO_2NH_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2$OH, —$SO_2NH_2$, —NHC(O)-alkyl, —C(O)O-alkyl, —C(O)-heterocycloalkyl or heteroaryl; and

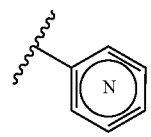

represents a pyridyl group, wherein the ring nitrogen atom can be at any of the five unsubstituted ring atom positions.

In a further embodiment, $R^1$ is —$CH_2$—; $R^2$ is —C(O)$OR^9$ or —C(O)N$(R^9)_2$, $R^{10}$ is:

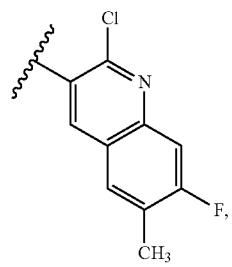

$R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —$C(O)NH_2$, —C(O)NH-alkyl, —C(O)OH, —OH, —$NH_2$, —$SO_2$-alkyl, —$SO_2NH$-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —O-haloalkyl, —$NHSO_2$-alkyl, —$NO_2$, —$C(O)NH_2$, —C(O)NH-alkyl, —C(O)OH, —OH, —$NH_2$, —$SO_2$-alkyl, —$SO_2NH$-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl; and

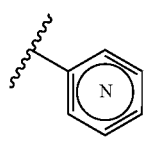

represents a pyridyl group, wherein the ring nitrogen atom can be at any of the five unsubstituted ring atom positions.

In one embodiment, $R^2$ is —$C(O)OR^9$ or —$C(O)N(R^9)_2$; $R^3$ is:

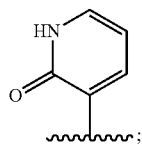 [SMILES: *c1ccc[nH]c1=O]

and $R^{10}$ is:

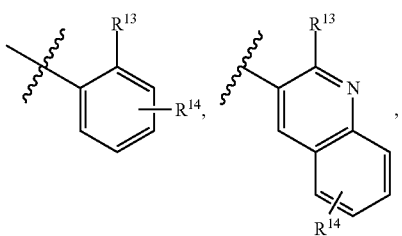

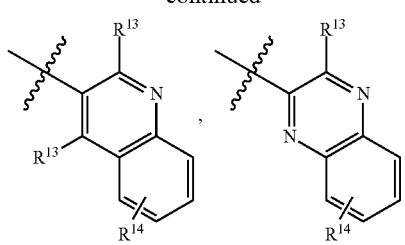

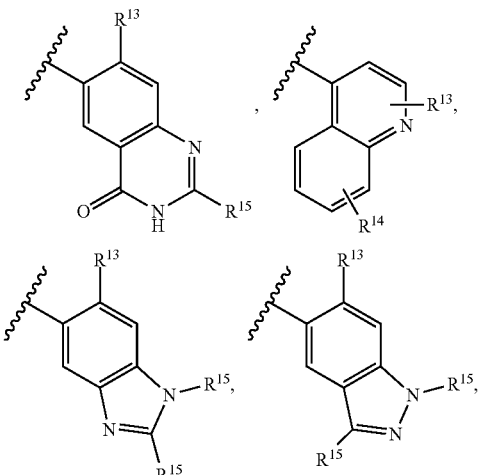

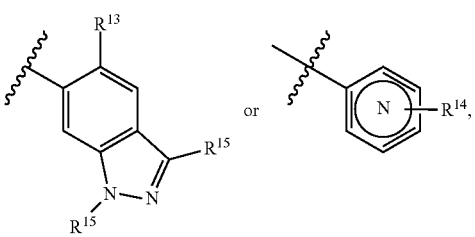

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —$C(O)NH_2$, —C(O)NH-alkyl, —C(O)OH, —OH, —$NH_2$, —$SO_2$-alkyl, —$SO_2NH$-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —O-haloalkyl, —$NHSO_2$-alkyl, —$NO_2$, —$C(O)NH_2$, —C(O)NH-alkyl, —C(O)OH, —OH, —$NH_2$, —$SO_2$-alkyl, —$SO_2NH$-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl; and

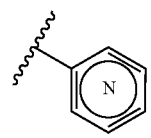

represents a pyridyl group, wherein the ring nitrogen atom can be at any of the five unsubstituted ring atom positions.

In another embodiment, $R^1$ is —[C(R$^{12}$)$_2$]$_r$—, $R^2$ is —C(O)OR$^9$ or —C(O)N(R$^9$)$_2$, and $R^3$ is:

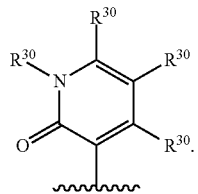

In another embodiment, $R^1$ is —CH$_2$—, —CH$_2$CH$_2$—, —CH(CH$_3$)— or

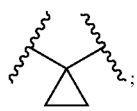

$R^2$ is —C(O)OR$^9$ or —C(O)N(R$^9$)$_2$; and $R^3$ is:

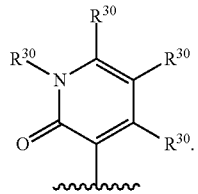

In still another embodiment, $R^1$ is —[C(R$^{12}$)$_2$]$_r$—, $R^2$ is —C(O)OR$^9$ or —C(O)N(R$^9$)$_2$, $R^3$ is:

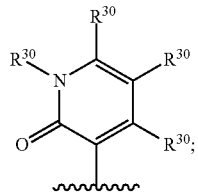

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —NH$_2$ or —CN, and $R^6$ is H, alkyl, —O-alkyl, —O-haloalkyl, cycloalkyl, halo, haloalkyl, —OH, hydroxyalkyl, —NH$_2$ or —CN.

In another embodiment, $R^1$ is —[C(R$^{12}$)$_2$]$_r$—, $R^2$ is —C(O)OR$^9$ or —C(O)N(R$^9$)$_2$, and $R^3$ is:

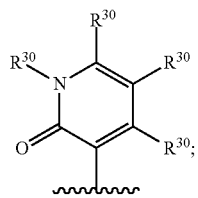

$R^4$ and $R^7$ are each H; $R^5$ is H, alkyl, —O-alkyl, —O-haloalkyl, cycloalkyl, halo, haloalkyl, —OH, hydroxyalkyl, —NH$_2$ or —CN, and $R^6$ is H, alkyl, —O-alkyl, —O-haloalkyl, cycloalkyl, halo, haloalkyl, —OH, hydroxyalkyl, —NH$_2$ or —CN.

In another embodiment, $R^1$ is —[C(R$^{12}$)$_2$]$_r$—, $R^2$ is —C(O)OR$^9$ or —C(O)N(R$^9$)$_2$, and $R^3$ is:

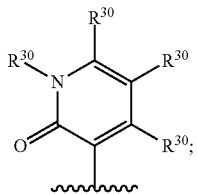

$R^4$ and $R^7$ are each H; and $R^5$ and $R^6$ are each other than H.

In yet another embodiment, $R^1$ is —[C(R$^{12}$)$_2$]$_r$—, $R^2$ is —C(O)OR$^9$ or —C(O)N(R$^9$)$_2$, and $R^3$ is:

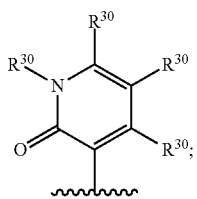

$R^4$ and $R^7$ are each H; and $R^5$ and $R^6$ are each independently selected from alkyl, halo and haloalkyl.

In a further embodiment, $R^1$ is —[C(R$^{12}$)$_2$]$_r$—, $R^2$ is —C(O)OR$^9$ or —C(O)N(R$^9$)$_2$, and $R^3$ is:

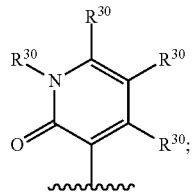

$R^4$ and $R^7$ are each H; and $R^5$ and $R^6$ are each independently selected from alkyl and halo.

In one embodiment, $R^1$ is —[C(R$^{12}$)$_2$]$_r$—, $R^2$ is —C(O)OR$^9$ or —C(O)N(R$^9$)$_2$, $R^3$ is:

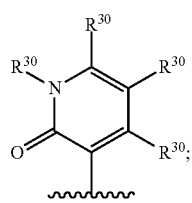

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; and $R^{10}$ is aryl or heteroaryl.

In another embodiment, $R^1$ is —[C(R$^{12}$)$_2$]$_r$—, $R^2$ is —C(O)OR$^9$ or —C(O)N(R$^9$)$_2$, $R^3$ is:

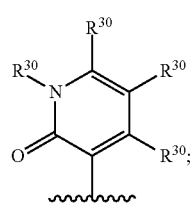

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; and $R^{10}$ is:

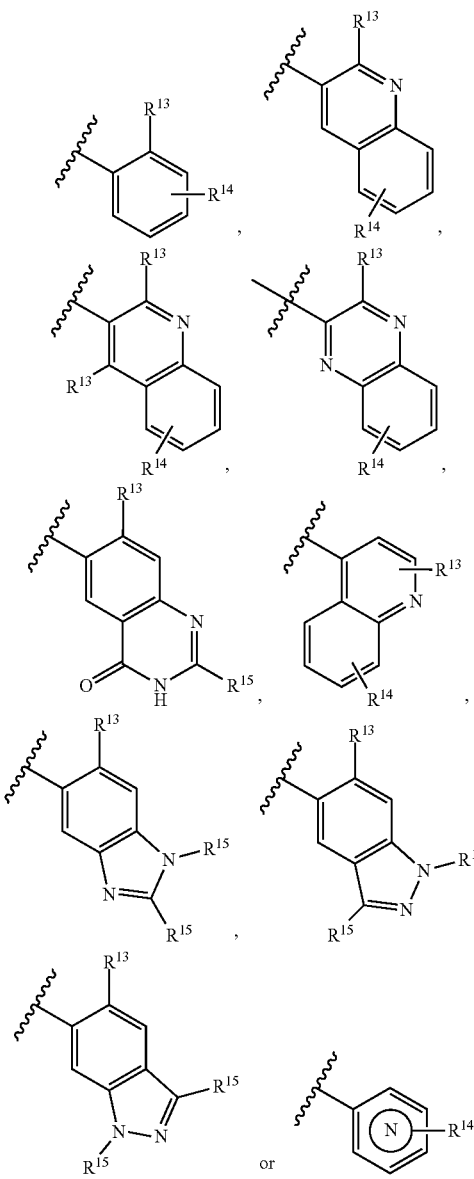

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of $R^{15}$ is independently alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and

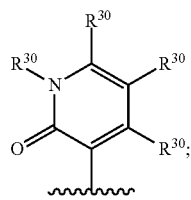

represents a pyridyl group, wherein the ring nitrogen atom can be at any of the five unsubstituted ring atom positions.

In another embodiment, $R^1$ is —[C(R$^{12}$)$_2$]$_r$—, $R^2$ is —C(O)OR$^9$ or —C(O)N(R$^9$)$_2$, $R^3$ is:

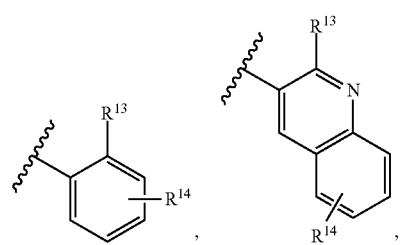

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; and $R^{10}$ is:

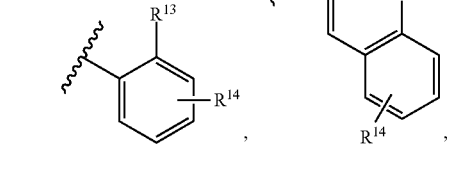

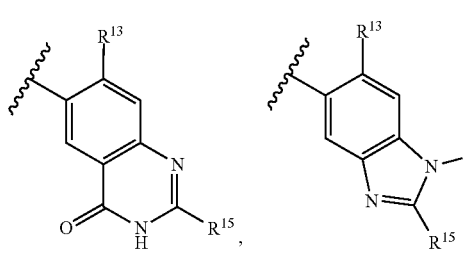

-continued

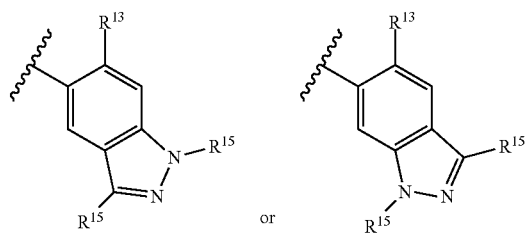

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In another embodiment, $R^1$ is —[C($R^{12}$)$_2$]$_r$—, $R^2$ is —C(O)O$R^9$ or —C(O)N($R^9$)$_2$, $R^3$ is:

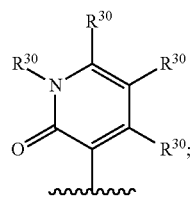

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —$NH_2$ or —CN; $R^6$ is H, alkyl, —O-alkyl, —O-haloalkyl, cycloalkyl, halo, haloalkyl, —OH, hydroxyalkyl, —$NH_2$ or —CN; and $R^{10}$ is:

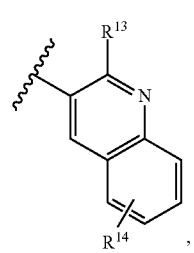

wherein $R^{13}$ is H, F, Br or Cl and $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl.

In still another embodiment, $R^1$ is —[C($R^{12}$)$_2$]$_r$—, $R^2$ is —C(O)O$R^9$ or —C(O)N($R^9$)$_2$, $R^3$ is:

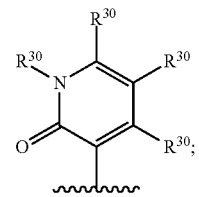

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —$NH_2$ or —CN; $R^6$ is H, alkyl, —O-alkyl, —O-haloalkyl, cycloalkyl, halo, haloalkyl, —OH, hydroxyalkyl, —$NH_2$ or —CN; and $R^{10}$ is:

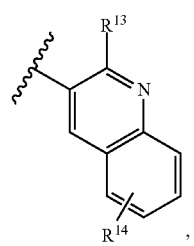

wherein $R^{13}$ is Cl and $R^{14}$ represents up to 4 optional and additional substituents, each independently selected from alkyl, cycloalkyl or halo.

In another embodiment, $R^1$ is —[C($R^{12}$)$_2$]$_r$—, $R^2$ is —C(O)O$R^9$ or —C(O)N($R^9$)$_2$, $R^3$ is:

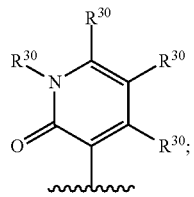

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —$NH_2$ or —CN; $R^6$ is H, alkyl, —O-alkyl, —O-haloalkyl, cycloalkyl, halo, haloalkyl, —OH, hydroxyalkyl, —$NH_2$ or —CN; and $R^{10}$ is:

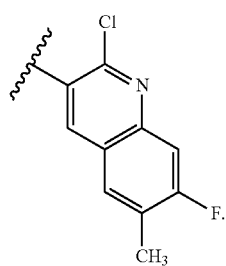 [SMILES: *c1cc2cc(C)c(F)cc2nc1Cl]

In another embodiment, $R^1$ is —$CH_2$—, $R^2$ is —C(O)$OR^9$ or —C(O)N($R^9$)$_2$, $R^3$ is:

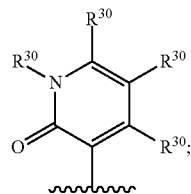

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —$NH_2$ or —CN; $R^6$ is H, alkyl, —O-alkyl, —O-haloalkyl, cycloalkyl, halo, haloalkyl, —OH, hydroxyalkyl, —$NH_2$ or —CN; and $R^{10}$ is:

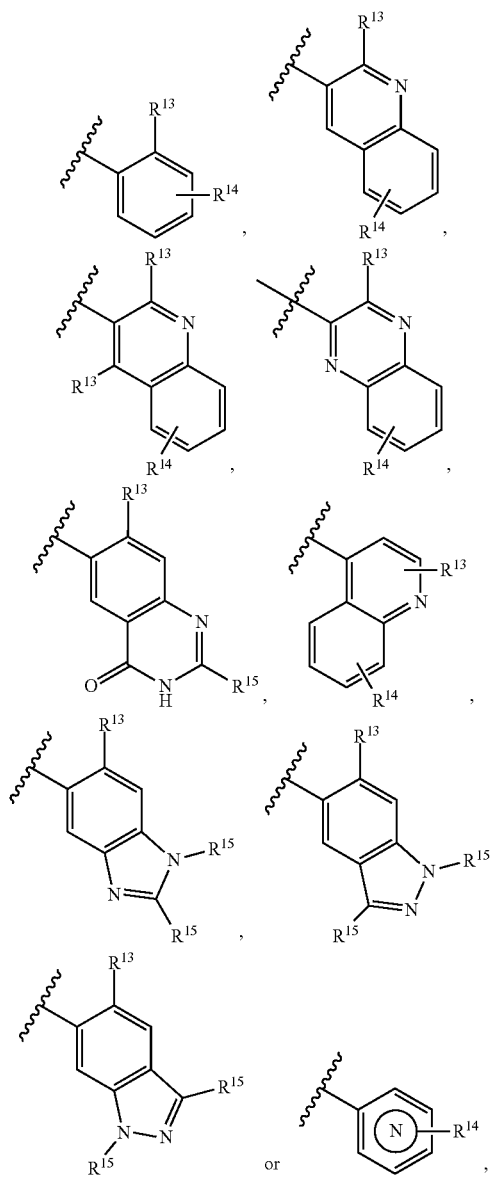

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2$OH, —$SO_2NH_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2$OH, —$SO_2NH_2$, —NHC(O)-alkyl, —C(O)O-alkyl, —C(O)-heterocycloalkyl or heteroaryl; and

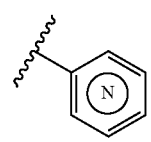

represents a pyridyl group, wherein the ring nitrogen atom can be at any of the five unsubstituted ring atom positions.

In still another embodiment, $R^1$ is —$CH_2$—, $R^2$ is —C(O)$OR^9$ or —C(O)N($R^9$)$_2$, $R^3$ is:

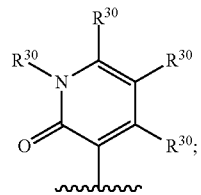

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —$NH_2$ or —CN; $R^6$ is H, alkyl, —O-alkyl, —O-haloalkyl, cycloalkyl, halo, haloalkyl, —OH, hydroxyalkyl, —$NH_2$ or —CN; and $R^{10}$ is:

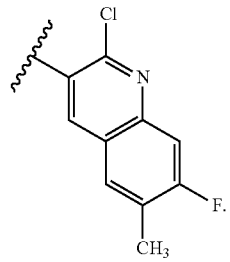 [SMILES: *c1cc2cc(C)c(F)cc2nc1Cl]

In another embodiment, $R^1$ is —$CH_2$—, $R^2$ is —C(O)OH; $R^3$ is:

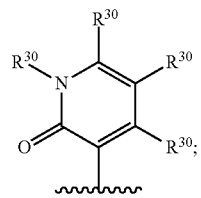

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; and $R^{10}$ is:

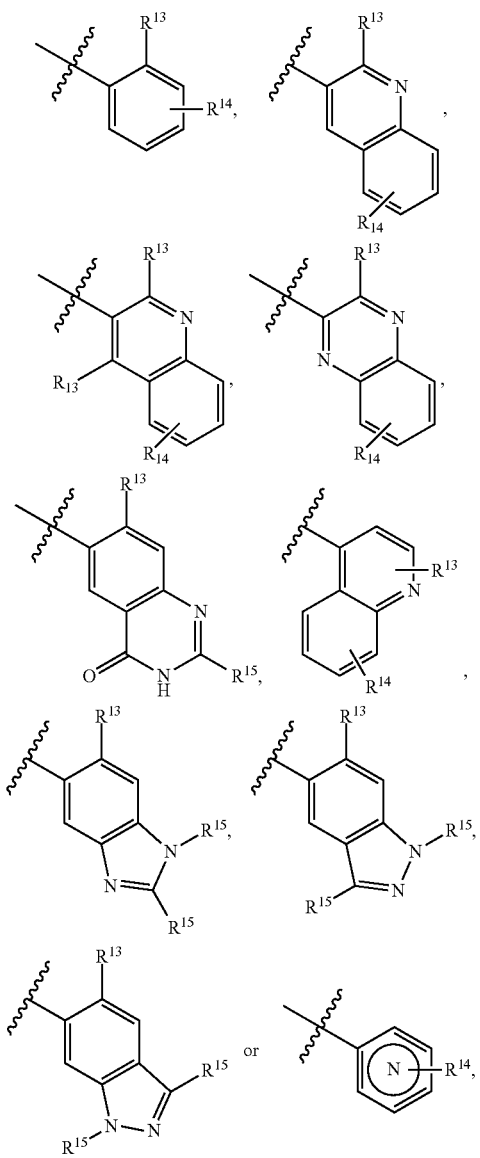

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of $R^{15}$ is independently alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and

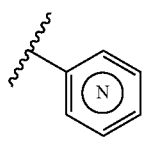

represents a pyridyl group, wherein the ring nitrogen atom can be at any of the five unsubstituted ring atom positions.

In another embodiment, $R^1$ is —CH$_2$—, $R^2$ is —C(O)OH; $R^3$ is:

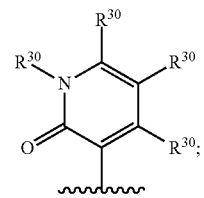

$R^4$ and $R^7$ are each independently H, alkyl, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; and $R^{10}$ is:

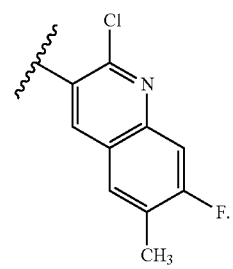 [SMILES: *c1cc2cc(C)c(F)cc2nc1Cl]

In one embodiment, for the compounds of formula (I), variables $R^1$, $R^2$, $R^3$, $R^4$, $R^5$, $R^6$, $R^7$ and $R^{10}$ are selected independently from each other.

In another embodiment, the compounds of formula (I) are in purified form.

In one embodiment, the compounds of formula (I) have the formula (Ia):

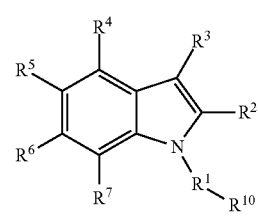

(Ia)

or a pharmaceutically acceptable salt, solvate, ester or prodrug thereof, wherein:

R$^1$ is —CH$_2$—, —CH$_2$CH$_2$—, —CH(CH$_3$)— or

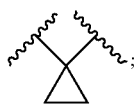 [SMILES: *C1(*)CC1]

R$^2$ is —C(O)OH, —C(O)Oalkyl, —C(O)O-cycloalkyl, —C(O)NH$_2$, —C(O)NHalkyl, or —C(O)NH-cycloalkyl;

R$^3$ is:

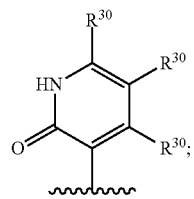

R$^4$, R$^5$, R$^6$ and R$^7$ are each, independently, H, alkyl, —[C(R$^{12}$)$_2$]$_q$-cycloalkyl, —[C(R$^{12}$)$_2$]$_q$-heterocycloalkyl, haloalkyl, halo, —OH, —OR$^9$ or —N(R$^9$)$_2$;

each occurrence of R$^9$ is independently H, alkyl, cycloalkyl, heterocycloalkyl, haloalkyl or hydroxyalkyl;

R$^{10}$ is:

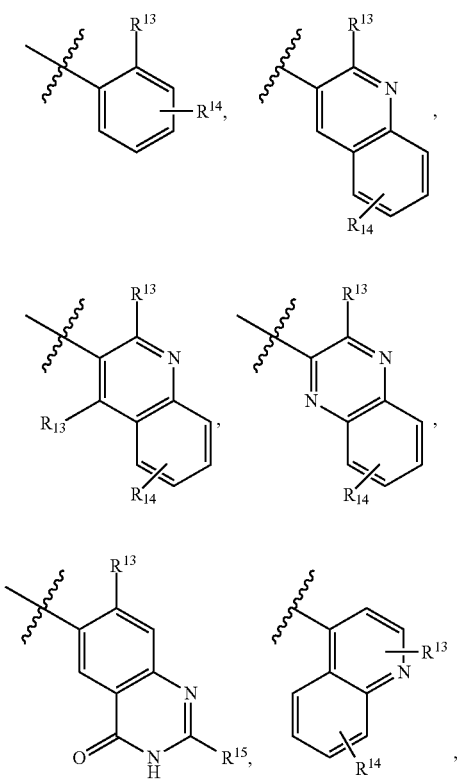

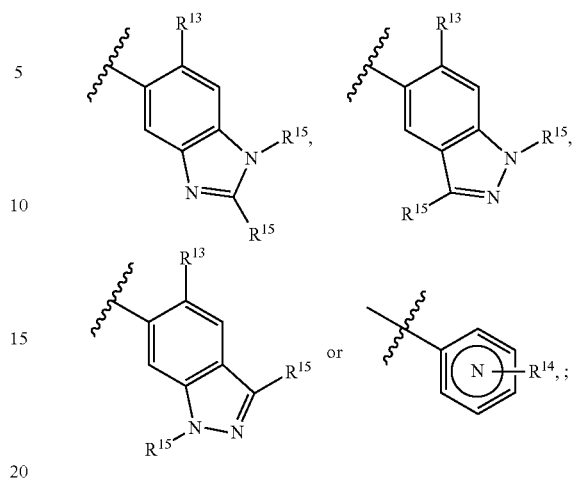

each occurrence of R$^{11}$ is independently alkyl, aryl, cycloalkyl, haloalkyl, heteroaryl, heterocycloalkyl or hydroxyalkyl;

each occurrence of R$^{12}$ is independently H, halo, —N(alkyl)$_2$, —OH, —O-alkyl, alkyl, cycloalkyl or heterocycloalkyl, or two R$^{12}$ groups, together with the carbon atoms to which they are attached, join to form a cycloalkyl, heterocycloalkyl or C═O group;

R$^{13}$ is H, F, Br or Cl;

R$^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl;

each occurrence of R$^{15}$ is independently alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl;

each occurrence of R$^{30}$ is independently, H, halo, —N(alkyl)$_2$, —OH, —O-alkyl, —O-haloalkyl, alkyl, cycloalkyl or heterocycloalkyl, or two adjacent R$^{30}$ groups, together with the carbon atoms to which they are attached, join to form a –3- to 7-membered ring selected from aryl, cycloalkyl, heteroaryl and heterocycloalkyl;

each occurrence of q is independently an integer ranging from 0 to 4;

each occurrence of r is independently an integer ranging from 1 to 4; and

represents a pyridyl group, wherein the ring nitrogen atom can be at any of the five unsubstituted ring atom positions.

The following embodiments pertain to the compounds of formula (Ia):

In one embodiment, R$^2$ is —C(O)OH or —C(O)O-alkyl.

In another embodiment, R$^2$ is —C(O)OH or —C(O)O-alkyl, and R$^3$ is:

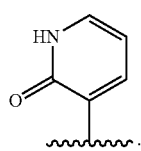 [SMILES: *c1ccc[nH]c1=O]

In another embodiment, R¹ is —CH₂—; R² is —C(O)OH or —C(O)O-alkyl; and R³ is:

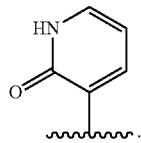 [SMILES: *c1ccc[nH]c1=O]

In still another embodiment, R¹ is —CH₂—; R² is —C(O)OH or —C(O)O-alkyl; R³ is:

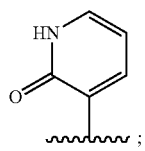

and R¹⁰ is:

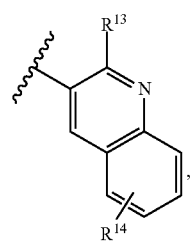

wherein R¹³ is Cl and R¹⁴ represents up to 4 optional and additional substituents, each independently selected from alkyl, cycloalkyl or halo.

In another embodiment, R¹ is —CH₂—; R² is —C(O)OH or —C(O)O-alkyl; R³ is:

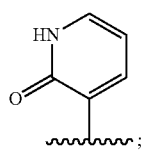 [SMILES: *c1ccc[nH]c1=O]

and R¹⁰ is:

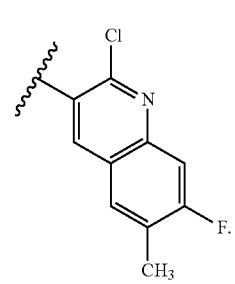

In another embodiment, R¹ is —CH₂—; R² is —C(O)OH or —C(O)O-alkyl; R³ is:

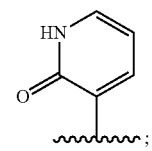

and R⁴ and R⁷ are each H.

In yet another embodiment, R¹ is —CH₂—; R² is —C(O)OH or —C(O)O-alkyl; R³ is:

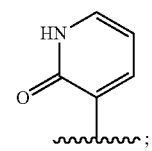

R⁴ and R⁷ are each H; and R⁵ and R⁶ are each independently H, alkyl, halo or haloalkyl.

In another embodiment, R¹ is —CH₂—; R² is —C(O)OH or —C(O)O-alkyl; R³ is:

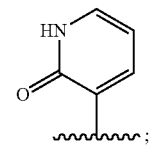

R⁴ and R⁷ are each H; and R⁵ and R⁶ are each independently alkyl or halo.

In a further embodiment, R¹ is —CH₂—; R² is —C(O)OH or —C(O)O-alkyl; R³ is:

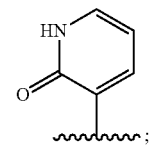

R⁴ and R⁷ are each H; R⁵ and R⁶ are each independently H, alkyl, halo or haloalkyl; and R¹⁰ is:

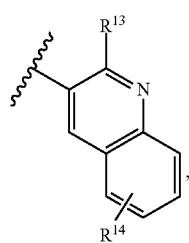

wherein $R^{13}$ is Cl and $R^{14}$ represents up to 4 optional and additional substituents, each independently selected from alkyl, cycloalkyl or halo.

In one embodiment, $R^1$ is —$CH_2$—; $R^2$ is —C(O)OH or —C(O)O-alkyl; $R^3$ is:

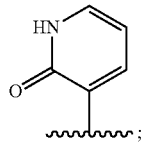

$R^4$ and $R^7$ are each H; $R^5$ and $R^6$ are each independently H, alkyl, halo or haloalkyl; and $R^{10}$ is:

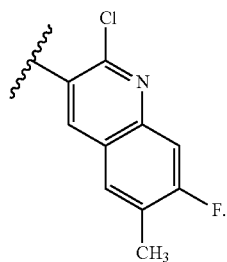

In one embodiment, for the compounds of formula (Ia), variables $R^1$, $R^2$, $R^3$, $R^4$, $R^5$, $R^6$, $R^7$ and $R^{10}$ are selected independently from each other.

In another embodiment, the compounds of formula (Ia) are in purified form.

The 2-Carboxy Substituted Indole Derivatives of Formula (II)

The present invention also provides 2-Carboxy Substituted Indole Derivatives having the formula:

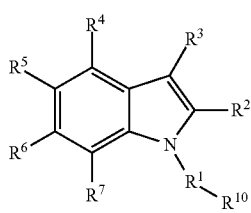

(II)

and pharmaceutically acceptable salts, solvates, esters and prodrugs thereof, wherein $R^1$, $R^2$, $R^4$, $R^5$, $R^6$, $R^7$ and $R^{10}$ are defined above for the compounds of formula (II).

In one embodiment, $R^1$ is bond.
In another embodiment, $R^1$ is —$[C(R^{12})_2]_r$—.
In another embodiment, $R^1$ is —$[C(R^{12})_2]_r$—O—$[C(R^{12})_2]_q$—.
In still another embodiment, $R^1$ is —$[C(R^{12})_2]_r$—N($R^9$)—$[C(R^{12})_2]_q$—.
In yet another embodiment, $R^1$ is —$[C(R^{12})_2]_q$—CH=CH—$[C(R^{12})_2]_q$—.
In another embodiment, $R^1$ is —$[C(R^{12})_2]_q$—C≡C—$[C(R^{12})_2]_q$—.
In a further embodiment, $R^1$ is —$[C(R^{12})_2]_q$—$SO_2$—$[C(R^{12})_2]_q$—.
In one embodiment, $R^1$ is —$CH_2$—, —$CH_2CH_2$—, —CH($CH_3$)— or

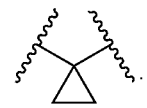 [SMILES: *C1(*)CC1]

In another embodiment, $R^1$ is —$CH_2$—.
In another embodiment, $R^1$ is:

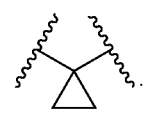 [SMILES: *C1(*)CC1]

In one embodiment, $R^{10}$ is aryl.
In another embodiment, $R^{10}$ is —H.
In another embodiment, $R^{10}$ is cycloalkyl.
In another embodiment, $R^{10}$ is cycloalkenyl.
In still another embodiment, $R^{10}$ is heterocycloalkenyl.
In another embodiment, $R^{10}$ is heteroaryl.
In another embodiment, $R^{10}$ is heterocycloalkyl.
In another embodiment, $R^{10}$ is phenyl.
In another embodiment, $R^{10}$ is phenyl, which is substituted with from 1-4 groups independently selected from: halo, —$NH_2$, —$NHSO_2$-alkyl, haloalkyl, methoxy, —O-haloalkyl, —$[C(R^{12})_2]_q$—NHC(O)NH-alkyl, alkyl, —OH, —CN, —C(O)$NH_2$ or —$[C(R^{12})_2]_q$—$NH_2$.
In yet another embodiment, $R^{10}$ is pyridyl.
In a further embodiment, $R^{10}$ is

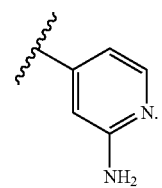 [SMILES: *c1ccnc(N)c1]

In another embodiment, —$R^{10}$ is:

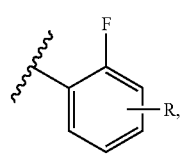

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —CH$_2$NH$_2$, —SO$_2$NH$_2$, —NHC(O)-alkyl, —C(O)O-alkyl, —C(O)-heterocycloalkyl and heteroaryl.

In another embodiment, R$^{10}$ is

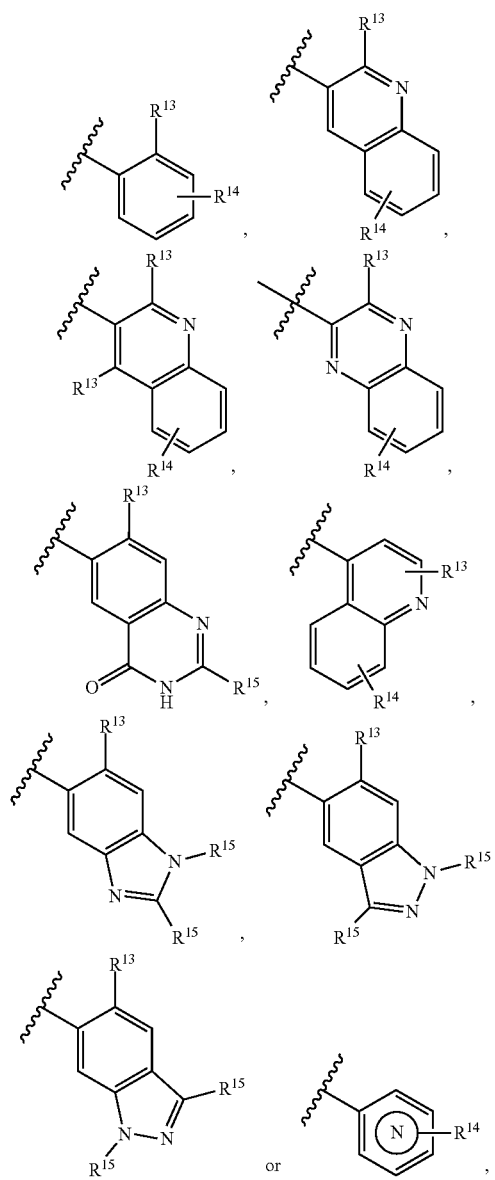

wherein R$^{13}$ is F or Cl; R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of R$^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, R$^1$ is —CH$_2$—, —CH$_2$CH$_2$—, —CH(CH$_3$)— or

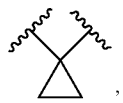 [SMILES: *C1(*)CC1]

and R$^{10}$ is aryl or heteroaryl.

In another embodiment, R$^1$ is —CH$_2$—, —CH$_2$CH$_2$—, —CH(CH$_3$)— or

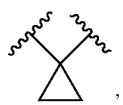

and R$^{10}$ is phenyl.

In another embodiment, R$^1$ is —CH$_2$—, —CH$_2$CH$_2$—, —CH(CH$_3$)— or

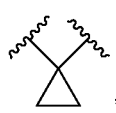

and R$^{10}$ is alkyl or cycloalkyl.

In another embodiment, R$^1$ is —CH$_2$— and R$^{10}$ is aryl or heteroaryl.

In still another embodiment, R$^1$ is —CH$_2$— or

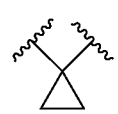

and R$^{10}$ is

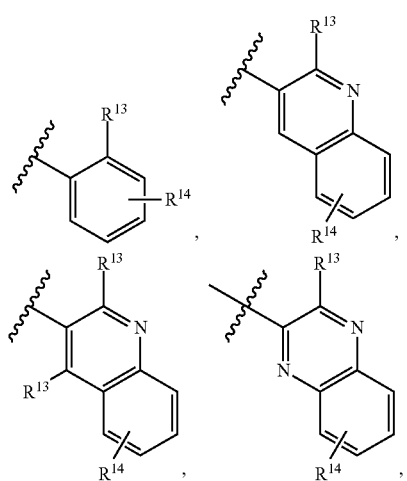

-continued

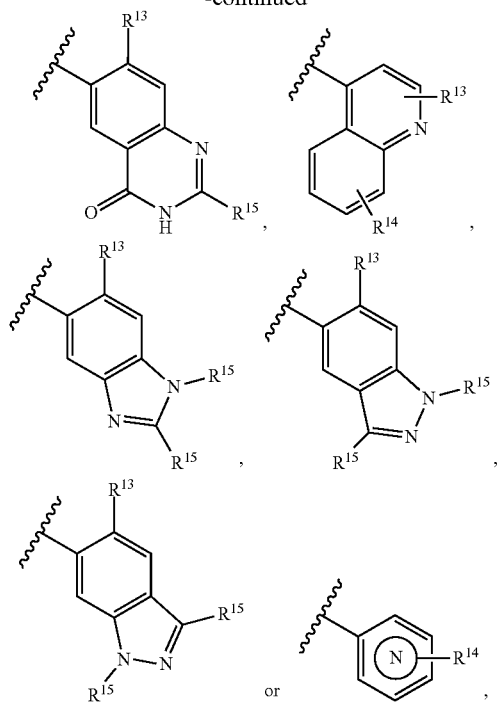

wherein $R^{13}$ is F or Cl; $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In one embodiment, —$R^1$-$R^{10}$ is benzyl.

In another embodiment, —$R^1$-$R^{10}$ is benzyl, wherein the phenyl moiety of the benzyl group is substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$.

In still another embodiment, —$R^1$-$R^{10}$ is

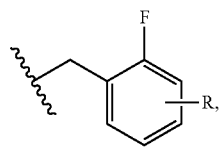

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —CH$_2$NH$_2$, —SO$_2$NH$_2$, —NHC(O)-alkyl, —C(O)O-alkyl, —C(O)-heterocycloalkyl and heteroaryl.

In another embodiment, —$R^1$-$R^{10}$ is

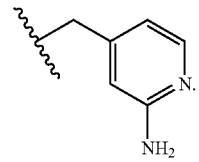

In still another embodiment, —$R^1$-$R^{10}$ is alkyl.

In yet another embodiment, —$R^1$-$R^{10}$ is —$R^1$-$R^{10}$ is benzyl, wherein the phenyl moiety of the benzyl group is substituted with 1 or 2 fluorine atoms.

In yet another embodiment, —$R^1$-$R^{10}$ is —$R^1$-$R^{10}$ is benzyl, wherein the phenyl moiety of the benzyl group is substituted with 1 or 2 methyl groups.

In yet another embodiment, —$R^1$-$R^{10}$ is —$R^1$-$R^{10}$ is benzyl, wherein the phenyl moiety of the benzyl group is substituted with one fluorine atom and one methyl group.

In another embodiment, —$R^1$-$R^{10}$ is haloalkyl.

In a further embodiment, —$R^1$-$R^{10}$ is —CH$_2$-cycloalkyl.

In another embodiment, —$R^1$-$R^{10}$ is other than H.

In another embodiment, $R^1$ is —CH$_2$— and $R^{10}$ is alkyl or cycloalkyl.

In another embodiment, $R^1$ is —CH$_2$— and $R^{10}$ is

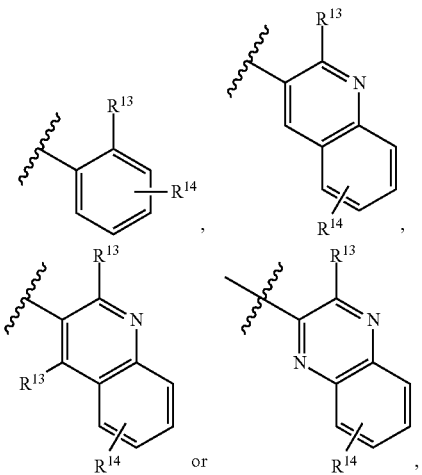

wherein $R^{13}$ is F or Cl and $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In one embodiment, $R^2$ is —C(O)$R^9$.
In another embodiment, $R^2$ is —C(O)O$R^9$.
In another embodiment, $R^2$ is —C(O)OCH$_2$O$R^9$.
In still another embodiment, $R^2$ is —C(O)N($R^9$)$_2$.
In yet another embodiment, $R^2$ is —[C($R^{12}$)$_2$]$_q$—C(O)O$R^9$.
In another embodiment, $R^2$ is —[C($R^{12}$)$_2$]$_q$—C(O)N($R^9$)$_2$.
In a further embodiment, $R^2$ is -alkyl.
In another embodiment, $R^2$ is —[C($R^{12}$)$_2$]$_q$-aryl.
In another embodiment, $R^2$ is —[C($R^{12}$)$_2$]$_q$-cycloalkyl.
In still another embodiment, $R^2$ is —[C($R^{12}$)$_2$]$_q$-cycloalkenyl.
In still another embodiment, $R^2$ is —[C($R^{12}$)$_2$]$_q$-heterocycloalkyl.

In yet another embodiment, $R^2$ is —[C($R^{12}$)$_2$]$_q$-heteroaryl.

In another embodiment, $R^2$ is —[C($R^{12}$)$_2$]$_q$-heterocycloalkenyl.

In a further embodiment, $R^2$ is —C(O)O$R^9$ or —C(O)OCH$_2$O$R^9$.

In another embodiment, $R^2$ is —C(O)O$R^9$ or —C(O)N($R^9$)$_2$.

In another embodiment, $R^2$ is —C(O)OH, —C(O)NH$_2$, —C(O)O-alkyl, —C(O)O-cycloalkyl, —C(O)NH-alkyl or —C(O)NH-cycloalkyl.

In another embodiment, $R^2$ is —C(O)OH.

In another embodiment, $R^2$ is —C(O)NH$R^9$.

In another embodiment, $R^2$ is —C(O)NH$_2$.

In still another embodiment, $R^2$ is —C(O)$R^9$, —C(O)O$R^9$, —C(O)OCH$_2$O$R^9$, —C(O)N($R^9$)$_2$, —[C($R^{12}$)$_2$]$_q$—C(O)O$R^9$, —[C($R^{12}$)$_2$]$_q$—C(O)N($R^9$)$_2$ or —[C($R^{12}$)$_2$]$_q$-heteroaryl wherein a heteroaryl group can be optionally substituted with up to 4 substituents, which are the same or different, and are selected from alkyl, alkenyl, alkynyl, aryl, —[C($R^{12}$)$_2$]$_q$-cycloalkyl, —[C($R^{12}$)$_2$]$_q$-cycloalkenyl, —[C($R^{12}$)$_2$]$_q$-heterocycloalkyl, —[C($R^{12}$)$_2$]$_q$-heterocycloalkenyl, —[C($R^{12}$)$_2$]$_q$-heteroaryl, —[C($R^{12}$)$_2$]$_q$-haloalkyl, —[C($R^{12}$)$_2$]$_q$-hydroxyalkyl, halo, —OH, —O$R^9$, —CN, —[C($R^{12}$)$_2$]$_q$—C(O)$R^8$, —[C($R^{12}$)$_2$]$_q$—C(O)O$R^9$, —[C($R^{12}$)$_2$]$_q$—C(O)N($R^9$)$_2$, —[C($R^{12}$)$_2$]$_q$—O$R^9$, —[C($R^{12}$)$_2$]$_q$—N($R^9$)$_2$, —[C($R^{12}$)$_2$]$_q$—NHC(O)$R^8$, —[C($R^{12}$)$_2$]$_q$—N$R^8$C(O)N($R^9$)$_2$, —[C($R^{12}$)$_2$]$_q$—NHSO$_2$$R^{11}$, —[C($R^{12}$)$_2$]$_q$—S(O)$_p$$R^{11}$, —[C($R^{12}$)$_2$]$_q$—SO$_2$N($R^9$)$_2$ and —SO$_2$N($R^9$)C(O)N($R^9$)$_2$.

In one embodiment, $R^3$ is

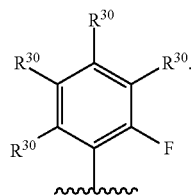

In another embodiment, $R^3$ is

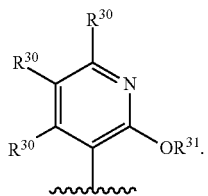

In another embodiment, $R^3$ is

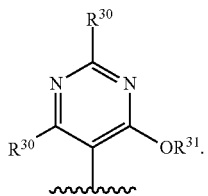

In another embodiment, $R^3$ is

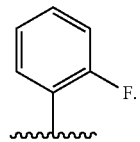

In one embodiment, $R^4$ is H.
In another embodiment, $R^4$ is H or F.
In another embodiment, $R^4$ is F.
In another embodiment, $R^5$ is H.
In another embodiment, $R^5$ is other than H.
In yet another embodiment, $R^6$ is H.
In another embodiment, $R^6$ is other than H.
In another embodiment, $R^6$ is H or F.
In a further embodiment, $R^6$ is F.
In one embodiment, $R^9$ is H and $R^{11}$ is methyl or ethyl.
In another embodiment, $R^9$ is H and $R^{11}$ is cyclopropyl.
In still another embodiment, $R^7$ is H.
In another embodiment, $R^4$ and $R^7$ are each independently H, halo or hydroxy.
In another embodiment, $R^4$ and $R^7$ are each independently H, F or hydroxy.
In another embodiment, $R^4$ and $R^7$ are each H.
In yet another embodiment, $R^4$, $R^6$ and $R^7$ are each H.
In another embodiment, $R^4$, $R^5$, $R^6$ and $R^7$ are each H.
In a further embodiment, $R^4$, $R^6$ and $R^7$ are each H and $R^5$ is other than H.
In another embodiment, $R^4$, $R^6$ and $R^7$ are each H and $R^5$ is alkyl.
In another embodiment, $R^4$, $R^6$ and $R^7$ are each H and $R^5$ is halo.
In another embodiment, $R^4$, $R^6$ and $R^7$ are each H and $R^5$ is methyl.
In a further embodiment, $R^4$, $R^6$ and $R^7$ are each H and $R^5$ is Cl.
In another embodiment, $R^4$ and $R^7$ are each H and $R^5$ and $R^6$ are other than H.
In another embodiment, $R^5$ is other than H.
In still another embodiment, $R^5$ is alkyl.
In yet another embodiment, $R^5$ is halo.
In still another embodiment, $R^5$ is methyl.
In another embodiment, $R^5$ is ethyl.
In another embodiment, $R^6$ is H.
In another embodiment, $R^6$ is other than H.
In a further embodiment, $R^6$ is alkyl.
In yet another embodiment, $R^6$ is halo.
In still another embodiment, $R^6$ is methyl.
In another embodiment, $R^6$ is F.
In one embodiment, $R^4$ is H or F; $R^5$ is methyl or ethyl; $R^6$ is H or F; and $R^7$ is H.

In one embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C($R^{12}$)$_2$]$_q$—NHC(O)NH-alkyl, alkyl, —OH, —CN, —C(O)NH$_2$ or —[C($R^{12}$)$_2$]$_q$—NH$_2$; and $R^2$ is —C(O)O$R^9$.

In one embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C($R^{12}$)$_2$]$_q$—NHC(O)NH-alkyl, alkyl, —OH, —CN, —C(O)NH$_2$ or —[C($R^{12}$)$_2$]$_q$—NH$_2$; and $R^2$ is —C(O)OH.

In another embodiment, $R^1$ is —CH$_2$—, —CH$_2$CH$_2$—, —CH(CH$_3$)— or

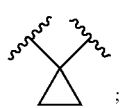 [SMILES: *C1(*)CC1]

$R^2$ is —C(O)OR$^9$; and $R^{10}$ is:

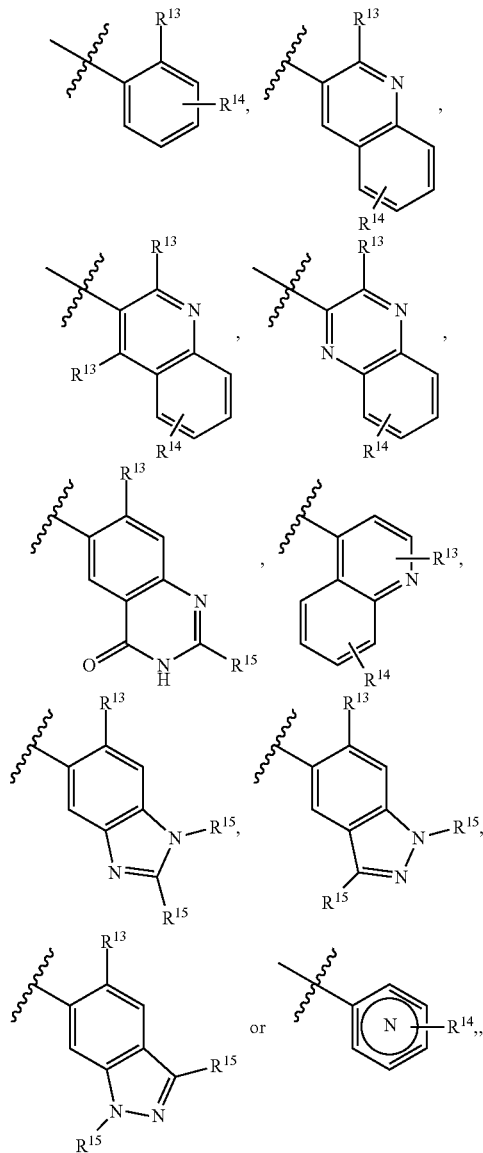

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, $R^1$ is —CH$_2$—, —CH$_2$CH$_2$—, —CH(CH$_3$)— or

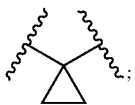 [SMILES: *C1(*)CC1]

$R^2$ is —C(O)OR$^9$; $R^5$ is alkyl, cycloalkyl, halo or hydroxy; $R^6$ is H, halo or hydroxy; and $R^{10}$ is:

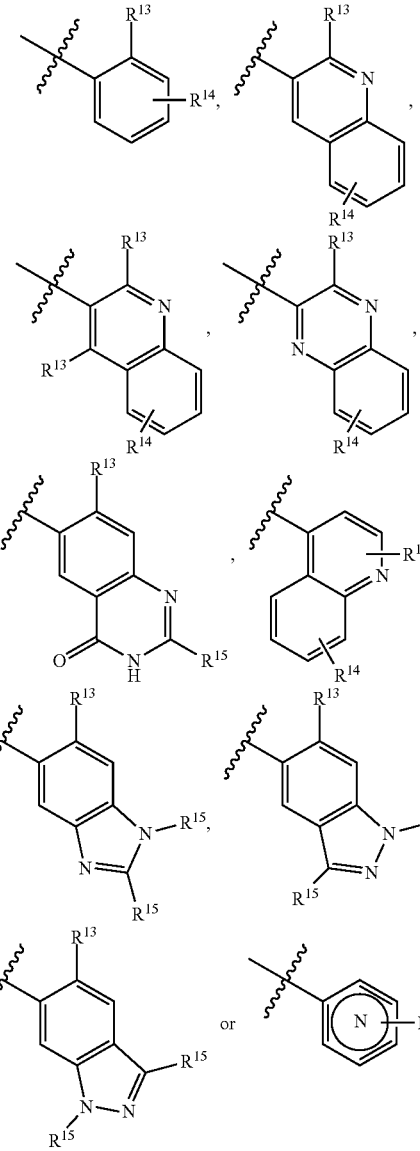

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of $R^{15}$ is independently alkyl, cycloalkyl, CF$_3$, —CN, halo, —O-alkyl, —NHSO$_2$-alkyl, —NO₂, —C(O)NH₂, —C(O)NH-alkyl, —C(O)OH, —OH, —NH₂, —SO₂-alkyl, —SO₂NH-alkyl, —S-alkyl, —CH₂NH₂, —CH₂OH, —SO₂NH₂, —NHC(O)-alkyl, —C(O)O-alkyl, —C(O)-heterocycloalkyl or heteroaryl.

In another embodiment, R¹ is —CH₂—, —CH₂CH₂—, —CH(CH₃)— or

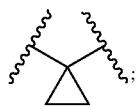 [SMILES: *C1(*)CC1]

R² is —C(O)OR⁹; R⁵ is methyl or ethyl; R⁶ is H, F or Cl; and R¹⁰ is:

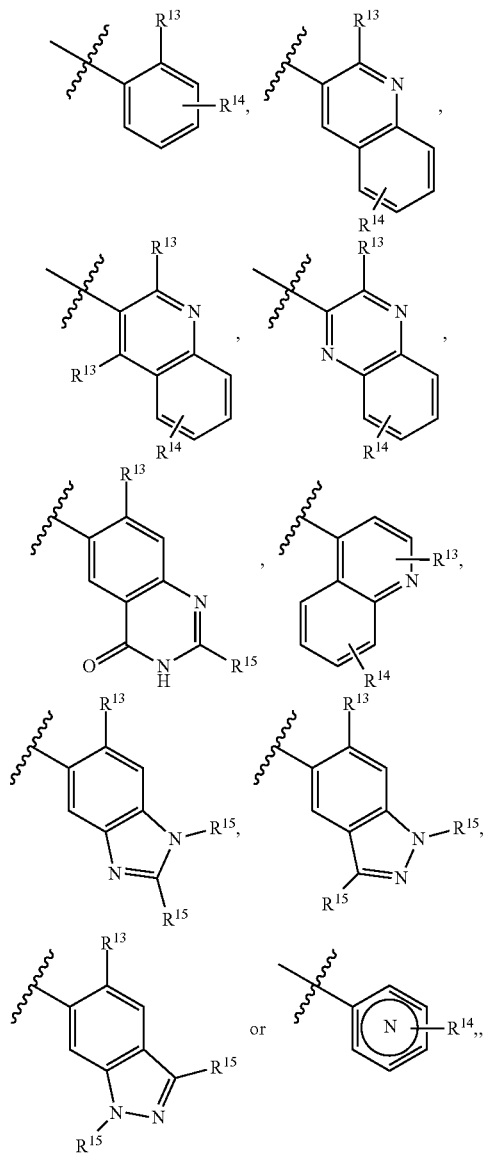

wherein R¹³ is H, F, Br or Cl; R¹⁴ represents up to 4 optional and additional substituents, each independently selected from alkyl, cycloalkyl, CF₃, —CN, halo, —O-alkyl, —NHSO₂-alkyl, —NO₂, —C(O)NH₂, —C(O)NH-alkyl, —C(O)OH, —OH, —NH₂, —SO₂-alkyl, —SO₂NH-alkyl, —S-alkyl, —CH₂NH₂, —CH₂OH, —SO₂NH₂, —NHC(O)-alkyl, —C(O)O-alkyl, —C(O)-heterocycloalkyl and heteroaryl; and each occurrence of R¹⁵ is independently alkyl, cycloalkyl, CF₃, —CN, halo, —O-alkyl, —NHSO₂-alkyl, —NO₂, —C(O)NH₂, —C(O)NH-alkyl, —C(O)OH, —OH, —NH₂, —SO₂-alkyl, —SO₂NH-alkyl, —S-alkyl, —CH₂NH₂, —CH₂OH, —SO₂NH₂, —NHC(O)-alkyl, —C(O)O-alkyl, —C(O)-heterocycloalkyl or heteroaryl.

In another embodiment, R¹ is —CH₂—, —CH₂CH₂—, —CH(CH₃)— or

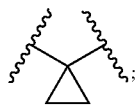

R² is —C(O)OR⁹; R⁵ is methyl or ethyl; R⁶ is H, F or Cl; R⁹ is H;

R¹⁰ is:

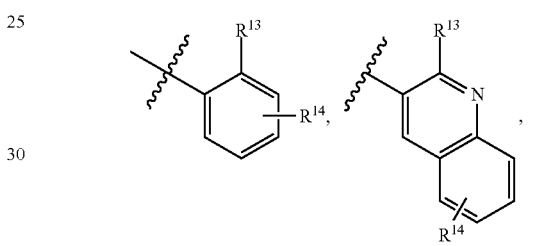

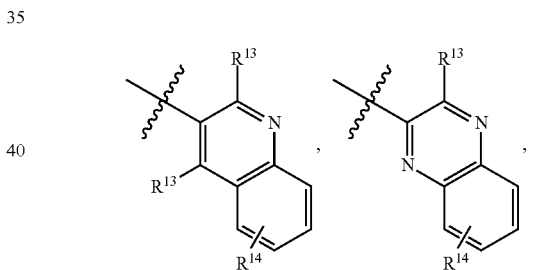

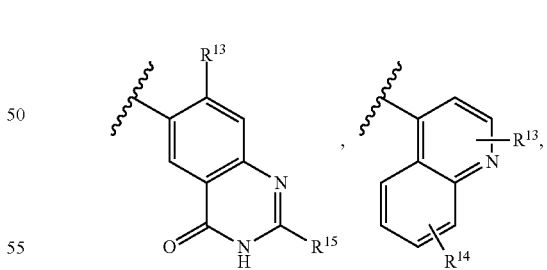

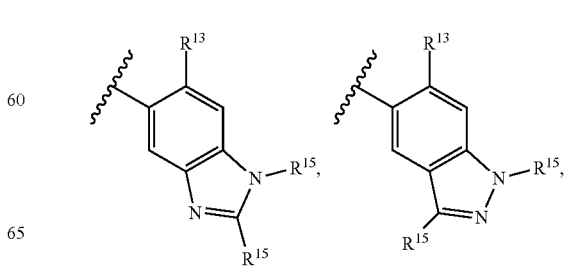

-continued

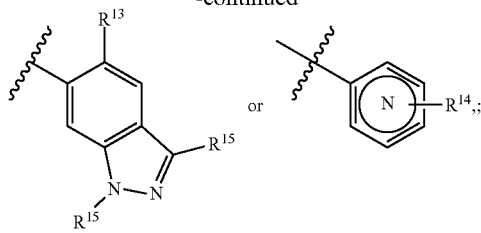
or

-continued

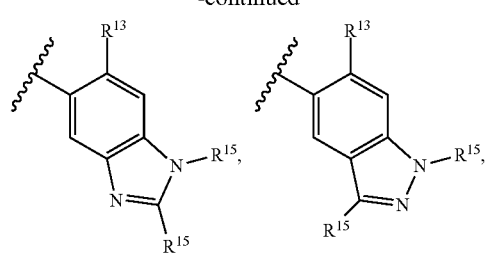

$R^{11}$ is methyl; $R^{13}$ is H, F, Br or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In another embodiment, $R^1$ is —$CH_2$—, —$CH_2CH_2$—, —$CH(CH_3)$— or

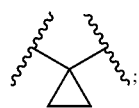

$R^2$ is —C(O)$OR^9$; $R^5$ is methyl or ethyl; $R^6$ is H, F or Cl; $R^9$ is H;
$R^{10}$ is:

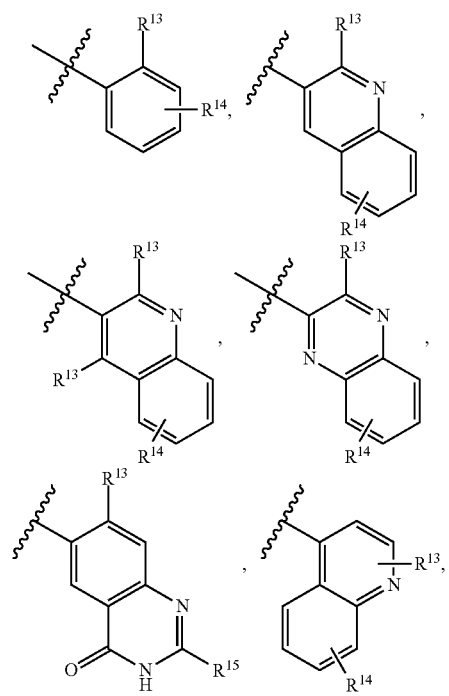

$R^{11}$ is cyclopropyl; $R^{13}$ is H, F, Br or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl; and each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl.

In one embodiment, $R^1$-$R^{10}$ is

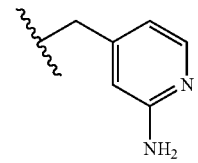 [SMILES: *Cc1ccnc(N)c1]

and $R^2$ is C(O)$OR^9$.

In one embodiment, $R^1$-$R^{10}$ is

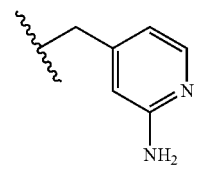 [SMILES: *Cc1ccnc(N)c1]

and $R^2$ is —C(O)OH.

In one embodiment, $R^1$-$R^{10}$ is

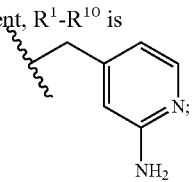

$R^2$ is $C(O)OR^9$; and $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$.

In one embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; $R^2$ is —C(O)OR$^9$; and $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$.

In one embodiment, $R^1$-$R^{10}$ is

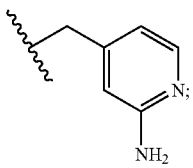 [SMILES: *Cc1ccnc(N)c1]

$R^2$ is $C(O)OR^9$; $R^4$, $R^6$ and $R^7$ are each H; and $R^5$ is other than H.

In another embodiment, $R^1$-$R^{10}$ is

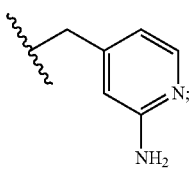 [SMILES: *Cc1ccnc(N)c1]

$R^2$ is $R^2$ is $C(O)OH$; $R^4$, $R^6$ and $R^7$ are each H; and $R^5$ is other than H.

In another embodiment, $R^1$-$R^{10}$ is

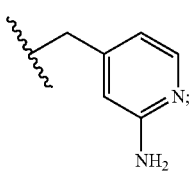 [SMILES: *Cc1ccnc(N)c1]

$R^2$ is $C(O)OR^9$, $R^{11}$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)alkyl, pyrazolyl or —OCH$_2$C(O)NH$_2$; $R^4$, $R^6$ and $R^7$ are each H; and $R^5$ is other than H.

In one embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; $R^2$ is $C(O)OR^9$; $R^4$, $R^6$ and $R^7$ are each H; and $R^5$ is other than H.

In another embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; $R^2$ is $C(O)OH$; $R^4$, $R^6$ and $R^7$ are each H; and $R^5$ is other than H.

In another embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; —$R^2$ is $C(O)OR^9$; $R^4$, $R^6$ and $R^7$ are each H; and $R^5$ is other than H.

In one embodiment, $R^1$-$R^{10}$ is

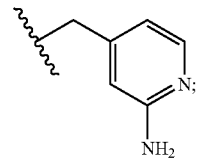

$R^2$ is $C(O)OR^9$; $R^4$ is H or F; $R^5$ is methyl or ethyl; $R^6$ is H or F; and $R^7$ is H.

In another embodiment, $R^1$-$R^{10}$ is

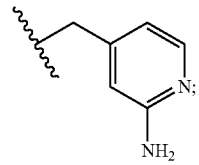 [SMILES: *Cc1ccnc(N)c1]

$R^2$ is $C(O)OR^9$; $R^4$ is H or F; $R^5$ is methyl or ethyl; $R^6$ is H or F; and $R^7$ is H.

In another embodiment, $R^1$-$R^{10}$ is

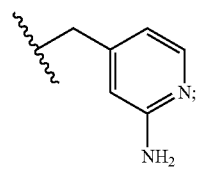 [SMILES: *Cc1ccnc(N)c1]

$R^2$ is $C(O)OR^9$, $R^9$ is H, alkyl, cycloalkyl; $R^4$ is H or F; $R^5$ is methyl or ethyl; $R^6$ is H or F; and $R^7$ is H.

In one embodiment, $R^1$-$R^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is C(O)OR$^9$; R$^4$ is H or F; R$^5$ is methyl or ethyl; R$^6$ is H or F; and R$^7$ is H.

In another embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is C(O)OR$^9$; R$^4$ is H or F; R$^5$ is methyl or ethyl; R$^6$ is H or F; and R$^7$ is H.

In another embodiment, R$^1$-R$^{10}$ is benzyl, wherein the phenyl moiety of the benzyl group is optionally substituted with from 1-4 groups independently selected from: halo, —NH$_2$, —NHSO$_2$-alkyl, haloalkyl, methoxy, —O-haloalkyl, —[C(R$^{12}$)$_2$]$_q$—NHC(O)NH-alkyl, alkyl, —OH, —CN, —C(O)NH$_2$ or —[C(R$^{12}$)$_2$]$_q$—NH$_2$; R$^2$ is K 1 C(O)OR$^9$; R$^H$ is phenyl, which is optionally substituted with up to 3 groups independently selected from: alkyl, F, Cl, methyl, —NH$_2$, —NO$_2$, methoxy, —SO$_2$NH$_2$, —COOH, —[C(R$^{12}$)$_2$]$_q$—C(O)O-alkyl, —OH, —NHSO$_2$-alkyl, —[C(R$^{12}$)$_2$]$_q$—SO$_2$-alkyl, —CF$_3$, —CN, thiazolyl, —C(O)NH-alkyl, —NHSO$_2$-phenyl, —NHSO$_2$-cyclopropyl, —NHSO$_2$-alkyl, —[C(R$^{12}$)$_2$]$_q$—NHC(O)-alkyl, pyrazolyl or —OCH$_2$C(O)NH$_2$; R$^4$ is H or F; R$^5$ is methyl or ethyl; R$^6$ is H or F; and R$^7$ is H.

In one embodiment, R$^1$ is —CH$_2$—; R$^2$ is C(O)OH; or —C(O)NH$_2$; R$^4$ is H or F; R$^5$ is methyl or ethyl; R$^6$ is H or F; R$^7$ is H; and —R$^{10}$ is:

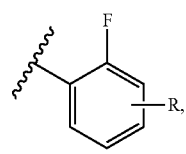

wherein R represents up to 2 optional and additional phenyl substituents, each independently selected from halo, —O-alkyl, alkyl, —CF$_3$, —CN, —NHSO$_2$-alkyl, —NO$_2$, —C(O)NH$_2$, —C(O)OH, —NH$_2$, —SO$_2$-alkyl, —SO$_2$NH-alkyl, —S-alkyl, —CH$_2$NH$_2$, —SO$_2$NH$_2$, —NHC(O)-alkyl, —C(O)O-alkyl, —C(O)-heterocycloalkyl and heteroaryl.

In another embodiment, R$^1$ is —CH$_2$—; R$^5$ is alkyl, cycloalkyl, halo or hydroxy; R$^6$ is H, halo or hydroxy; and R$^{10}$ is

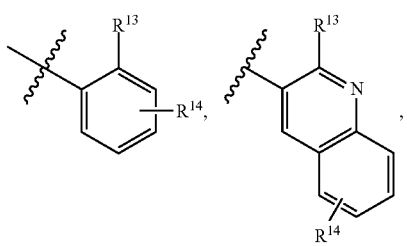

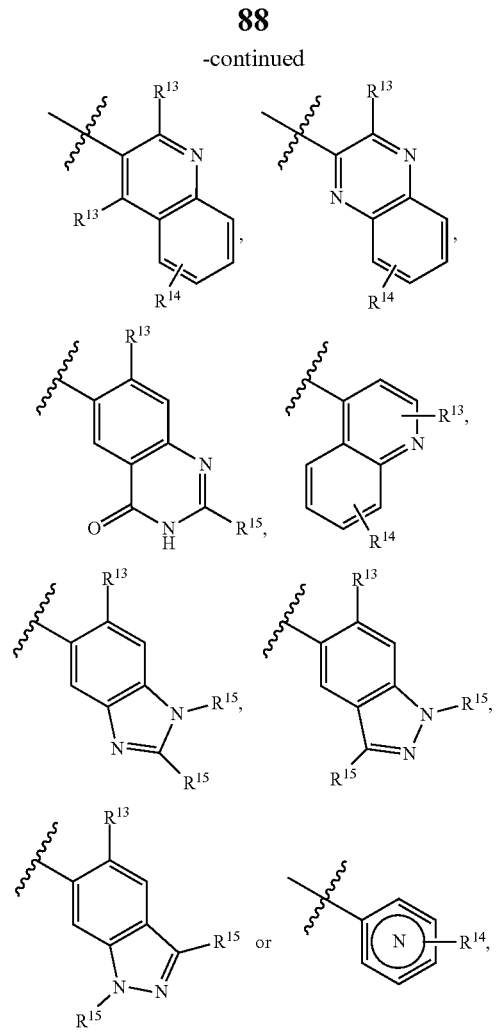

wherein R$^{13}$ is F or Cl; R$^{14}$ represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; and each occurrence of R$^{15}$ is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl.

In another embodiment, R$^1$ is —CH$_2$—; R$^5$ is methyl or ethyl; R$^6$ is H or F; and R$^{10}$ is

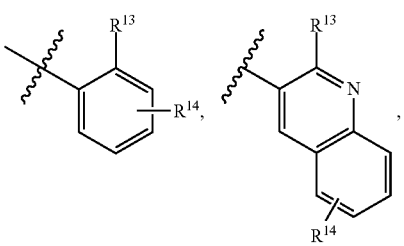

-continued

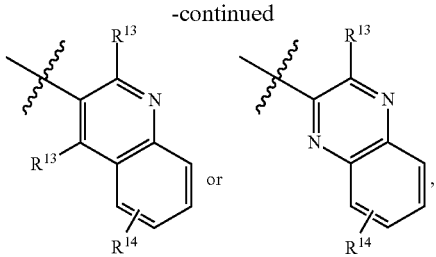

wherein $R^{13}$ is F or Cl and $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$alkyl, —SO$_2$NHalkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl.

In still another embodiment, $R^1$ is —CH$_2$—; $R^9$ is H; $R^{10}$ is

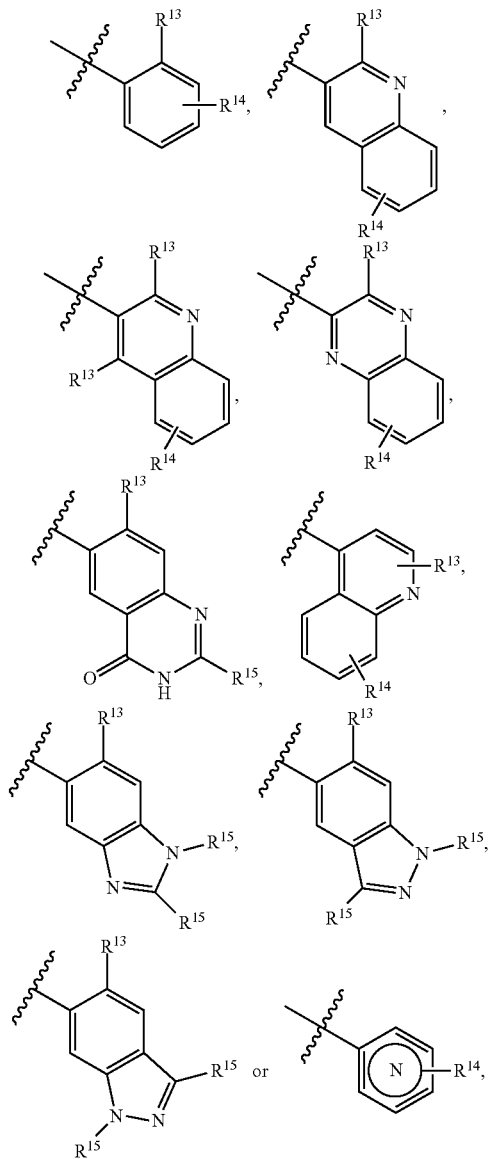

wherein $R^{13}$ is F or Cl; $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and $R^{11}$ is methyl.

In another embodiment, $R^1$ is —CH$_2$—; $R^9$ is H; $R^{10}$ is

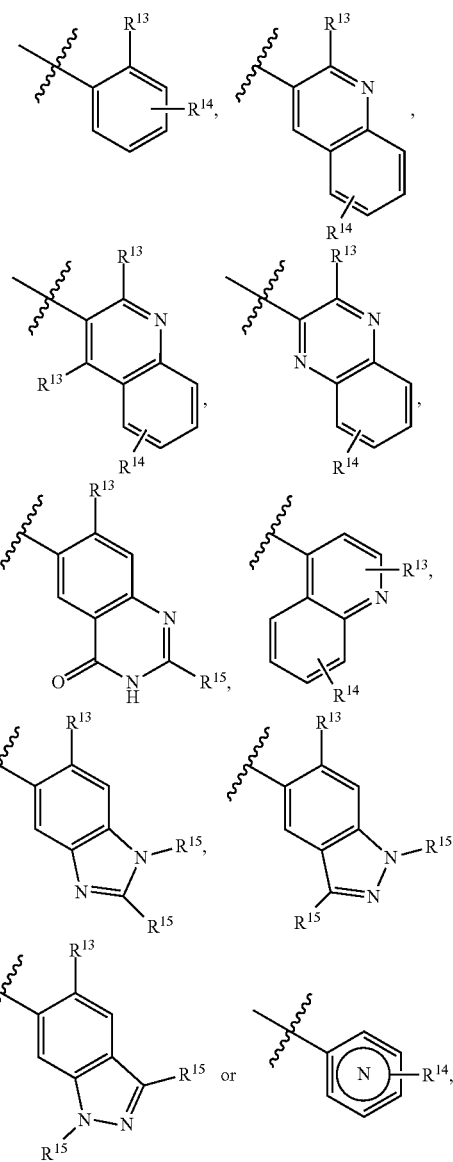

wherein $R^{13}$ is F or Cl, $R^{14}$ represents up to 4 optional and additional substituents, each independently selected from alkyl, cycloalkyl, $CF_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2$OH, —$SO_2NH_2$, —NHC(O)-alkyl, —C(O)O-alkyl, —C(O)-heterocycloalkyl or heteroaryl; and $R^{11}$ is cyclopropyl.

In one embodiment, —C(O)$OR^9$ or —C(O)N($R^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl.

In another embodiment, $R^2$ is —C(O)$OR^9$ or —C(O)N($R^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group.

In another embodiment, $R^2$ is —C(O)$OR^9$ or —C(O)N($R^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; and $R^1$ is —[C($R^{12}$)$_2$]$_r$—.

In still another embodiment, $R^2$ $R^2$ is —C(O)$OR^9$ or —C(O)N($R^9$)$_2$, wherein $R^9$ is H, alkyl, aryl, cycloalkyl, heteroaryl or heterocycloalkyl; and $R^1$ is —$CH_2$—, —$CH_2CH_2$—, —CH($CH_3$)— or

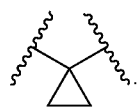 [SMILES: *C1(*)CC1]

In another embodiment, $R^2$ is —C(O)$OR^9$ or —C(O)N($R^9$)$_2$, wherein $R^9$ is H, alkyl, aryl, cycloalkyl, heteroaryl or heterocycloalkyl; and wherein $R^4$ and $R^7$ are each independently H, alkyl, halo or —OH, $R^5$ is H, alkyl, —O-alkyl, —O-haloalkyl, cycloalkyl, halo, haloalkyl, —OH, hydroxyalkyl, —$NH_2$ or —CN, and $R^6$ is H, alkyl, —O-alkyl, —O-haloalkyl, cycloalkyl, halo, haloalkyl, —OH, hydroxyalkyl, —$NH_2$ or —CN.

In yet another embodiment, $R^2$ is —C(O)$OR^9$ or —C(O)N($R^9$)$_2$, wherein $R^9$ is H, alkyl, aryl, cycloalkyl, heteroaryl or heterocycloalkyl; and $R^{10}$ is aryl or heteroaryl.

In yet another embodiment, $R^2$ is $R^2$ is —C(O)$OR^9$ or —C(O)N($R^9$)$_2$, wherein $R^9$ is H, alkyl, aryl, cycloalkyl, heteroaryl or heterocycloalkyl; and $R^{10}$ is:

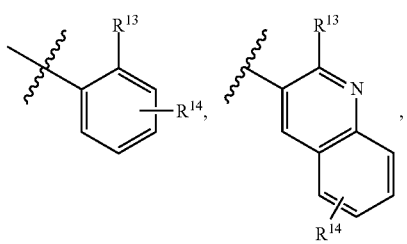

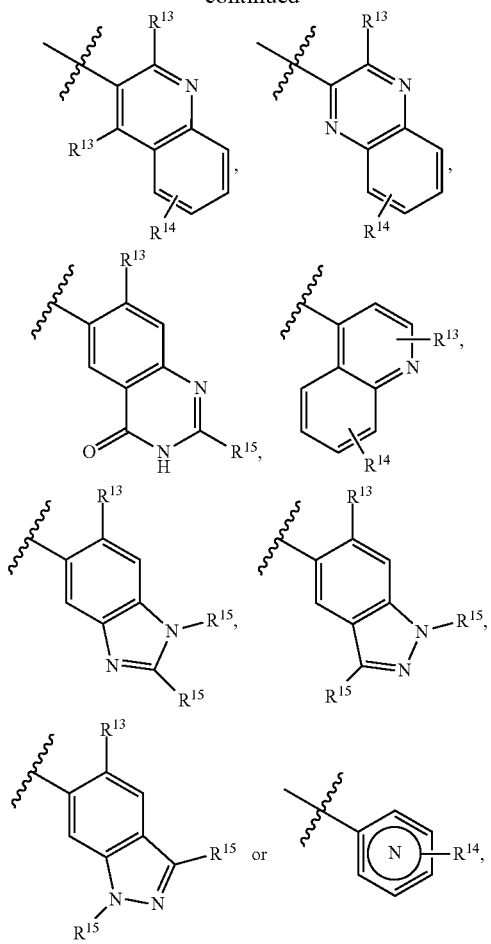

wherein $R^{13}$ is H, F, Br or Cl; $R^{14}$ represents up to 4 optional and additional substituents, each independently selected from alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2$OH, —$SO_2NH_2$, —NHC(O)-alkyl, —C(O)O-alkyl, —C(O)-heterocycloalkyl and heteroaryl; each occurrence of $R^{15}$ is independently alkyl, cycloalkyl, $CF_3$, —CN, halo, —O-alkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2$OH, —$SO_2NH_2$, —NHC(O)-alkyl, —C(O)O-alkyl, —C(O)-heterocycloalkyl or heteroaryl; and

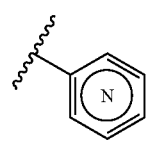

represents a pyridyl group, wherein the ring nitrogen atom can be at any of the five unsubstituted ring atom positions.

In yet another embodiment, $R^2$ is —C(O)$OR^9$ or —C(O)N($R^9$)$_2$, wherein $R^9$ is H, alkyl, aryl, cycloalkyl, heteroaryl or heterocycloalkyl and $R^{11}$ is alkyl, aryl, cycloalkyl, haloalkyl, heteroaryl, heterocycloalkyl or hydroxyalkyl; $R^{10}$ is:

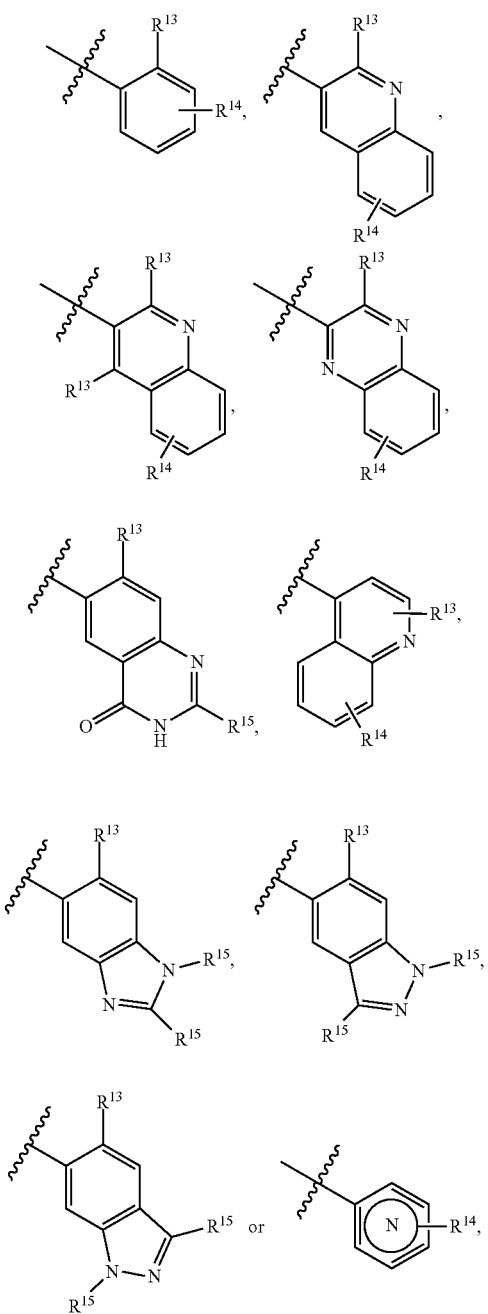

wherein R[13] is H, F, Br or Cl; R[14] represents up to 4 optional and additional substituents, each independently selected from alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of R[15] is independently alkyl, cycloalkyl, CF$_3$, —CN, halo, —O-alkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl;

represents a pyridyl group, wherein the ring nitrogen atom can be at any of the five unsubstituted ring atom positions; and R[4] and R[7] are each independently H, halo or hydroxy; R[5] is H, alkyl, —O-alkyl, —O-haloalkyl, cycloalkyl, halo, haloalkyl, —OH, hydroxyalkyl, —NH$_2$ or —CN; and R[6] is H, alkyl, —O-alkyl, —O-haloalkyl, cycloalkyl, halo, haloalkyl, —OH, hydroxyalkyl, —NH$_2$ or —CN.

In one embodiment, R[2] is —C(O)OR[9] or —C(O)N(R[9])$_2$, wherein R[9] is H, alkyl, aryl, cycloalkyl, heteroaryl or heterocycloalkyl.

In another embodiment, R[2] is —C(O)OR[9] or —C(O)N(R[9])$_2$; R[9] is H, alkyl, aryl, cycloalkyl, heteroaryl or heterocycloalkyl; and each occurrence of R[30] is independently, H, halo, —N(alkyl)$_2$, —OH, —O-alkyl, —O-haloalkyl, alkyl, cycloalkyl or heterocycloalkyl, or two adjacent R[30] groups, together with the carbon atoms to which they are attached, join to form an aryl, cycloalkyl, heteroaryl or heterocycloalkyl group.

In another embodiment, R[1] is —[C(R[12])$_2$]$_r$—; R[2] is —C(O)OR[9] or —C(O)N(R[9])$_2$; and R[9] is H, alkyl, aryl, cycloalkyl, heteroaryl or heterocycloalkyl.

In still another embodiment, R[1] is —CH$_2$—, —CH$_2$CH$_2$—, —CH(CH$_3$)— or

R[2] is —C(O)OR[9] or —C(O)N(R[9])$_2$; and R[9] is H, alkyl, aryl, cycloalkyl, heteroaryl or heterocycloalkyl.

In another embodiment, R[1] is —CH$_2$; R[2] is —C(O)OR[9] or —C(O)N(R[9])$_2$; and R[9] is H, alkyl, aryl, cycloalkyl, heteroaryl or heterocycloalkyl.

In another embodiment, R[2] is —C(O)OR[9] or —C(O)N(R[9])$_2$; R[4] and R[7] are each independently H, halo or —OH; R[5] is H, alkyl, —O-alkyl, —O-haloalkyl, cycloalkyl, halo, haloalkyl, —OH, hydroxyalkyl, —NH$_2$ or —CN; R[6] is H, alkyl, —O-alkyl, —O-haloalkyl, cycloalkyl, halo, haloalkyl, —OH, hydroxyalkyl, —NH$_2$ or —CN; R[9] is H, alkyl, aryl, cycloalkyl, heteroaryl or heterocycloalkyl; and each occurrence of R[30] is independently, H, halo, —N(alkyl)$_2$, —OH, —O-alkyl, —O-haloalkyl, alkyl, cycloalkyl or heterocycloalkyl, or two adjacent R[30] groups, together with the carbon atoms to which they are attached, join to form an aryl, cycloalkyl, heteroaryl or heterocycloalkyl group.

In yet another embodiment, R[2] is —C(O)OR[9] or —C(O)N(R[9])$_2$; R[4] and R[7] are each independently H, halo or —OH; R[5] is H, alkyl, —O-alkyl, —O-haloalkyl, cycloalkyl, halo, haloalkyl, —OH, hydroxyalkyl, —NH$_2$ or —CN; R[6] is H, alkyl, —O-alkyl, —O-haloalkyl, cycloalkyl, halo, haloalkyl, —OH, hydroxyalkyl, —NH$_2$ or —CN; R[9] is H, alkyl, aryl, cycloalkyl, heteroaryl or heterocycloalkyl; and each occurrence of R[30] is independently, H, halo, —N(alkyl)$_2$, —OH, —O-alkyl, —O-haloalkyl, alkyl, cycloalkyl or heterocycloalkyl, or two adjacent R[30] groups, together with the carbon atoms to which they are attached, join to form an aryl, cycloalkyl, heteroaryl or heterocycloalkyl group; and $R^{10}$ is aryl or heteroaryl.

In another embodiment, $R^2$ is —C(O)O$R^9$ or —C(O)N($R^9$)$_2$; $R^4$ and $R^7$ are each independently H, halo or —OH; $R^5$ is H, alkyl, —O-alkyl, —O-haloalkyl, cycloalkyl, halo, haloalkyl, —OH, hydroxyalkyl, —NH$_2$ or —CN; $R^6$ is H, alkyl, —O-alkyl, —O-haloalkyl, cycloalkyl, halo, haloalkyl, —OH, hydroxyalkyl, —NH$_2$ or —CN; $R^9$ is H, alkyl, aryl, cycloalkyl, heteroaryl or heterocycloalkyl; and each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group; and $R^{10}$ is:

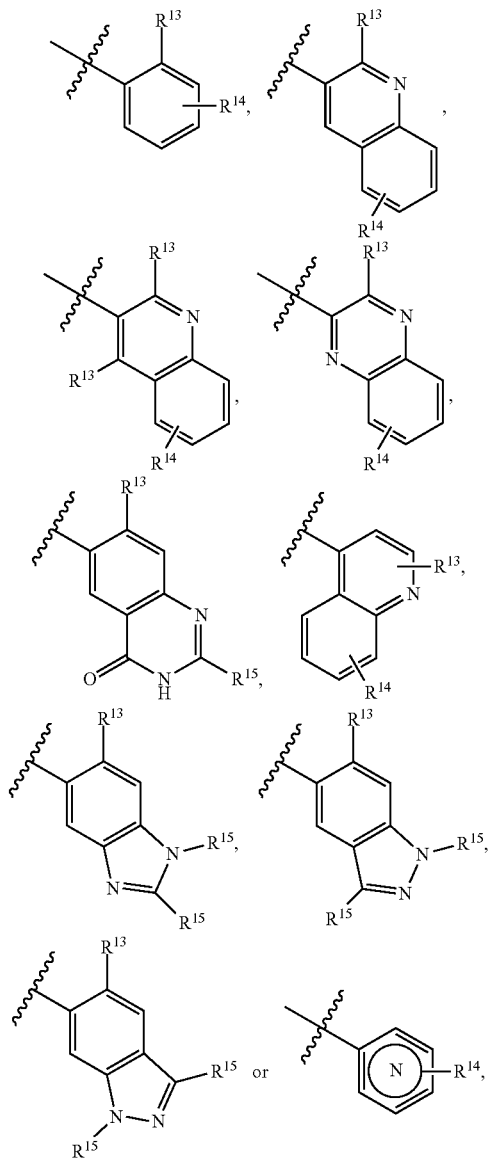

wherein $R^{13}$ is H, F, Br or Cl; $R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl and heteroaryl; each occurrence of $R^{15}$ is independently alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl; and

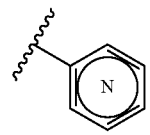

represents a pyridyl group, wherein the ring nitrogen atom can be at any of the five unsubstituted ring atom positions.

In one embodiment, for the compounds of formula (II), variables $R^1$, $R^2$, $R^3$, $R^4$, $R^5$, $R^6$, $R^7$ and $R^{10}$ are selected independently from each other.

In another embodiment, the compounds of formula (II) are in purified form.

In one embodiment, the compounds of formula (II) have the formula (IIa):

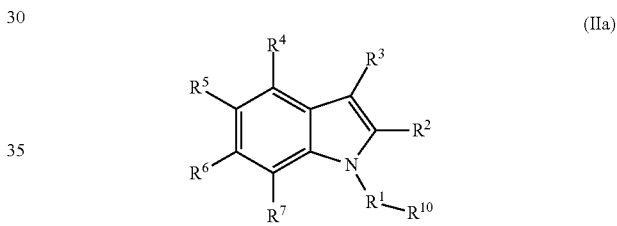

(IIa)

or a pharmaceutically acceptable salt, solvate, ester or prodrug thereof,
wherein:
$R^1$ is —CH$_2$—, —CH$_2$CH$_2$—, —CH(CH$_3$)— or

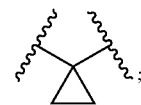 [SMILES: *C1(*)CC1]

$R^2$ is —C(O)O$R^9$ or —C(O)N($R^9$)$_2$;
$R^3$ is:

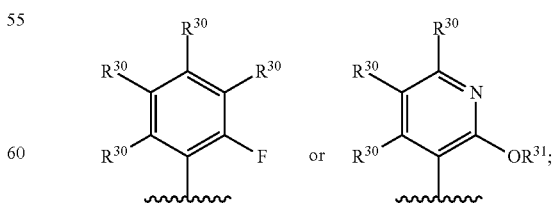

$R^4$, $R^5$, $R^6$ and $R^7$ are each, independently, H, alkyl, cycloalkyl, heterocycloalkyl, haloalkyl, halo, —OH, —OH, —O-alkyl, —O-haloalkyl, —NH$_2$, —NH-alkyl or —N(alkyl)$_2$;

each occurrence of $R^9$ is independently H, alkyl, cycloalkyl, heterocycloalkyl, haloalkyl or hydroxyalkyl;

$R^{10}$ is:

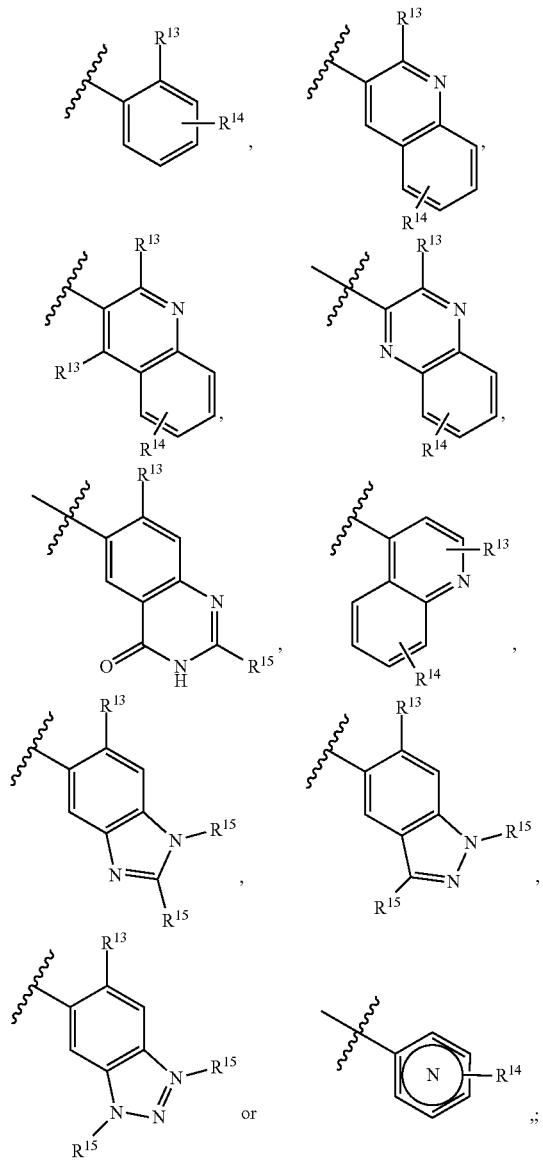

each occurrence of $R^{11}$ is independently alkyl, aryl, cycloalkyl, haloalkyl, heteroaryl, heterocycloalkyl or hydroxyalkyl;

$R^{13}$ is H, F, Br or Cl;

$R^{14}$ represents up to 4 optional and additional substituents, each independently selected from alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl and heteroaryl;

each occurrence of $R^{15}$ is independently alkyl, cycloalkyl, $CF_3$, —CN, halo, —O-alkyl, —O-haloalkyl, —$NHSO_2$-alkyl, —$NO_2$, —C(O)$NH_2$, —C(O)NH-alkyl, —C(O)OH, —OH, —$NH_2$, —$SO_2$-alkyl, —$SO_2$NH-alkyl, —S-alkyl, —$CH_2NH_2$, —$CH_2OH$, —$SO_2NH_2$, —NHC(O)-alkyl, —C(O)O-alkyl, —C(O)-heterocycloalkyl or heteroaryl;

each occurrence of $R^{30}$ is independently, H, halo, —N(alkyl)$_2$, —OH, —O-alkyl, —O-haloalkyl, alkyl, cycloalkyl or heterocycloalkyl, or two adjacent $R^{30}$ groups, together with the carbon atoms to which they are attached, join to form an aryl, cycloalkyl, heteroaryl or heterocycloalkyl group;

each occurrence of q is independently an integer ranging from 0 to 4;

each occurrence of r is independently an integer ranging from 1 to 4; and

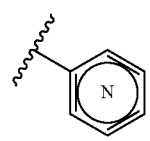

represents a pyridyl group, wherein the ring nitrogen atom can be at any of the five unsubstituted ring atom positions.

In one embodiment, for the compounds of formula (IIa), variables $R^1$, $R^2$, $R^3$, $R^4$, $R^5$, $R^6$, $R^7$ and $R^{10}$ are selected independently from each other.

In another embodiment, the compounds of formula (IIa) are in purified form.

Non-limiting illustrative examples of the compounds of the present invention are set forth below in Table 1 and in the Examples section below.

TABLE 1

| No. | STRUCTURE | M + H |
|---|---|---|
| 1 | 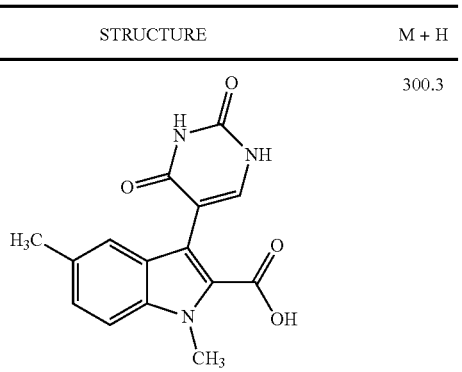 | 300.3 |
| 2 | 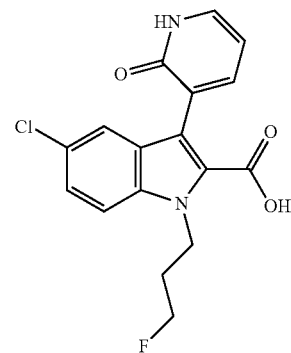 [SMILES: O=C(O)c1c(-c2ccc[nH]c2=O)c2cc(Cl)ccc2n1CCCF] | 349.8 |

TABLE 1-continued

| No. | STRUCTURE | M + H |
|---|---|---|
| 3 | 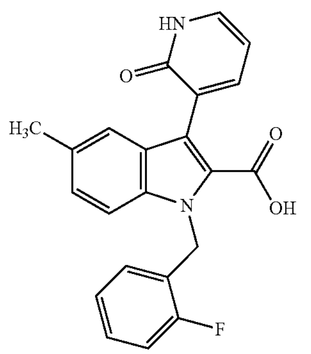 [SMILES: Cc1ccc2c(c1)c(-c1ccc[nH]c1=O)c(C(=O)O)n2Cc1ccccc1F] | 377.4 |
| 4 | 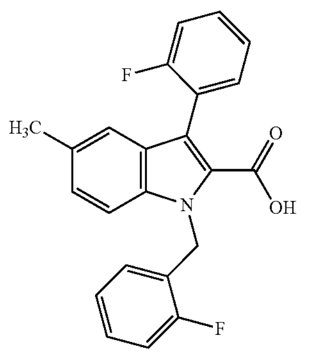 [SMILES: Cc1ccc2c(c1)c(-c1ccccc1F)c(C(=O)O)n2Cc1ccccc1F] | 378.4 |
| 5 | 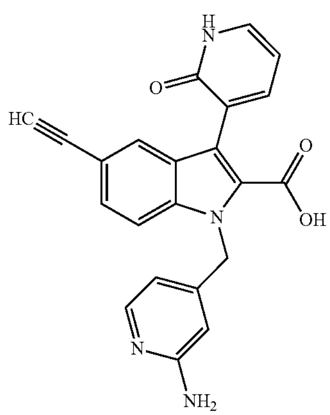 [SMILES: C#Cc1ccc2c(c1)c(-c1ccc[nH]c1=O)c(C(=O)O)n2Cc1ccnc(N)c1] | 385.4 |
| 6 | 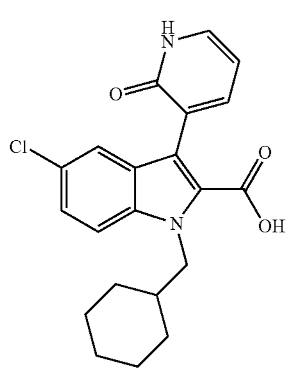 [SMILES: O=C(O)c1c(-c2ccc[nH]c2=O)c2cc(Cl)ccc2n1CC1CCCCC1] | 385.9 |
| 7 | | 387.5 |
| 8 | | 391.4 |
| 9 | | 391.4 |
| 10 | | 391.4 |

TABLE 1-continued
| No. | STRUCTURE | M + H |
|---|---|---|
| 11 | 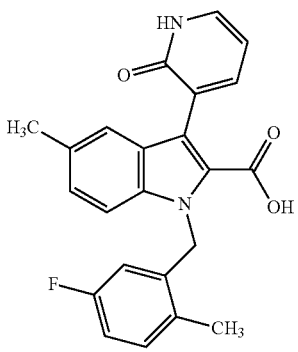 [SMILES: Cc1ccc2c(c1)c(-c1ccc[nH]c1=O)c(C(=O)O)n2Cc1cc(F)ccc1C] | 391.4 |
| 12 | 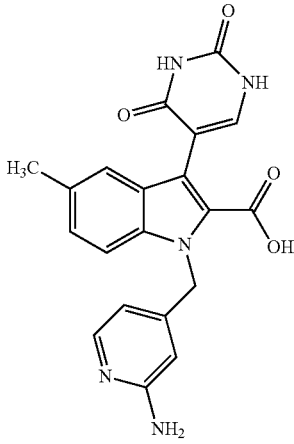 [SMILES: Cc1ccc2c(c1)c(-c1c[nH]c(=O)[nH]c1=O)c(C(=O)O)n2Cc1ccnc(N)c1] | 392.4 |
| 13 | 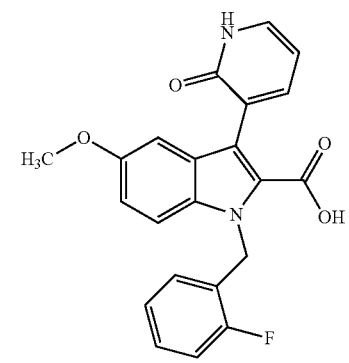 [SMILES: COc1ccc2c(c1)c(-c1ccc[nH]c1=O)c(C(=O)O)n2Cc1ccccc1F] | 393.4 |
| 14 | 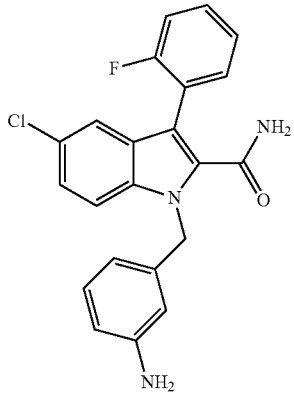 [SMILES: NC(=O)c1c(-c2ccccc2F)c2cc(Cl)ccc2n1Cc1cccc(N)c1] | 394.9 |
| 15 | 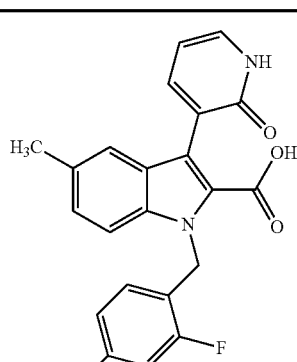 | 395.4 |
| 16 | 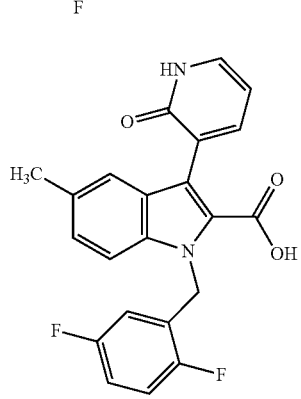 | 395.4 |
| 17 | 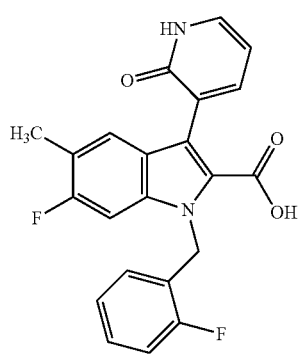 [SMILES: Cc1cc2c(-c3ccc[nH]c3=O)c(C(=O)O)n(Cc3ccccc3F)c2cc1F] | 395.4 |
| 18 | 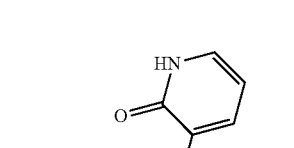 | 395.8 |

TABLE 1-continued
| No. | STRUCTURE | M + H |
|---|---|---|
| 19 | 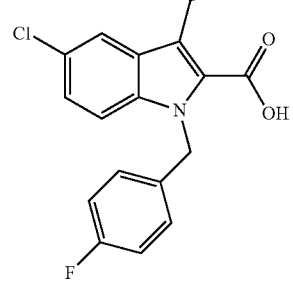 | 395.8 |
| 20 | 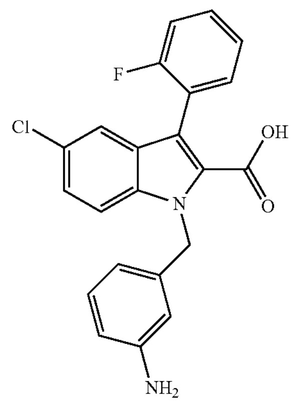 [SMILES: Nc1cccc(Cn2c(C(=O)O)c(-c3ccccc3F)c3cc(Cl)ccc32)c1] | 395.8 |
| 21 | 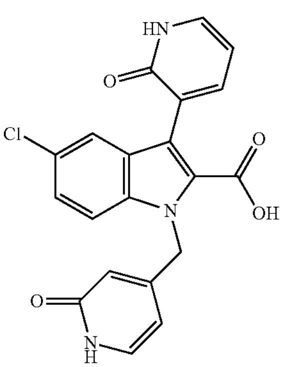 [SMILES: O=C(O)c1c(-c2ccc[nH]c2=O)c2cc(Cl)ccc2n1Cc1cc[nH]c(=O)c1] | 396.8 |
| 22 | 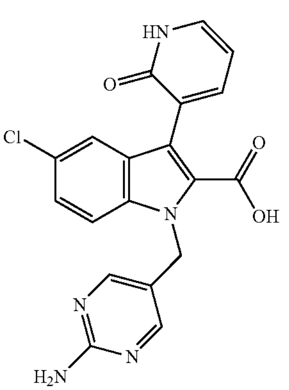 [SMILES: Nc1ncc(Cn2c(C(=O)O)c(-c3ccc[nH]c3=O)c3cc(Cl)ccc32)cn1] | 396.8 |
TABLE 1-continued
| No. | STRUCTURE | M + H |
|---|---|---|
| 23 | 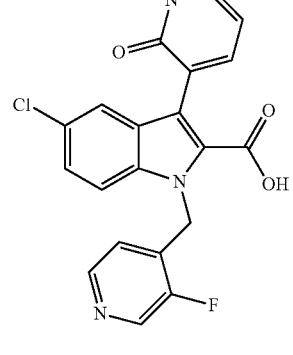 | 397.8 |
| 24 | 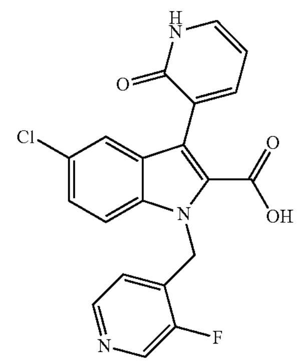 [SMILES: O=C(O)c1c(-c2ccc[nH]c2=O)c2cc(Cl)ccc2n1Cc1ccncc1F] | 398.8 |
| 25 | 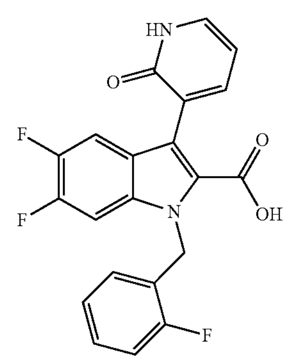 [SMILES: O=C(O)c1c(-c2ccc[nH]c2=O)c2cc(F)c(F)cc2n1Cc1ccccc1F] | 399.3 |
| 26 | 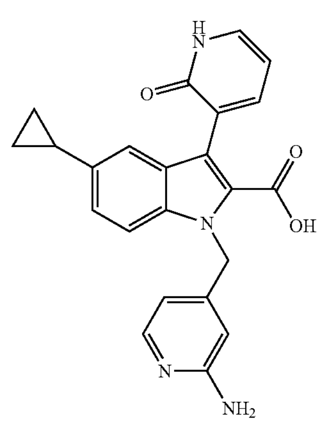 [SMILES: Nc1cc(Cn2c(C(=O)O)c(-c3ccc[nH]c3=O)c3cc(C4CC4)ccc32)ccn1] | 401.4 |

TABLE 1-continued

| No. | STRUCTURE | M + H |
|-----|-----------|-------|
| 27 | 5-ethyl-3-(2-oxo-1,2-dihydropyridin-3-yl)-1-(2,4-dimethylbenzyl)-1H-indole-2-carboxylic acid | 401.5 |
| 28 | 5-chloro-3-(2-oxo-1,2-dihydropyridin-3-yl)-1-((2-aminothiazol-4-yl)methyl)-1H-indole-2-carboxylic acid | 401.8 |
| 29 | 5-acetyl-3-(2-oxo-1,2-dihydropyridin-3-yl)-1-((2-aminopyridin-4-yl)methyl)-1H-indole-2-carboxylic acid | 403.4 |
| 30 | 5-methoxy-3-(2-oxo-1,2-dihydropyridin-3-yl)-1-(2,4-dimethylbenzyl)-1H-indole-2-carboxylic acid | 403.5 |
| 31 | 5-methyl-3-(2-oxo-1,2-dihydropyridin-3-yl)-1-(3-nitrobenzyl)-1H-indole-2-carboxylic acid | 404.4 |
| 32 | 5-ethyl-3-(2-oxo-1,2-dihydropyridin-3-yl)-1-(2-fluoro-3-methylbenzyl)-1H-indole-2-carboxylic acid | 405.4 |
| 33 | 5-isopropyl-3-(2-oxo-1,2-dihydropyridin-3-yl)-1-(2-fluorobenzyl)-1H-indole-2-carboxylic acid | 405.4 |
| 34 | 5-ethoxy-3-(2-oxo-1,2-dihydropyridin-3-yl)-1-(2-fluorobenzyl)-1H-indole-2-carboxylic acid | 407.4 |

TABLE 1-continued

| No. | STRUCTURE | M + H |
|-----|-----------|-------|
| 35 | 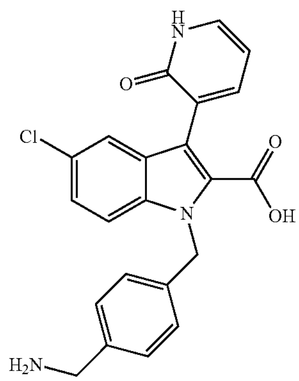 [SMILES: NCc1ccc(Cn2c(C(=O)O)c(-c3ccc[nH]c3=O)c3cc(Cl)ccc32)cc1] | 408.9 |
| 36 | 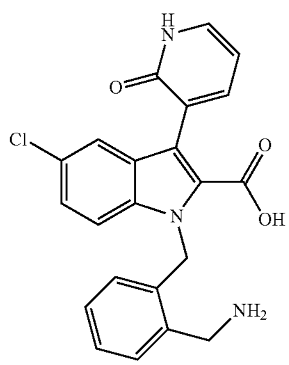 [SMILES: NCc1ccccc1Cn1c(C(=O)O)c(-c2ccc[nH]c2=O)c2cc(Cl)ccc21] | 408.9 |
| 37 | 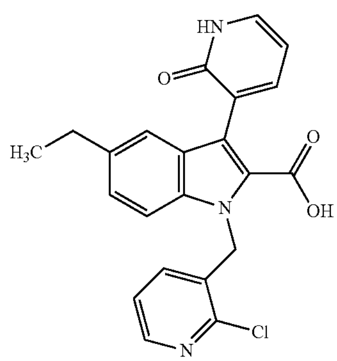 [SMILES: CCc1ccc2c(c1)c(-c1ccc[nH]c1=O)c(C(=O)O)n2Cc1cccnc1Cl] | 408.9 |
| 38 | 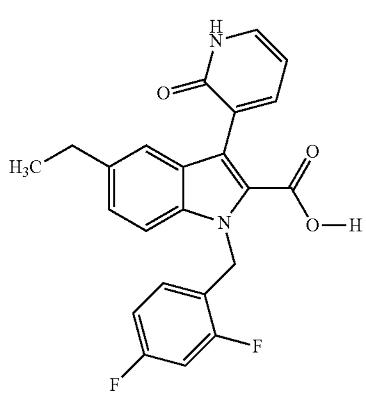 [SMILES: CCc1ccc2c(c1)c(-c1ccc[nH]c1=O)c(C(=O)O)n2Cc1ccc(F)cc1F] | 409.4 |
| 39 | | 409.4 |
| 40 | | 409.8 |
| 41 | | 409.8 |
| 42 | | 410.8 |

TABLE 1-continued

| No. | STRUCTURE | M + H |
|---|---|---|
| 43 | 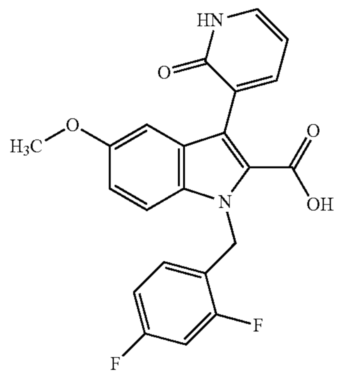 [SMILES: COc1ccc2c(c1)c(-c1ccc[nH]c1=O)c(C(=O)O)n2Cc1ccc(F)cc1F] | 411.4 |
| 44 | 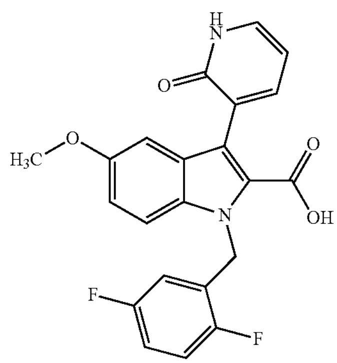 [SMILES: COc1ccc2c(c1)c(-c1ccc[nH]c1=O)c(C(=O)O)n2Cc1cc(F)ccc1F] | 411.4 |
| 45 | 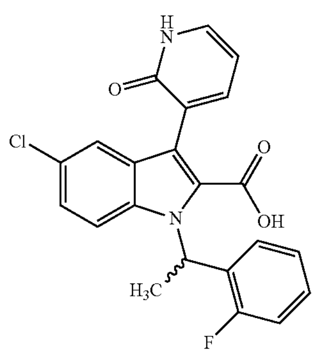 [SMILES: CC(c1ccccc1F)n1c(C(=O)O)c(-c2ccc[nH]c2=O)c2cc(Cl)ccc21] | 411.8 |
| 46 | 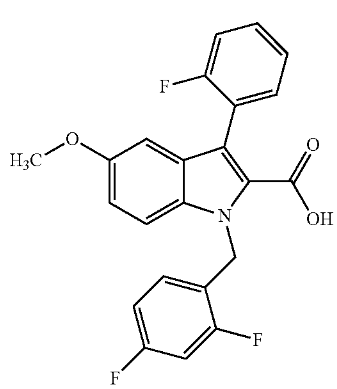 [SMILES: COc1ccc2c(c1)c(-c1ccccc1F)c(C(=O)O)n2Cc1ccc(F)cc1F] | 412.4 |
| 47 | | 412.4 |
| 48 | | 412.8 |
| 49 | | 415.8 |
| 50 | | 416.8 |

TABLE 1-continued

| No. | STRUCTURE | M + H |
|---|---|---|
| 51 | 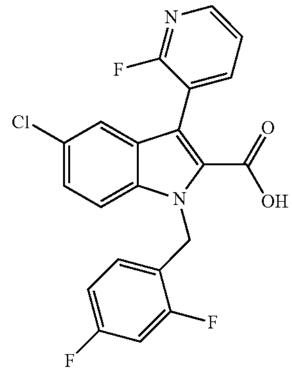 [SMILES: O=C(O)c1c(-c2cccnc2F)c2cc(Cl)ccc2n1Cc1ccc(F)cc1F] | 417.8 |
| 52 | 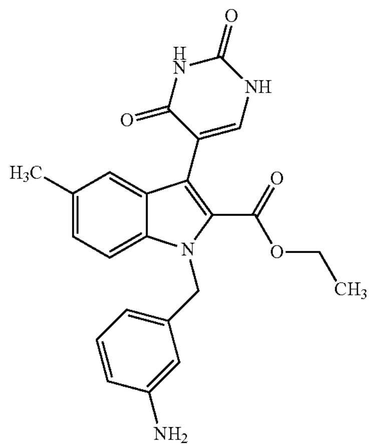 [SMILES: CCOC(=O)c1c(-c2c[nH]c(=O)[nH]c2=O)c2cc(C)ccc2n1Cc1cccc(N)c1] | 419.5 |
| 53 | 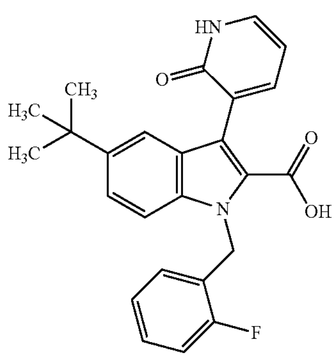 [SMILES: CC(C)(C)c1ccc2c(c1)c(-c1ccc[nH]c1=O)c(C(=O)O)n2Cc1ccccc1F] | 419.5 |
| 54 | 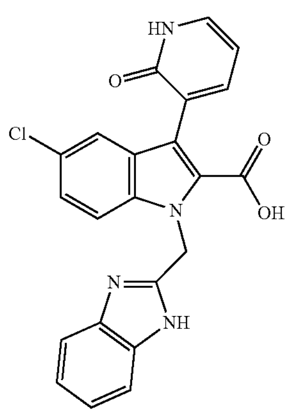 [SMILES: O=C(O)c1c(-c2ccc[nH]c2=O)c2cc(Cl)ccc2n1Cc1nc2ccccc2[nH]1] | 419.8 |
| 55 | | 419.8 |
| 56 | | 420.5 |
| 57 | | 420.5 |
| 58 | | 420.8 |

TABLE 1-continued

| No. | STRUCTURE | M + H |
|-----|-----------|-------|
| 59  | 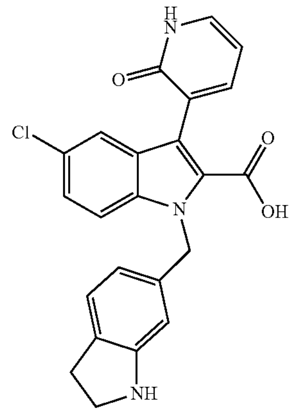 [SMILES: O=C(O)c1c(-c2ccc[nH]c2=O)c2cc(Cl)ccc2n1Cc1ccc2c(c1)NCC2]          | 420.9 |
| 60  | 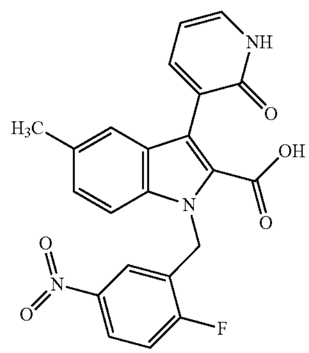 [SMILES: Cc1ccc2c(c1)c(-c1ccc[nH]c1=O)c(C(=O)O)n2Cc1cc([N+](=O)[O-])ccc1F]          | 422.4 |
| 61  | 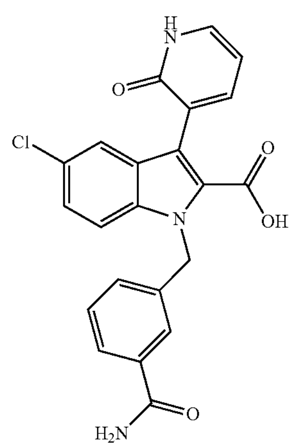 [SMILES: NC(=O)c1cccc(Cn2c(C(=O)O)c(-c3ccc[nH]c3=O)c3cc(Cl)ccc32)c1]          | 422.8 |
| 62  | 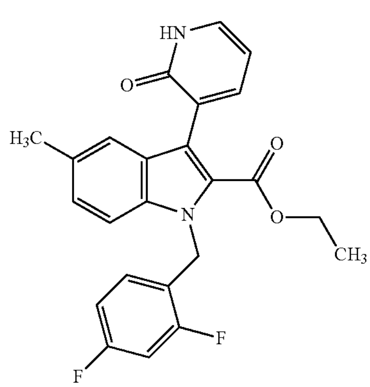 [SMILES: CCOC(=O)c1c(-c2ccc[nH]c2=O)c2cc(C)ccc2n1Cc1ccc(F)cc1F]          | 423.4 |
| 63  |           | 423.9 |
| 64  |           | 424.2 |
| 65  |           | 425.4 |
| 66  |           | 425.4 |

TABLE 1-continued
| No. | STRUCTURE | M + H |
|---|---|---|
| 67 | 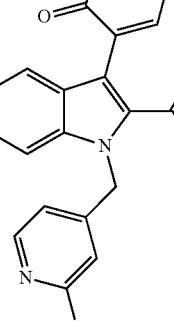 | 425.8 |
| 68 | 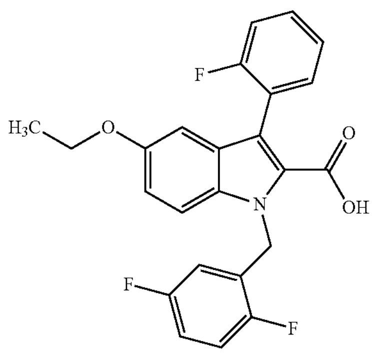 [SMILES: CCOc1ccc2c(c1)c(-c1ccccc1F)c(C(=O)O)n2Cc1cc(F)ccc1F] | 426.4 |
| 69 | 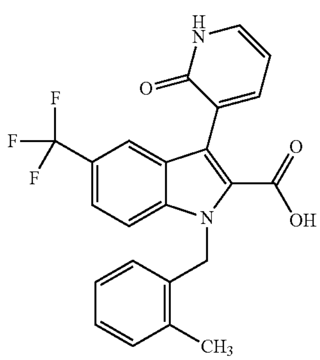 [SMILES: Cc1ccccc1Cn1c(C(=O)O)c(-c2ccc[nH]c2=O)c2cc(C(F)(F)F)ccc21] | 427.4 |
| 70 | 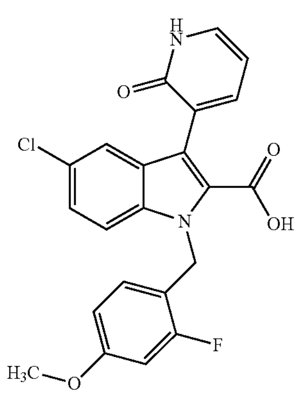 [SMILES: COc1ccc(Cn2c(C(=O)O)c(-c3ccc[nH]c3=O)c3cc(Cl)ccc32)c(F)c1] | 427.8 |
| 71 | 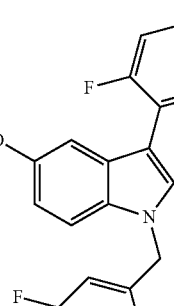 | 429.4 |
| 72 | 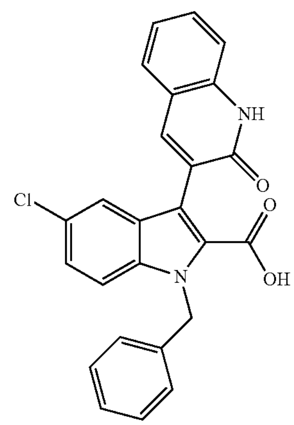 [SMILES: O=C(O)c1c(-c2cc3ccccc3[nH]c2=O)c2cc(Cl)ccc2n1Cc1ccccc1] | 429.9 |
| 73 | 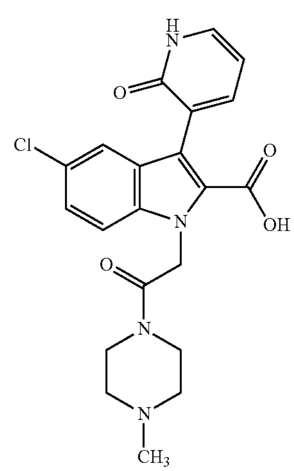 [SMILES: CN1CCN(C(=O)Cn2c(C(=O)O)c(-c3ccc[nH]c3=O)c3cc(Cl)ccc32)CC1] | 429.9 |

TABLE 1-continued
| No. | STRUCTURE | M + H |
|---|---|---|
| 74 | 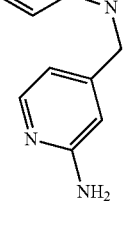 | 430.3 |
| 75 | 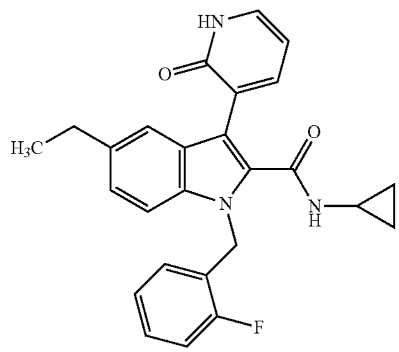 [SMILES: CCc1ccc2c(c1)c(-c1ccc[nH]c1=O)c(C(=O)NC1CC1)n2Cc1ccccc1F] | 430.5 |
| 76 | 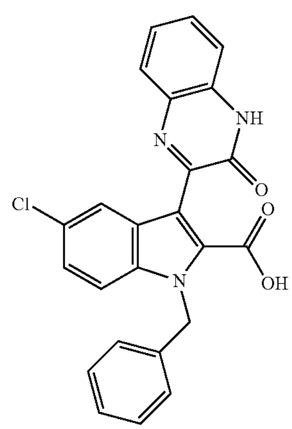 [SMILES: O=C(O)c1c(-c2nc3ccccc3[nH]c2=O)c2cc(Cl)ccc2n1Cc1ccccc1] | 430.9 |
| 77 | 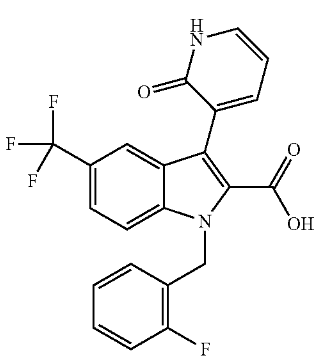 [SMILES: O=C(O)c1c(-c2ccc[nH]c2=O)c2cc(C(F)(F)F)ccc2n1Cc1ccccc1F] | 431.4 |
TABLE 1-continued
| No. | STRUCTURE | M + H |
|---|---|---|
| 78 | 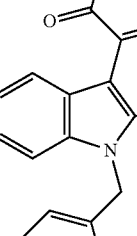 | 432.3 |
| 79 | 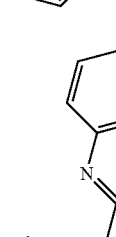 | 432.8 |
| 80 | 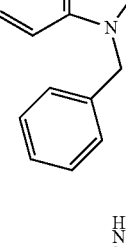 | 432.8 |

TABLE 1-continued

| No. | STRUCTURE | M + H |
|---|---|---|
| 81 | 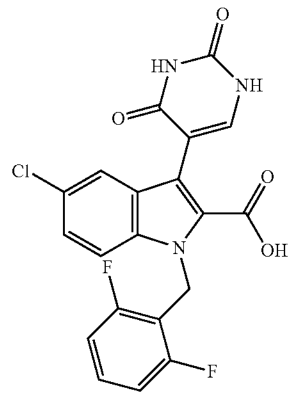 [SMILES: O=C(O)c1c(-c2c[nH]c(=O)[nH]c2=O)c2cc(Cl)ccc2n1Cc1c(F)cccc1F] | 432.8 |
| 82 | 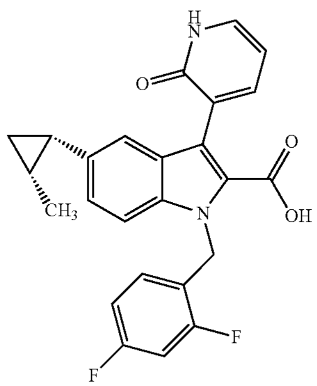 [SMILES: C[C@@H]1C[C@@H]1c1ccc2c(c1)c(-c1ccc[nH]c1=O)c(C(=O)O)n2Cc1ccc(F)cc1F] | 435.4 |
| 83 | 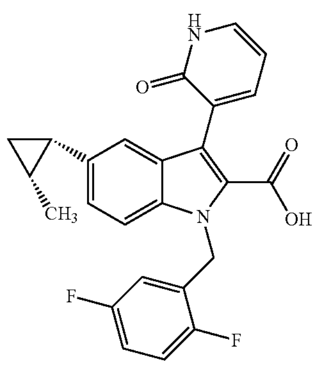 [SMILES: C[C@@H]1C[C@@H]1c1ccc2c(c1)c(-c1ccc[nH]c1=O)c(C(=O)O)n2Cc1cc(F)ccc1F] | 435.4 |
| 84 | 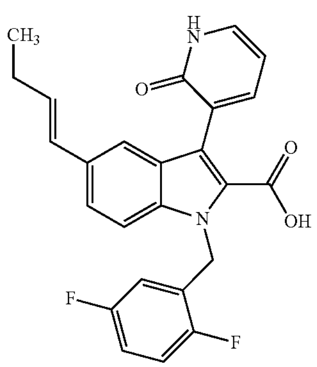 [SMILES: CC/C=C/c1ccc2c(c1)c(-c1ccc[nH]c1=O)c(C(=O)O)n2Cc1cc(F)ccc1F] | 435.4 |
| 85 | | 435.4 |
| 86 | | 436.4 |
| 87 | | 436.4 |
| 88 | | 437.5 |

TABLE 1-continued

| No. | STRUCTURE | M + H |
|---|---|---|
| 89 | 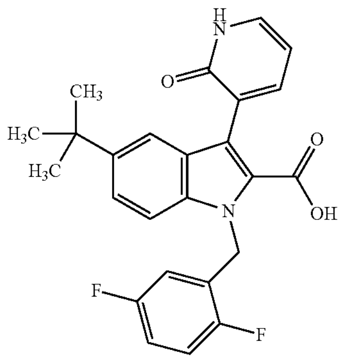 [SMILES: CC(C)(C)c1ccc2c(c1)c(-c1ccc[nH]c1=O)c(C(=O)O)n2Cc1cc(F)ccc1F] | 437.5 |
| 90 | 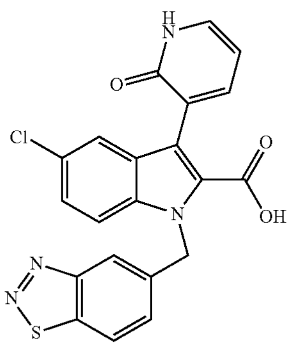 [SMILES: O=C(O)c1c(-c2ccc[nH]c2=O)c2cc(Cl)ccc2n1Cc1ccc2snnc2c1] | 437.9 |
| 91 | 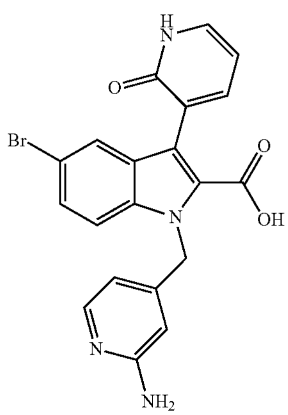 [SMILES: Nc1cc(Cn2c(C(=O)O)c(-c3ccc[nH]c3=O)c3cc(Br)ccc32)ccn1] | 440.3 |
| 92 | 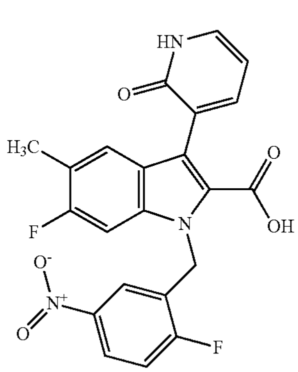 [SMILES: Cc1cc2c(-c3ccc[nH]c3=O)c(C(=O)O)n(Cc3cc([N+](=O)[O-])ccc3F)c2cc1F] | 440.4 |
| 93 | 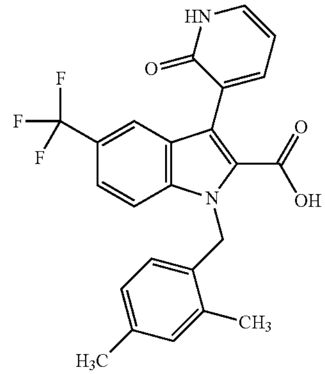 [SMILES: Cc1ccc(Cn2c(C(=O)O)c(-c3ccc[nH]c3=O)c3cc(C(F)(F)F)ccc32)c(C)c1] | 441.4 |
| 94 | 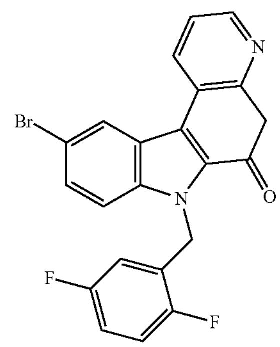 [SMILES: O=C1Cc2ncccc2-c2c1n(Cc1cc(F)ccc1F)c1ccc(Br)cc21] | 442.2 |
| 95 | 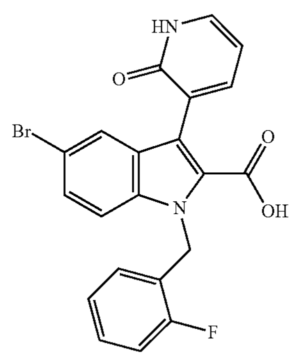 [SMILES: O=C(O)c1c(-c2ccc[nH]c2=O)c2cc(Br)ccc2n1Cc1ccccc1F] | 442.3 |
| 96 | 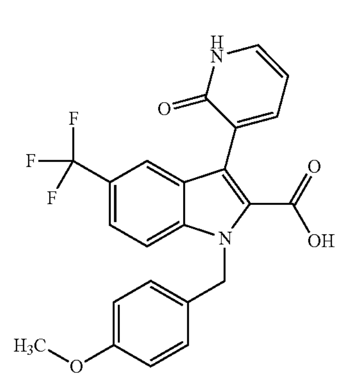 [SMILES: COc1ccc(Cn2c(C(=O)O)c(-c3ccc[nH]c3=O)c3cc(C(F)(F)F)ccc32)cc1] | 443.4 |

TABLE 1-continued

| No. | STRUCTURE | M + H |
|---|---|---|
| 97 | 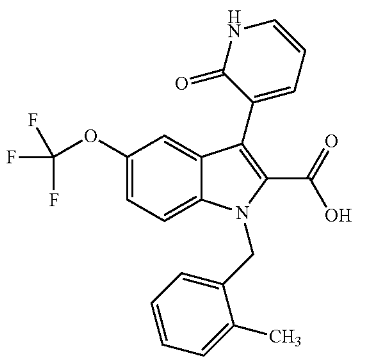 [SMILES: Cc1ccccc1Cn1c(C(=O)O)c(-c2ccc[nH]c2=O)c2cc(OC(F)(F)F)ccc21] | 443.4 |
| 98 | 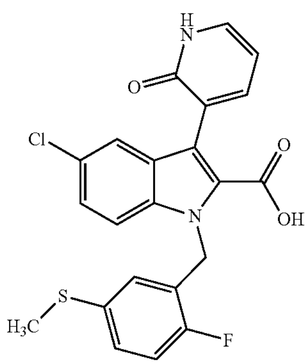 [SMILES: CSc1ccc(F)c(Cn2c(C(=O)O)c(-c3ccc[nH]c3=O)c3cc(Cl)ccc32)c1] | 443.9 |
| 99 | 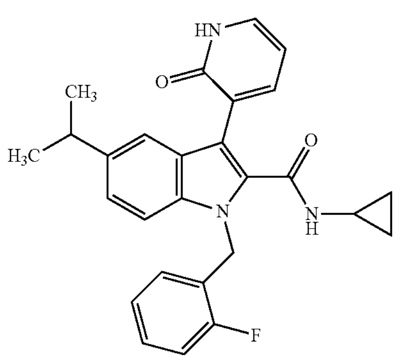 [SMILES: CC(C)c1ccc2c(c1)c(-c1ccc[nH]c1=O)c(C(=O)NC1CC1)n2Cc1ccccc1F] | 444.5 |
| 100 | 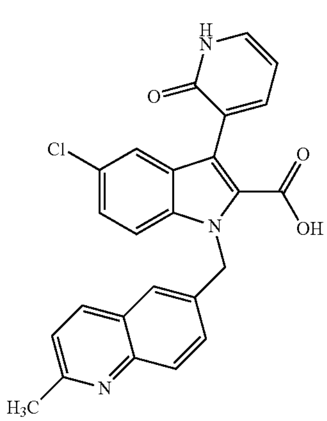 [SMILES: Cc1ccc2cc(Cn3c(C(=O)O)c(-c4ccc[nH]c4=O)c4cc(Cl)ccc43)ccc2n1] | 444.9 |
| 101 | | 445.4 |
| 102 | | 445.4 |
| 103 | | 445.4 |
| 104 | | 445.8 |

TABLE 1-continued

| No. | STRUCTURE | M + H |
|---|---|---|
| 105 | 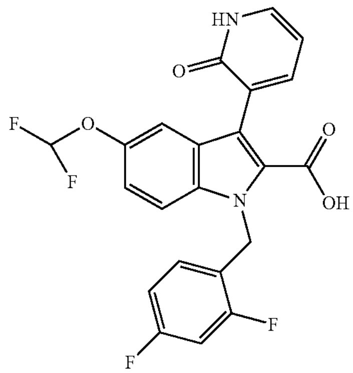 [SMILES: O=C(O)c1c(-c2ccc[nH]c2=O)c2cc(OC(F)F)ccc2n1Cc1ccc(F)cc1F] | 447.4 |
| 106 | 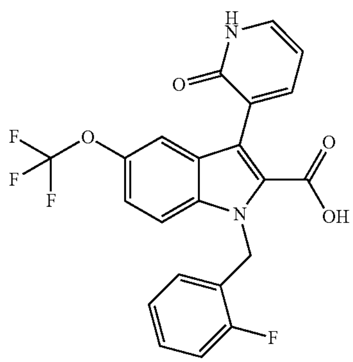 [SMILES: O=C(O)c1c(-c2ccc[nH]c2=O)c2cc(OC(F)(F)F)ccc2n1Cc1ccccc1F] | 447.4 |
| 107 | 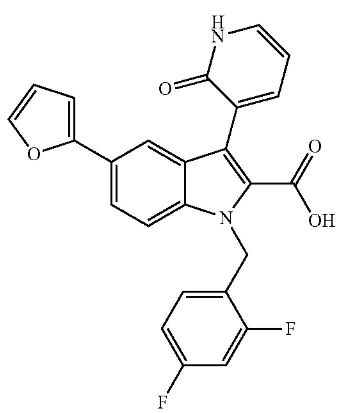 [SMILES: O=C(O)c1c(-c2ccc[nH]c2=O)c2cc(-c3ccco3)ccc2n1Cc1ccc(F)cc1F] | 447.4 |
| 108 | 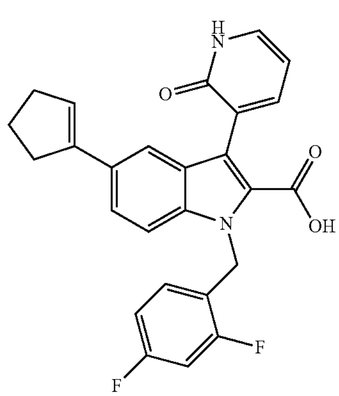 [SMILES: O=C(O)c1c(-c2ccc[nH]c2=O)c2cc(C3=CCCC3)ccc2n1Cc1ccc(F)cc1F] | 447.5 |
| 109 | | 447.8 |
| 110 | | 449.4 |
| 111 | | 449.4 |
| 112 | | 449.5 |

TABLE 1-continued

| No. | STRUCTURE | M + H |
|---|---|---|
| 113 | 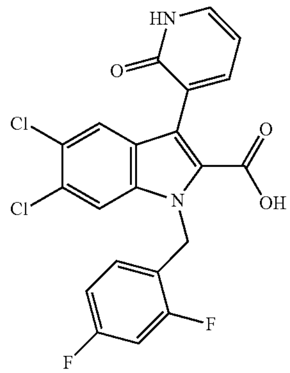 [SMILES: O=C(O)c1c(-c2ccc[nH]c2=O)c2cc(Cl)c(Cl)cc2n1Cc1ccc(F)cc1F] | 450.2 |
| 114 | 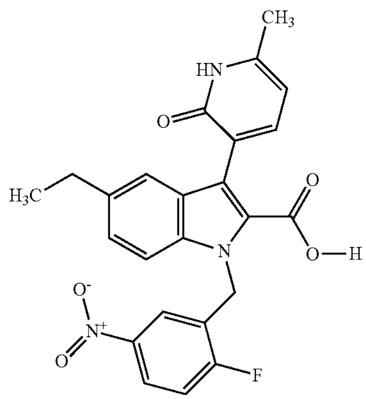 [SMILES: CCc1ccc2c(c1)c(-c1ccc(C)[nH]c1=O)c(C(=O)O)n2Cc1cc([N+](=O)[O-])ccc1F] | 450.4 |
| 115 | 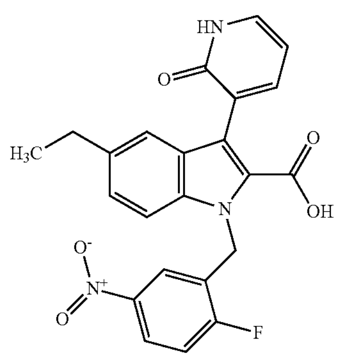 [SMILES: CCc1ccc2c(c1)c(-c1ccc[nH]c1=O)c(C(=O)O)n2Cc1cc([N+](=O)[O-])ccc1F] | 452.9 |
| 116 | 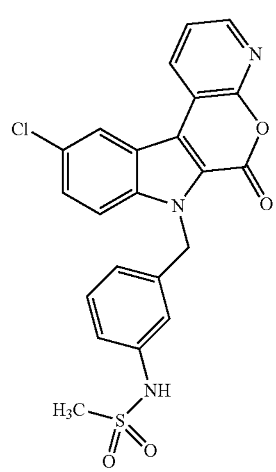 [SMILES: CS(=O)(=O)Nc1cccc(Cn2c3ccc(Cl)cc3c3c4cccnc4oc(=O)c32)c1] | 454.9 |
| 117 | | 455.5 |
| 118 | | 456.5 |
| 119 | | 458.9 |
| 120 | | 459.5 |

TABLE 1-continued

| No. | STRUCTURE | M + H |
|---|---|---|
| 121 | 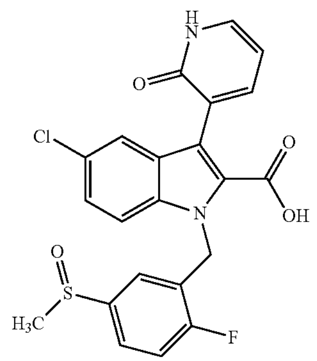 [SMILES: CS(=O)c1ccc(F)c(Cn2c(C(=O)O)c(-c3ccc[nH]c3=O)c3cc(Cl)ccc32)c1] | 459.9 |
| 122 | 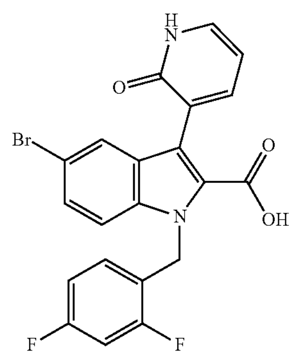 [SMILES: O=C(O)c1c(-c2ccc[nH]c2=O)c2cc(Br)ccc2n1Cc1ccc(F)cc1F] | 460.3 |
| 123 | 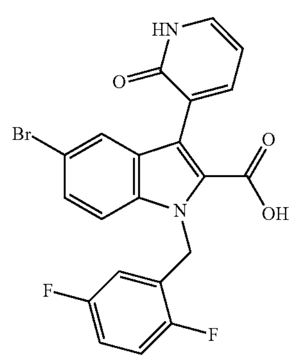 [SMILES: O=C(O)c1c(-c2ccc[nH]c2=O)c2cc(Br)ccc2n1Cc1cc(F)ccc1F] | 460.3 |
| 124 | 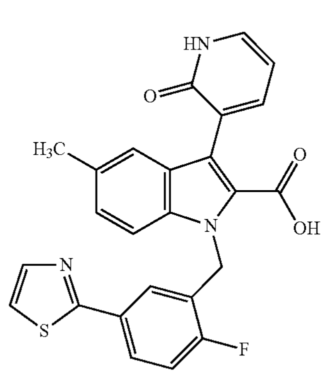 [SMILES: Cc1ccc2c(c1)c(-c1ccc[nH]c1=O)c(C(=O)O)n2Cc1cc(-c2nccs2)ccc1F] | 460.5 |
| 125 | | 461.4 |
| 126 | | 462.5 |
| 127 | | 463.4 |
| 128 | | 463.5 |

TABLE 1-continued
| No. | STRUCTURE | M + H |
|---|---|---|
| 129 | 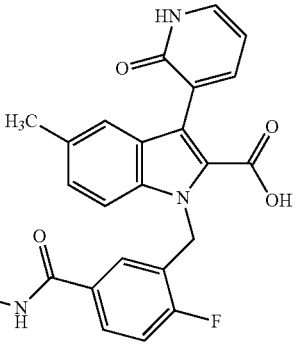 | 464.5 |
| 130 | 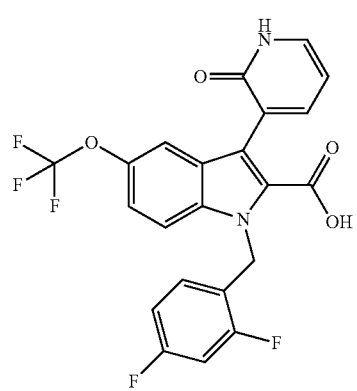 [SMILES: O=C(O)c1c(-c2ccc[nH]c2=O)c2cc(OC(F)(F)F)ccc2n1Cc1ccc(F)cc1F] | 465.4 |
| 131 | 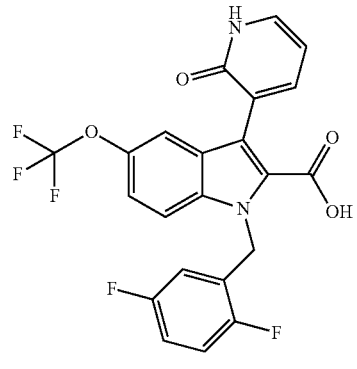 [SMILES: O=C(O)c1c(-c2ccc[nH]c2=O)c2cc(OC(F)(F)F)ccc2n1Cc1cc(F)ccc1F] | 465.4 |
| 132 | 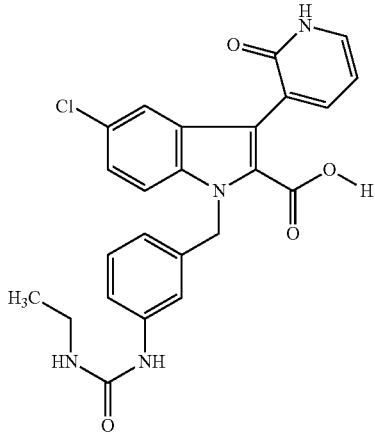 [SMILES: CCNC(=O)Nc1cccc(Cn2c(C(=O)O)c(-c3ccc[nH]c3=O)c3cc(Cl)ccc32)c1] | 465.9 |
| 133 | 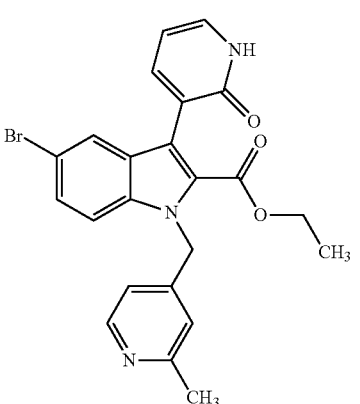 | 468.3 |
| 134 | 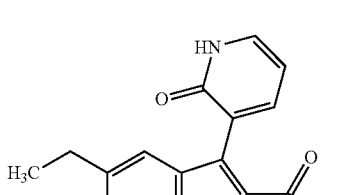 | 469.5 |
| 135 | 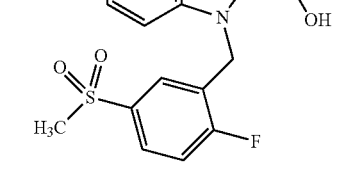 | 470.5 |
| 136 | 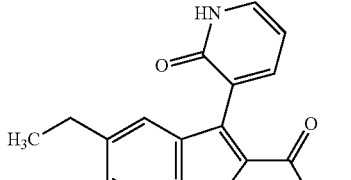 | 471.5 |

US 8,614,229 B2
TABLE 1-continued
| No. | STRUCTURE | M + H |
|---|---|---|
| 137 | 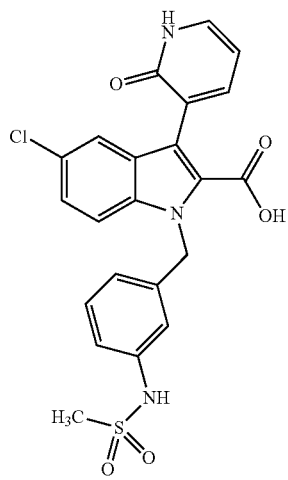 [SMILES: CS(=O)(=O)Nc1cccc(Cn2c(C(=O)O)c(-c3ccc[nH]c3=O)c3cc(Cl)ccc32)c1] | 472.9 |
| 138 | 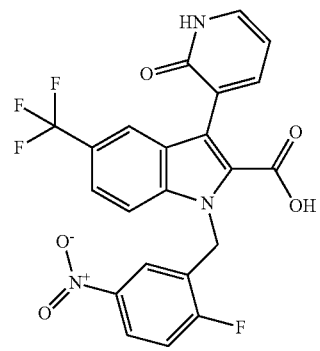 [SMILES: O=C(O)c1c(-c2ccc[nH]c2=O)c2cc(C(F)(F)F)ccc2n1Cc1cc([N+](=O)[O-])ccc1F] | 476.4 |
| 139 | 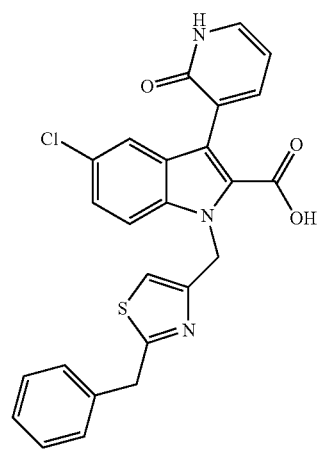 [SMILES: O=C(O)c1c(-c2ccc[nH]c2=O)c2cc(Cl)ccc2n1Cc1csc(Cc2ccccc2)n1] | 477.0 |
TABLE 1-continued
| No. | STRUCTURE | M + H |
|---|---|---|
| 140 | 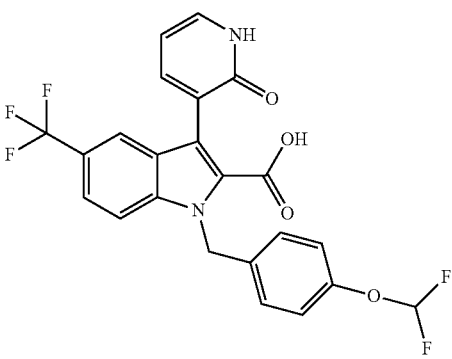 [SMILES: O=C(O)c1c(-c2ccc[nH]c2=O)c2cc(C(F)(F)F)ccc2n1Cc1ccc(OC(F)F)cc1] | 479.4 |
| 141 | 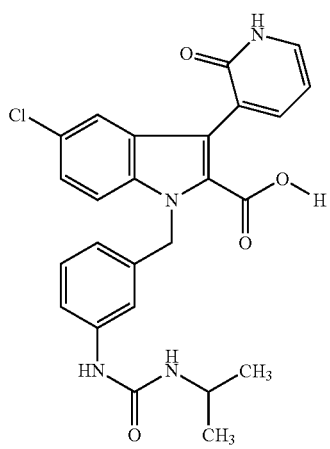 [SMILES: CC(C)NC(=O)Nc1cccc(Cn2c(C(=O)O)c(-c3ccc[nH]c3=O)c3cc(Cl)ccc32)c1] | 479.9 |
| 142 | 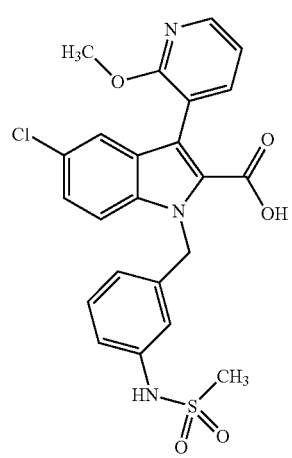 [SMILES: COc1ncccc1-c1c(C(=O)O)n(Cc2cccc(NS(C)(=O)=O)c2)c2ccc(Cl)cc12] | 486.9 |

TABLE 1-continued

| No. | STRUCTURE | M + H |
|-----|-----------|-------|
| 143 | 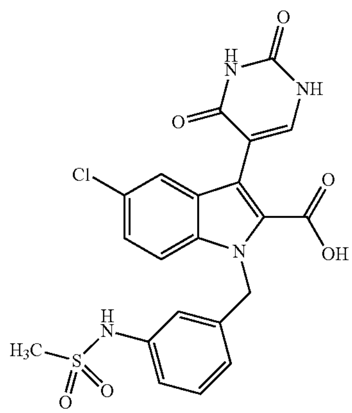 [SMILES: CS(=O)(=O)Nc1cccc(Cn2c(C(=O)O)c(-c3c[nH]c(=O)[nH]c3=O)c3cc(Cl)ccc32)c1] | 489.9 |
| 144 | 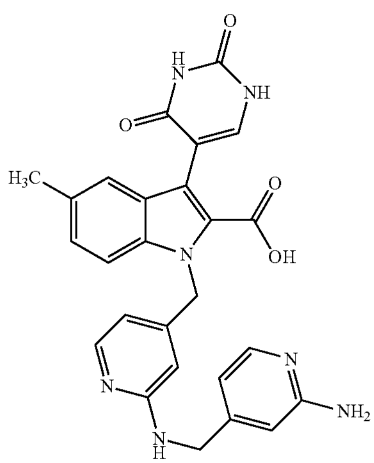 [SMILES: Cc1ccc2c(c1)c(-c1c[nH]c(=O)[nH]c1=O)c(C(=O)O)n2Cc1ccnc(NCc2ccnc(N)c2)c1] | 498.5 |
| 145 | 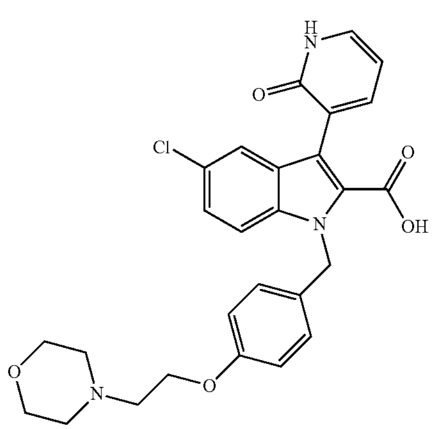 [SMILES: O=C(O)c1c(-c2ccc[nH]c2=O)c2cc(Cl)ccc2n1Cc1ccc(OCCN2CCOCC2)cc1] | 509.0 |
| 146 | 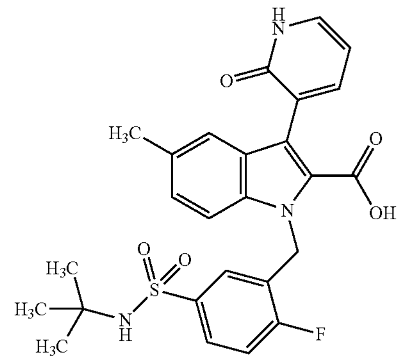 [SMILES: Cc1ccc2c(c1)c(-c1ccc[nH]c1=O)c(C(=O)O)n2Cc1cc(S(=O)(=O)NC(C)(C)C)ccc1F] | 512.6 |
| 147 | 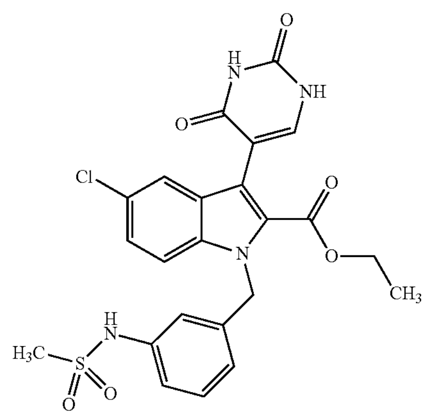 [SMILES: CCOC(=O)c1c(-c2c[nH]c(=O)[nH]c2=O)c2cc(Cl)ccc2n1Cc1cccc(NS(C)(=O)=O)c1] | 518.0 |
| 148 | 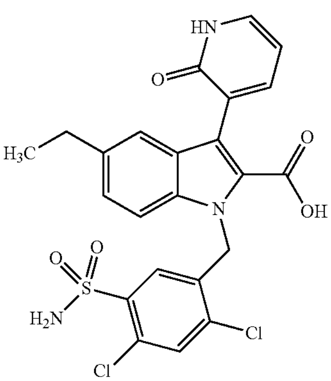 [SMILES: CCc1ccc2c(c1)c(-c1ccc[nH]c1=O)c(C(=O)O)n2Cc1cc(S(N)(=O)=O)c(Cl)cc1Cl] | 521.4 |
| 149 | 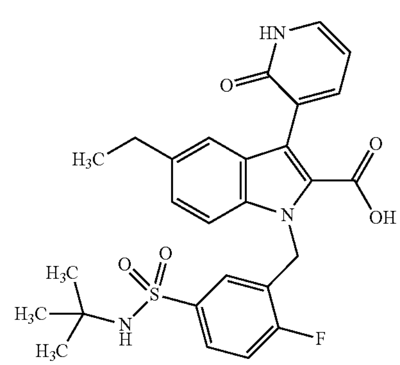 [SMILES: CCc1ccc2c(c1)c(-c1ccc[nH]c1=O)c(C(=O)O)n2Cc1cc(S(=O)(=O)NC(C)(C)C)ccc1F] | 526.6 |

TABLE 1-continued
| No. | STRUCTURE | M + H |
|---|---|---|
| 150 | 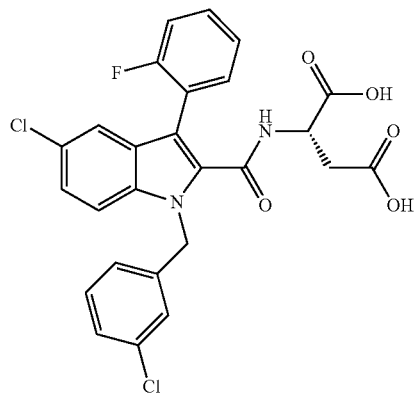 [SMILES: O=C(O)C[C@H](NC(=O)c1c(-c2ccccc2F)c2cc(Cl)ccc2n1Cc1cccc(Cl)c1)C(=O)O] | 530.4 |
| 151 | 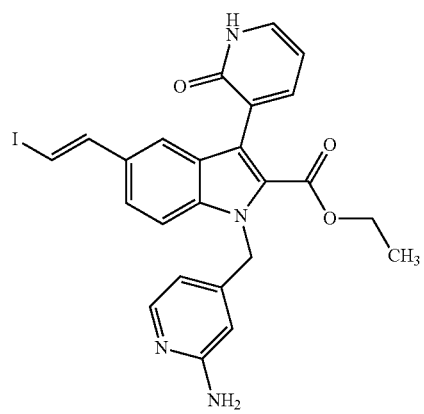 [SMILES: CCOC(=O)c1c(-c2ccc[nH]c2=O)c2cc(/C=C/I)ccc2n1Cc1ccnc(N)c1] | 541.4 |
| 152 | 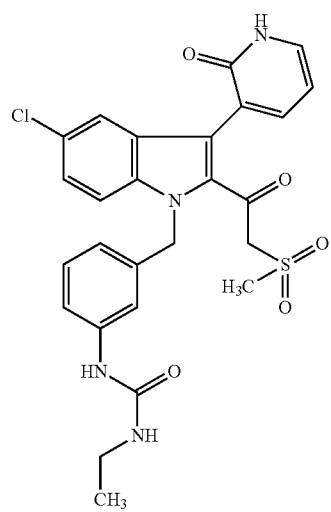 [SMILES: CCNC(=O)Nc1cccc(Cn2c(C(=O)CS(C)(=O)=O)c(-c3ccc[nH]c3=O)c3cc(Cl)ccc32)c1] | 542.0 |
TABLE 1-continued
| No. | STRUCTURE | M + H |
|---|---|---|
| 153 | 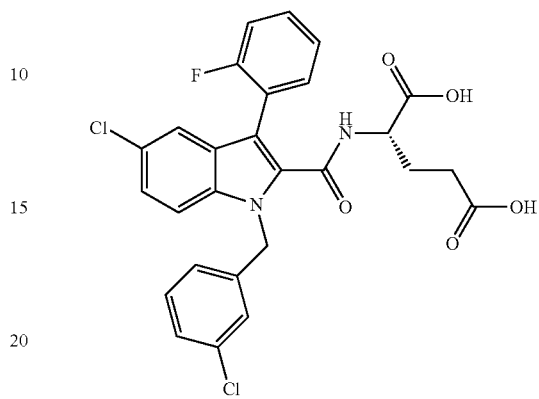 | 544.4 |
| 154 | 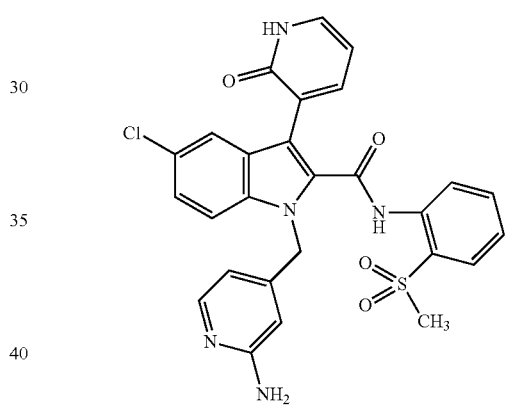 | 549.0 |
| 155 | 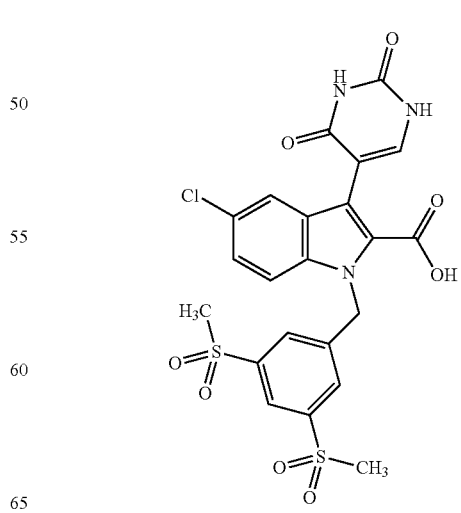 | 553.0 |

TABLE 1-continued
| No. | STRUCTURE | M + H |
|---|---|---|
| 156 | 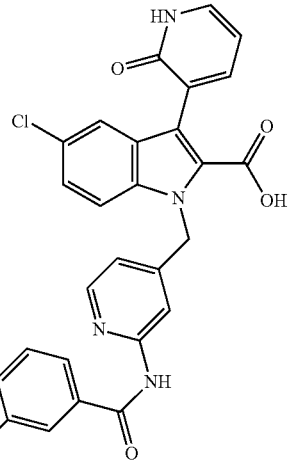 | 585.9 |
| 157 | 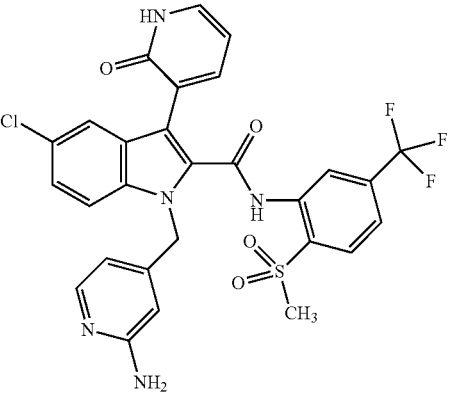 [SMILES: CS(=O)(=O)c1ccc(C(F)(F)F)cc1NC(=O)c1c(-c2ccc[nH]c2=O)c2cc(Cl)ccc2n1Cc1ccnc(N)c1] | 617.0 |
| 158 | 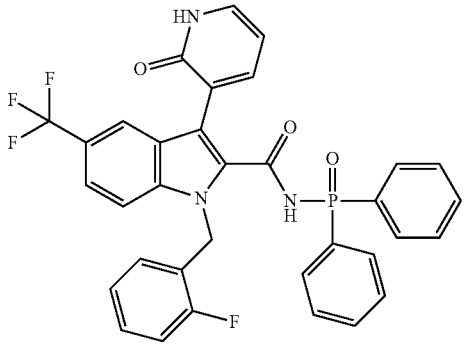 [SMILES: O=C(NP(=O)(c1ccccc1)c1ccccc1)c1c(-c2ccc[nH]c2=O)c2cc(C(F)(F)F)ccc2n1Cc1ccccc1F] | 630.6 |
| 159 | 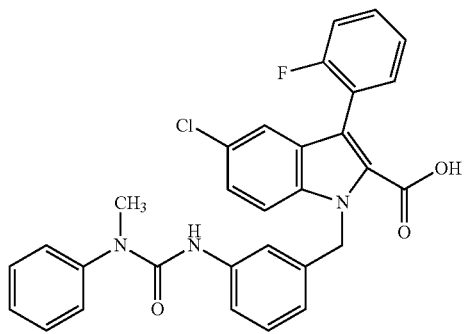 [SMILES: CN(C(=O)Nc1cccc(Cn2c(C(=O)O)c(-c3ccccc3F)c3cc(Cl)ccc32)c1)c1ccccc1] | 529 |
| 160 | 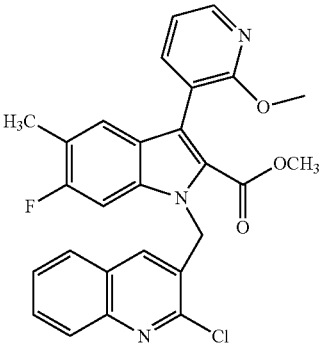 | 491 |
| 161 | 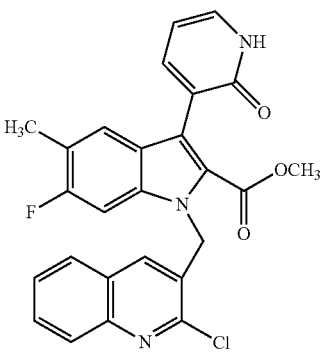 [SMILES: COC(=O)c1c(-c2ccc[nH]c2=O)c2cc(C)c(F)cc2n1Cc1cc2ccccc2nc1Cl] | 477 |
| 162 | 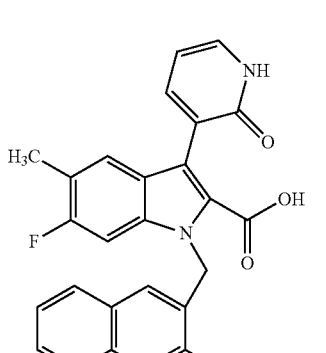 | 462 |
| 163 | 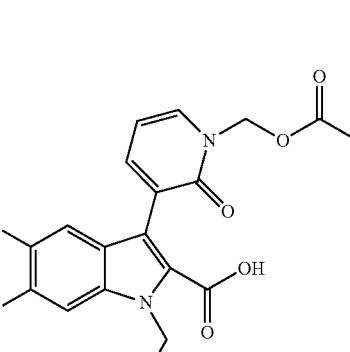 | 577 |

TABLE 1-continued

| No. | STRUCTURE | M + H |
|-----|-----------|-------|
| 164 | 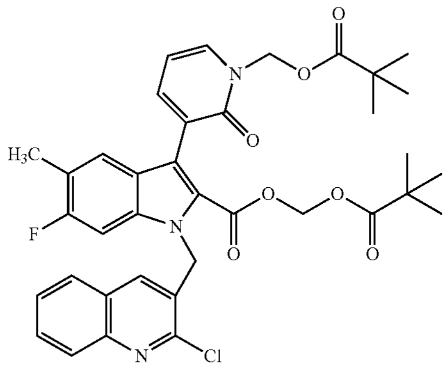 [SMILES: Cc1cc2c(-c3cccn(COC(=O)C(C)(C)C)c3=O)c(C(=O)OCOC(=O)C(C)(C)C)n(Cc3cc4ccccc4nc3Cl)c2cc1F] | 690 |
| 165 | 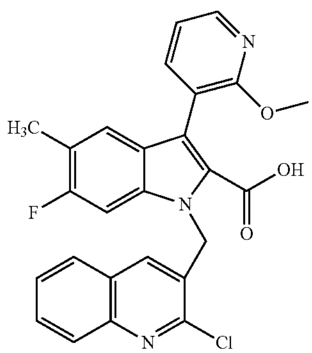 | 477 |
| 166 | 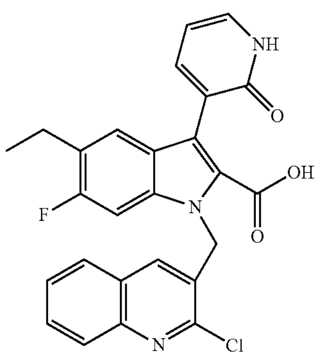 [SMILES: CCc1cc2c(-c3ccc[nH]c3=O)c(C(=O)O)n(Cc3cc4ccccc4nc3Cl)c2cc1F] | 477 |
| 167 | 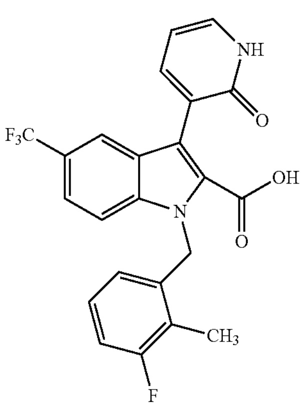 [SMILES: Cc1c(F)cccc1Cn1c(C(=O)O)c(-c2ccc[nH]c2=O)c2cc(C(F)(F)F)ccc21] | 639 |
| 168 | | 405 |
| 169 | | 440 |
| 170 | | NA |

NA = not available and pharmaceutically acceptable salts, solvates, esters and prodrugs thereof.

Additional illustrative examples of the compounds of the present invention, include but are not limited to, the compounds set forth below in Table 2.

TABLE 2
| No. | STRUCTURE | M + 1 |
|---|---|---|
| 171 | 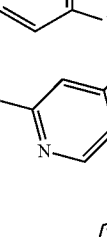 | 393.4 |
| 172 | 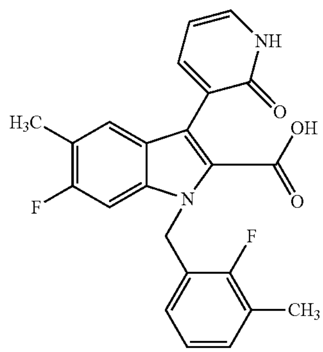 [SMILES: Cc1cc2c(-c3ccc[nH]c3=O)c(C(=O)O)n(Cc3cccc(C)c3F)c2cc1F] | 409.4 |
| 173 | 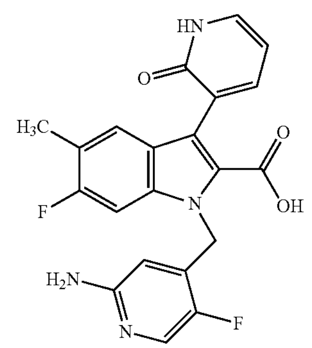 [SMILES: Cc1cc2c(-c3ccc[nH]c3=O)c(C(=O)O)n(Cc3cc(N)ncc3F)c2cc1F] | 411.4 |
| 174 | 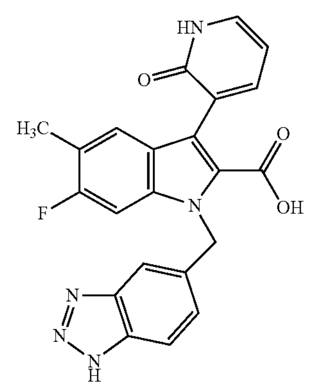 [SMILES: Cc1cc2c(-c3ccc[nH]c3=O)c(C(=O)O)n(Cc3ccc4[nH]nnc4c3)c2cc1F] | 418.4 |
TABLE 2-continued
| No. | STRUCTURE | M + 1 |
|---|---|---|
| 175 | 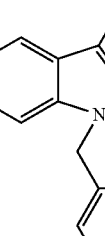 | 426.4 |
| 176 | 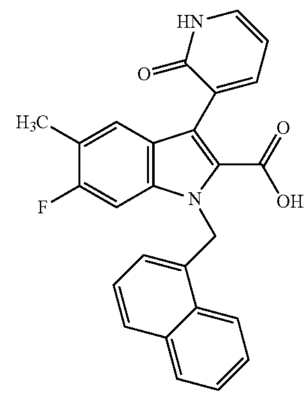 [SMILES: Cc1cc2c(-c3ccc[nH]c3=O)c(C(=O)O)n(Cc3cccc4ccccc34)c2cc1F] | 427.5 |
| 177 | 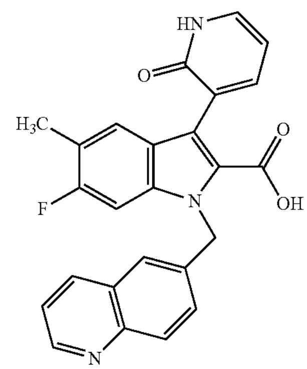 [SMILES: Cc1cc2c(-c3ccc[nH]c3=O)c(C(=O)O)n(Cc3ccc4ncccc4c3)c2cc1F] | 428.4 |
| 178 | 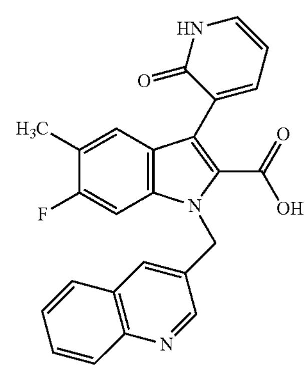 [SMILES: Cc1cc2c(-c3ccc[nH]c3=O)c(C(=O)O)n(Cc3cnc4ccccc4c3)c2cc1F] | 428.4 |

TABLE 2-continued
| No. | STRUCTURE | M + 1 |
|---|---|---|
| 179 | 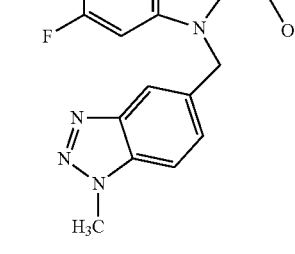 | 432.4 |
| 180 | 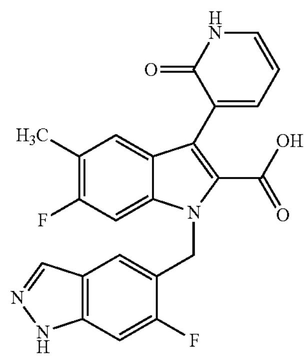 [SMILES: Cc1cc2c(-c3ccc[nH]c3=O)c(C(=O)O)n(Cc3cc4cn[nH]c4cc3F)c2cc1F] | 435.4 |
| 181 | 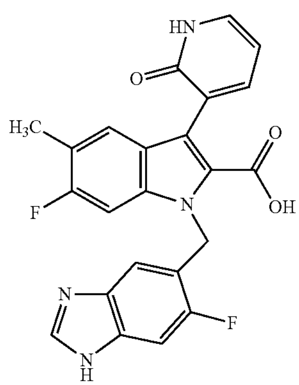 [SMILES: Cc1cc2c(-c3ccc[nH]c3=O)c(C(=O)O)n(Cc3cc4nc[nH]c4cc3F)c2cc1F] | NA |
| 182 | 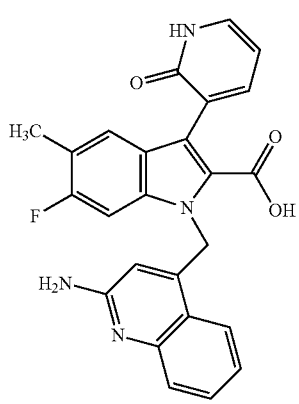 [SMILES: Cc1cc2c(-c3ccc[nH]c3=O)c(C(=O)O)n(Cc3cc(N)nc4ccccc34)c2cc1F] | 443.5 |
| 183 | 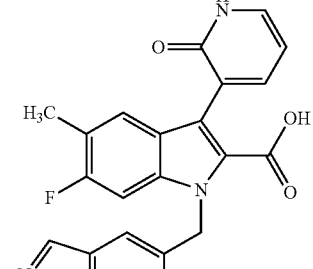 | 444.4 |
| 184 | 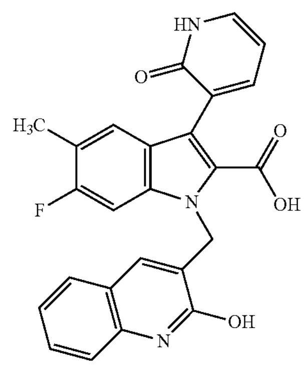 [SMILES: Cc1cc2c(-c3ccc[nH]c3=O)c(C(=O)O)n(Cc3cc4ccccc4nc3O)c2cc1F] | 444.4 |
| 185 | 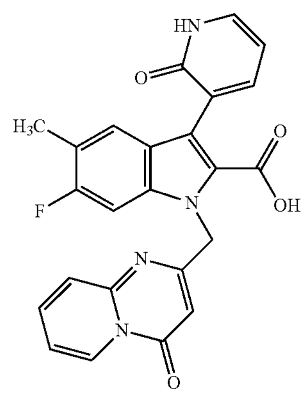 [SMILES: Cc1cc2c(-c3ccc[nH]c3=O)c(C(=O)O)n(Cc3cc(=O)n4ccccc4n3)c2cc1F] | 445.4 |
| 186 | 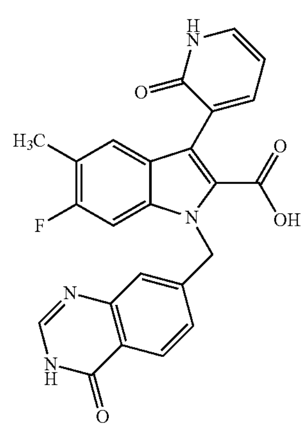 [SMILES: Cc1cc2c(-c3ccc[nH]c3=O)c(C(=O)O)n(Cc3ccc4c(=O)[nH]cnc4c3)c2cc1F] | 445.4 |

TABLE 2-continued

| No. | STRUCTURE | M + 1 |
|---|---|---|
| 187 | 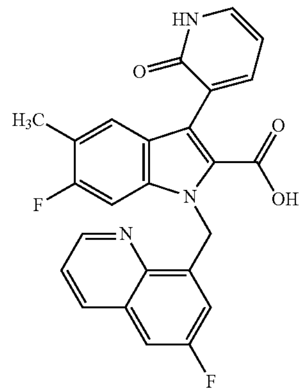 [SMILES: Cc1cc2c(-c3ccc[nH]c3=O)c(C(=O)O)n(Cc3cc(F)cc4cccnc34)c2cc1F] | 446.4 |
| 188 | 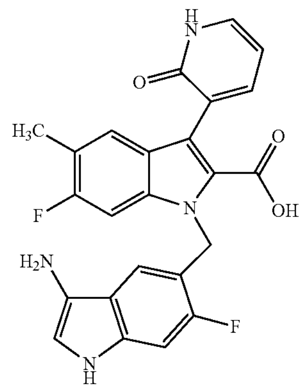 [SMILES: Cc1cc2c(-c3ccc[nH]c3=O)c(C(=O)O)n(Cc3cc4c(N)c[nH]c4cc3F)c2cc1F] | 449.4 |
| 189 | 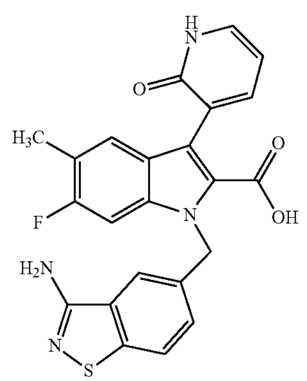 [SMILES: Cc1cc2c(-c3ccc[nH]c3=O)c(C(=O)O)n(Cc3ccc4snc(N)c4c3)c2cc1F] | 449.5 |
| 190 | 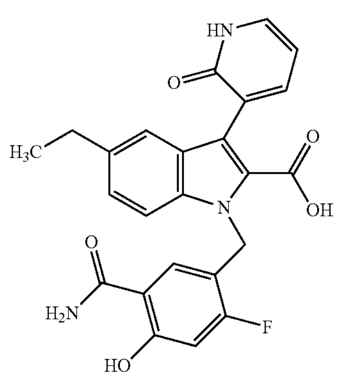 [SMILES: CCc1ccc2c(c1)c(-c1ccc[nH]c1=O)c(C(=O)O)n2Cc1cc(C(N)=O)c(O)cc1F] | 450.4 |
| 191 | | 451.5 |
| 192 | | 451.9 |
| 193 | | 451.9 |
| 194 | | NA |

TABLE 2-continued
| No. | STRUCTURE | M + 1 |
|---|---|---|
| 195 | 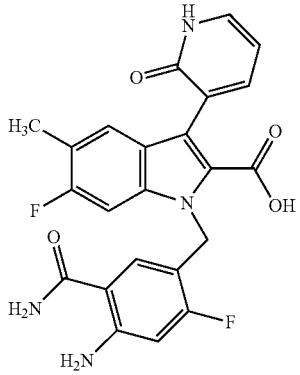 [SMILES: Cc1cc2c(-c3ccc[nH]c3=O)c(C(=O)O)n(Cc3cc(C(N)=O)c(N)cc3F)c2cc1F] | 453.4 |
| 196 | 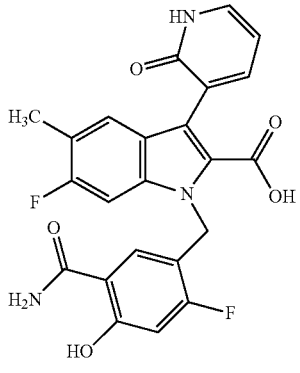 [SMILES: Cc1cc2c(-c3ccc[nH]c3=O)c(C(=O)O)n(Cc3cc(C(N)=O)c(O)cc3F)c2cc1F] | 454.4 |
| 197 | 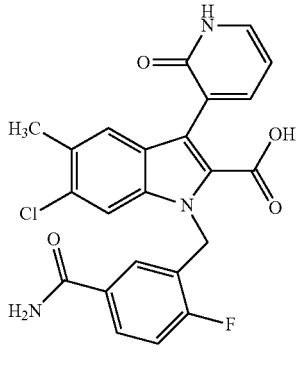 [SMILES: Cc1cc2c(-c3ccc[nH]c3=O)c(C(=O)O)n(Cc3cc(C(N)=O)ccc3F)c2cc1Cl] | 454.9 |
| 198 | 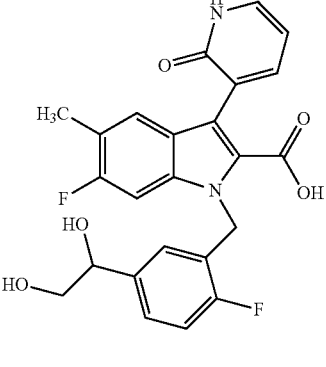 | 455.4 |
| 199 | 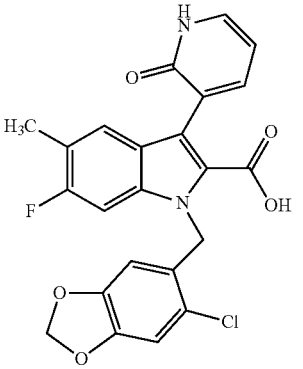 [SMILES: Cc1cc2c(-c3ccc[nH]c3=O)c(C(=O)O)n(Cc3cc4c(cc3Cl)OCO4)c2cc1F] | 455.8 |
| 200 | 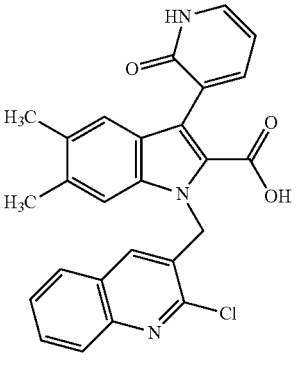 [SMILES: Cc1cc2c(-c3ccc[nH]c3=O)c(C(=O)O)n(Cc3cc4ccccc4nc3Cl)c2cc1C] | 458.9 |
| 201 | 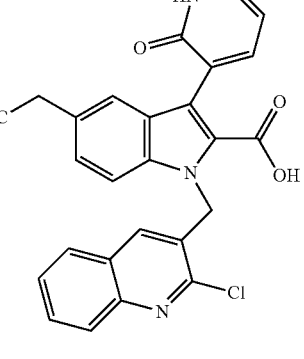 | 458.9 |
| 202 | 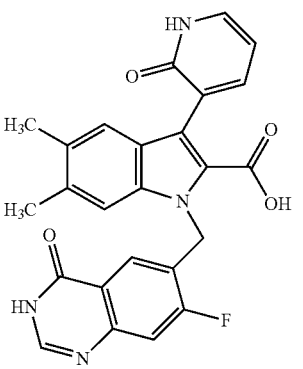 [SMILES: Cc1cc2c(-c3ccc[nH]c3=O)c(C(=O)O)n(Cc3cc4c(=O)[nH]cnc4cc3F)c2cc1C] | 459.5 |

TABLE 2-continued
| No. | STRUCTURE | M + 1 |
|---|---|---|
| 203 | 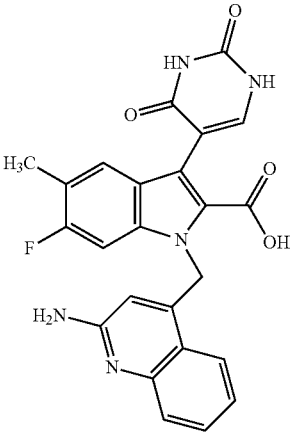 [SMILES: Cc1cc2c(-c3c[nH]c(=O)[nH]c3=O)c(C(=O)O)n(Cc3cc(N)nc4ccccc34)c2cc1F] | 460.4 |
| 204 | 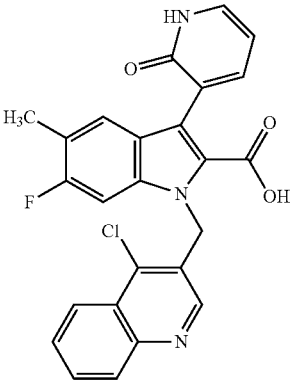 [SMILES: Cc1cc2c(-c3ccc[nH]c3=O)c(C(=O)O)n(Cc3cnc4ccccc4c3Cl)c2cc1F] | 462.9 |
| 205 | 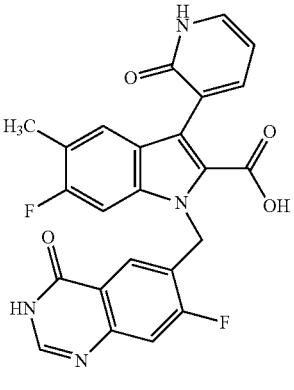 [SMILES: Cc1cc2c(-c3ccc[nH]c3=O)c(C(=O)O)n(Cc3cc4c(=O)[nH]cnc4cc3F)c2cc1F] | 463.4 |
| 206 | 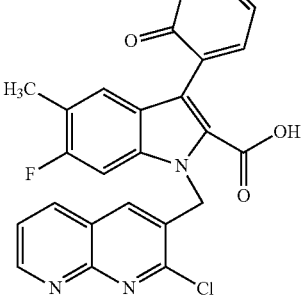 | NA |
| 207 | 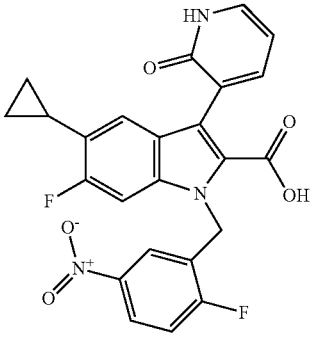 [SMILES: O=C(O)c1c(-c2ccc[nH]c2=O)c2cc(C3CC3)c(F)cc2n1Cc1cc([N+](=O)[O-])ccc1F] | 466.4 |
| 208 | 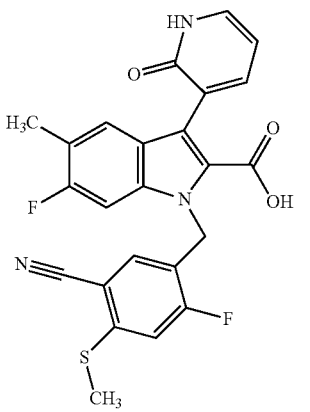 [SMILES: CSc1cc(F)c(Cn2c(C(=O)O)c(-c3ccc[nH]c3=O)c3cc(C)c(F)cc32)cc1C#N] | 466.5 |
| 209 | 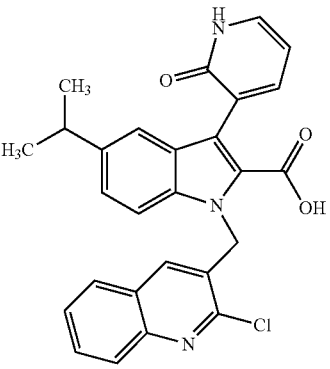 [SMILES: CC(C)c1ccc2c(c1)c(-c1ccc[nH]c1=O)c(C(=O)O)n2Cc1cc2ccccc2nc1Cl] | 472.9 |
| 210 | 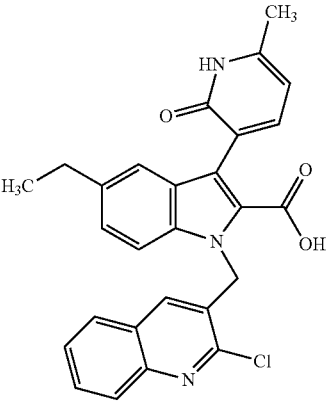 [SMILES: CCc1ccc2c(c1)c(-c1ccc(C)[nH]c1=O)c(C(=O)O)n2Cc1cc2ccccc2nc1Cl] | 472.9 |

US 8,614,229 B2
153
TABLE 2-continued
| No. | STRUCTURE | M + 1 |
|---|---|---|
| 211 | 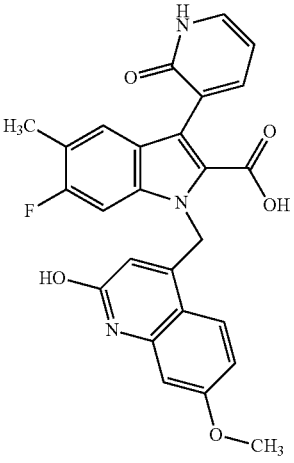 [SMILES: COc1ccc2c(Cn3c(C(=O)O)c(-c4ccc[nH]c4=O)c4cc(C)c(F)cc43)cc(O)nc2c1] | 474.5 |
| 212 | 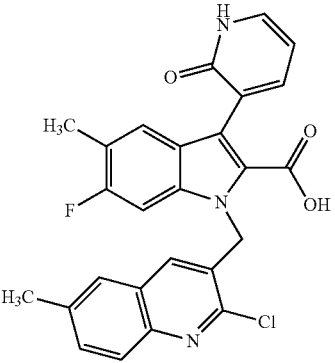 [SMILES: Cc1ccc2nc(Cl)c(Cn3c(C(=O)O)c(-c4ccc[nH]c4=O)c4cc(C)c(F)cc43)cc2c1] | 476.9 |
| 213 | 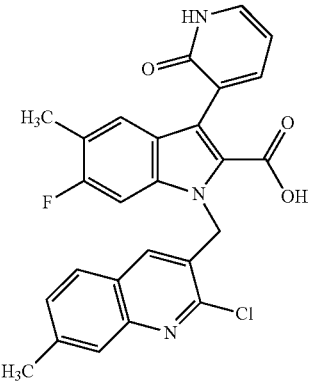 [SMILES: Cc1ccc2cc(Cn3c(C(=O)O)c(-c4ccc[nH]c4=O)c4cc(C)c(F)cc43)c(Cl)nc2c1] | 476.9 |
154
TABLE 2-continued
| No. | STRUCTURE | M + 1 |
|---|---|---|
| 214 | 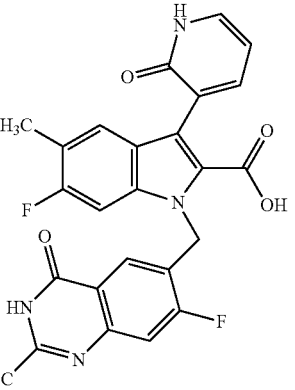 | 477.4 |
| 215 | 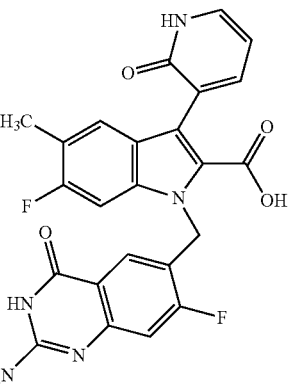 | NA |
| 216 | 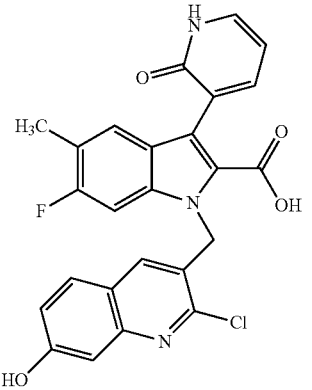 [SMILES: Cc1cc2c(-c3ccc[nH]c3=O)c(C(=O)O)n(Cc3cc4ccc(O)cc4nc3Cl)c2cc1F] | 478.9 |
| 217 | 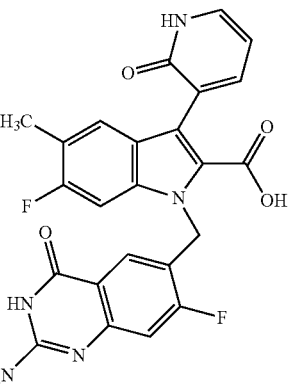 | 479.3 |

TABLE 2-continued
| No. | STRUCTURE | M + 1 |
|---|---|---|
| 218 | 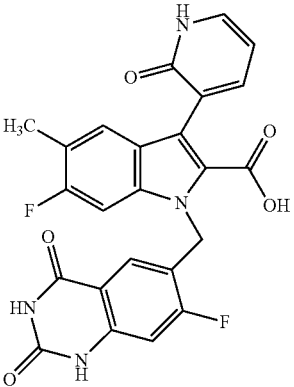 [SMILES: Cc1cc2c(-c3ccc[nH]c3=O)c(C(=O)O)n(Cc3cc4c(=O)[nH]c(=O)[nH]c4cc3F)c2cc1F] | 479.4 |
| 219 | 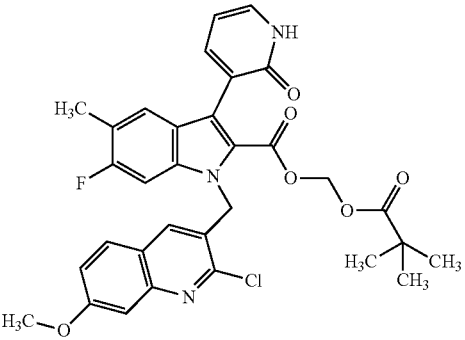 [SMILES: COc1ccc2cc(Cn3c(C(=O)OCOC(=O)C(C)(C)C)c(-c4ccc[nH]c4=O)c4cc(C)c(F)cc43)c(Cl)nc2c1] | NA |
| 220 | 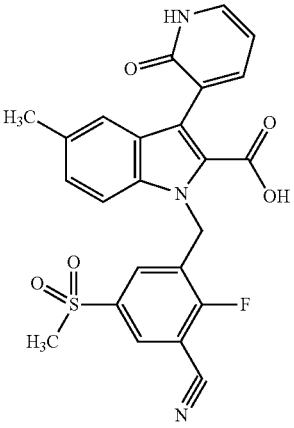 [SMILES: Cc1ccc2c(c1)c(-c1ccc[nH]c1=O)c(C(=O)O)n2Cc1cc(S(C)(=O)=O)cc(C#N)c1F] | 480.5 |
| 221 | 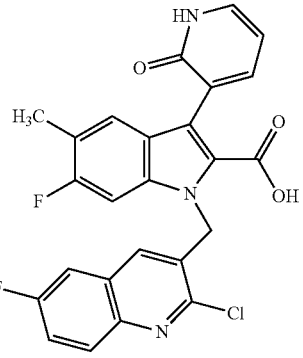 | 480.9 |
| 222 | 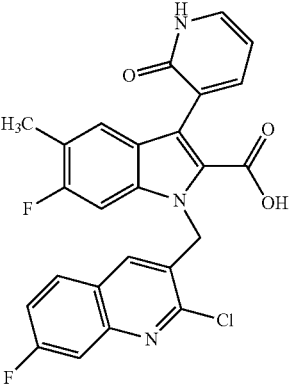 [SMILES: Cc1cc2c(-c3ccc[nH]c3=O)c(C(=O)O)n(Cc3cc4ccc(F)cc4nc3Cl)c2cc1F] | 480.9 |
| 223 | 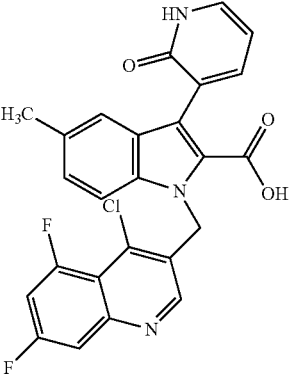 [SMILES: Cc1ccc2c(c1)c(-c1ccc[nH]c1=O)c(C(=O)O)n2Cc1cnc2cc(F)cc(F)c2c1Cl] | 480.9 |
| 224 | 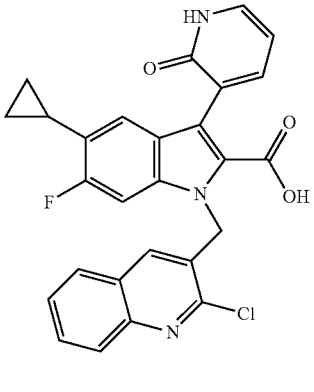 [SMILES: O=C(O)c1c(-c2ccc[nH]c2=O)c2cc(C3CC3)c(F)cc2n1Cc1cc2ccccc2nc1Cl] | 488.9 |
| 225 | 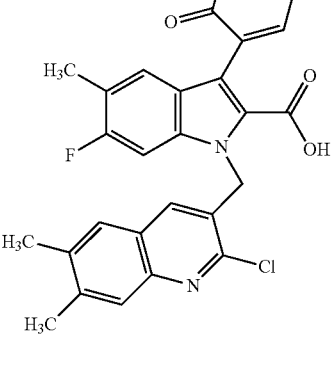 | 490.9 |

TABLE 2-continued
| No. | STRUCTURE | M + 1 |
|---|---|---|
| 226 | 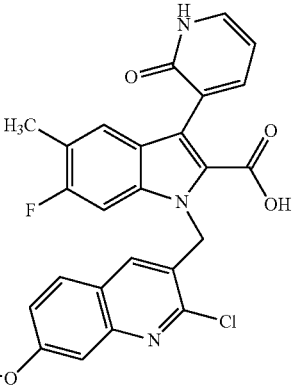 | 492.9 |
| 227 | 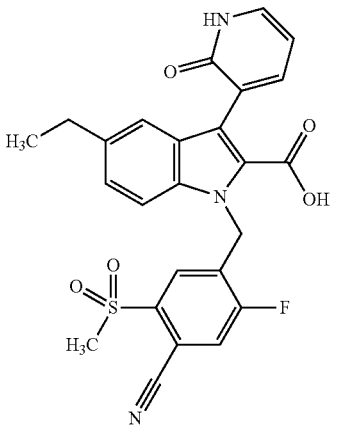 [SMILES: CCc1ccc2c(c1)c(-c1ccc[nH]c1=O)c(C(=O)O)n2Cc1cc(S(C)(=O)=O)c(C#N)cc1F] | 494.5 |
| 228 | 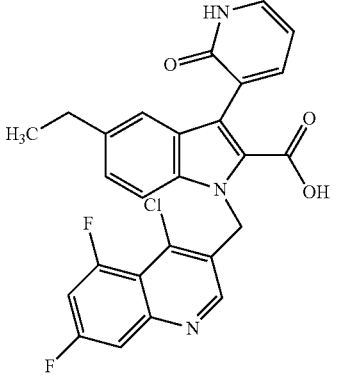 [SMILES: CCc1ccc2c(c1)c(-c1ccc[nH]c1=O)c(C(=O)O)n2Cc1cnc2cc(F)cc(F)c2c1Cl] | 494.9 |
| 229 | 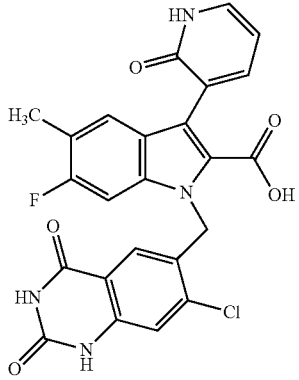 [SMILES: Cc1cc2c(-c3ccc[nH]c3=O)c(C(=O)O)n(Cc3cc4c(=O)[nH]c(=O)[nH]c4cc3Cl)c2cc1F] | 495.0 |
| 230 | 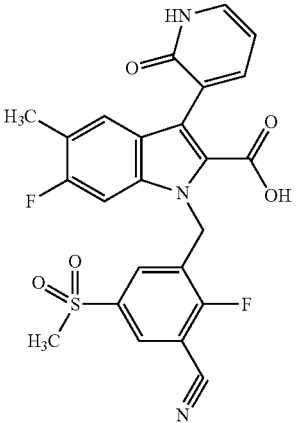 [SMILES: Cc1cc2c(-c3ccc[nH]c3=O)c(C(=O)O)n(Cc3cc(S(C)(=O)=O)cc(C#N)c3F)c2cc1F] | 498.5 |
| 231 | 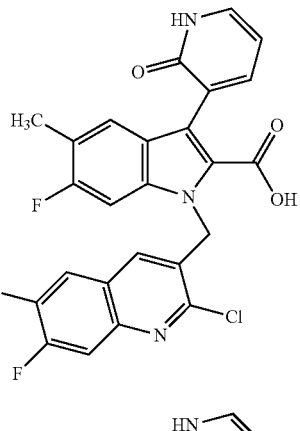 | 498.9 |
| 232 | 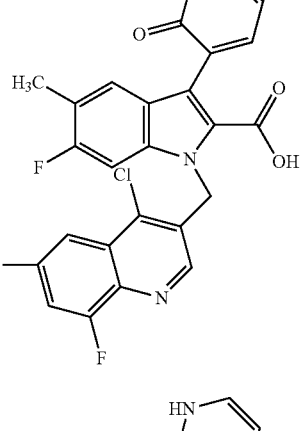 | 498.9 |
| 233 | 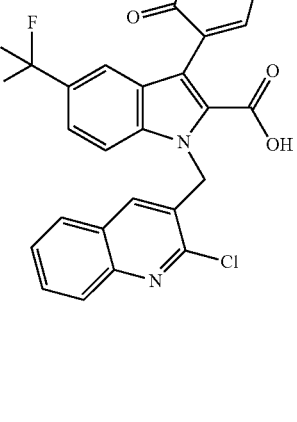 | 498.9 |

TABLE 2-continued
| No. | STRUCTURE | M + 1 |
|---|---|---|
| 234 | 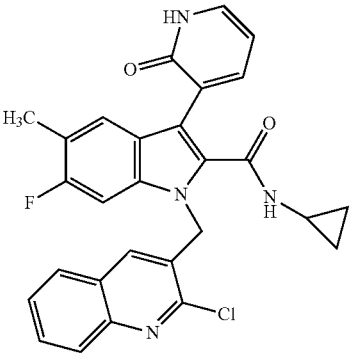 [SMILES: Cc1cc2c(-c3ccc[nH]c3=O)c(C(=O)NC3CC3)n(Cc3cc4ccccc4nc3Cl)c2cc1F] | 502.0 |
| 235 | 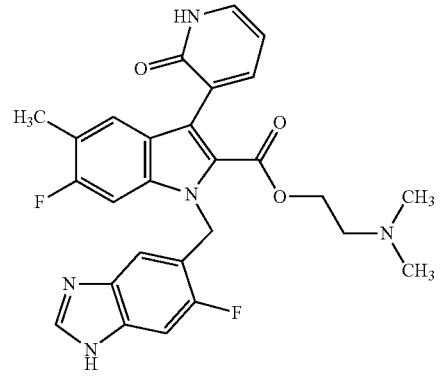 | NA |
| 236 | 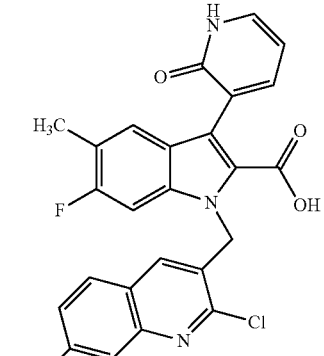 | NA |
| 237 | 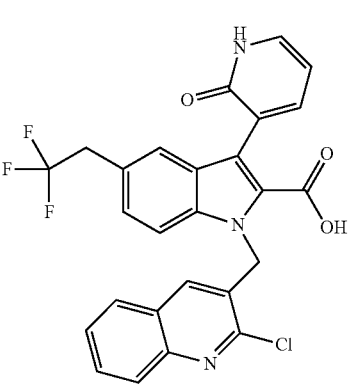 | 507.5 |
| 238 | 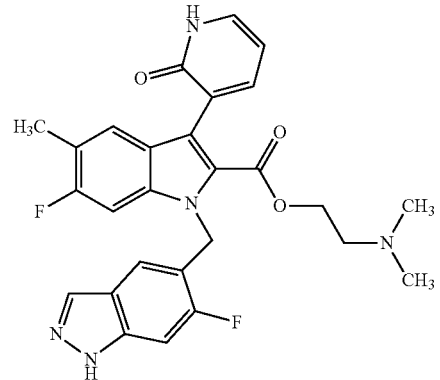 | 509.0 |
| 239 | 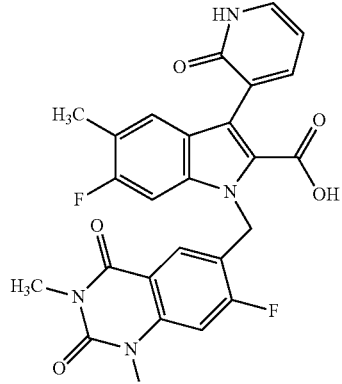 | 509.5 |
| 240 | 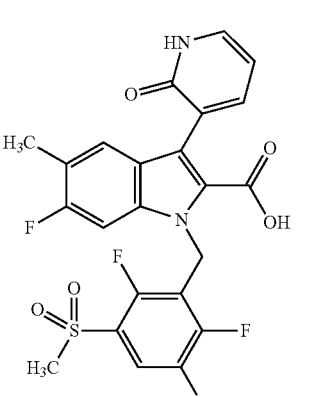 | 512.9 |
| 241 | 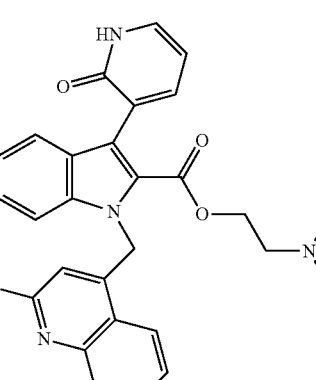 | NA |

TABLE 2-continued

| No. | STRUCTURE | M + 1 |
|-----|-----------|-------|
| 242 | 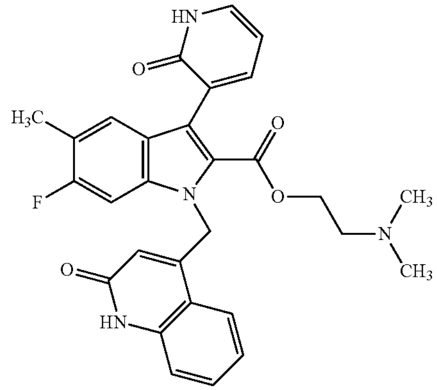 | NA |
| 243 | 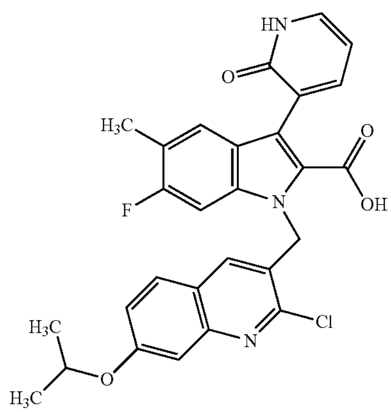 [SMILES: Cc1cc2c(-c3ccc[nH]c3=O)c(C(=O)O)n(Cc3cc4ccc(OC(C)C)cc4nc3Cl)c2cc1F] | 521.0 |
| 244 | 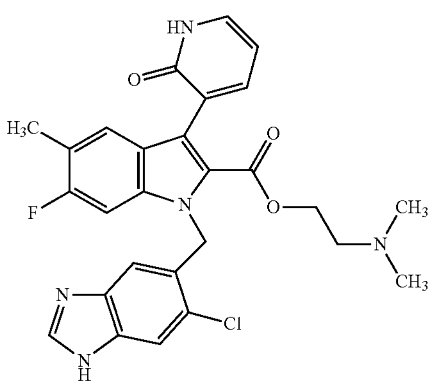 | NA |
| 245 | 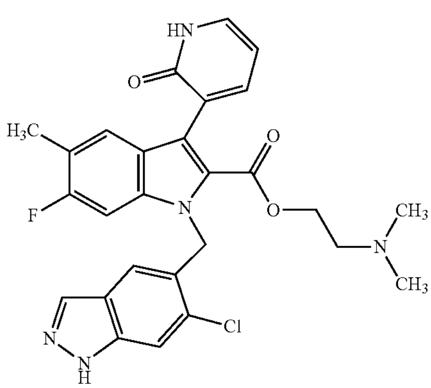 | NA |
| 246 | | 534.0 |
| 247 | | 535.0 |
| 248 | | NA |
| 249 | | NA |

TABLE 2-continued
| No. | STRUCTURE | M + 1 |
|---|---|---|
| 250 | 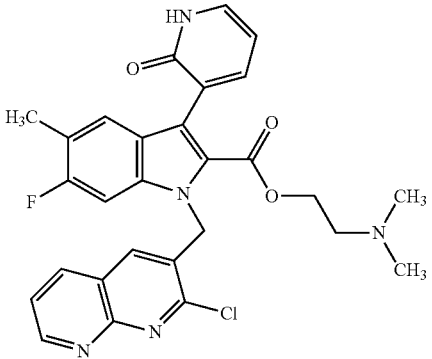 [SMILES: Cc1cc2c(-c3ccc[nH]c3=O)c(C(=O)OCCN(C)C)n(Cc3cc4cccnc4nc3Cl)c2cc1F] | NA |
| 251 | 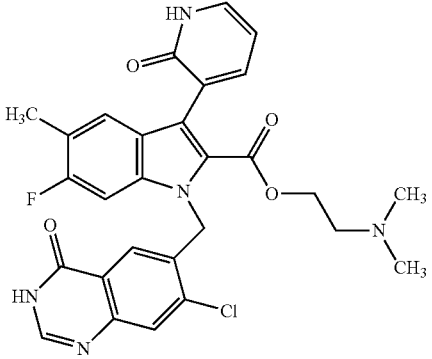 [SMILES: Cc1cc2c(-c3ccc[nH]c3=O)c(C(=O)OCCN(C)C)n(Cc3cc4c(=O)[nH]cnc4cc3Cl)c2cc1F] | NA |
| 252 | 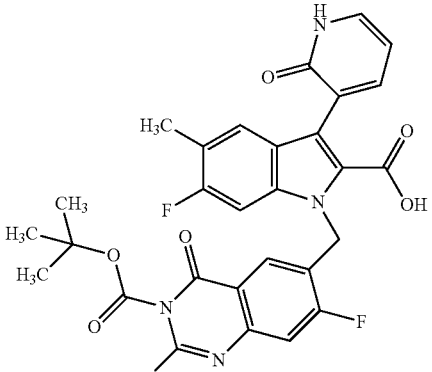 | 577.6 |
| 253 | 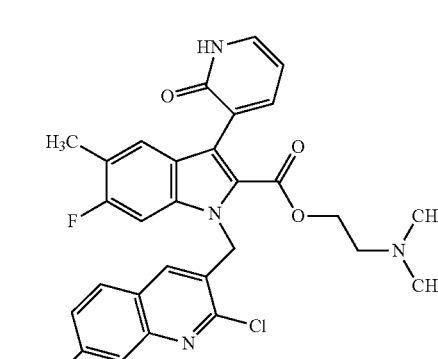 | NA |
| 254 | 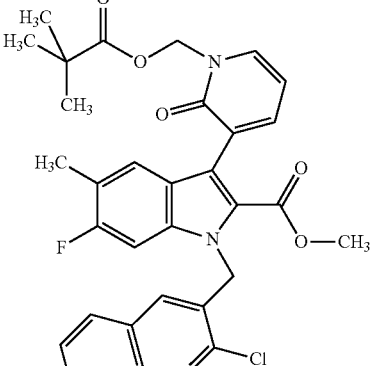 | 591.1 |
| 255 | 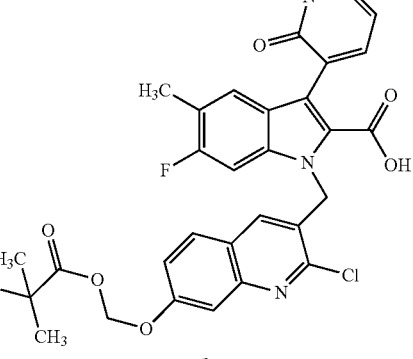 | 593.0 |
| 256 | 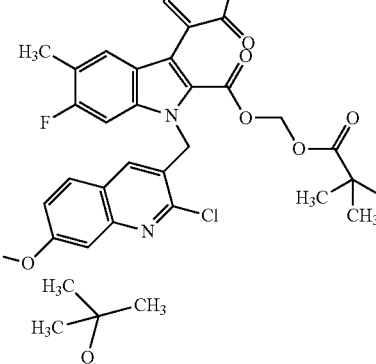 | 607.1 |
| 257 | 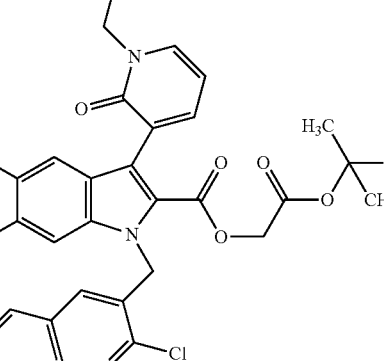 | 691.2 |

TABLE 2-continued

| No. | STRUCTURE | M + 1 |
|---|---|---|
| 258 | 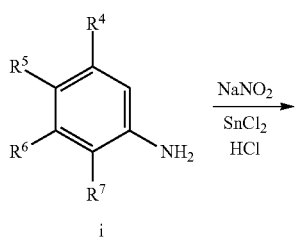 | 476.0 |

NA = not available and pharmaceutically acceptable salts, solvates, esters and prodrugs thereof.

Methods for Making the 2-Carboxy Substituted Indole Derivatives

Methods useful for making the 2-Carboxy Substituted Indole Derivatives are set forth in the Examples below and generalized in Schemes 1-5. Examples of commonly known methodologies useful for the synthesis of indoles are set forth, for example, in G. R. Humphrey and J. T. Kuethe, *Chemical Reviews* 106:2875-2911, 2006.

Scheme 1 shows a method useful for making compounds of formula iv, which are useful intermediates for making the 2-Carboxy Substituted Indole Derivatives.

Scheme 1

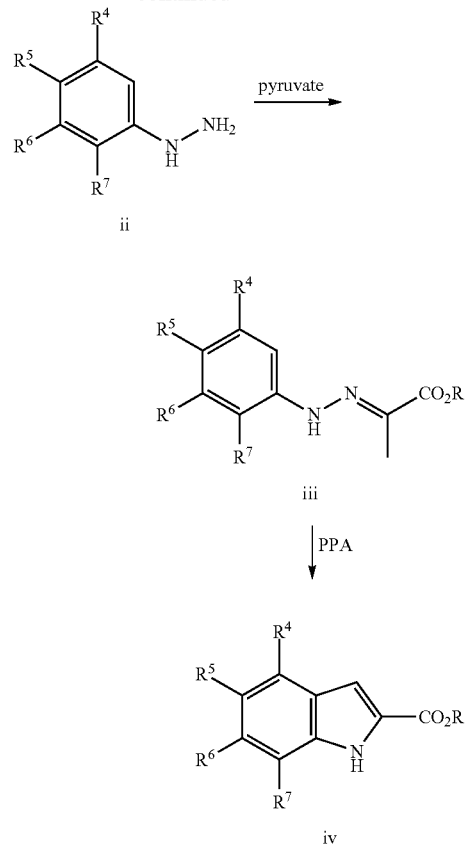

wherein $R^4$-$R^7$ are defined above for the compounds of formula (I) and R is H, alkyl or aryl.

An aniline compound of formula i can be converted to an indole compound of formula iv using various indole syntheses that are well-known to those skilled in the art of organic synthesis, including but not limited to, a Fischer indole synthesis through intermediates of type ii and iii, the method set forth in Nazare et al., *Angew. Chem.*, 116:4626-4629 (2004).

Scheme 2 shows methods useful for making compounds viii and x, which are useful intermediates for making of the 2-Carboxy Substituted Indole Derivatives.

Scheme 2

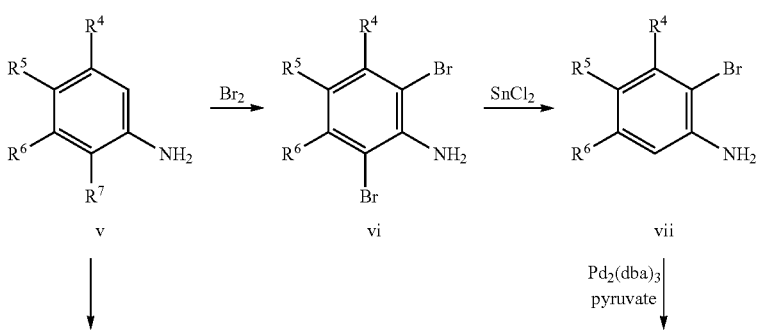

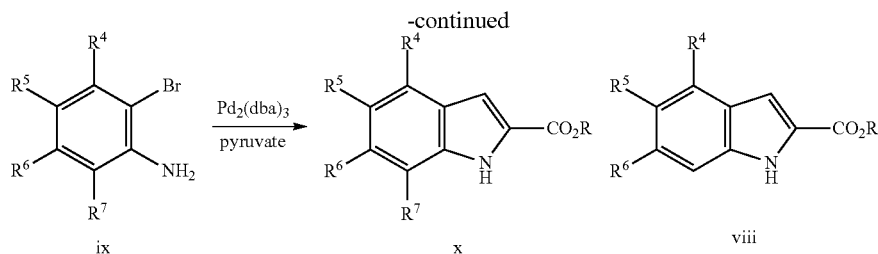

wherein $R^4$-$R^7$ are defined above for the compounds of formula (I) and R is H, alkyl or aryl.

A benzene derivative of formula v, wherein $R^7$ is H, can be di-brominated to provide compound vi. Selective de-bromination provides the corresponding monobromo analog vii, which under palladium catalyzed cyclization conditions provides the desired intermediate viii, wherein $R^7$ is H. Alternatively a compound of formula v, wherein $R^7$ is other than H, can be monobrominated to provide compound ix. A compound of formula ix can then undergo under palladium catalyzed cyclization conditions provides the desired intermediate x, wherein $R^7$ is other than H.

Scheme 3 illustrates methods by which intermediate compounds of formula xi can be further derivatized to provide the 2-Carboxy Substituted Indole Derivatives, which are intermediates to the title 2-Carboxy Substituted Indole Derivatives.

$R^3$-M (wherein M is —B(OH)$_2$, —Si(alkyl)$_2$OH, —Sn(alkyl)$_3$, —MgBr, —MgCl, —ZnBr, —ZnCl, or any metal which can participate in an organometallic cross-coupling reaction) using an organometallic cross-coupling method. Alternatively, a compound of formula xii, wherein X is —B(OH)$_2$, —Si(alkyl)$_2$OH, —Sn(alkyl)$_3$, —MgBr, —MgCl, —ZnBr, —ZnCl, or any metal which can participate in an organometallic cross-coupling reaction, can then be coupled with an appropriate compound of formula $R^3$-M (wherein M is halo or —O-triflate) using an organometallic cross-coupling method. Suitable cross-coupling methods include, but not limited to, a Stille coupling (see Choshi et al., *J. Org. Chem.*, 62:2535-2543 (1997), and Scott et al., *J. Am. Chem. Soc.*, 106:4630 (1984)), a Suzuki coupling (see Miyaura et al., *Chem. Rev.*, 95:2457 (1995)), a Negishi coupling (see Thou et al., *J. Am. Chem. Soc.*, 127:12537-12530 (2003)), a silanoate-based coupling (see Denmark et al.,

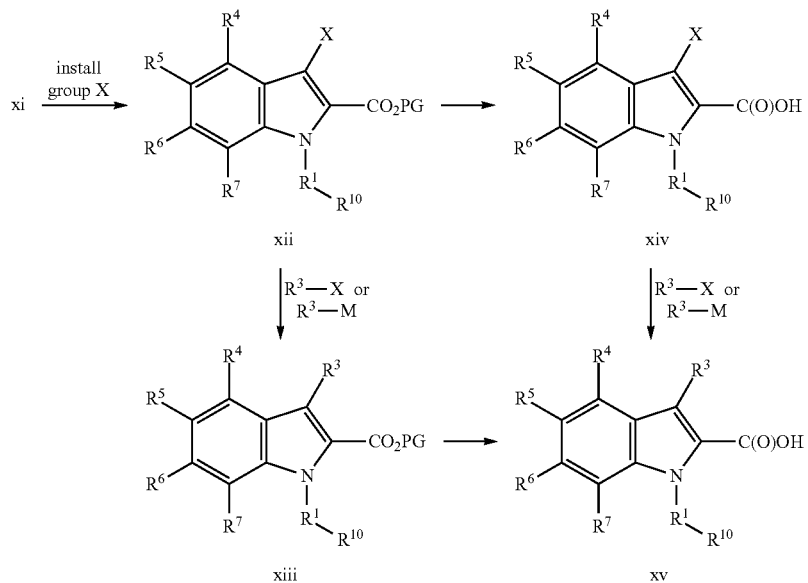

Scheme 3 wherein $R^1$, $R^3$, $R^4$-$R^7$ and $R^{10}$ are defined above for the compounds of formula (I); PG is a carboxy protecting group; and X is halo, —O-triflate, —B(OH)$_2$, —Si(alkyl)$_2$OH, —Sn(alkyl)$_3$, —MgBr, —MgCl, —ZnBr, or —ZnCl; and M is any metal which can participate in an organometallic cross-coupling reaction.

An intermediate compound of formula xi can be converted to a 3-substituted indole of formula xii using methods well-known to one skilled in the art of organic synthesis. A compound of formula xii, wherein X is halo or —O-triflate can then be coupled with an appropriate compound of formula

*Chem. Eur. J.* 12:4954-4963 (2006)) and a Kumada coupling (see Kumada, *Pure Appl. Chem.*, 52:669 (1980) and Fu et al., *Angew. Chem.* 114:4363 (2002)) to provide a compound of formula F. The carboxy protecting group, PG, can then be removed from the compound of formula xiv and the resulting carboxylic acid can be derivatized using the methods described below in order to make the appropriate $R^2$ groups and make the compounds of formula xv, which correspond to the compounds of formula (I), wherein $R^2$ is —C(O)OH. Alternatively, a compound of formula xii can first be deprotected and the $R^2$ group attached using the above methods to provide a compound of formula xiii. A compound of formula xiii can then be cross-coupled with a compound of R³—X or R³-M as described above to provide make the compounds of formula xv.

Scheme 4 shows a method useful for making the 2-Carboxy Substituted Indole Derivatives, wherein R² is —C(O)N(R⁹)₂.

Scheme 4

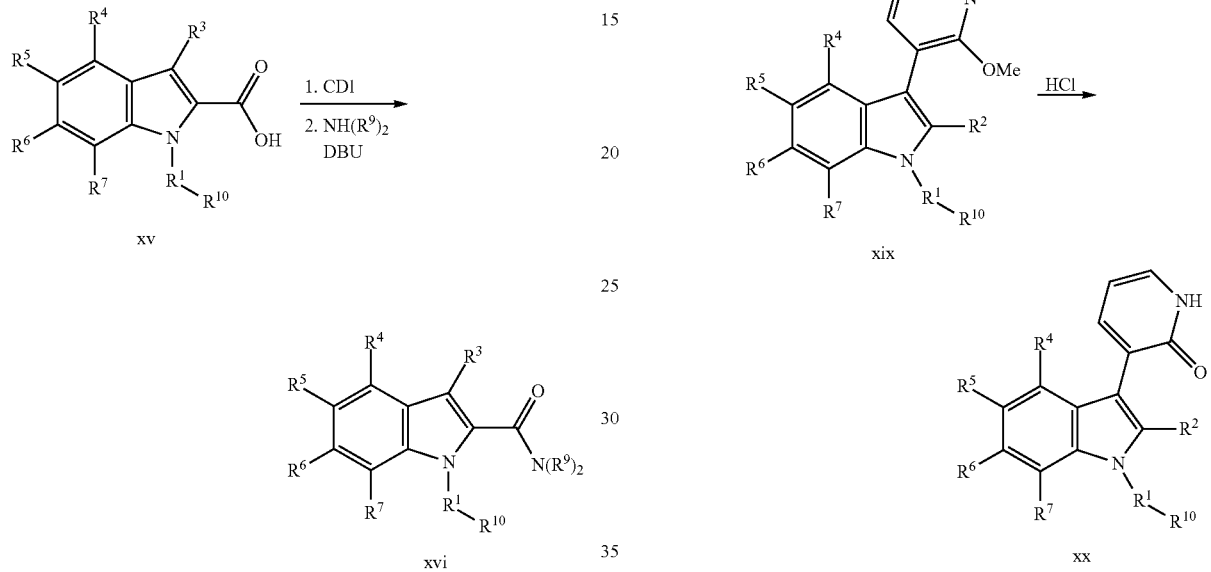

wherein R¹, R³, R⁴-R⁷, R⁹ and R¹⁰ are defined above for the compounds of formula (I).

A 2-carboxy indole compound of formula xv can be coupled with an amine of formula NH(R⁹)₂ in the presence of carbonyldiimidazole (CDI) and 1,8-diazabicyclo[5.4.0]undec-7-ene (DBU) to provide the compounds of formula xvi, which correspond to the 2-Carboxy Substituted Indole Derivatives wherein R² is —C(O)N(R⁹)₂.

Scheme 5 shows a method useful for making the 2-Carboxy Substituted Indole Derivatives, wherein R³ is 1H-pyridin-2-one-3-yl.

Scheme 5

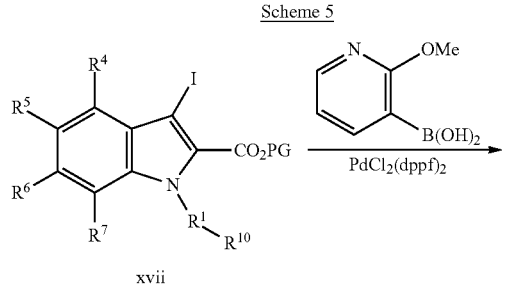

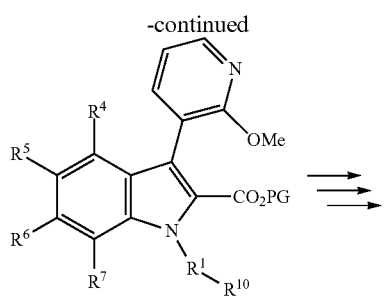

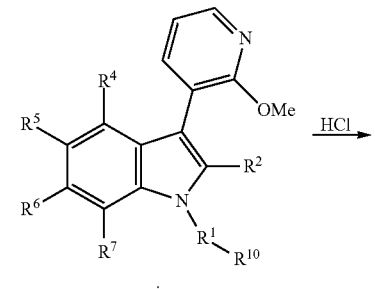

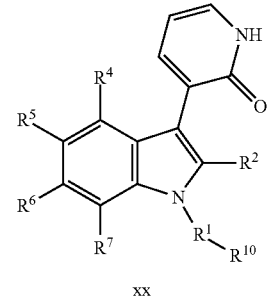

wherein R¹, R², R⁴-R⁷, R⁹ and R¹⁰ are defined above for the compounds of formula (I) and PG is a carboxy protecting group.

A 3-iodoindole compound of formula xvii can be coupled with 2-hydroxypyridine-3-boronic acid using a Suzuki coupling reaction to provide the R³-substituted indole compounds of formula xviii. A compound of formula xviii can be further elaborated using methods set forth above to provide the compounds of formula xix. The 2-hydroxypyridyl moiety of a compound of formula xix can then be reacted with strong acid, such as hydrochloric acid to provide the compounds of formula xx, which correspond to the 2-Carboxy Substituted Indole Derivatives, wherein R³ is 1H-pyridin-2-one-3-yl.

The starting material and reagents depicted in Schemes 1-5 are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art will recognize that the synthesis of 2-Carboxy Substituted Indole Derivatives may require the need for the protection of certain functional groups (i.e., derivatization for the purpose of chemical compatibility with a particular reaction condition). Suitable protecting groups for the various functional groups of the 2-Carboxy Substituted Indole Derivatives and methods for their installation and removal may be found in Greene et al., *Protective Groups in Organic Synthesis*, Wiley-Interscience, New York, (1999).

One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (i.e. non-linear or preassembly of certain portions of the molecule) is a more efficient method of assembly of the target compounds. Methods suitable for the preparation of 2-Carboxy Substituted Indole Derivatives are set forth above in Schemes 1-5.

The starting materials and the intermediates prepared using the methods set forth in Schemes 1-5 may be isolated and purified if desired using conventional techniques, including but not limited to filtration, distillation, crystallization, chromatography and the like. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance 500 (500 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minute—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific.

Example 1

Preparation of Compounds 14 and 159

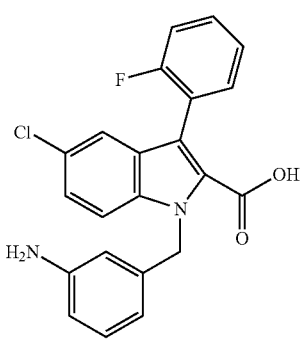

14

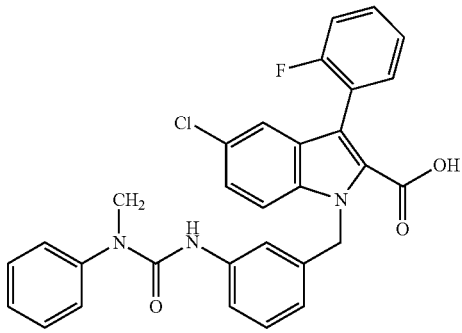

159

Step 1:

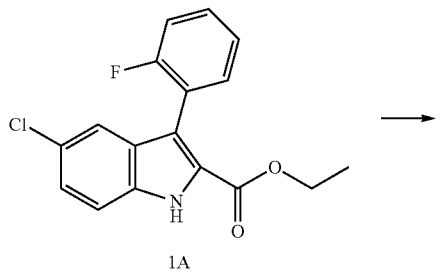

1A

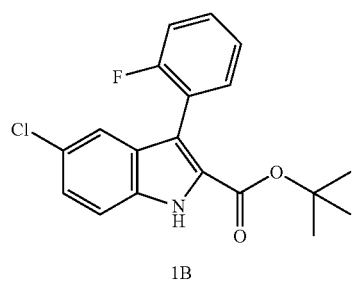

1B

A solution of ethyl-5-chloro-3-ortho-fluorophenylindole-2-carboxylate, (1A, 10 g, 31.5 mmol) in 0.5 M LiOH in MeOH (125 mL) was allowed to stir at reflux for 4 hours. The mixture was cooled down to room temperature and then concentrated in vacuo. Water was added to the residue and the resulting suspension acidified with aqueous 1N HCl solution. The solids were collected by filtration, and then were dissolved into EtOAc. The organic solution was dried over sodium sulfate, filtered and concentrated in vacuo to a solid residue. The resulting residue was resuspended in anhydrous toluene (150 mL) at 80° C. and Me$_2$N—[O-(tBu)]$_2$ (20 mL, 84.0 mmol) was added to the heated suspension dropwise. The reaction mixture was allowed to stir at 80° C. for 3 h and then cooled to room temperature. The mixture was diluted with toluene, washed with aqueous saturate sodium bicarbonate solution (×2) and brine respectively. The organic layer was dried and concentrated in vacuo to provide a residue. The resulting residue was triturated from hexanes to provide compound 1B (9.3 g, 85% yield) as a white powder. $^1$H NMR (400 MHz, CDCl$_3$): δ9.08 (s, 1H), 7.46-7.33 (m, 4H), 7.30 & 7.28 (dd, J=1.47 Hz & 8.79 Hz, 1H), 7.25-7.21 (m, 1H), 7.17 (t, J=9.15 Hz, 1H), 1.40 (s, 9H).

Step 2:

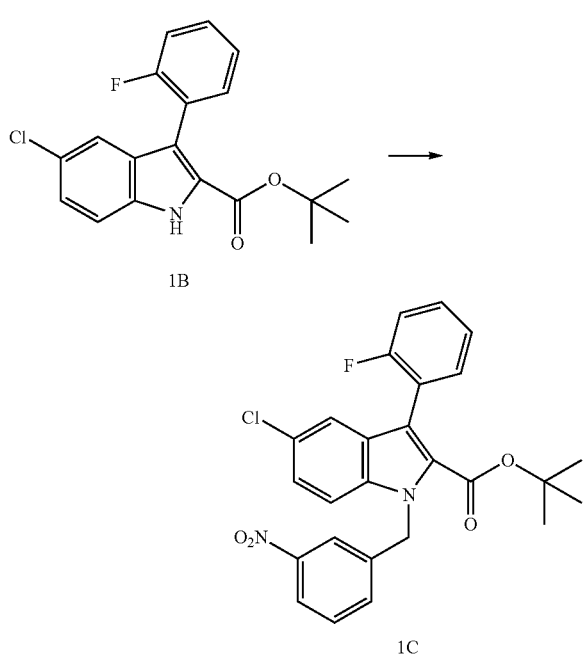

To a solution of 5-chloro-3-(2-fluoro-phenyl)-1H-indole-2-carboxylic acid tert-butyl ester, 1B (3 g, 8.68 mmol) in DMF at 0° C. was added potassium tert-butoxide (10.4 mL). The mixture was allowed to stir at 0° C. for 10 minutes and then 3-nitrobenzylbromide (2.15 g, 9.95 mmol) was added. The reaction mixture was then allowed to warm slowly over 6-8 h to room temperature, and stir an additional 12 hours. DMF was removed in vacuo, and the resulting residue was re-dissolved into ethyl acetate. The solution was washed twice with aqueous 5% sodium bicarbonate solution. The separated organic layer was dried, filtered and concentrated in vacuo. The crude product was purified using flash chromatography to provide compound 1C (4 g, 96% yield).

Step 3:

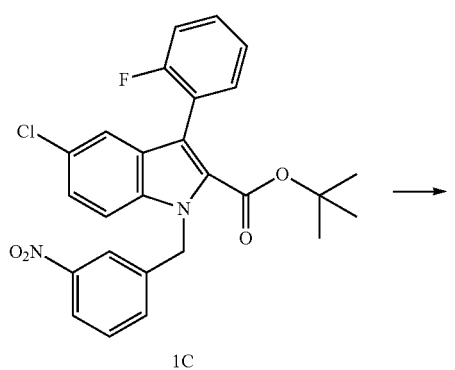

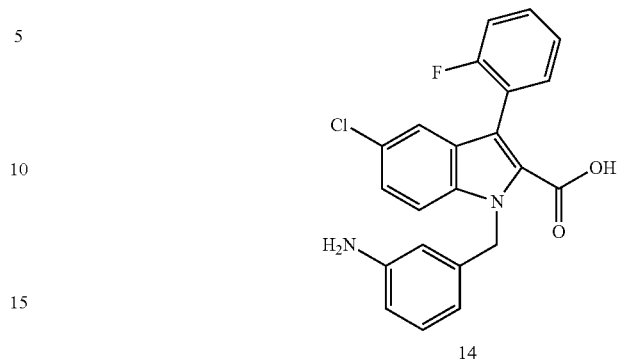

A mixture of 5-chloro-3-(2-fluoro-phenyl)-1-(3-nitro-benzyl)-1H-indole-2-carboxylic acid tert-butyl ester, 1C (4.0 g, 8.32 mmol) and SnCl$_2$.2H$_2$O (11.28 g, 50.0 mmol) in ethanol (40 mL) was allowed to stir at 85° C. for 2 hours. The mixture was cooled to room temperature, and concentrated in vacuo. The resulting residue was re-dissolved into ethyl acetate, aqueous 1N sodium hydroxide solution was added until the pH value of the aqueous layer reaches 7~8. The resulting suspension was filtered through a pad of celite. The filtrate was treated again with an aqueous 1N sodium hydroxide solution and filtered. The filtrate was washed with brine, dried, filtered and concentrated in vacuo. The resulting residue was purified through column chromatography to provide compound 14 (2.0 g, 60% yield). $^1$H NMR (400 MHz, CDCl3): δ7.45-7.34 (m, 3H), 7.29 (d, J=8.79 Hz, 1H), 7.24 & 7.22 (dd, J=2.20 Hz & 8.79 Hz, 2H), 7.19-7.14 (m, 1H), 7.06 (t, J=8.06 Hz, 1H), 6.55-6.52 (m, 2H), 6.38 (s, 1H), 5.72 (s, 2H), 2.05 (s, 2H), 1.25 (s, 9H).

Step 4:

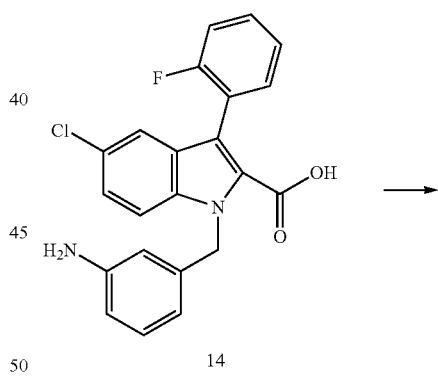

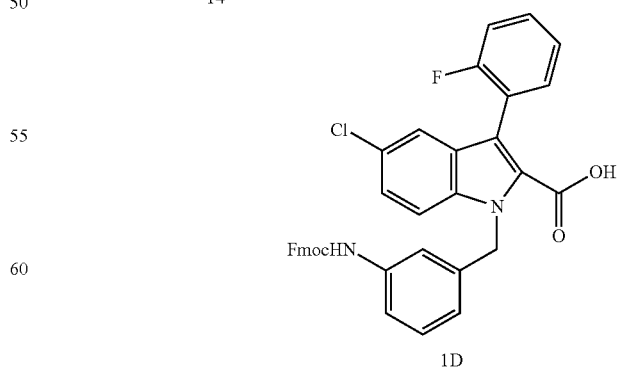

To a solution of compound 14 (2.9 g, 7.35 mmol) in 1,4-dioxane (40 mL) was added N-(9-Fluorenylmethoxycarbonyloxy)succinimide (4.95 g, 14.69 mmol). The resulting reaction mixture was allowed to stir at 50° C. for 18 hours. The mixture was then cooled to room temperature and concentrated in vacuo. The residue obtained was dissolved into dichloromethane, washed with aqueous 5% sodium bicarbonate solution. The separated organic layer was dried over sodium sulfate, filtered and concentrated in vacuo. The residue obtained was purified using flash chromatography to provide compound 1D (2.2 g, 49% yield). $^1$H NMR (400 MHz, CDCl3): δ 7.75 (d, J=7.32 Hz, 2H), 7.56 (d, J=5.86 Hz, 2H), 7.45-7.35 (m, 6H), 7.33-7.27 (m, 6H), 7.19-7.14 (m, 3H), 6.70 (d, J=7.32 Hz, 1H), 5.78 (s, 2H), 4.49 (d, J=6.59 Hz, 2H), 4.21 (t, J=5.49 Hz, 1H).

Step 5:

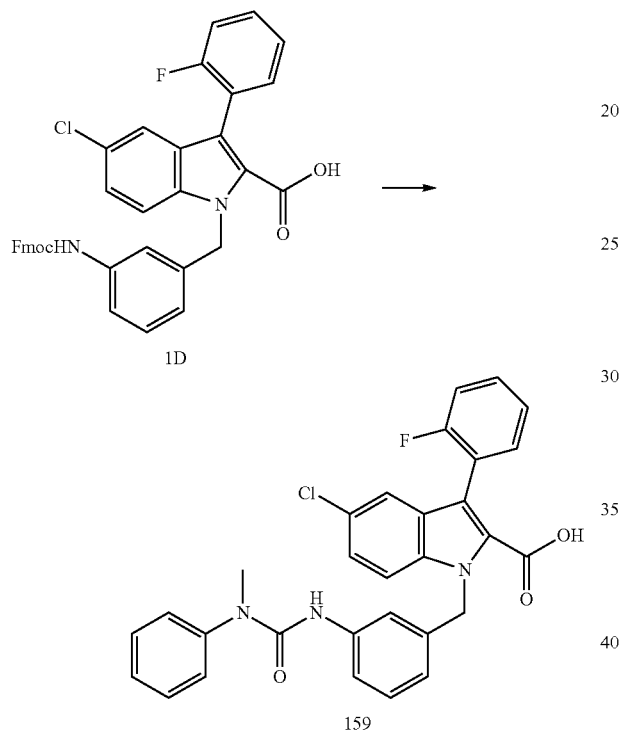

The mixture of 5-chloro-1-[3-(9H-fluoren-9-ylmethoxy-carbonylamino)-benzyl]-3-(2-fluoro-phenyl)-1H-indole-2-carboxylic acid, 1D (2.0 g, 3.24 mmol) and DIEA (5.0 mL, 12.96 mmol) in dichloromethane (35 mL) was added dropwise to trityl chloride polystyrene resin (7.05 g, 6.49 mmol) in dichloromethane (35 mL). The resulting mixture was allowed to stir at room temperature for 18 hours. The mixture was quenched with DIEA/MeOH, and washed with DMF (4×) to provide a resin-attached Fmoc-intermediate. This Fmoc-intermediate was treated with 20% piperidine in DMF. The mixture was allowed to stir for 1 h and then washed with DMF (4×) to provide the corresponding resin-attached free amine-intermediate. This free amine-intermediate was treated with N-methyl-N-phenylcarbamoyl chloride (32.4 mmol) and DIPEA (64.8 mmol)). The mixture was stirred in DMF for 48 h before washed with DMF (2×), THF (2×), methanol (2×) and dichloromethane (2×) respectively to provide the corresponding resin-attached urea-intermediate. This urea intermediate was then cleared off of the resin by treatment with 2% trifluoroacetic acid in dichloromethane to provide Compound 159. MS=528 (M+H)

Example 2

Preparation of Compound 14

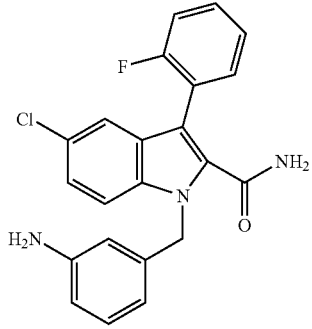

Step 1:

To a solution of compound 1A, 1.0 g, 3.15 mmol) in DMF (10 mL) in an ice-bath was added potassium t-butyl oxide (446 mg, 3.97 mmol). The mixture was stirred in the ice-bath for 10 minutes before 3-nitrobenzyl bromide (801 mg, 3.71 mmol) was added. The reaction mixture was allowed to stir at room temperature for 48 hours. The reaction was then quenched, and DMF was removed from the mixture. The resulting residue was dissolved into ethyl acetate, and washed with aqueous 5% sodium bicarbonate solution (3×). The separated organic layer was dried over sodium sulfate, filtered and concentrated in vacuo. The crude product was purified using column chromatography to provide compound 2A. $^1$H NMR (400 MHz, CDCl3): δ 8.13 (d, J=8.79 Hz, 1H), 8.06 (s, 1H), 7.52 (d, J=2.20 Hz, 1H), 7.49-7.45 (m, 2H), 7.43-7.36 (m, 3H), 7.31 (d, J=1.47 Hz, 1H), 7.29 (s, 1H), 7.18 (t, J=9.15 Hz, 1H), 5.92 (s, 2H), 4.14 (q, J=6.59 Hz & 7.32 Hz, 2H), 0.98 (t, J=7.32 Hz, 3H).

Step 2:

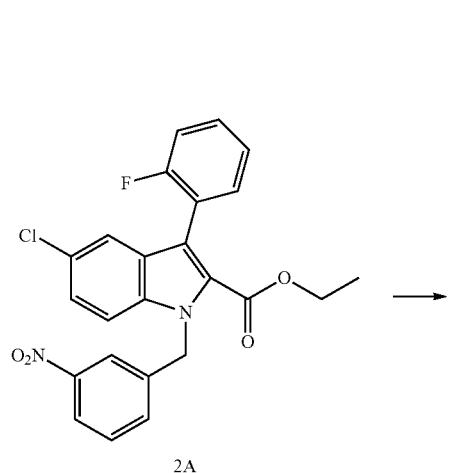

2A

A solution comprising compound 2A (0.93 g, 2.05 mmol) in LiOH (0.5 M solution in methanol, 30 mL) was placed in microwave reactor for 10 minutes (150 watts). To the mixture was added aqueous 1N HCl solution to precipitate out the products. The filtered solid was washed with aqueous 1N HCl solution (2×), and was then dissolved into ethyl acetate. The resulting solution was dried over sodium sulfate, filtered and concentrated in vacuo to provide compound 2B (0.87 g, 100% yield).

Step 3:

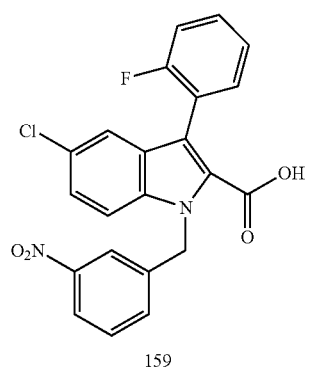

159

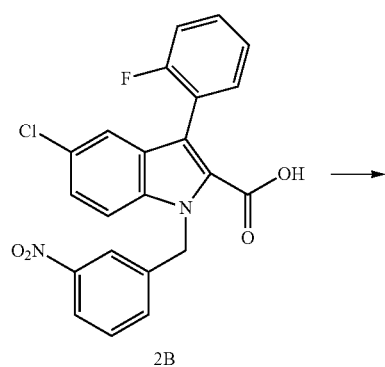

2B

-continued

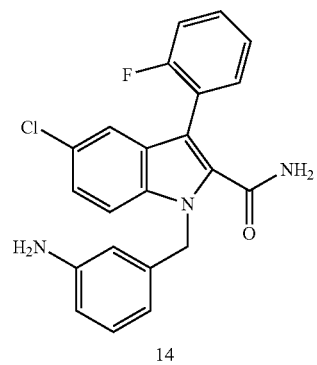

14

To the sieber amide resin (64.5 mg, 0.04 mmol) was added 20% piperidine in DMF (10 mL). The resulting mixture was allowed to stir at room temperature for 40 minutes before being washed with DMF (3×) to get a de-protected resin. To the de-protected resin in DMF (2 mL) were added 5-chloro-3-(2-fluoro-phenyl)-1-(3-nitro-benzyl)-1H-indole-2-carboxylic acid, 2B (16 mg, 0.038 mmol), HATU and DIPEA. The mixture was allowed to stir at room temperature for 18 h before treated with 2 M $SnCl_2$ in DMF. The mixture was then washed with DMF (3×), THF (3×), and dichloromethane (3×) respectively to get the resin-attached intermediate. The resin is cleaved by the treatment with 4% trifluoroacetic acid in dichloromethane to provide compound 14. $^1$H NMR (400 MHz, CDCl3): δ 10.32 (s, 2H), 7.47 (s, 2H), 7.36 (s, 2H), 7.18-7.10 (m, 3H), 7.06-6.98 (m, 2H), 6.79 (s, 1H), 5.98 (s, 1H), 5.39 (s, 2H), 3.65 (s, 1H), 3.07 (s, 1H).

Example 3

Preparation of Compound 101

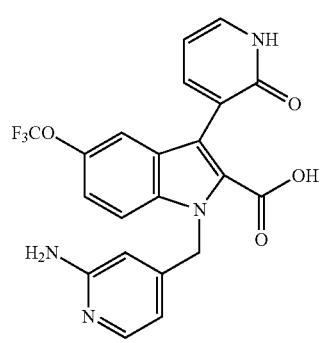

101

Step 1:

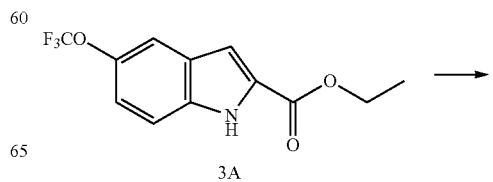

3A

-continued

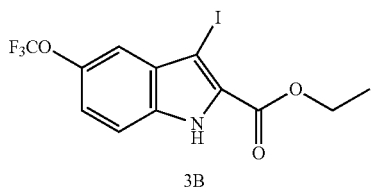

3B

To a solution of ethyl 5-(trifluoromethoxy)-1H-indole-2-carboxylate, 3A (1.95 g, 7.14 mmol) in acetone (40 mL) was added N-iodosuccinimide (1.61 g, 7.14 mmol). The resulting suspension was allowed to stir at room temperature for 3.75 hours. The reaction was quenched with aqueous sodium thiosulfate solution (50 mL). The volatiles was evaporated under reduced pressure, and the resulting residue was dissolved into ethyl acetate (500 mL) and water (100 mL) The mixture was washed with aqueous saturated sodium thiosulfate solution (100 mL). The layers were separated, and the aqueous layer was extracted with ethyl acetate (2×100 mL) The combined organic layer was washed with aqueous 1N sodium bicarbonate solution (100 mL) and brine (50 mL). The organic layer was then dried over magnesium sulfate, filtered and concentrated in vacuo to provide the crude product 3B (2.8 g, 98% yield). $^1$H NMR (400 MHz, CDCl3) δ 9.28 (s, 1H), 7.44 (s, 1H), 7.40 (d, J=8.79 Hz, 1H), 7.24 (s, 1H), 4.48 (q, J=6.59 Hz & 7.32 Hz, 2H), 1.48 (t, J=7.32 Hz, 3H).

Step 2:

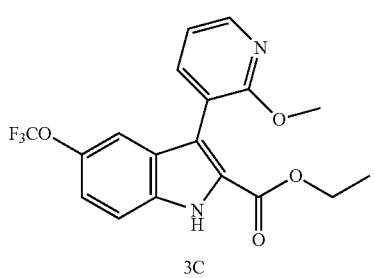

3B

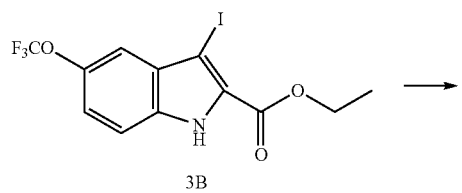

3C

To a solution of 3-iodo-5-trifluoromethoxy-1H-indole-2-carboxylic acid ethyl ester, 3B (2.80 g, 7.02 mmol) in 1,2-dimethoxyethane (90 mL) was added PdCl$_2$(dppf)$_2$ (573 mg, 0.70 mmol). The resulting mixture was de-gassed with nitrogen bubbling for 10 minutes. In a second flask, the mixture of 2-methoxy-3-pyridine boronic acid (1.29 g, 8.42 mmol) and potassium carbonate (4.85 g, 35.1 mmol) in dimethoxyethane (30 mL) and water (30 mL) was de-gassed with nitrogen bubbling for 5 minutes. The mixture was then transferred slowly to the first flask. The resulting biphasic mixture was vigorously stirred at 90° C. for 4.25 h before it was cooled to room temperature. The reaction was quenched by the addition of a solution of sodium sulfite (5 g) in water (100 mL) at room temperature. Ethyl acetate (100 mL) was added, and the layers were separated. The aqueous layer was extracted with ethyl acetate (2×100 mL). The combined organic layer was dried over magnesium sulfate, filtered and concentrated in vacuo to provide the crude product 3C (1.44 g, 54% yield). M.S. found for C18H15F3N2O4: 381.04 (M+H)$^+$.

Step 3:

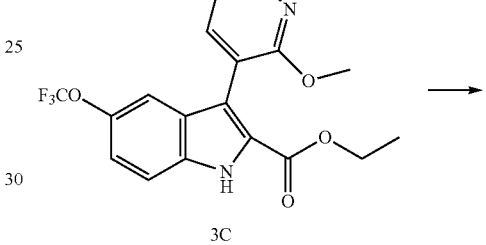

3C

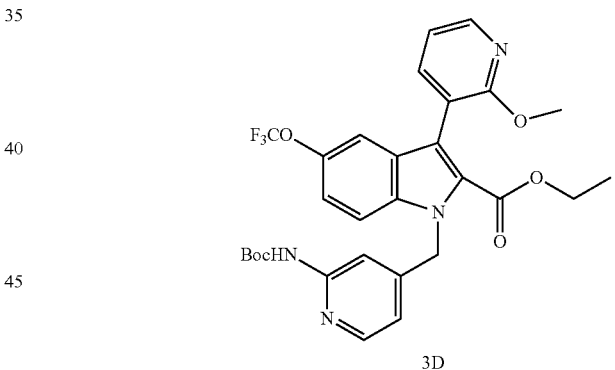

3D 3-(2-Methoxy-pyridin-3-yl)-5-trifluoromethoxy-1H-indole-2-carboxylic acid ethyl ester, 3C (1.0 g, 2.63 mmol) was dissolved into DMF (100 mL) at room temperature. To the mixture were added (4-bromomethyl-pyridin-2-yl)-carbamic acid tert-butyl ester (0.83 g, 2.89 mmol) and cesium carbonate (1.29 g, 3.95 mmol). The resulting suspension was allowed to stir at room temperature for 18 hours. The reaction mixture was diluted with ethyl acetate (500 mL), and was washed with water (3×80 mL), aqueous saturate sodium bicarbonate (2×50 mL) and brine respectively. The separated organic layer was dried over magnesium sulfate, filtered and concentrated in vacuo. The crude product obtained was purified using flash chromatography to provide compound 3D (1.44 g, 93% yield). M.S. found for C29H29F3N4O6: 587.51 (M+H)$^+$.

Step 4:

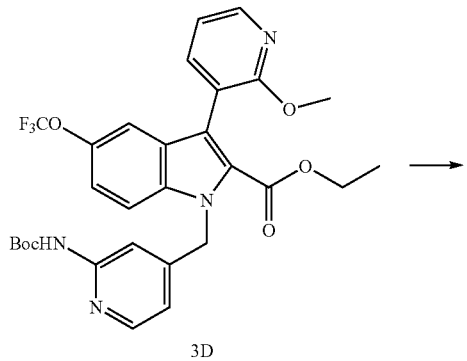

3D

To a solution of 1-(2-tert-butoxycarbonylamino-pyridin-4-ylmethyl)-3-(2-methoxy-pyridin-3-yl)-5-trifluoromethoxy-1H-indole-2-carboxylic acid ethyl ester, 3D (1.42 g, 2.42 mmol) in THF (15 mL) and water (3 mL) was added aqueous 1N lithium hydroxide solution (12.1 mL, 12.10 mmol). The resulting suspension was refluxed at 70° C. for 22 hours. The mixture was cooled down to room temperature, and the aqueous layer was acidified to pH=2 with addition of aqueous 1N HCl solution. The mixture was extracted twice with 100 mL of THF/ethyl acetate (1:1). The combined organic layer was dried over magnesium sulfate, filtered and concentrated in vacuo to yield the crude product 3E (100% yield). M.S. found for C27H25F3N4O6: 559.21 (M+H)$^+$.

Step 5:

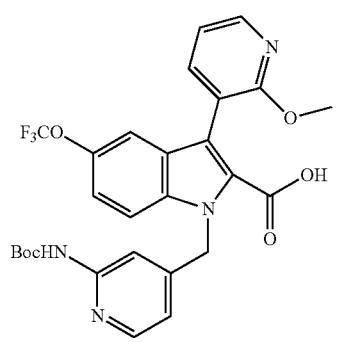

3E

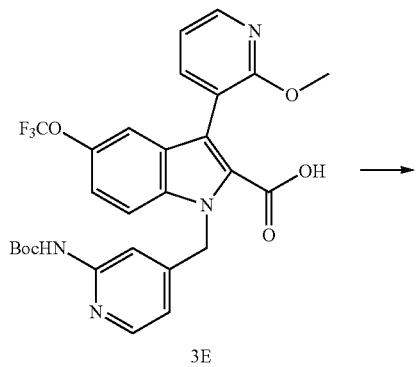

3E

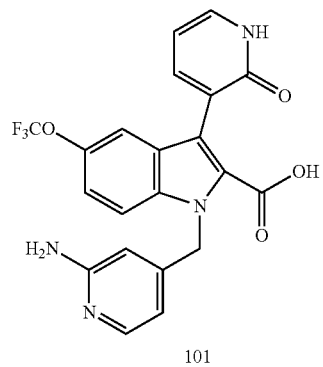

101

1-(2-tert-Butoxycarbonylamino-pyridin-4-ylmethyl)-3-(2-methoxy-pyridin-3-yl)-5-trifluoromethoxy-1H-indole-2-carboxylic acid, 3E (24 mg, 0.04 mmol) was dissolved into 4N HCl in 1,4-dioxane (2 mL) in a tube. Water (1 drop) was added afterwards. The reaction mixture was allowed to stir at 90° C. in the sealed tube for 3 hours. The reaction mixture was cooled down to room temperature before being concentrated in vacuo to provide compound 101 (100% yield). M.S. found for C$_{21}$H$_{15}$F$_3$N$_4$O$_4$: 445.2 (M+H)$^+$.

Example 4

Preparation of Intermediate Compound 4F

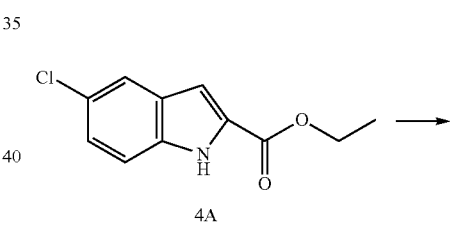

4A

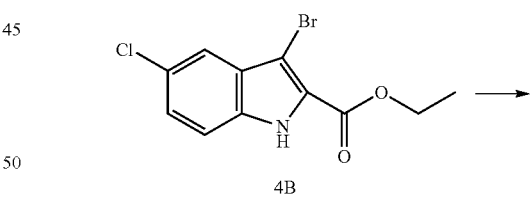

4B

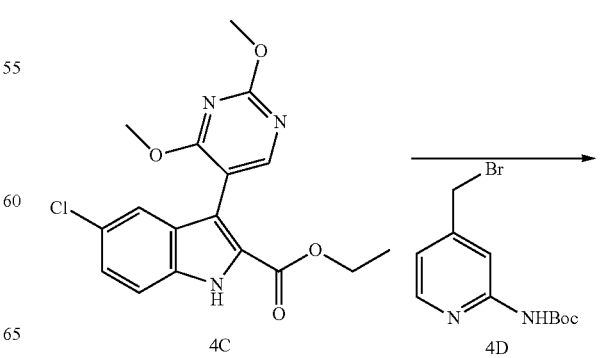

4C 4D

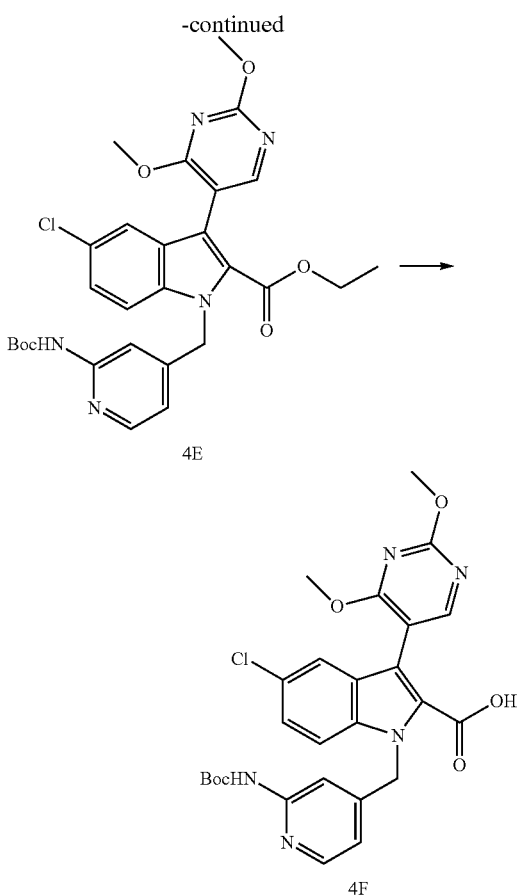

4E

4F

Step 1:

To a solution of ethyl 5-chloroindole-2-carboxylate, 4A (20 g, 89.6 mmol) in THF (200 mL) in a cooled water bath was added NBS (16.0 g, 89.9 mmol) slowly. The resulting reaction mixture was allowed to stir at room temperature for 18 h before water (700 mL) was added. The mixture was continued to stir at room temperature for 20 minutes and then filtered. The solids were washed with water (2×100 mL), and dried to afford the crude product 4B (25.8 g, 90% yield). $^1$H NMR (500 MHz, CDCl3) δ 9.06 (s, 1H), 7.66-7.65 (m, 1H), 7.35-7.31 (m, 2H), 4.47 (q, J=7.25 Hz, 2H), 1.46 (t, J=7.09 Hz, 3H).

Step 2:

To a mixture of 3-bromo-5-chloro-1H-indole-2-carboxylic acid ethyl ester, 4B (1.00 g, 3.31 mmol), 2,4-dimethoxypyrimidine-5-boronic acid (0.73 g, 3.97 mmol), [1,1'-bis(diphenylphosphino)ferrocene]dichloropalladium(II) with dichloromethane complex (1:1) (0.26 g, 0.32 mmol) in DME (15 mL) was added a solution of sodium carbonate (4.5 mL of 1.5 M, 6.75 mmol) via a syringe. The reaction mixture was allowed to stir at reflux for 6 h before cooled down to room temperature. The mixture was diluted with dichloromethane (50 mL), and was filtered through a pad of celite. The filtrate was concentrated in vacuo. The resulting residue was purified using flash chromatography on silica gel (20% ethyl acetate in hexanes) to provide the product 4C as a white solid (0.47 g, 39% yield). M.S. found for $C_{17}H_{16}ClN_3O_4$: 362.2 (M+H)$^+$.

Step 3:

To a solution of 5-chloro-3-(2,4-dimethoxy-pyrimidin-5-yl)-1H-indole-2-carboxylic acid ethyl ester, 4C (620 mg, 1.71 mmol) in DMF were added (4-bromomethyl-pyridin-2-yl)- carbamic acid tert-butyl ester, 4D (490 mg, 1.71 mmol) and cesium carbonate (1100 mg, 3.39 mmol). The resulting suspension was allowed to stir at room temperature for 17 hours. The mixture was then diluted with ethyl acetate (80 mL), and washed with water (3×50 mL). The organic layer was dried over sodium sulfate, filtered and concentrated in vacuo. The resulting residue was purified using chromatography on silica gel using 30% ethyl acetate in hexanes to deliver the product 4E (705 mg, 73% yield). M.S. found for $C_{28}H_{30}ClN_5O_6$: 568.3 (M+H)$^+$.

Step 4:

To a solution of 1-(2-tert-butoxycarbonylamino-pyridin-4-ylmethyl)-5-chloro-3-(2,4-dimethoxy-pyrimidin-5-yl)-1H-indole-2-carboxylic acid ethyl ester, 4E (500 mg, 0.88 mmol) in THF (10 mL) was added an aqueous solution of lithium hydroxide (2.0 ml of 1 M, 2.9 mmol). The resulting reaction mixture was allowed to stir at reflux for 16 hours. The Reaction was then cooled and concentrated in vacuo. The resulting residue was dissolved in methanol (80 mL), neutralized with 1.0 M HCl aqueous solution (2.5 mL, 2.5 mmol) and then concentrated again under reduced pressure. The resulting residue was extracted with dichloromethane (3×30 mL). The combined organic layer was concentrated in vacuo, and dried on house vacuum to provide compound 4F (440 mg, 92%). M.S. found for $C_{26}H_{26}ClN_5O_6$: 540.3 (M+H)$^+$.

Example 5

Preparation of Compound 167

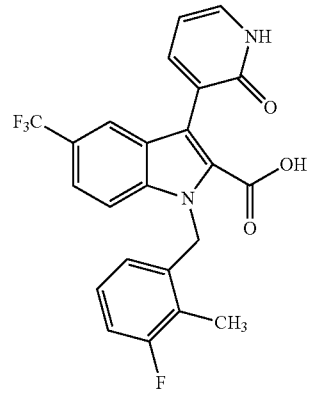

167

Step 1:

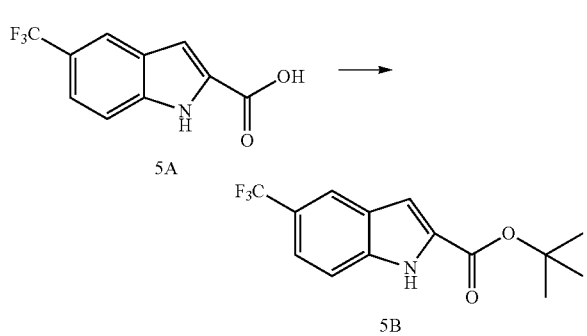

5A

5B

To a solution of the indole 5A (1.6 g, 6.9 mmol) in toluene (5.0 mL) was added N,N-dimethylformamide di-tert butyl acetal (5 mL), and heated to 90° C. for 12 h, cooled to room temperature, another aliquot of N,N-dimethylformamide di-tert butyl acetal (5 mL) was added and the reaction mixture was heated to 90° C. for 12 h, cooled to room temperature, diluted with ethyl acetate (10.0 mL), washed with water (2×10.0 mL), brine, dried over MgSO$_4$, filtered and concentrated to yield compound 5B (1.2 g, 60%) as a white solid. $^1$H NMR (400 MHz, CDCl3): δ 9.17 (s, 1H), 7.97 (s, 1H), 7.51 (s, 2H), 7.21 (s, 1H), 1.63 (s, 9H).

Step 2:

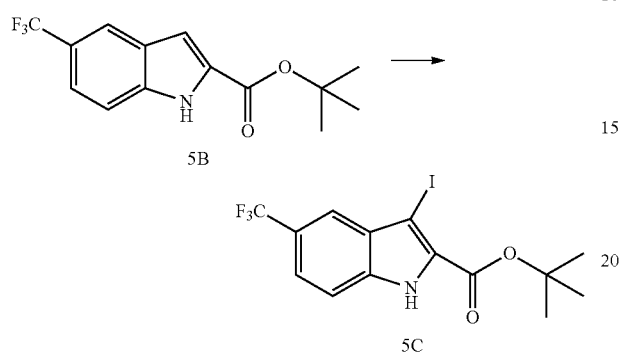

To a solution of 5B (1.2 g, 4.2 mmol) in CHCl$_3$ (25 mL) was added N-iodosuccinimide (946 mg, 4.2 mmol) and the reaction allowed to stir at room temperature for 12 hours. The reaction mixture concentrated in vacuo, diluted with water and extracted in EtOAc (200 mL). The combined organic layers were dried (MgSO$_4$), filtered, and concentrated in vacuo. The brown resulting residue was taken in minimum amount of CH$_2$Cl$_2$ and triturated with hexanes. Compound 5C was separated out as a brown solid which was filtered, and dried in vacuo. (1.23 g, 72% yield). $^1$H NMR (400 MHz, CDCl3): δ 9.34 (s, 1H), 7.87 (s, 1H), 7.57 (d, J=8.06 Hz, 1H), 7.49 (d, J=8.79 Hz, 1H), 1.68 (s, 9H).

Step 3:

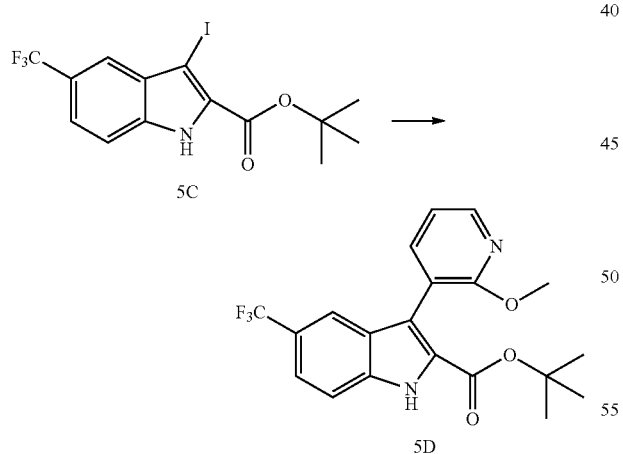

To a solution of compound 5C (1.23 g, 3.0 mmol) in DME (30 mL) under nitrogen atmosphere was added with 2-methoxy-3-pyridyl boronic acid (0.482 g, 3.15 mmol) and Pd (dppf)$_2$Cl$_2$ (245 mg, 0.3 mmol) and the resulting reaction was allowed to stir at room temperature under nitrogen for 0.5 hours. The reaction mixture was then treated with a solution of potassium carbonate (1.6 g, 12 mmol) in water (12 mL) and the resulting solution was heated to 90° C. and allowed to stir at this temperature for 1 hour. The reaction mixture was then diluted with EtOAc (200 mL) and the resulting solution was concentrated in vacuo to provide a crude residue which was purified using flash column chromatography (EtOAc/Hexanes, 0 to 30% EtOAc) to provide the product 5D as a solid (820.0 mg). M.S. found for C20H19F3N2O3: 393.2 (M+H)$^+$.

Step 4:

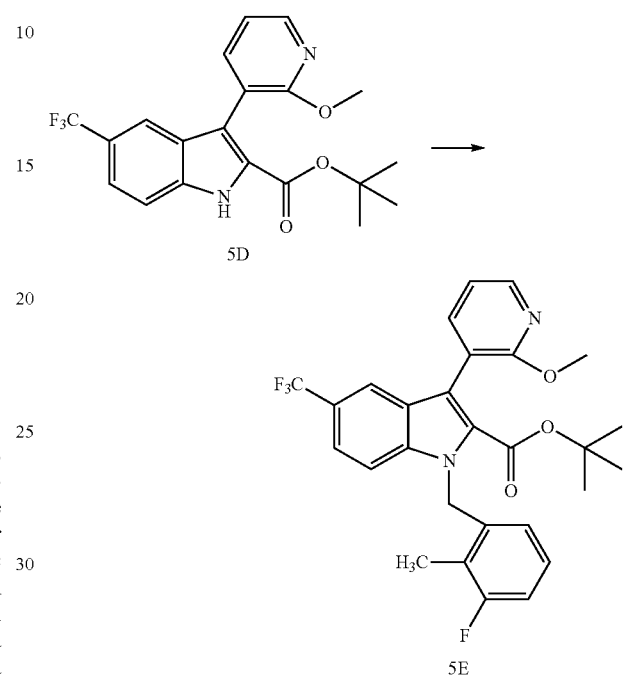

To a solution of indole 5D (10.0 g, 25.4 mmol) in DMF (100 mL) was added cesium carbonate (9.93 g, 30.5 mmol) and 3-fluoro-3-methylbenzyl bromide (3.57 mL, 30.5 mmol) and allowed to stir at room temperature for 12 hours. The reaction mixture was diluted with EtOAc (500 mL), washed with water (3×100 mL) and with brine (2×100 mL). The combined organic layers were dried (MgSO$_4$), filtered, and concentrated in vacuo and purified using flash column chromatography on silica gel to provide the product 5E as a colorless solid.

Step 5:

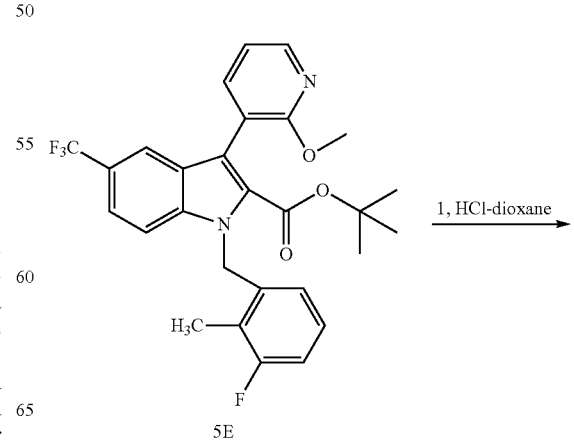

187
-continued

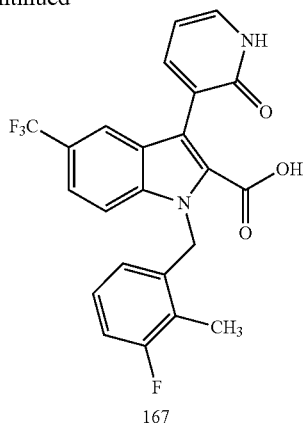
167

A solution of compound 5E (1.0 g, 1.94 mmol) was dissolved in 4N HCl in dioxane (20 mL) and heated at 80° C. overnight. After cooling the volatiles were removed under reduced pressure to provide compound 167 as a white solid.

Example 6

Preparation of Compound 168

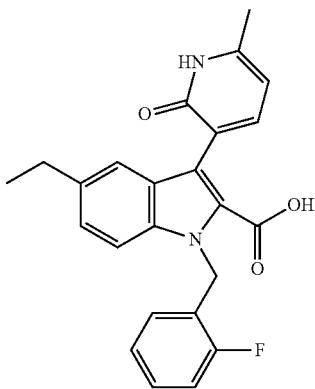 [SMILES: CCc1ccc2c(c1)c(-c1ccc(C)[nH]c1=O)c(C(=O)O)n2Cc1ccccc1F]

Step 1:

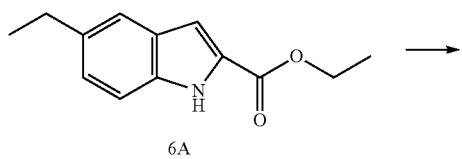

The starting materials 6A (15.0 g, 69.04 mmol) and THF (100 mL) were added to a 1000 ml round-bottomed flask. The resulting solution was cooled with a water bath. To this stirring solution, MS (15.30 g, 68.80 mmol) was added slowly.

188

The resulting solution was allowed to stir at room temperature for 5 hours before 700 ml of water was added. The resulting mixture was continued to stir at room temperature for 30 minutes and then filtered. The cake was washed with water (2×40 mL), dried by air and then on house vacuum to provide compound 6B as an off-white solid (23.0 g, 97%). M.S. found for $C_{13}H_{14}INO_2$: 344.2 (M+H)+.

Step 2:

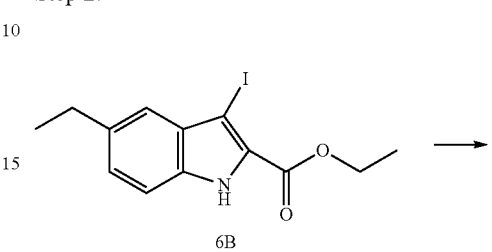

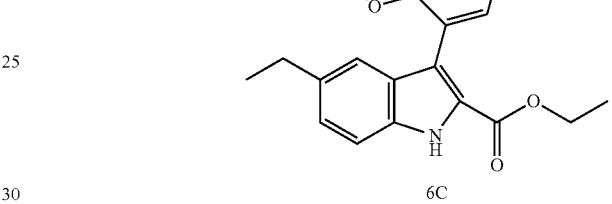

A 200 ml round-bottomed flask was charged with 6B (2.45 g, 7.14 mmol), 6-methyl-2-methoxypyridine-3-boronic acid (0.98 g, 5.87 mmol), [1,1' bis(diphenylphosphino)ferrocene] dichloropalladium(II) complex with dichloromethane (1:1) (0.58 g, 0.71 mmol), and DME (50 mL). To the stirring solution, a solution of sodium carbonate (10 ml of 1.5 M, 15.0 mmol) was added via a syringe. The reaction mixture was maintained reflux for 4 hours before cooled to room temperature. After concentration, the resulting residue was taken up with ethyl acetate (200 mL), washed with water (3×100 mL), and dried over sodium sulfate. The solvent was removed by distillation under reduced pressure and the resulting residue was purified using Combiflash chromatography on silica gel using 0-10% ethyl acetate in hexanes as the solvent to provide the product 6C as a white solid (1.51 g, 76%). M.S. found for $C_{20}H_{22}N_2O_3$: 339.2 (M+H)+.

Step 3:

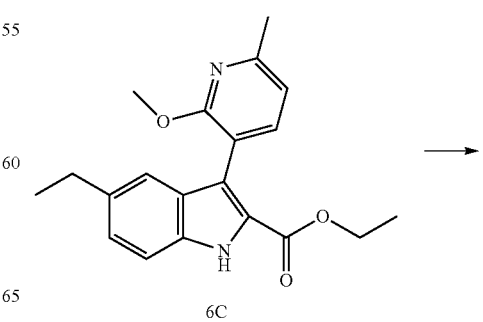

-continued

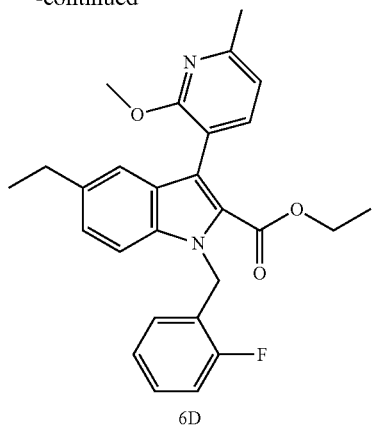

6D

The reaction materials 6C (200 mg, 0.59 mmol), 2-fluorobenzylchloride (170 mg, 1.76 mmol), cesium carbonate (700 mg, 2.16 mmol), and DMF (3 mL) were added to a 100 ml round-bottomed flask. The resulting suspension was allowed to stir at room temperature for 16 hours, diluted with ethyl acetate (100 mL), and washed with water (3×40 mL): The organic solution was dried over sodium sulfate and concentrated. The resulting residue was purified using Combiflash chromatography on silica gel using 0-10% ethyl acetate in hexanes as the eluent to deliver the product 6D as a gel (205 mg, 78%).
Step 4:

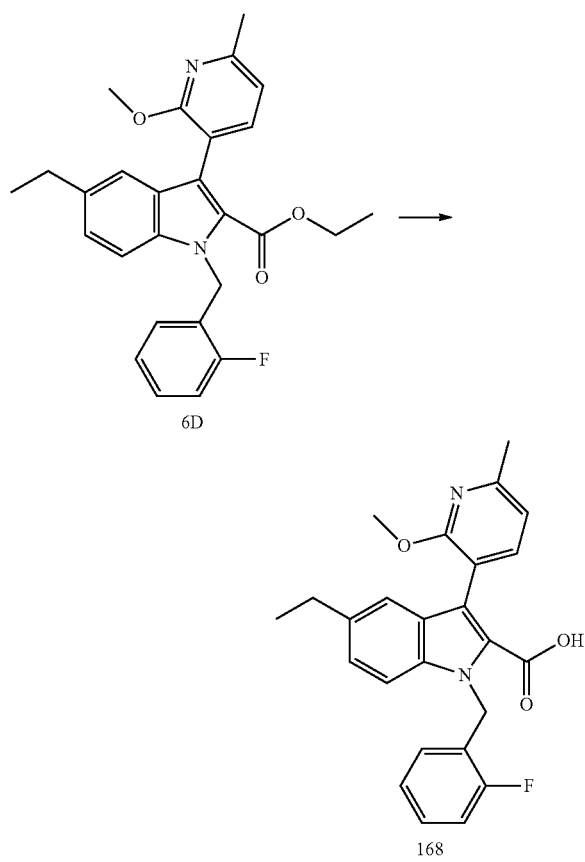

6D

168

To the stirring mixture of 6D (200 mg, 0.45 mmol) in THF (5 mL) in a 100 ml round-bottomed flask was added with a solution of lithium hydroxide (2.5 ml of 1 M, 2.5 mmol). The resulting solution was maintained at reflux for 4 days before cooled to room temperature. After concentration in vacuo, the resulting residue was dissolved in methanol (5 mL), neutralized with 1.0 M HCl aqueous solution (2.5 mL, 2.5 mmol) and then concentrated again. The resulting residue was extracted with ethyl acetate (3×40 mL). The combined organic solutions were concentrated and dried on house vacuum to provide compound 168 as a white wax (190 mg, ~100%). M.S. found for $C_{27}H_{25}ClFN_2O_3S$: 542.3 $(M+H)^+$.

Example 7

Preparation of Compound 7C

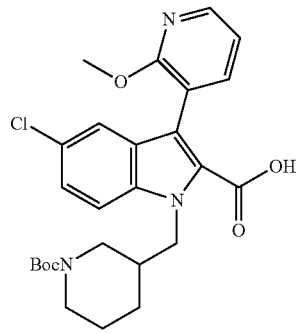

7C

Step 1:

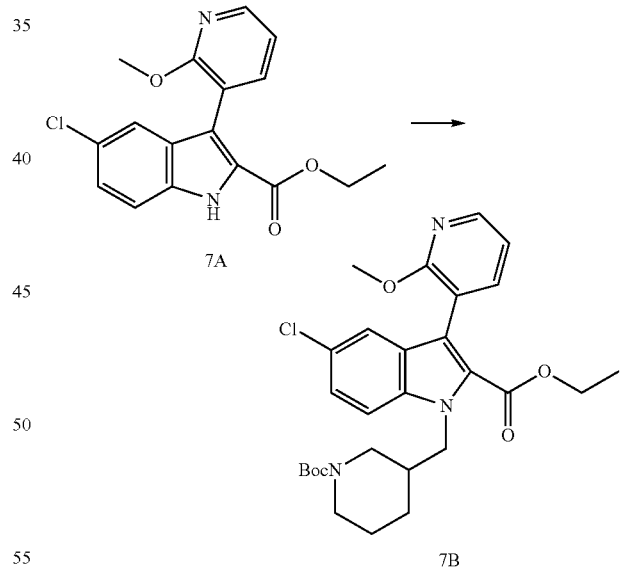

7A

7B

To a solution of 5-chloro-3-(2-methoxy-pyridin-3-yl)-1H-indole-2-carboxylic acid ethyl ester, 7A (500 mg, 1.51 mmol) in DMF (3 mL) were added 1-N-boc-3-bromomethylpiperidine, (500 mg, 1.78 mmol) and cesium carbonate. The resulting suspension was allowed to stir at 50° C. for 20 hours. The mixture was cooled down to room temperature, diluted with ethyl acetate (100 mL), and washed with water (3×20 mL). The organic layer was dried over sodium sulfate, filtered and concentrated in vacuo. The resulting residue was purified using Combiflash chromatography on silica gel using 0-10% ethyl acetate in hexanes to provide compound 7B (780 mg, 97% yield). ¹H NMR (500 MHz, CDCl3) δ 8.21 & 8.20 (dd, J=1.89 Hz & 5.04 Hz, 1H), 7.61 & 7.60 (dd, J=1.58 Hz & 7.25 Hz, 1H), 7.41 (d, J=1.58 Hz, 1H), 7.33 (d, J=8.51 Hz, 1H), 7.31 & 7.29 (dd, J=1.89 Hz & 8.83 Hz, 1H), 7.01 (q, J=5.04 Hz & 2.21 Hz, 1H), 4.48 (s, 2H), 4.14 (q, J=6.94 Hz & 7.25 Hz, 2H), 3.94 (d, J=13.24 Hz, 1H), 3.86 (s, 3H), 2.78-2.72 (m, 1H), 2.63 (t, J=11.67 Hz, 1H), 1.58 (s, 6H), 1.38 (s, 9H), 1.00 (t, J=7.09 Hz, 3H).

Step 2:

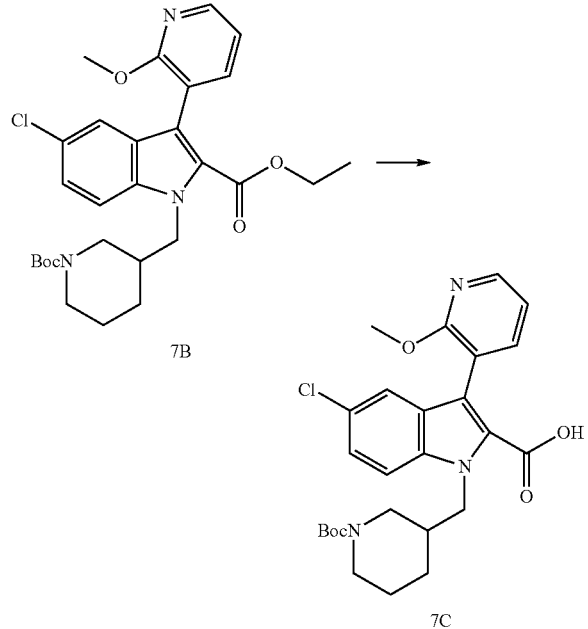

To a solution of 1-(1-tert-butoxycarbonyl-piperidin-3-yl-methyl)-5-chloro-3-(2-methoxy-pyridin-3-yl)-1H-indole-2-carboxylic acid ethyl ester, 7B (370 mg, 0.70 mmol) in THF (50 mL) was added an aqueous solution of lithium hydroxide (2.0 mL of 1 M, 2.0 mmol). The resulting mixture was allowed to stir at reflux for 2 days before cooled down to room temperature. The mixture was concentrated in vacuo. The resulting residue was dissolved into methanol (5 mL), neutralized with aqueous 1.0 M HCl solution (2.0 mL, 2.0 mmol) and then concentrated again under reduced pressure. The resulting residue was triturated with ethyl acetate (3×30 mL), and the combined organic layer was concentrated and dried on house vacuum to provide compound 7C (290 mg, 83% yield).

Example 8

Preparation of Compound 8E

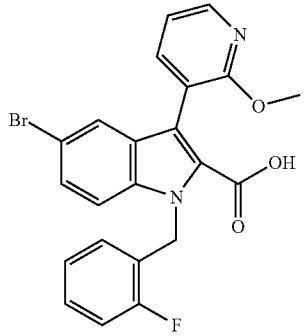

Step 1:

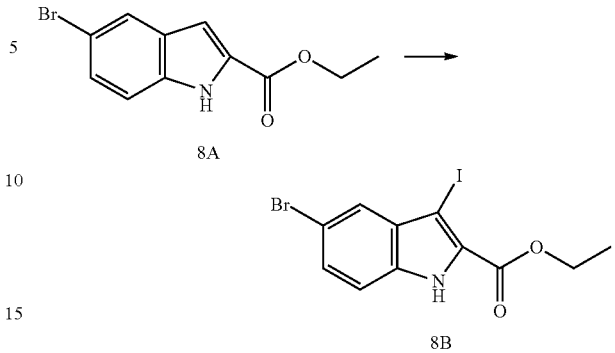

Ethyl 5-bromo 2-indole carboxylate, 8A (4.0 g, 14.9 mmol) was dissolved into acetone (200 mL) at room temperature. To the mixture was added N-iodosuccinimide (3.65 g, 15.4 mmol). The resulting suspension was allowed to stir at room temperature for 3 hours. The mixture was concentrated in vacuo, and the resulting residue was dissovled into ethyl acetate (150 mL). The mixture was washed with saturated aqueous sodium thiosulfate solution (50 mL). The layers were separated, and the aqueous layer was extracted with ethyl acetate (2×100 mL). The combined organic layer was dried (magnesium sulfate), filtered and concentrated in vacuo to provide the crude product 8B (100% yield). ¹H NMR (400MHz, d₆-DMSO): δ 12.48 (s, 1H), 7.55 (s, 1H), 7.45-7.44 (m, 2H), 4.39 (q, J=6.59 Hz & 7.32 Hz, 2H), 1.38 (t, J=7.32 Hz, 3H).

Step 2:

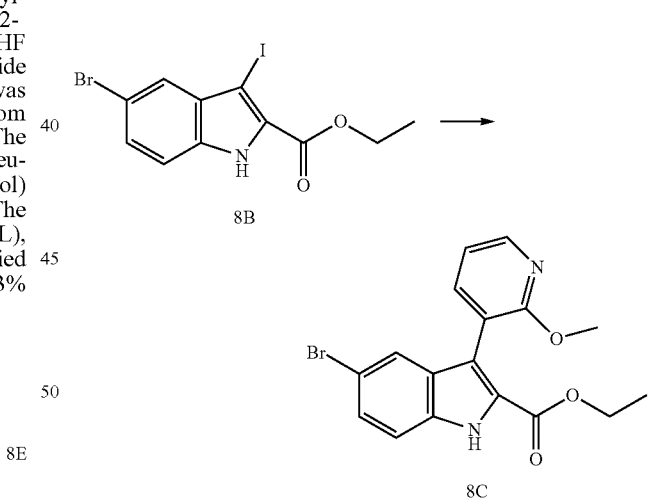

5-Bromo-3-iodo-1H-indole-2-carboxylic acid ethyl ester, 8B (8.66 g, 21.9 mmol) was dissolved into 1,2-dimethoxyethane (400 mL). And PdCl₂(dppf)₂ (1.80 g, 2.20 mmol) was added. The resulting mixture was de-gassed with nitrogen bubbling for 5 minutes before it was heated to 90° C. and stirred for 15 minutes. In a second flask, the mixture of 2-methoxy-3-pyridine boronic acid (3.72 g, 24.3 mmol) and potassium carbonate (15.2 g, 110 mmol) in dimethoxyethane (100 mL) and water (100 mL) was de-gassed with nitrogen bubbling for 5 minutes. The mixture was then transferred in three portions to the first flask. The resulting bi-phasic mixture was vigorously stirred at 90° C. for 3.5 h before it was cooled to room temperature. The reaction was quenched by addition of a solution of sodium sulfite (15 g) in water (200 mL) at room temperature. Ethyl acetate (200 mL) was added, and the layers were separated. The aqueous layer was extracted with ethyl acetate (2×300 mL). The combined organic layer was dried (magnesium sulfate), filtered and concentrated in vacuo to provide the crude product 8C (100% yield). M.S. calc'd for C17H15BrN2O3: 375.22. Found: 377.00.

Step 3:

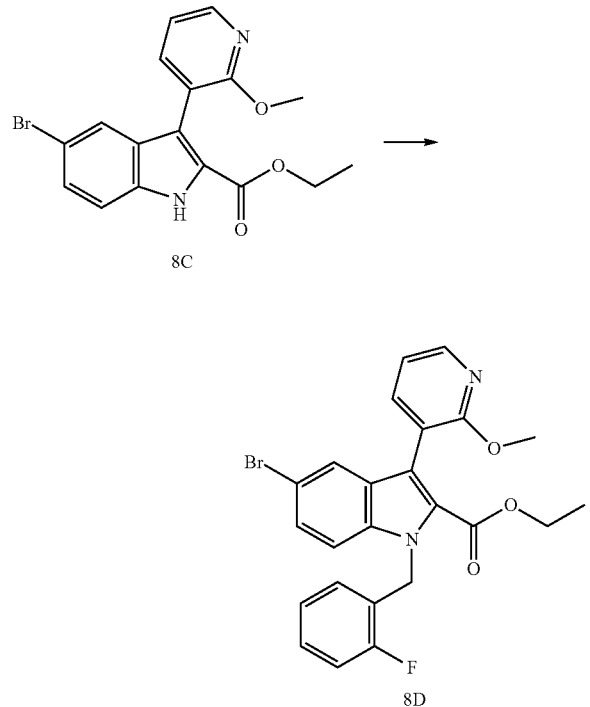

8C

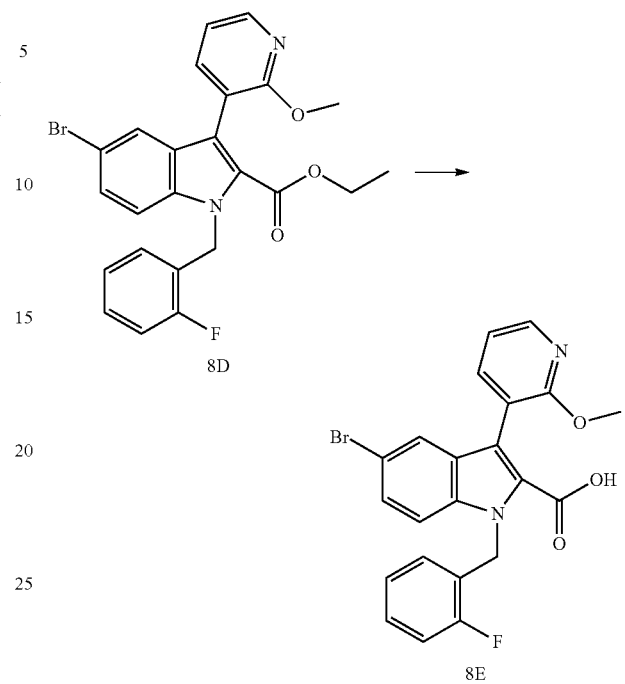

8D

5-Bromo-3-(2-methoxy-pyridin-3-yl)-1H-indole-2-carboxylic acid ethyl ester, 8C (0.66 g, 1.59 mmol) was dissolved into DMF (50 mL) at room temperature. To the mixture were added 2-fluorobenzyl bromide (0.42 g, 2.23 mmol) and cesium carbonate (0.84 g, 2.40 mmol). The resulting suspension was allowed to stir at room temperature for 18 hours. Ethyl acetate (200 mL) and water (100 mL) were added to the reaction mixture, and the layers were separated. The aqueous layer was extracted with ethyl acetate (2×100 mL). The combined organic layer was washed with water (2×100 mL). The separated organic layer was dried (magnesium sulfate), filtered and concentrated in vacuo to provide the crude product. The crude product was purified using flash chromatography to provide product 8D (0.32 g, 42% yield). M.S. calc'd for C24H2ON2O3BrF: 483.33. Found: 485.3.

Step 4:

8D

8E

To a solution of 5-bromo-1-(2-fluoro-benzyl)-3-(2-methoxy-pyridin-3-yl)-1H-indole-2-carboxylic acid ethyl ester, 8D (0.32 g, 0.66 mmol) in methanol (5 mL) was added lithium hydroxide monohydrate (110 mg, 2.64 mmol). And water (0.2 mL) was added to improve the solubility. The resulting suspension was allowed to stir at room temperature for 5 minutes before being placed in microwave reactor for 20 minutes (120° C., high power). The mixture was concentrated in vacuo. Ethyl acetate (50 mL) and water (50 mL) were added to the residue. The aqueous layer was acidified to pH=2 by adding aqueous 1N HCl solution, and was saturated with NaCl salts. The layers were seperated, and the aqueous layer was further extracted with ethyl acetate (2×50 mL). The combined organic layer was dried (magnesium sulfate) and filtered and concentrated in vacuo to provide compound 8E (93% yield) which was used without further purification. M.S. calc'd for C22H16N2O3BrF: 455.28. Found: 456.01 (M+H)+.

Example 9

Preparation of Compound 77

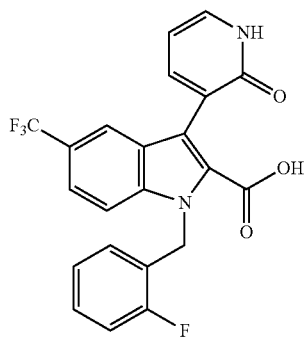

77

Step 1:

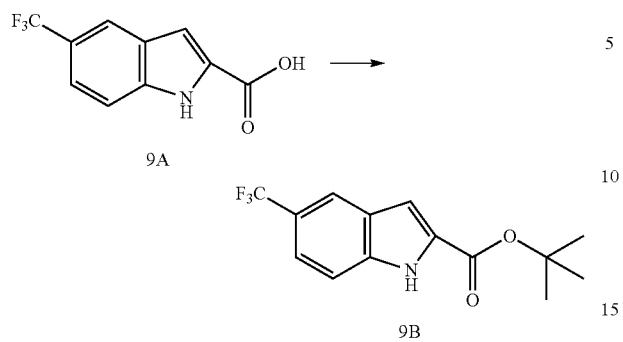

To a solution of 5-(trifluoromethyl)indole-2-carboxylic acid, 9A (1.6 g, 6.9 mmol) in toluene (5.0 mL) at room temperature was added N,N-dimethylformamide di-tert-butyl acetal (5.0 mL). The mixture was allowed to stir at 90° C. for 12 hours, and then was cooled to room temperature. Another aliquot of N,N-dimethylformamide di-tert butyl acetal (5 mL) was added. The reaction mixture was heated to 90° C. for another 12 hours, cooled to room temperature, and was diluted with ethyl acetate (10 mL). The mixture was washed with water (2×10 mL), and brine respectively. The separated organic layer was dried over MgSO$_4$, filtered and concentrated to yield the product 9B (1.2 g, 60% yield). $^1$H NMR (400 MHz, CDCl$_3$): δ9.17 (s, 1H), 7.97 (s, 1H), 7.51 (s, 2H), 7.21 (s, 1H), 1.63 (s, 9H).

Step 2:

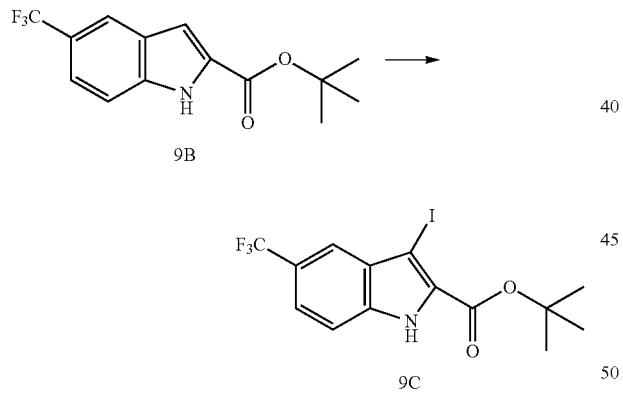

To a solution of 5-trifluoromethyl-1H-indole-2-carboxylic acid tert-butyl ester, 9B (1.2 g, 4.2 mmol) in CHCl$_3$ (25 mL) was added N-iodosuccinimide (946 mg, 4.2 mmol). The reaction mixture was allowed to stir at room temperature for 12 hours, before it was concentrated in vacuo. The resulting residue was diluted into water (100 mL), and was extracted with EtOAc (200 mL). The separated organic layer was dried over MgSO$_4$, filtered, and concentrated in vacuo. The brown resulting residue was taken in minimum amount of CH$_2$Cl$_2$ and triturated with hexanes. The product 9C was separated out as a brown solid after filtration, and dried in vacuo (1.23 g, 72% yield), $^1$H NMR (400 MHz, CDCl3): δ 9.34 (s, 1H), 7.87 (s, 1H), 7.57 (d, J=8.06 Hz, 1H), 7.49 (d, J=8.79 Hz, 1H), 1.68 (s, 9H).

Step 3:

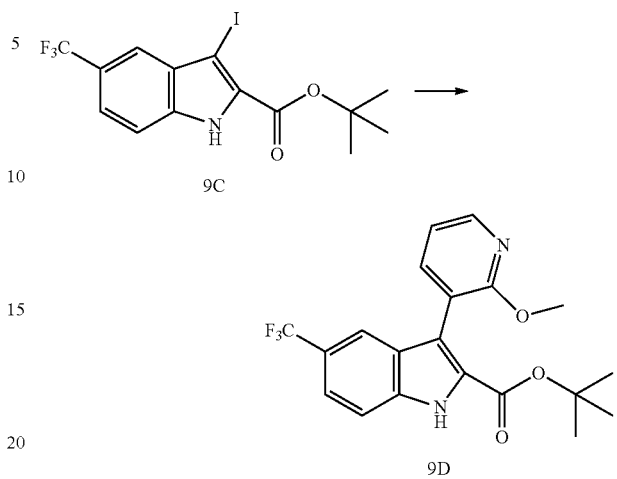

To a solution of 3-iodo-5-trifluoromethyl-1H-indole-2-carboxylic acid tert-butyl ester, 9C (1.23 g, 3.0 mmol) in DME (30 mL) under nitrogen atmosphere was added 2-methoxy-3-pyridyl boronic acid (0.48 g, 3.15 mmol) and Pd(dppf)$_2$Cl$_2$ (245 mg, 0.3 mmol). The resulting reaction was allowed to stir at room temperature under nitrogen for 0.5 hours. The reaction mixture was then treated with a solution of potassium carbonate (1.6 g, 12 mmol) in water (12 mL), and the resulting solution was allowed to stir at 90° C. for 1 hour. The reaction mixture was then diluted with EtOAc (200 mL), and the resulting solution was concentrated in vacuo. The resulting residue was purified using flash column chromatography to provide the product 9D (820 mg, 70% yield). M.S. found for C20H19F3N2O3: 393.2 (M+H)$^+$.

Step 4:

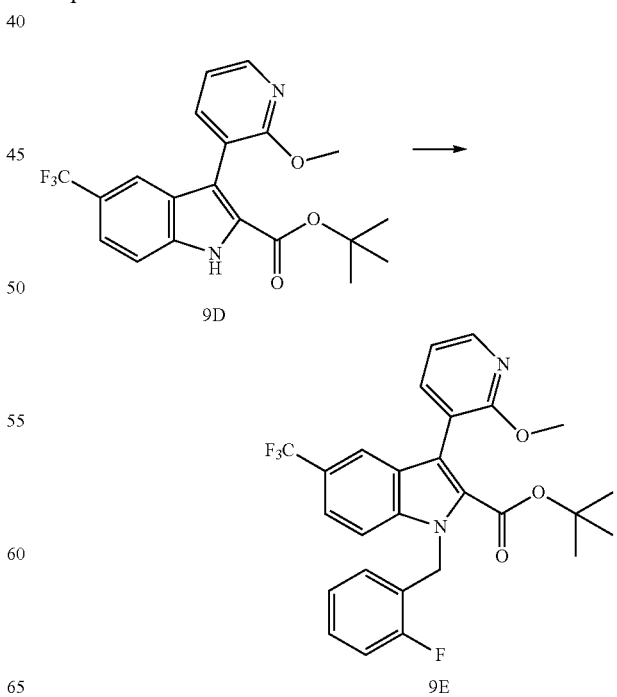

To a solution of 3-(2-methoxy-pyridin-3-yl)-5-trifluoromethyl-1H-indole-2-carboxylic acid tert-butyl ester, 9D (400 mg, 1.02 mmol) in DMF (8 mL) were added 2-fluorobenzyl bromide (0.14 mL, 1.12 mmol) and cesium carbonate (365 mg, 1.12 mmol). The resulting mixture was allowed to stir at room temperature for 18 hours. Ethyl acetate (200 mL) and water (100 mL) were added to the reaction mixture, and the layers were separated. The organic layer was washed with water (2×100 mL) and brine (50 mL). The separated organic layer was dried over sodium sulfate, filtered and concentrated in vacuo to provide the crystallized product 9E (100% yield). M.S. found for C27H24F4N2O3: 501.11 (M+H)+.

Step 5:

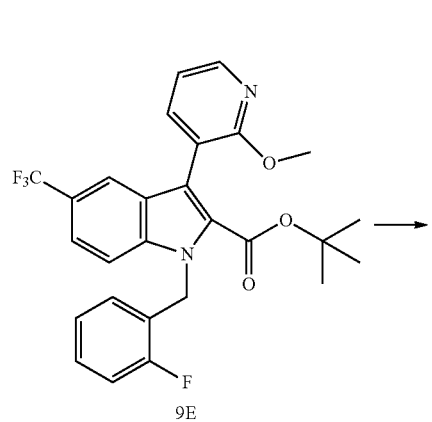

9E

To a solution of 1-(2-fluoro-benzyl)-3-(2-methoxy-pyridin-3-yl)-5-trifluoromethyl-1H-indole-2-carboxylic acid tert-butyl ester, 9E (510 mg, 1.02 mmol) in CH2Cl2 was added trifluoroacetic acid (3 mL). The reaction mixture was allowed to stir at room temperature for 18 hours. The solvent was removed under reduced pressure. The resulting residue was dissolved into ethyl acetate (200 mL). The ethyl acetate solution was washed with water (4×50 mL) and brine. The separated organic layer was dried over sodium sulfate, filtered and concentrated in vacuo to provide compound 9F (100% yield). M.S. found for C23H16F4N2O3: 445.06 (M+H)+.

Step 6:

9F

Compound J5 was stirred with 1 N HCl overnight to afford compound 77. MS=431 (M+H).

Example 10

Preparation of Compound 170

170

Step 1:

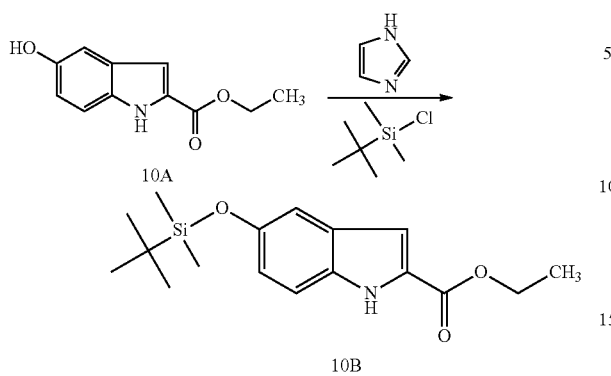

A solution of ethyl 5-hydroxy-1H-indole-2-carboxylate (10A, 6.0 g; 29.24 mmol) in 300 mL of dichloromethane was treated with imidazole (4.0 eq, 7.96 g) and tert-butyldimethylsilyl chloride (2.0 eq, 8.82 g). The reaction was allowed to stir at room temp for 3 hours. A small sample (1 mL) was taken from reaction mixture, diluted with dichloromethane (10 mL) and washed with water. Evaporation of the solvent and NMR analysis showed all starting material had been consumed. The reaction mixture was diluted with dichloromethane (300 mL) and washed with water (2×100 mL) and brine (100 mL) The organic layer was dried over magnesium sulfate, filtered and concentrated to provide compound 10B (9.20 g; 98%) as a white solid.

Step 2:

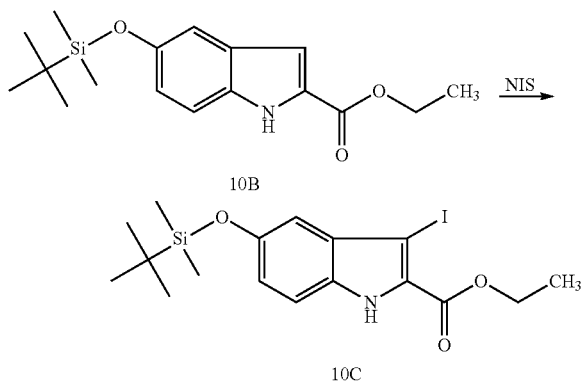

A solution of ethyl 5-tert-butyldimethylsilyloxy-1H-indole-2-carboxylate 10B (9.0 g) in 300 mL of chloroform was ice-cooled and treated with N-iodosuccinimide (1.1 eq, 6.97 g). The mixture was allowed to stir at 0° C. for 10 minutes and then at room temp for 2 hours. NMR analysis of a small aliquot showed complete conversion of starting material. The reaction mixture was diluted with dichloromethane (300 mL) and washed with aq saturated sodium thiosulfate (150 mL), aq saturated sodium bicarbonate (150 mL) and brine (100 mL). The organic layer was dried over magnesium sulfate, filtered and concentrated to provide compound 10C (11.58 g; 92%) as a white solid. M.S. found for C17H24INO3Si: 446.36 (M+H)$^+$.

Step 3:

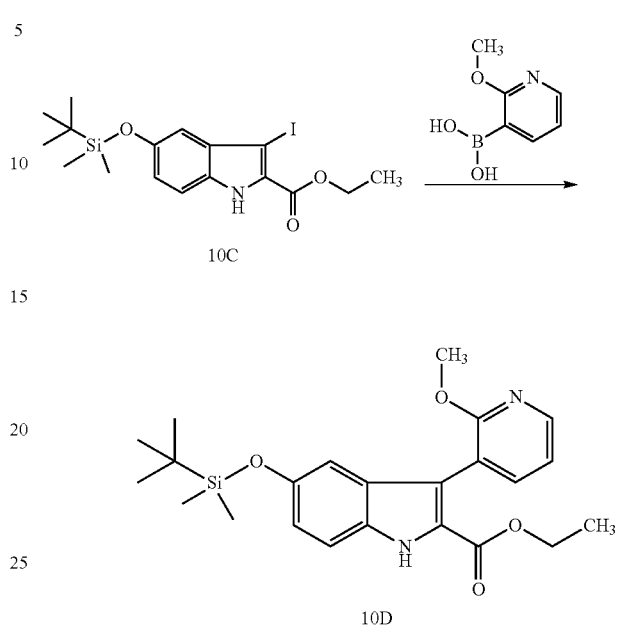

The 2-methoxy-3-pyridine boronic acid (1.05 eq, 3.27 g) was added to a solution of 10C (9.06 g; 20.345 mmol) in 100 mL of 1,2-dimethoxyethane. The mixture was degassed (vacuum/argon flush) and PdCl$_2$(dppf)$_2$ (10 mol %, 1.66 g) was added and the resulting orange solution was allowed to stir for 30 minutes at room temp. A solution of potassium carbonate (4.0 eq, 81 mL of aq 1M soln) was added and the resulting brown solution was allowed to stir at 90° C. for 2 hours. The reaction mixture was cooled to room temperature and concentrated. The resulting residue was diluted with ethyl acetate (600 mL) and washed with aq saturated sodium bicarbonate (100 mL) and brine (100 mL). The organic layer was dried over magnesium sulfate, filtered and concentrated. The resulting residue was divided into two equal portions and each was purified using silica gel chromatography (Biotage 75-M column; gradient: 0 to 30% ethyl acetate in hexanes) to provide compound 10D as a white solid (6.76 g; 65%). M.S. found for C23H30N2O4Si: 427.56 (M+H)$^+$.

Step 4:

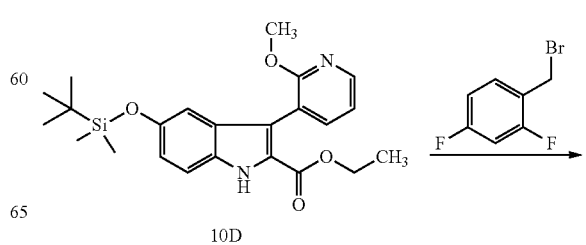

-continued

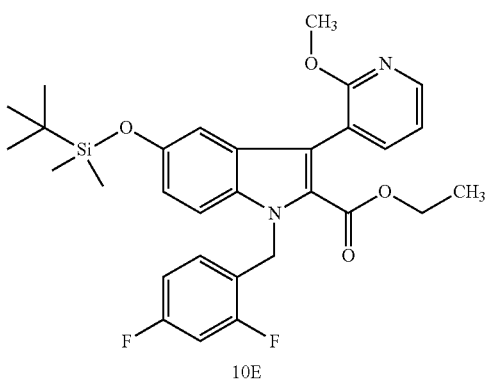

10E

A solution of indole derivative 10D (6.5 g, 15.237 mmol) in 50 mL of dry THF was added to an ice-cooled suspension of sodium hydride (1.3 eq, 792 mg of 60% susp in mineral oil) in 50 mL of dry THF. The resulting solution was allowed to stir for 10 minutes followed by addition of 2,4-difluorobenzyl bromide (1.3 eq, 2.54 mL, d 1.613). A catalytic amount of tetrabutylammonium iodide (0.2 eq, 1.12 g) was added to the reaction mixture and stirring was continued for 18 h (temperature from 0 to 25° C.). The reaction was quenched by addition of water (10 mL) and the mixture was diluted with ethyl acetate (500 mL). The organic layer was washed with water (2×100 mL) and brine (80 mL), dried over magnesium sulfate, filtered and concentrated to afford the crude product 10E as a colorless foam contaminated with undesired bis-N,O-difluorobenzyl product. The crude mixture was used for next reaction without further any further purification. M.S. found for C30H34N2O4Si: 553.65 (M+H)$^+$.

Step 5:

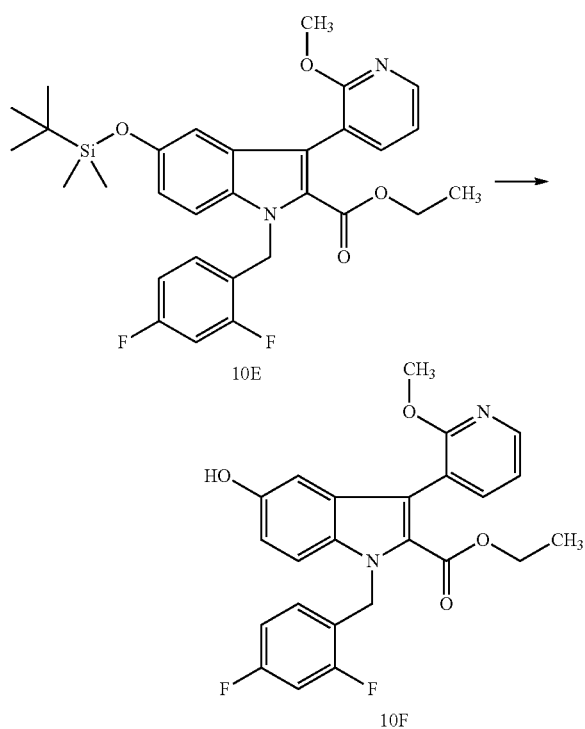

A solution of crude silylether 10E (15.237 mmol; 8.4 g) in 100 mL of THF (NOTE: 10E contains an impurity identified as the bis-N,O-difluorobenzyl compound) was ice-cooled and treated with ca 1.0 eq of TBAF (15 mL of 1.0M soln in THF). The mixture immediately turned yellow-green in color and TLC after 5 minutes (30% ethyl acetate in hexanes) showed no more starting material left. The mixture was diluted with ethyl acetate (500 mL) and washed with water (100 mL), aq saturated sodium bicarbonate (100 mL) and brine (100 mL). The organic layer was dried over magnesium sulfate, filtered and concentrated. The resulting residue was purified using silica gel chromatography (Biotage 75-M column; gradient: 10 to 50% ethyl acetate in hexanes) to provide compound 10F as a white solid (5.8 g; 88% for two steps). $^1$H NMR (400 MHz, d$_6$-DMSO): δ 9.09 (s, 1H), 8.17 & 8.16 (dd, J=2.20 & 5.13 Hz, 1H), 7.71 & 7.69 (dd, J=1.46 & 7.32 Hz, 1H), 7.45 (d, J=8.79 Hz, 1H), 7.26 (t, J=10.98 Hz, 1H), 7.10-7.06 (m, 1H), 6.97 (dt, J=8.79 & 2.20 Hz, 1H), 6.88 & 6.86 (dd, J=8.79 & 2.20 Hz, 1H), 6.76-6.71 (m, 1H), 6.67 (d, J=2.20 Hz, 1H), 5.77 (s, 2H), 3.99 (q, J=7.32 Hz, 2H), 3.75 (s, 3H), 0.85 (t, J=7.32 Hz, 3H).

Step 6:

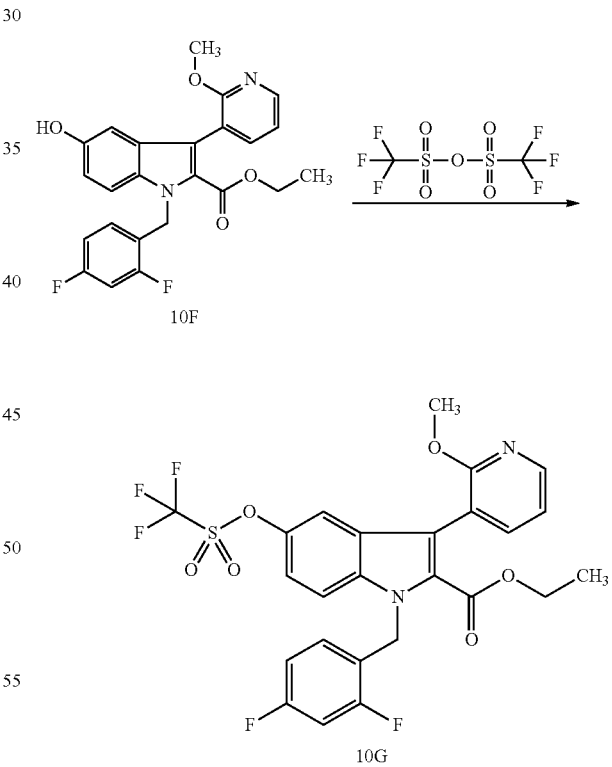

A solution of 1-(2,4-Difluoro-benzyl)-5-hydroxy-3-(2-methoxy-pyridin-3-yl)-1H-indole-2-carboxylic acid ethyl ester 10F (2.0 g; 4.56 mmol) in 20 mL of dry dichloromethane was ice cooled and treated with pyridine (4 mL) and triflic anhydride (2.1 eq, 1.61 mL, d 1.677). The mixture was allowed to stir for 10 minutes and treated with a catalytic amount of 4-dimethylamino pyridine. The cooling bath was removed and the reaction was allowed to stir for 2 hours. TLC (10% ethyl acetate in hexanes) showed no more starting material left and the mixture was diluted with ethyl acetate (200 mL) and washed with water (50 mL) and brine (50 mL). The organic layer was dried over magnesium sulfate, filtered and concentrated. The resulting residue was purified using silica gel chromatography (Biotage 40-M column; gradient: 0 to 20% ethyl acetate in hexanes) to provide compound 10G (2.50 g; 96%) as a colorless oil. MS found for C25H19F5N2O6S: 571.12 (M+H)$^+$.

Step 7:

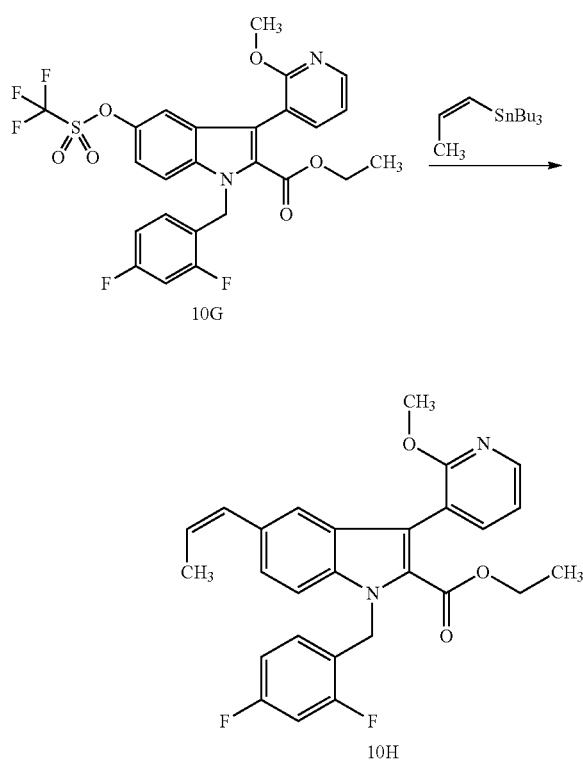

A solution of 1-(2,4-difluoro-benzyl)-3-(2-methoxy-pyridin-3-yl)-5-trifluoromethanesulfonyloxy-1H-indole-2-carboxylic acid ethyl ester 10G (650 mg; 1.13 mmol) in 10 mL of THF was treated with lithium chloride (7.0 eq, 336 mg) and (Z)-1-propenyltributyl stannane (1.5 eq, 0.51 mL, d 1.1). The mixture was degassed (vacuum/nitrogen flush) and tetrakis (triphenylphosphine)palladium was added (10 mol %, 130 mg). The reaction mixture was heated to 70° C. and stirred overnight. TLC (10% ethyl acetate in hexanes) and MS analyses showed complete conversion of starting material. The mixture was diluted with ethyl acetate (80 mL) and washed successively with water (10 mL), 10% aq ammonium hydroxide (10 mL), water (10 mL), and brine (10 mL). The organic layer was dried over magnesium sulfate, filtered and concentrated in rotavap. The resulting residue was purified using silica gel chromatography (Biotage 25-M column; gradient: 80 mL of hexanes then 0 to 25% ethyl acetate in hexanes) to provide compound 10H (400 mg; 77%) as a colorless oil. MS found for C27H24F2N2O3: 463.30 (M+H)$^+$.

Step 8:

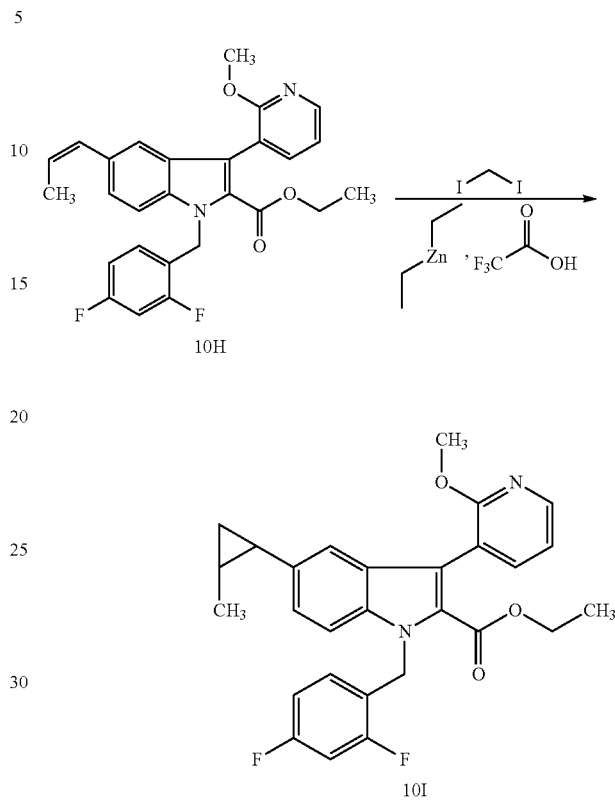

To a vigorously stirred solution of diethylzinc (10.0 eq, 3.9 mL of 1M soln in heptane) in 2 mL of dry dichloromethane at 0° C. (ice-water bath) was added dropwise a solution of trifluoroacetic acid (10.0 eq, 0.299 mL, d 1.480) in 0.5 mL of dichloromethane. The resulting mixture was allowed to stir for 10 minutes after which a solution of diiodomethane (10.0 eq, 0.31 mL, d 3.325) in 0.5 mL of dichloromethane was added dropwise. The mixture was allowed to stir for 10 minutes followed by addition of a solution of 1-(2,4-difluoro-benzyl)-3-(2-methoxy-pyridin-3-yl)-5-prop-Z-enyl-1H-indole-2-carboxylic acid ethyl ester 10H (180 mg; 0.389 mmol) in 1 mL of dry dichloromethane. The reaction was allowed to stir at 0° C. and monitored by TLC and MS analyses (NOTE: Rf of starting material and product is the same in different solvent systems). After 4 h the reaction was quenched by addition of aq saturated sodium bicarbonate (10 mL). The mixture was extracted with ethyl acetate (50 mL). The organic layer was washed with aq 1M HCl (10 mL), aq saturated sodium bicarbonate (10 mL), and brine (10 mL). The organic layer was dried over magnesium sulfate, filtered and concentrated. The resulting residue was purified using silica gel chromatography (Biotage 12-S column, gradient: 0 to 20% ethyl acetate in hexanes) to provide compound 10I as a colorless oil. M.S. found for C28H26F2N2O3: 477.26 (M+H)$^+$.

Step 9:

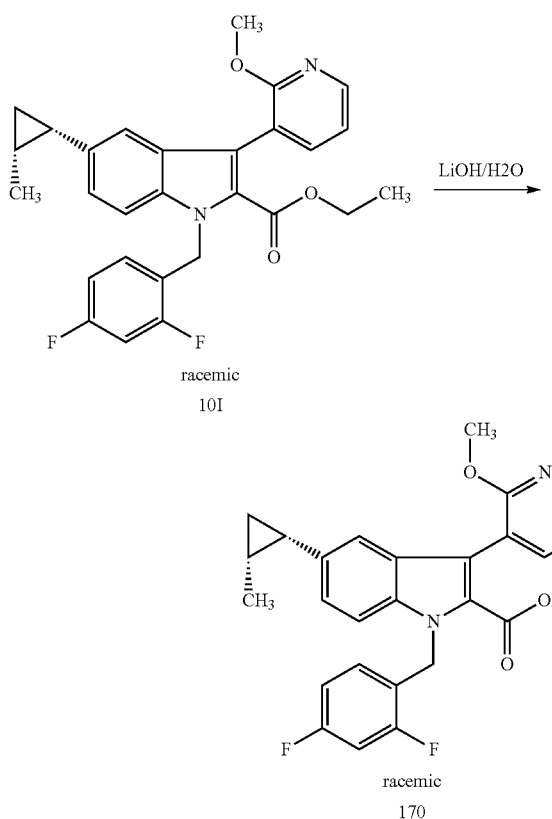

A solution of 1-(2,4-difluoro-benzyl)-3-(2-methoxy-pyridin-3-yl)-5-(2-cis-methyl-cyclopropyl)-1H-indole-2-carboxylic acid ethyl ester 10I (230 mg; 0.482 mmol) in 10 mL of a 5:1:1 THF/water/methanol mixture was treated with lithium hydroxide monohydrate (5.0 eq, 101 mg). The mixture was heated to 50° C. for 5 hours. TLC (20% ethyl acetate in hexanes) showed complete consumption of the starting material. The mixture was diluted with aq 1M HCl (40 mL) and the product was taken into dichloromethane (3×25 mL). The combined organic layers were dried over magnesium sulfate, filtered and concentrated to provide compound 170 (205 mg; 95% yield) as a white solid.

Example 11

Preparation of Compound 169

Step 1:

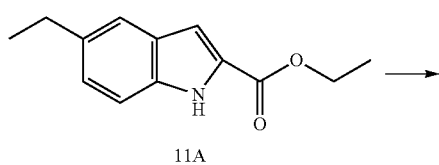

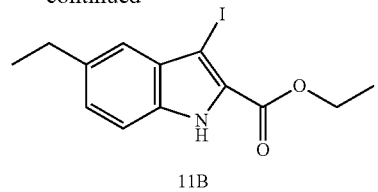

The starting materials 11A (15.0 g, 69.04 mmol) and THF (100 mL) were added to a 1000 ml round-bottomed flask. The resulting solution was cooled with a water bath. To this stirring solution, MS (15.30 g, 68.80 mmol) was added slowly. The resulting solution was allowed to stir at room temperature for 5 hours before 700 ml of water was added. The resulting mixture was continued to stir at room temperature for 30 minutes and then filtered. The cake was washed with water (2×40 mL), dried by air and then on house vacuum to provide compound 11B as an off-white solid (23.0 g, 97%). MS found 344.2 for $C_{13}H_{14}INO_2+H^+$.

Step 2:

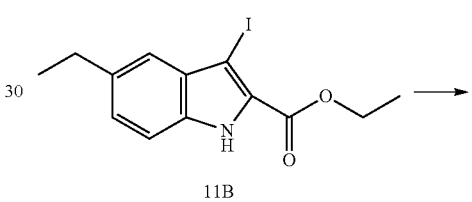

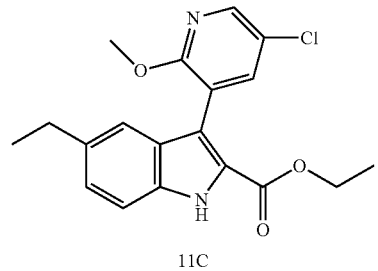

A 250 ml round-bottomed flask was charged with 11B (3.60 g, 10.49 mmol), 5-chloro-2-methoxypyridine-3-boronic acid (2.0 g, 10.67 mmol), [1,1'-bis(diphenylphosphino)ferrocene]dichloropalladium(II) complex with dichloromethane (1:1) (0.87 g, 1.06 mmol), and DME (50 mL). To the stirring solution, a solution of sodium carbonate (10 ml of 1.5 M, 15.0 mmol) was added via a syringe. The reaction mixture was maintained at reflux for 6 hours before cooled to room temperature. After concentration, the resulting residue was taken up with ethyl acetate (200 mL), washed with water (100 mL), and dried over sodium sulfate. The solvent was removed by distillation under reduced pressure and the resulting residue was purified using Combiflash chromatography on silica gel using 0-10% ethyl acetate in hexanes as the solvent to provide the product 11C as a white solid (2.4 g, 64%). M.S. found for $C_{19}H_{19}ClN_2O_3$: 359.2 $(M+H)^+$.

Step 3:

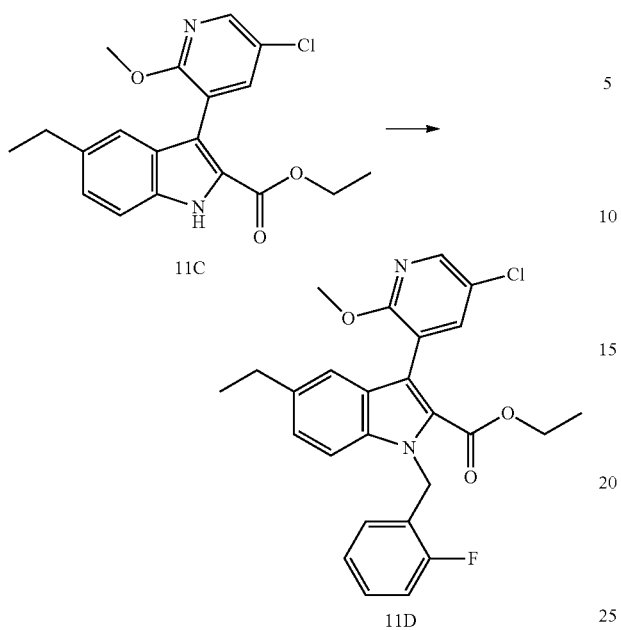

A suspension of 11C (280 mg, 0.78 mmol), 2-fluorobenzylchloride (300 mg, 2.07 mmol), cesium carbonate (400 mg, 1.23 mmol) and DMF (3 mL) was allowed to stir at room temperature for 19 hours, diluted with ethyl acetate (100 mL), and washed with water (3×50 mL). The organic solution was dried over sodium sulfate and concentrated. The resulting residue was purified using Combiflas chromatography on silica gel using 0-5% ethyl acetate in hexanes as the eluent to provide compound 11D as a gel (318 mg, 87%).

Step 4:

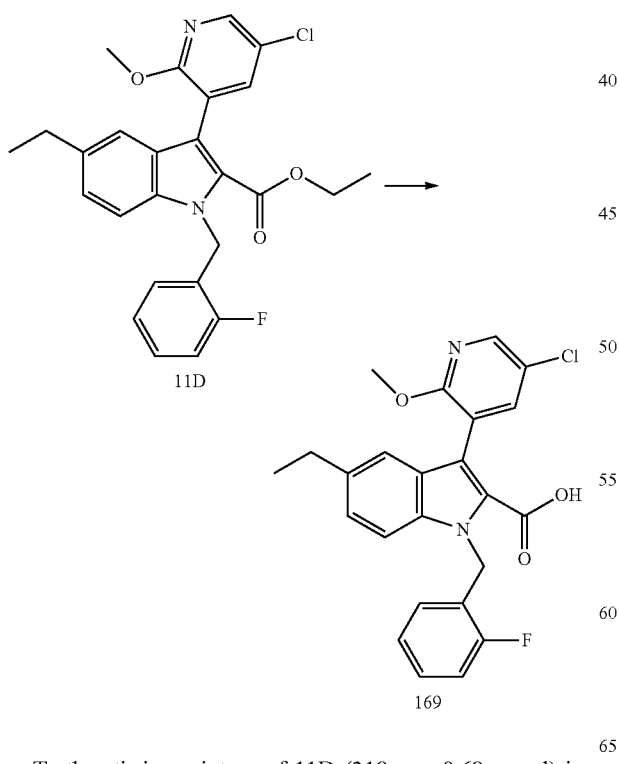

To the stirring mixture of 11D (318 mg, 0.68 mmol) in TI-LF (10 mL) in a 100 ml round-bottomed flask was added with a solution of lithium hydroxide (2.0 ml of 1 M, 2.0 mmol). The resulting solution was maintained at reflux for 5 days before cooled to room temperature. After concentration in vacuo, the resulting residue was dissolved in methanol (5 mL), neutralized with 1.0 M HCl aqueous solution (2.0 mL, 2.0 mmol) and then concentrated again. The resulting residue was extracted with ethyl acetate (3×40 mL) The combined organic solutions were concentrated and dried on house vacuum to provide compound 169 as a white solid (280 mg, 94%). M.S. found for $C_{24}H_{20}ClFN_2O_3$: 439.2 $(M+H)^+$.

Example 12

Preparation of Compound 160, 161 and 162

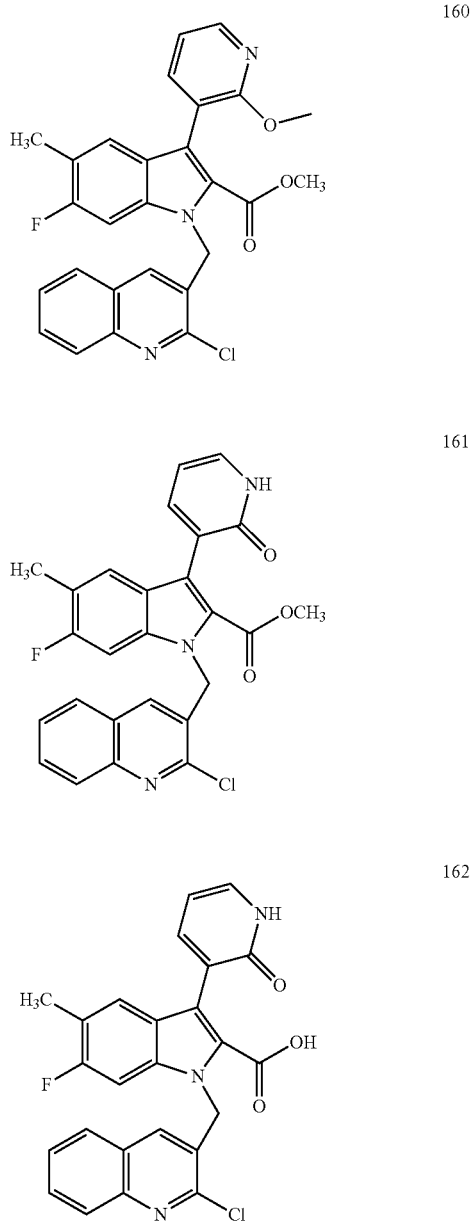

Step 1—Synthesis of Compound 12B

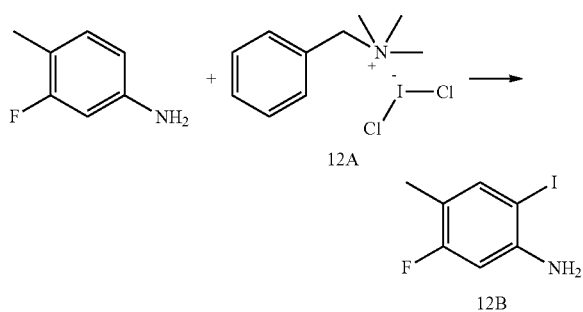

3-Fluoro-4-methylaniline (94.5 g, 755 mmol), dichloromethane (3 L), and methanol (1 L) were charged into a 5000 ml three-necked flask equipped with mechanic stirrer. The resulting solution was cooled to 0° C. using an ice-water bath and to the cooled solution was added calcium carbonate powder (151 g, 1509 mmol) followed by iodate salt 12A (275 g, 790 mmol). The resulting suspension was maintained at ~0° C. for 2 hours then the cool bath was removed and the reaction mixture warmed to room temperature while stirring for an additional 15 hours. The reaction mixture was then filtered and the filtrate was concentrated in vacuo. The resulting residue was dissolved in dichloromethane (1 L), washed sequentially with water (500 mL), saturated sodium carbonate solution (500 mL) and water (500 mL), then dried over sodium sulfate, filtered and concentrated in vacuo. The resulting brown oil residue was dried under house vacuum to provide compound 12B (179 g, 95% yield, >90% purity by NMR) which was used without further purification.

Step 2—Synthesis of Compound 12E

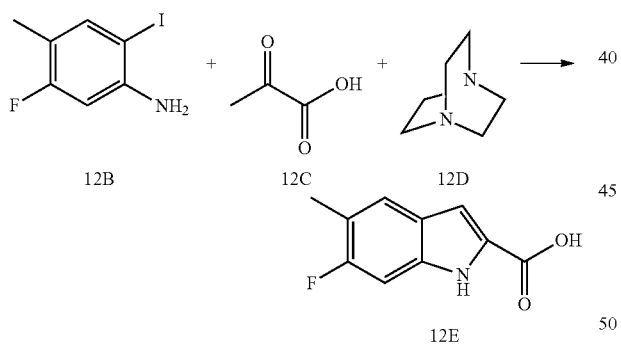

Compound 12B (74.66 g, 279 mmol) and diamine compound 12D (101.32 g, 903 mmol) were DMF (300 mL) were charged into a 1000 ml three-necked flask. The resulting solution was placed in a room temperature water bath and pyruvic acid (12C, 62.7 mL, 902 mmol) was added to the stirred solution. The resulting solution was degassed, then palladium diacetate (3.5 g, 15.6 mmol) was added and the resulting reaction mixture was degassed again, then heated to ~105° C. and allowed to stir at this temperature for 4 hours. The reaction mixture was allowed to cool to room temperature, then was partitioned between ethyl acetate (1000 mL) and water (600 mL) The aqueous phase was set aside and the organic phase was washed with brine (2×200 mL), dried over sodium sulfate, filtered and concentrated in vacuo. The resulting residue was recrystallized from ethyl acetate/hexanes to provide compound 12E as a brown solid (28.2 g). The aqueous phase was acidified to pH=3 using conc. HCl and the resulting acidic solution was extracted with ethyl acetate (2×300 mL). The combined organic extracts were washed with brine, dried over sodium sulfate, filtered and concentrated in vacuo, and the resulting residue was triturated using ethyl acetate/hexanes to provide an additional amount of compound 12E as a brown solid (18.0 g). The combined crude yield was 80% (>80% purity).

Step 3—Synthesis of Compound 12F

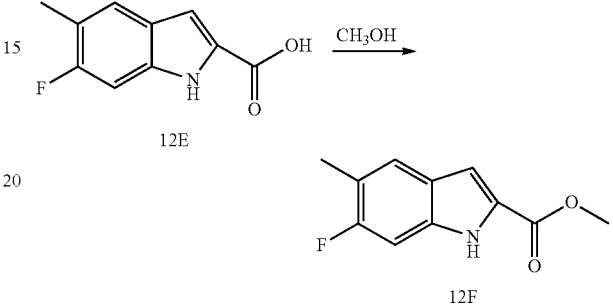

A solution of compound 12E (26.52 g, 137 mmol) in methanol (400 mL) was placed in a room temperature water bath. To the solution was slowly added thionyl chloride (30 mL) and the resulting reaction was allowed to stir maintained at room temperature for two days, then was concentrated in vacuo. The resulting residue was dissolved in ethyl acetate (300 mL), washed sequentially with brine (200 mL), saturated sodium carbonate solution (100 mL) and water (200 mL), then dried over sodium sulfate, filtered and concentrated in vacuo. The resulting residue was dried under house vacuum to provide compound 12F as a brown solid (18.6 g, 65%).

Step 4—Synthesis of Compound 12G

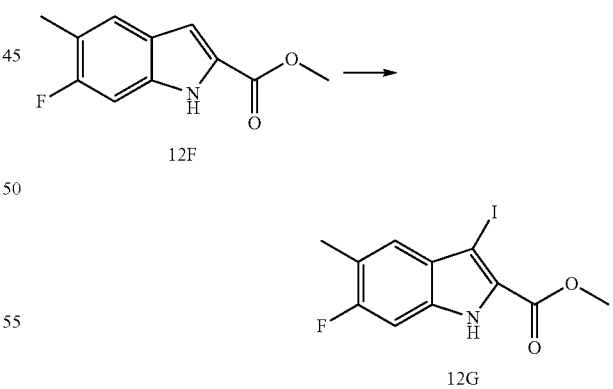

A solution of compound 12F (35.0 g, 169 mmol) in THF (200 mL) was placed in a room temperature water bath. To the solution was slowly added N-iodosuccinimide (38.0 g, 169 mmol) and the resulting reaction was allowed to stir at room temperature for 3.5 hours. Water (1500 mL) was then added to the reaction mixture and the resulting suspension was allowed to stir at room temperature for 2 hours, then filtered. The collected solid was washed with water (2×200 mL) and dried under house vacuum to provide compound 12G as a grey solid (51.5 g, 91%). MS=334 (M+H).

Step 5—Synthesis of Compound 12I

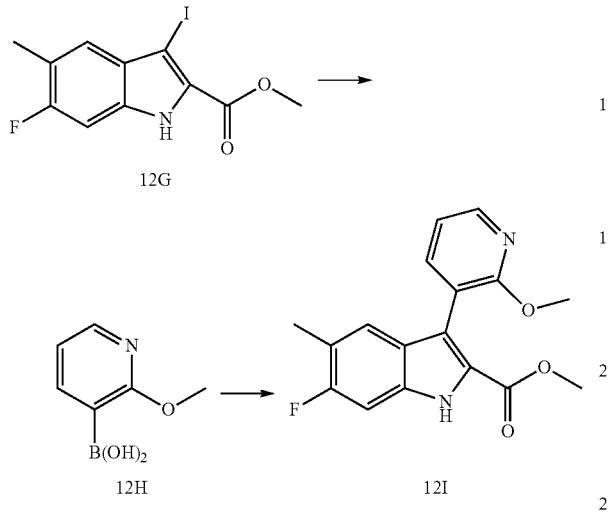

A suspension of compound 12G (25.0 g, 75 mmol), compound 12H (16.0 g, 104.6 mmol), and [1,1'-bis(diphenylphosphino)ferrocene]dichloropalladium (II) complex with dichloromethane (6.0 g, 7.34 mmol) in THF was heated to reflux and allowed to stir at this temperature for 4 hours. The reaction mixtures was then cooled to room temperature and concentrated in vacuo. The resulting residue was diluted with ethyl acetate (500 mL) and the resulting solution was washed with water (2×200 mL). The organic phase was dried over sodium sulfate, filtered and concentrated in vacuo. The residue obtained was crystallized from ethyl acetate to provide compound 12I (14.76 g, 63%) as a light brown solid. MS=315 (M+H).

Step 6—Synthesis of Compound 160

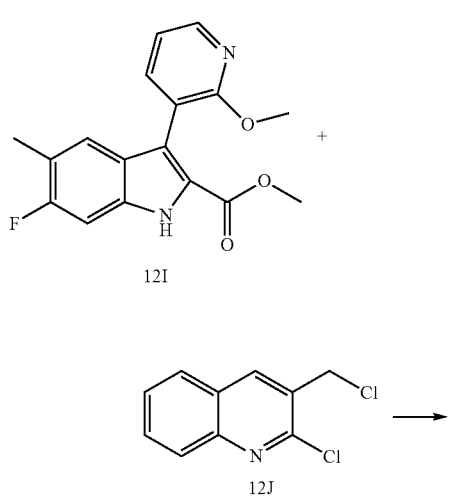

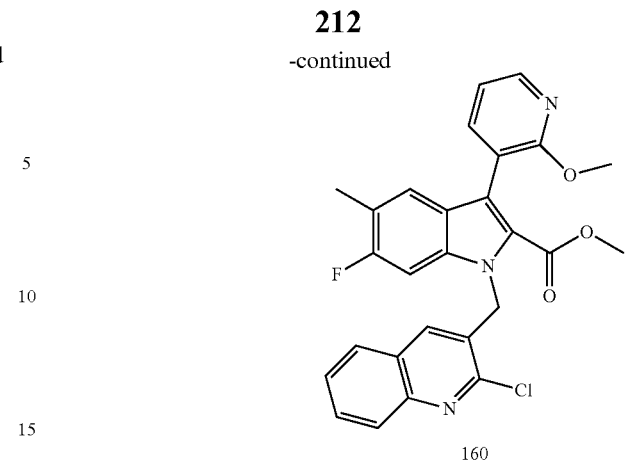

A suspension of compound 12I (3.0 g, 9.54 mmol), compound 12J (Maybridge, 2.6 g, 12.26 mmol) and cesium carbonate (7.0 g, 21.58 mmol) in DMF was allowed to stir at room temperature for about 15 hours. Ethyl acetate (300 mL) was then added to the reaction mixture and the resulting solution was washed with water (3×200 mL), dried over sodium sulfate, filtered and concentrated in vacuo. The resulting residue was purified using Combi-flash chromatography with 0-30% ethyl acetate in hexanes as the eluent to provide compound 160 as a white solid (3.6 g, 77%). MS=490 (M+H).

Step 7—Synthesis of Compound 161

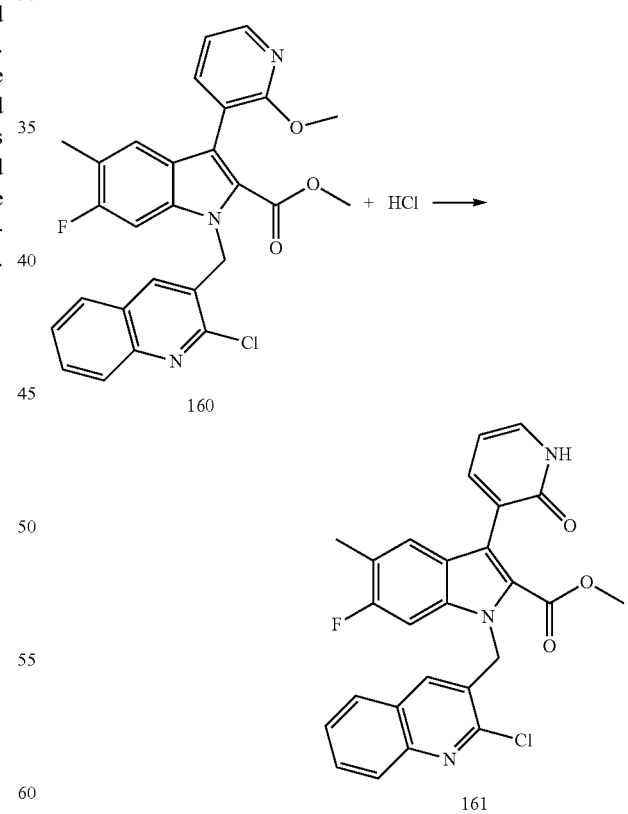

A 350 mL pressure vessel was charged with a solution of compound 160 (940 mg, 1.92 mmol) in HCl in dioxane (4.0 M, 50 mL, 200 mmol) and the resulting reaction was heated to 90° C. and allowed to stir at this temperature for 6 hours. The reaction mixture was then cooled to room temperature and concentrated in vacuo. The resulting residue was crystallized from methanol to provide compound 161 as a white solid (510 mg, 56%). MS=476 (M+H).

Step 8—Synthesis of Compound 162

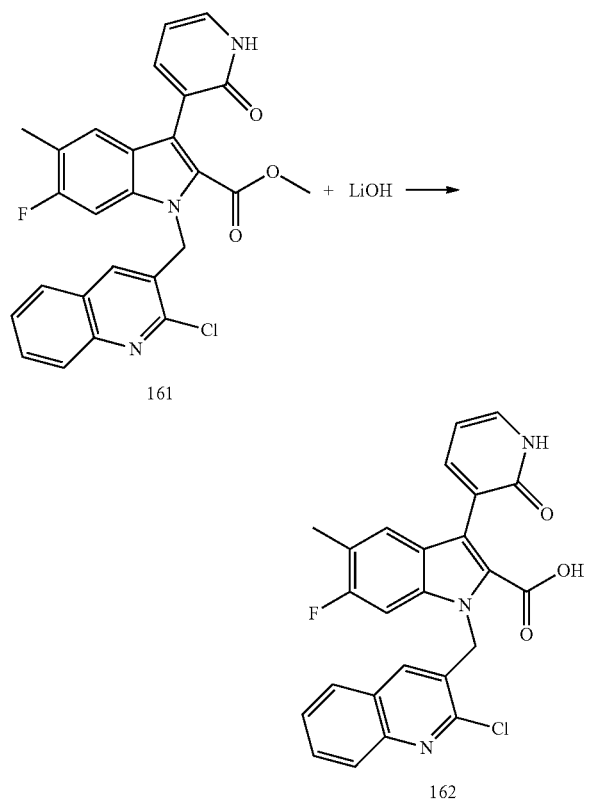

A solution of compound 161 (510 mg, 1.07 mmol), aqueous lithium hydroxide (4.0 mL, 1.0 M, 4.0 mmol), and THF (10 mL) was heated to reflux and allowed to stir at this temperature for about 15 hours. The reaction mixture was then cooled to room temperature, and the resulting suspension was concentrated in vacuo. The resulting residue was diluted with methanol (10 mL) and the resulting solution was neutralized using 1.0 M HCl (4.0 mL, 4.0 mmol), then concentrated in vacuo. The resulting solid residue was washed sequentially with water (3×10 mL), methanol (20 mL) and ethyl acetate (30 mL), then vacuum dried to provide compound 162 as a white powder (450 mg, 91%). MS=462 (M+H).

Step 9—Preparation of the Sodium Salt of Compound 162

Compound 162 (1.055 g, 2.28 mmol) was diluted with methanol (150 mL), and to the resulting suspension was slowly added aqueous sodium hydroxide (0.5 M, 4.7 mL, 2.35 mmole) with stirring. The resulting reaction was allowed to stir for 10 minutes and was then concentrated in vacuo to provide the sodium salt of compound 162. MS=485 (M+Na)

Step 10—Preparation of the Choline Salt of Compound 162

Compound 162 (0.5 g, 1.08 mmol) was dissolved in isopropanol (10 mL) and to the resulting solution was added choline hydroxide (20 wt % in water, 0.7 mL) The reaction mixture was heated slowly to about 65° C., then water (0.5 mL) was added. The reaction mixture was then filtered hot and the collected solids were washed with isopropanol. The filtrate was allowed to cool to room temperature on its own over a one hour period (during which time most of the solvent evaporated), and was then cooled in an ice bath for about 2 hours. The resulting cooled solution was then filtered and the collected solid was dried overnight in a vacuum oven to provide the choline salt of compound 162 (0.53 g, 88% yield).

Example 13

Preparation of Compound 163

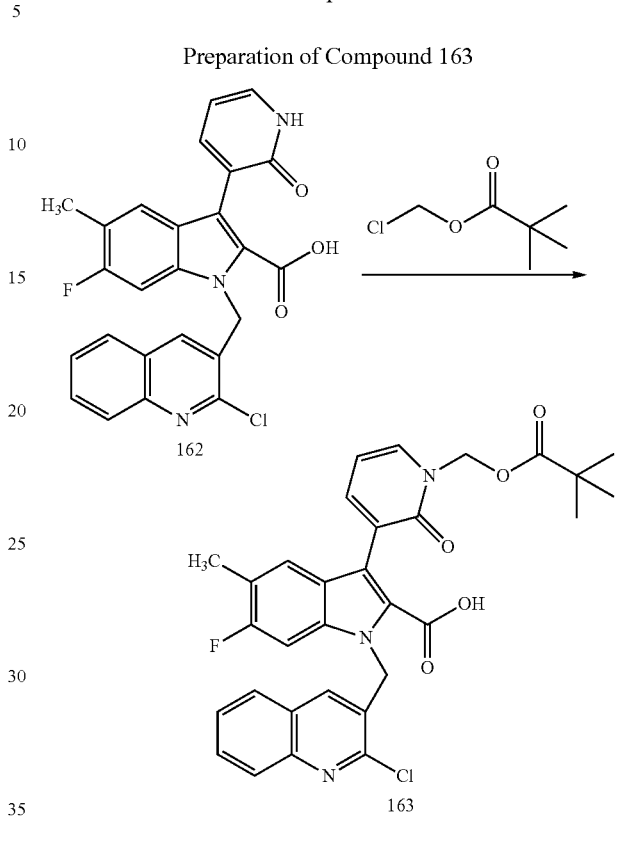

The mixture of compound 162 (100 mg, 0.217 mmol), chloromethyl pivolate (30 mg, 0.199 mmol), cesium carbonate (100 mg, 0.308 mmol), and DMF (3 mL) was allowed to stir at room temperature. After for 6 h ethyl acetate (100 mL) was added and the mixture was washed with water (3×40 mL), dried over sodium sulfate, and concentrated. The resulting residue was purified using Combi-Flash chromatography using 0-5% methanol in dichloromethane as the eluent to afford compound 163 as a white gel (33 mg, 29%). MS=576 (M+H).

Example 14

Preparation of Compound 164

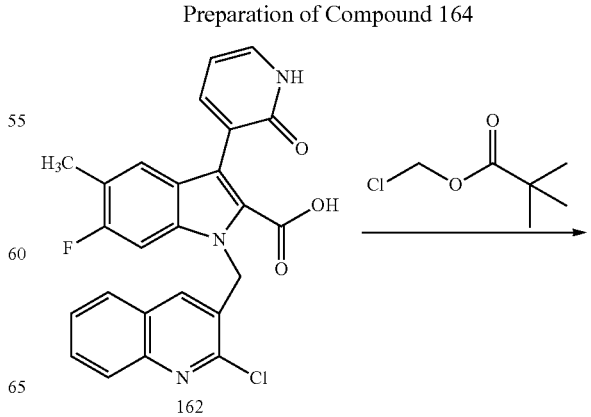

-continued

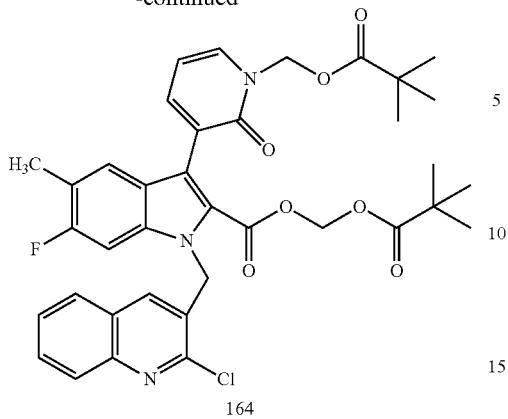
164

The mixture of 162 (70 mg, 0.152 mmol), chloromethyl pivolate (70 mg, 0.465 mmol), cesium carbonate (150 mg, 0.462 mmol), and DMF (3 mL) was allowed to stir at room temperature for 6 hours. Ethyl acetate (100 mL) was then added and the mixture was washed with water (3×40 mL), dried over sodium sulfate, and concentrated. The resulting residue was purified using Combi-Flash chromatography using 30% ethyl acetate in hexanes as the eluent to afford 164 as a white solid (26 mg, 25%). MS=690 (M+H).

Example 15

Preparation of Compound 165

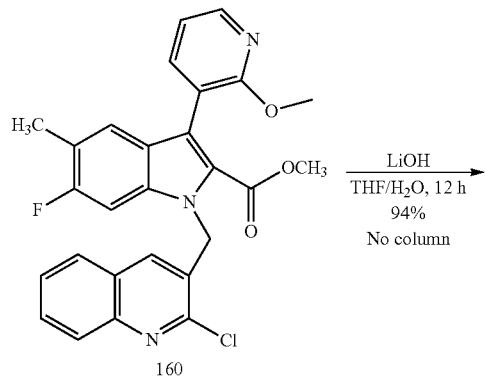

A mixture of 160 (275 mg, 0.56 mmol), aqueous lithium hydroxide (3.0 mL, 1.0 M, 3.0 mmol), and THF (4 mL) was refluxed overnight. After cooling to room temperature, the suspension was concentrated in vacuo. The resulting residue was mixed with methanol (5 mL), neutralized with 1.0 M HCl (3.0 mL, 3.0 mmol) and concentrated again. The resulting solid was extracted with ethyl acetate (3×40 mL). The combined organic solutions were concentrated and dried under vacuum to afford 165 as an orange solid (250 mg, 94%). MS=476 (M+H).

Example 16

Preparation of Compound 166

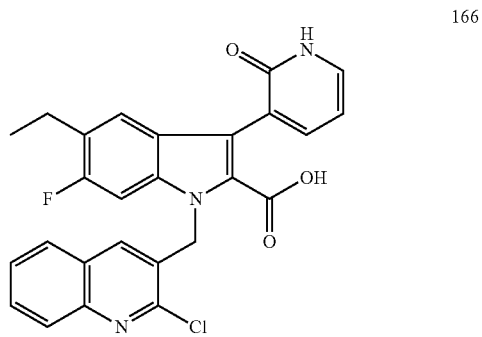 [SMILES: CCc1cc2c(-c3ccc[nH]c3=O)c(C(=O)O)n(Cc3cc4ccccc4nc3Cl)c2cc1F]
166

Step 1:

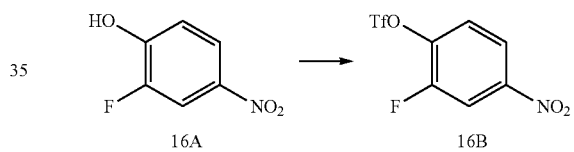
16A     16B

A solution of 2-fluoro-4-nitro-phenol (16A) (2.53 g; 16.1 mmol) in 60 mL of dry dichloromethane and 5 mL of dry THF was ice cooled and treated with pyridine (10 mL) and triflic anhydride (1.1 eq, 5.0 g, d 1.677). The mixture was allowed to stir for 10 minutes and treated with a catalytic amount of 4-dimethylamino pyridine (tip of spatula). The cooling bath was removed and the reaction was allowed to stir for 1 hour. TLC (10% ethyl acetate in hexanes) showed no more starting material left and the mixture was diluted with ethyl acetate (300 mL) and washed with aq saturated sodium bicarbonate (80 mL) and brine (80 mL). The organic layer was dried over magnesium sulfate, filtered and concentrated in vacuo. The resulting residue was purified on silica gel (Biotage 40-M column; gradient: 0 to 10% ethyl acetate in hexanes) to provide compound 16B (4.0 g; 87%) as a colorless oil.

Step 2:

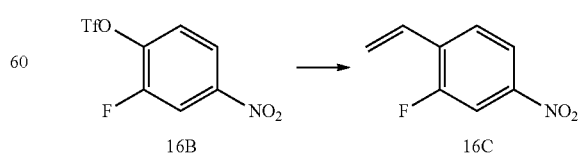
16B     16C

A solution of trifluoro-methanesulfonic acid 2-fluoro-4-nitro-phenyl ester (16B) (13.2 g; 45.64 mmol) in 225 mL of THF was treated with lithium chloride (7.0 eq, 13.5 g) and tributyl(vinyl)tin (2.0 eq, 26.6 mL, d 1.085). The mixture was degassed (vacuum/nitrogen flush) and tetrakis(triphenylphosphine)palladium was added (10 mol %, 5.26 g). The reaction mixture was heated to 80° C. and stirred overnight. TLC (5% ethyl acetate in hexanes) showed complete consumption of starting material. The mixture was diluted with water (100 mL) and extracted with 1:1 ether/ethyl acetate (900 mL). The organic layer was washed with 10% aqueous ammonium hydroxide (100 mL), water (100 mL) and brine (100 mL). The organic layer was dried over magnesium sulfate, filtered and concentrated in vacuo. The resulting residue was adsorbed on silica gel and purified on a Biotage 40-S column (gradient: 0 to 4% ethyl acetate in hexanes) to provide compound 16C (7.6 g; 99%) as a slightly yellow oil which contains some stannane impurities (ca. 1.4 g)

Step 3:

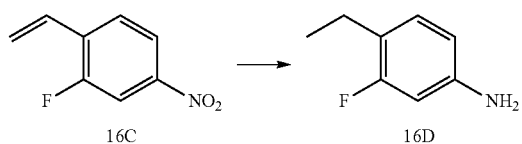

A solution of 2-fluoro-4-nitro-1-vinyl-benzene (16C) (42.65 mmol) in 140 mL of methanol was treated with a catalytic amount of 10% palladium on carbon (aprox 1.0 g). The mixture was hydrogenated at 35 psi for 2 hours. TLC (10% ethyl acetate in hexanes) showed complete consumption of starting material. The mixture was diluted with dichloromethane (100 mL) and filtered thru a short path of celite. The solids were washed with dichloromethane (100 mL). The filtrate, which contains the product 16D, was used directly in the next step.

Step 4:

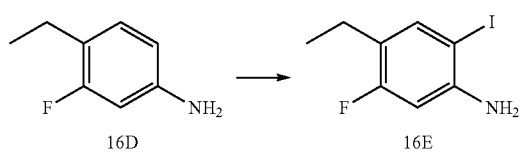

A solution of 4-ethyl-3-fluoro-phenylamine (16D) (the filtrate solution from previous step) was treated with benzyltrimethylammonium dichloroiodate (1.1 eq, 16.3 g) and calcium carbonate (2.0 eq, 8.53 g). The suspension was allowed to stir at room temp for 1 hour. TLC (10% ethyl acetate in hexanes) showed complete consumption of starting material. The solids were removed by filtration (whatman #1) and the filtrate was concentrated in rotavap. The resulting residue was partitioned between 800 mL of 1:1 ether/ethyl acetate and aqueous 5% sodium hydrogen sulfate (200 mL). The organic layer was washed with water (200 mL) and brine (200 mL). The organic layer was dried over magnesium sulfate, filtered and concentrated in rotavap. The resulting residue was adsorbed on silica gel and chromatographed on a Biotage 65-M column (gradient: 0 to 10% ether in hexanes) to provide compound 16E (8.5 g; 76%) as a yellow oil which contains some stannane impurities from a previous step.

Step 5:

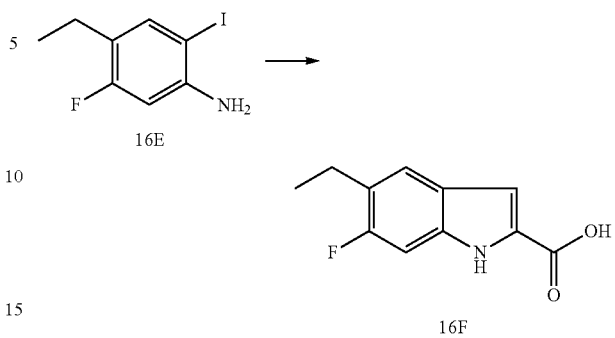

A solution of 4-ethyl-5-fluoro-2-iodo-phenylamine (16E) (7.29 g; 27.50 mmol) in 60 mL of dry DMF was treated with pyruvic acid (3.0 eq, 7.26 g, d 1.267) and DABCO (3.0 eq, 9.24 g). The mixture was degassed (vacuum/nitrogen flush) and palladium(II) acetate (0.05 eq, 308 mg) was added. The resulting solution was heated to 105° C. for 3 hours. The volatiles were removed in rotavap (high vacuum pump) and the resulting residue was partitioned between ethyl acetate (200 mL) and water (200 mL). The aqueous layer was back extracted with ethyl acetate (4×100 mL). The combined organic layers were washed with brine, dried over magnesium sulfate, filtered and concentrated in rotavap to provide the crude product 16F as a dark brown oil. No further purification was carried out.

Step 6:

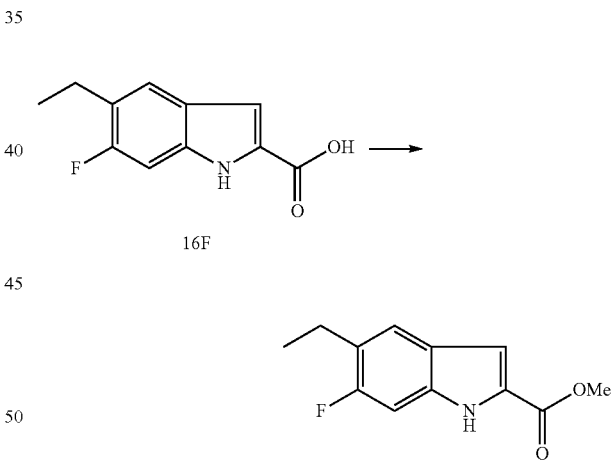

To an ice-cooled solution of 5-ethyl-6-fluoro-1H-indole-2-carboxylic acid (16F) (27.5 mmol) in 300 mL of 2:1 toluene/methanol was slowly added a solution of TMS-diazomethane in ether (2.0 eq, 27.5 mL of 2.0M). After addition was completed the cooling bath was removed and the reaction mixture was allowed to stir for 1 hour. The mixture was concentrated in rotavap to provide the crude product as a brown solid. The mixture was adsorbed on silica gel and purified on a Biotage 65-M column (gradient: 10 to 50% dichloromethane in hexanes) to provide compound 16G (3.0 g; 50% for two steps) as a white solid.

Step 7:

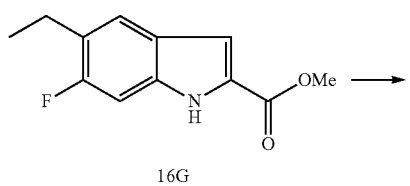

A solution of 5-ethyl-6-fluoro-1H-indole-2-carboxylic acid methyl ester (16G) (2.6 g; 11.75 mmol) in 60 mL of 1:1 THF-chloroform was ice-cooled and treated with N-iodosuccinimide (1.15 eq, 3.04 g). The cooling bath was removed and the mixture was allowed to stir for 2 hours. TLC (20% ethyl acetate in hexanes) showed almost complete consumption of starting material. The reaction mixture was diluted with ethyl acetate (300 mL) and washed with aq saturated sodium bicarbonate (2×60 mL) and brine (50 mL). The organic layer was dried over magnesium sulfate, filtered and concentrated in vacuo to provide the crude product 16H (4.0 g; 99%) as a slightly yellow solid which was used without further purification.

Step 8:

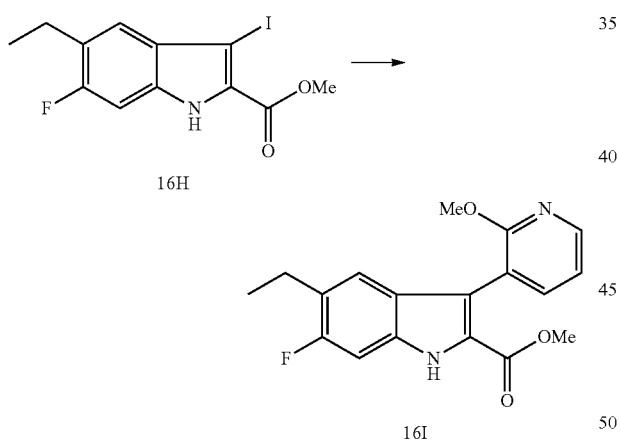

2-Methoxypyridine-3-boronic acid (1.5 eq, 2.69 g) was added to a solution of 5-ethyl-6-fluoro-3-iodo-1H-indole-2-carboxylic acid methyl ester (16H) (11.75 mmol) in 120 mL of 1,2-dimethoxyethane. The mixture was degassed (vaccum/argon flush) and palladium catalyst (10 mol %, 960 mg of PdCl$_2$(dppf)$_2$) was added and the resulting orange solution was allowed to stir for 10 minutes at room temp. A solution of potassium carbonate (4.0 eq, 23.5 mL of aqueous 2M soln) was added and the resulting brown mixture was allowed to stir at 85° C. for 2 h at which point TLC (20% ethyl acetate in hexanes) showed almost complete consumption of starting material. The reaction mixture was cooled to room temp and diluted with ethyl acetate (300 mL), washed with aq saturated sodium bicarbonate (100 mL) and brine (100 mL). The organic layer was dried over magnesium sulfate, filtered and concentrated in rotavap. The crude product was adsorbed on silica gel and purified on a Biotage 65-M column (gradient: 0 to 15% ethyl acetate in 1:1 hexanes-dichloromethane) to provide compound 16I (3.3 g; 86%) as a white solid.

Step 9:

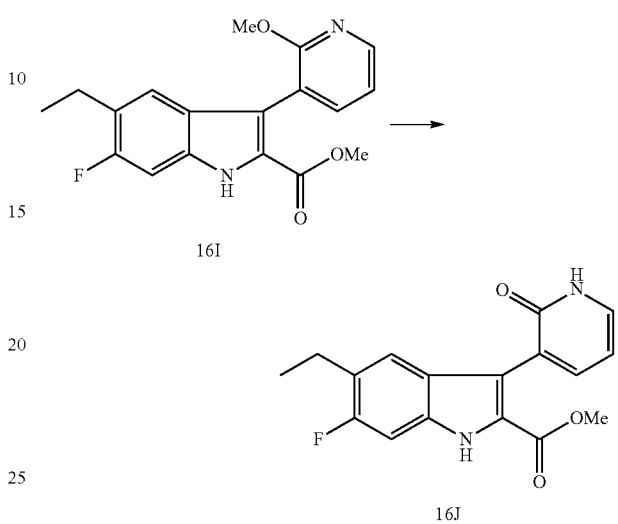

The 5-ethyl-6-fluoro-3-(2-methoxy-pyridin-3-yl)-1H-indole-2-carboxylic acid methyl ester (16I) (3.3 g; 10.05 mmol) was partially dissolved in 10 mL of methanol followed by addition of 40 mL of 4M HCl solution in dioxane. The resulting solution was heated in a sealed tube at 85° C. for 3 hours. TLC (40% acetone in 1:1 DCM-hexanes) showed aprox 40% conversion. All the volatiles were removed in vacuo and the resulting residue was re-dissolved in 4M HCl soln in dioxane (40 mL). The mixture was heated in a sealed tube (90° C.) for 3 hours. TLC showed some starting material left. All the volatiles were again removed in vacuo and the resulting residue was adsorbed on silica gel. Purification on a Biotage 40-M column (gradient: 20 to 60% acetone in 1:1 DCM-hexanes) gave the product 16J (2.0 g; 63%) as a yellow solid.

Step 10:

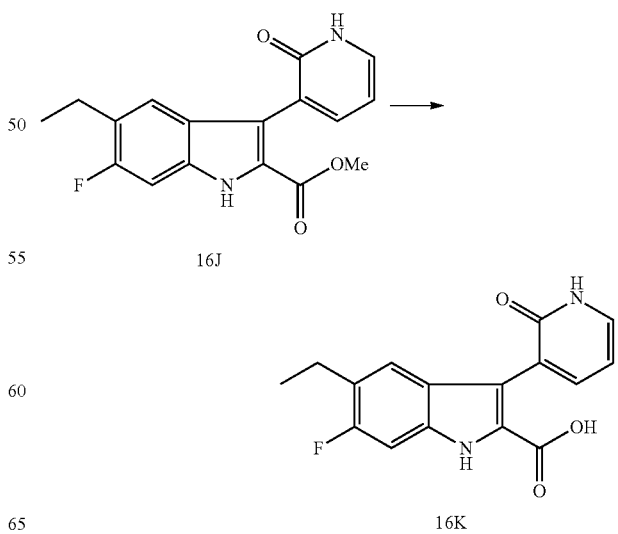

A solution of 5-ethyl-6-fluoro-3-(2-oxo-1,2-dihydro-pyridin-3-yl)-1H-indole-2-carboxylic acid methyl ester (16J) (1.9 g; 6.04 mmol) in 100 mL of 6:1:1 THF/water/methanol was treated with lithium hydroxide monohydrate (2.5 eq, 634 mg). The reaction mixture was allowed to stir at 50° C. and monitored by TLC (50% acetone in 1:1 DCM-hexanes). All the starting material had been consumed after 3 h (the product precipitated in the reaction mixture). The mixture was treated with aqueous 1M HCl (100 mL) and the product 16K (1.80 g; 99%) was recovered by filtration (whatman #1) as a white solid.

Step 11:

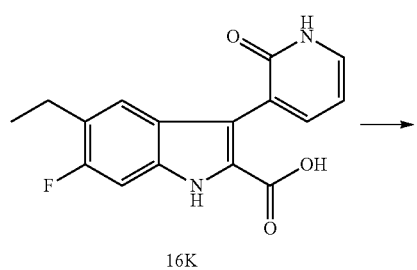

16K

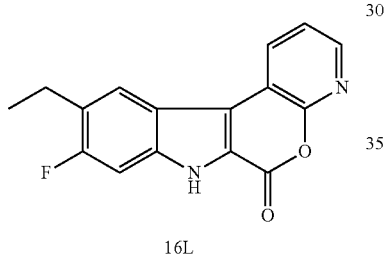

16L

The 5-ethyl-6-fluoro-3-(2-oxo-1,2-dihydro-pyridin-3-yl)-1H-indole-2-carboxylic acid (6K) (500 mg; 1.665 mmol) was suspended in dry DMF (40 mL) and treated with EDCI (2.0 eq, 638 mg) and triethylamine (10.0 eq, 2.33 mL, d 0.72). The mixture was stirred overnight at room temperature. The mixture was concentrated to dryness in vacuo. The resulting residue was treated with methanol (10 mL) to make a homogeneus suspension. The product was recovered by filtration (whatman #1) and washed with methanol (2×5 mL). The product 16L (282 mg; 60%) was thus obtained as a white solid.

Step 12:

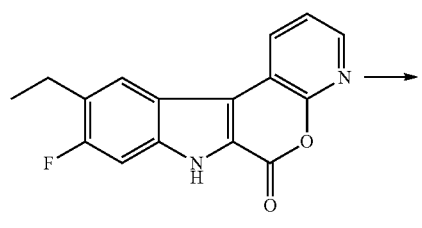

16L

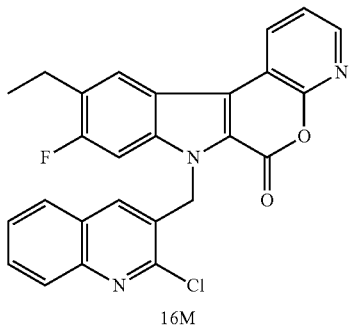

16M

The lactone 16L (40 mg, 0.141 mmol) was suspended in 2 mL of dry DMF and treated with 2-chloro-3-chloromethyl-quinoline (1.2 eq, 36 mg) and cesium carbonate (2.0 eq, 92 mg). A catalytic amount of tetrabutylammonium iodide (tip of spatula) was added and the mixture was allowed to stir at room temp. TLC (30% ethyl acetate in hexanes) showed complete consumption of starting material after 1 hour. The mixture was diluted with 50 mL of 4:1 DCM-THF and washed with water (10 mL). The organic layer was concentrated in vacuo to provide the crude product 16M (65 mg, 99%) which was used without further purification.

Step 13

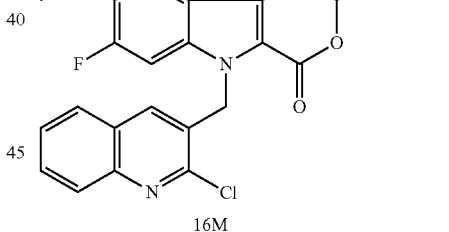

16M

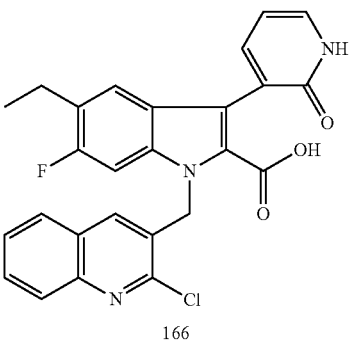

166

Lactone 16M (100 mg) was dissolved in 1,4-dioxane (10 mL) and water (1 mL). Lithium hydroxide hydrate (10 mg)

was added and the reaction mixture stirred for 12 h. The reaction mixture was concentrated to dryness to afford the lithium salt of 166.

Example 17

Preparation of Compound 86

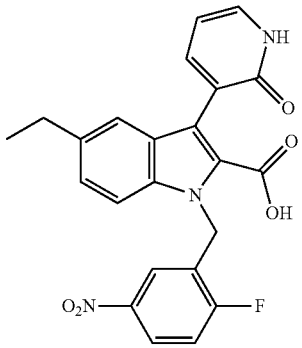

86

Step 1:

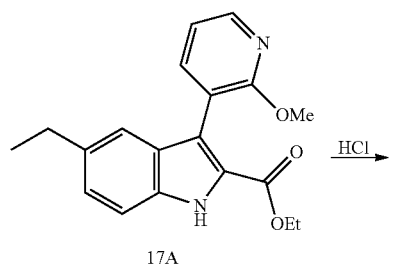

17A

To compound 17A (12.00 g, 24.7 mmol) in a thick-walled tube (ChemGlass) was added hydrogen chloride in p-dioxane (4 M, 150 mL). The tube was sealed with a Teflon stopcock and placed in a 90° C. in an oil bath for 3.5 hours. The reaction mixture was then cooled to room temperature, transferred to a flask and concentrated in vacuo to provide compound 17B (14.0 g, quant.), which was used without further purification. MS found for $C_{18}H_{18}N_2O_3$: 311.2 (M+H)$^+$.

Step 2:

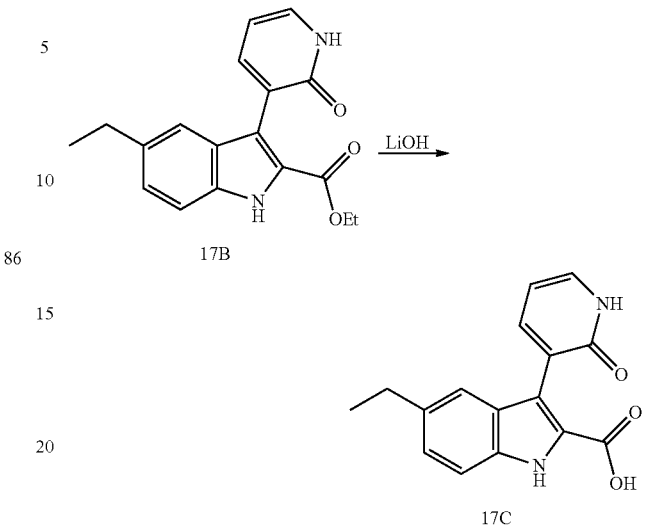

The crude product 17B from Step 1 was dissolved in THF (200 mL) and to this solution was added an aqueous solution of lithium hydroxide (4.6 g, mmol in 200 mL water). The mixture was heated at 80° C. for 16 hours, cooled to room temperature, acidified to pH~2 using 1 N aqueous HCl solution, and extracted with ethyl acetate (3×200 mL). The combined organic solution was washed with water (500 mL), dried over magnesium sulfate, filtered and concentrated in vacuo. The crude product 17C (11.1 g, quant.) was used without further purification. MS found for $C_{16}H_{14}N_2O_3$: 283.0 (M+H)$^+$.

Step 3:

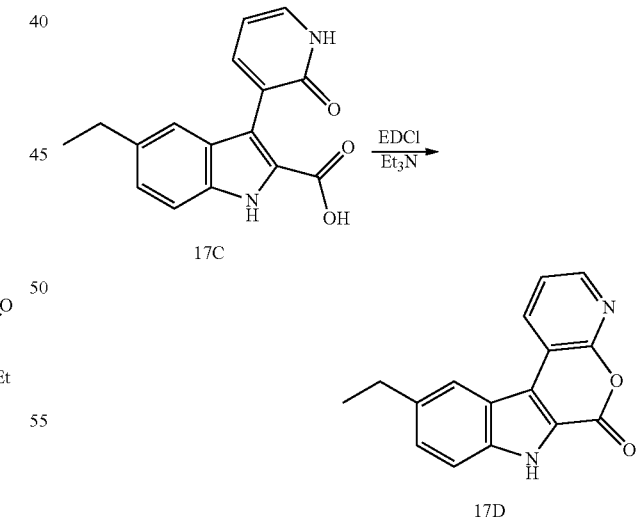

To a solution of 17C (6.94 g, 24.6 mmol) in DMF (300 mL) at room temperature was added 1-(3-dimethylaminopropyl)-3-ethylcarbodiimide hydrochloride (EDCI) (10.0 g, 52.2 mmol) and Et$_3$N (10.5 mL, 75.4 mmol) and the reaction mixture was allowed to stir for 16 hours. The mixture was then diluted with ethyl acetate (600 mL) and was washed with water (600 mL). The aqueous layer was extracted with ethyl acetate (2×500 mL). The combined organic solution was washed with water (2×1.5 L), dried over MgSO$_4$ and concentrated in vacuo to yield the crude product 17D (6.10 g, 94%). MS found for C$_{16}$H$_{12}$N$_2$O$_2$: 265.0 (M+H)$^+$.

Step 4:

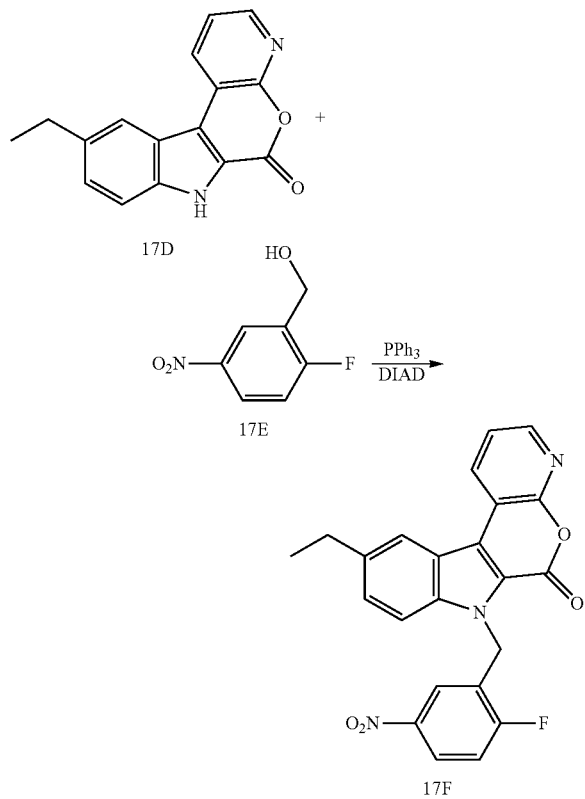

To a solution of compound 17D (600 mg, 2.27 mmol), triphenylphosphine (1.19 g, 4.54 mmol) and 2-fluoro-5-nitrobenzyl alcohol (17E) in anhydrous THF (50 mL) at room temperature was added diisopropyl azodicarboxylate (DIAD) (0.88 mL, 4.54 mmol) and the reaction mixture was allowed to stir for 4 hours. The mixture was then concentrated in vacuo. The crude product was purified using flash chromatography to provide compound 17F (1.61 g, quant.), which contained some triphenylphosphine oxide. MS found for C$_{23}$H$_{16}$FN$_3$O$_4$: 418.0 (M+H)$^+$.

Step 5:

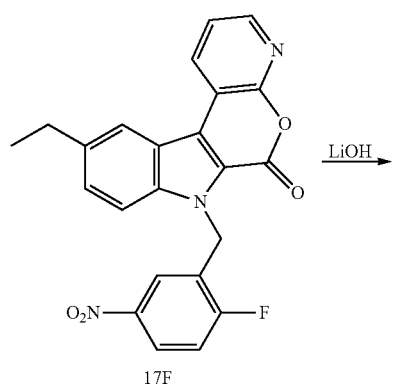

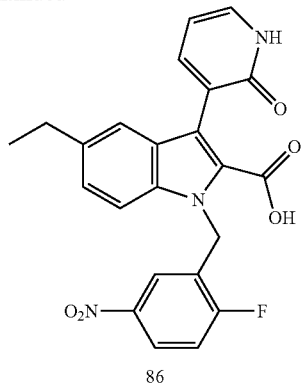

Compound 17F (400 mg, 0.958 mmol) was dissolved in tetrahydrofuran (50 mL) at room temperature and to this solution was added an aqueous solution of lithium hydroxide (50 mg, 1.19 mmol in 50 mL water). After stirred for 4 hours, the mixture was acidified to pH~2 using 1 N aqueous HCl solution, and extracted with ethyl acetate (3×60 mL). The combined organic solution was washed with water (100 mL), dried over magnesium sulfate, filtered and concentrated in vacuo. The crude product was purified using reverse-phase HPLC on a Waters Sunfire C$_{18}$ (10 μM, 50×250 mm) using 20-100% acetonitrile/water as eluent to provide compound 86 (190 mg, 46%). MS found for C$_{23}$H$_{18}$FN$_3$O$_5$: 436.0 (M+H)$^+$.

Example 18

Preparation of Intermediate Compound 18C

Step A—Synthesis of Compound 18A

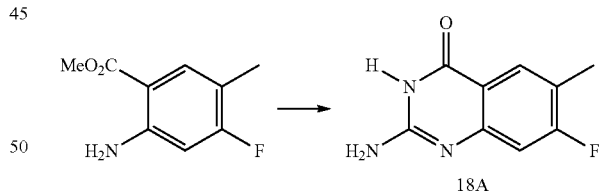

A solid mixture of methyl 2-amino-4-fluoro-5-methylbenzoate (2.66 g, 14.5 mmol), chloroformamidinium hydrochloride (2.6 g, 22.6 mmol) and methyl sulfone (8.5 g, 90.3 mmol) was heated to 150-160° C. in an oil bath with vigorous stirring. It became a clear solution after about 10 minutes. Heating was continued for a total of 2 hours. When cooled to room temperature, it became a solid. The material was taken up with water (200 mL), basified with commercial ammonium hydroxide. After stirred for 1 hour, the solid was collected through filtration. It was washed with water (20 mL) and dried under vacuum to provide crude product 18A (2.93 g, quant.). MS found for C$_9$H$_8$FN$_3$O: 194.2 (M+H)$^+$.

Step B—Synthesis of Compound 18B

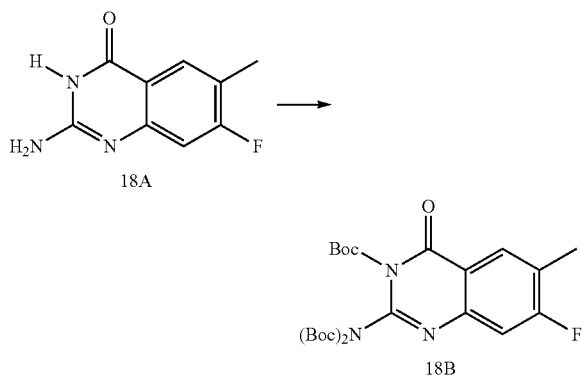

Compound 18B was prepared from 18A according the procedures described, and using 4 equivalents of (Boc)₂O. MS found for $C_{24}H_{32}FN_3O_7$: 394.3 $(M+H-100)^+$.

Step C—Synthesis of Compound 18C

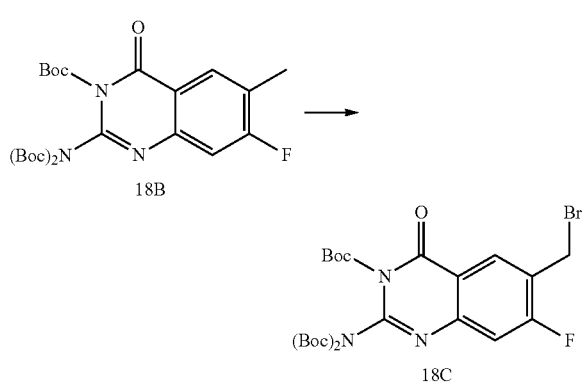

A solution of compound 18B (4.83 g, 9.8 mmol), N-bromosuccinimide (2.70 g, 15.2 mmol) and benzoyl peroxide (600 mg, 2.48 mmol) in carbon tetrachloride (300 mL) was heated to reflux and allowed to stir at this temperature for 18 hours. The reaction mixture was cooled to room temperature, concentrated in vacuo and the residue obtained was dissolved in EtOAc (300 mL). The resulting solution was washed with aqueous sodium thiosulfate (100 mL), brine (100 mL), dried (MgSO₄), filtered, and concentrated in vacuo to provide intermediate compound 18C, which was used without further purification. MS found for $C_{24}H_{31}BrFN_3O_7$: 472.3 $(M+H-100)^+$.

Example 19

Preparation of Intermediate Compound 19G

Step A—Synthesis of Compound 19B

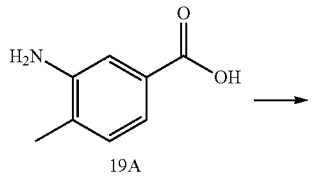

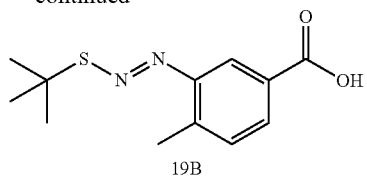

To a stirred solution of aqueous HCl (15 mL of conc HCl in 50 mL of water) was added 3-amino-4-methyl benzoic acid (19A, 5.0 g; 33.0 mmol). The mixture was cooled in an ice-water bath followed by slow addition of a solution of sodium nitrite (1.1 eq, 2.50 g) in water (12 mL). The mixture was allowed to stir for 30 minutes at which point the mixture was a homogeneous dark solution. A saturated aqueous solution of sodium acetate was added until pH 6 was attained. Sodium t-butylthiolate (0.5 eq, 1.85 g) was added in one portion. The reaction was allowed to stir for 2 h and the resulting precipitate was collected by filtration (whatman #1), washed with water (20 mL) and dried under vacuum to provide the product 19B (2.7 g; 64%) as a tan solid.

Step B—Synthesis of Compound 19C

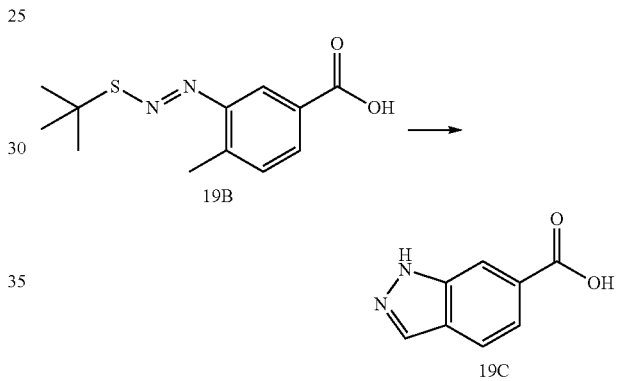

To a stirred solution of potassium tert-butoxide (10.0 eq, 12.0 g) in DMSO (50 mL) was added a solution of t-butyl-diazaenyl benzoic acid 19B (2.7 g; 10.70 mmol) in DMSO (30 mL). The mixture was allowed to stir for 6 h and then diluted with ice and acidified with aqueous 1 M HCl until pH 5-6 was attained. The mixture was extracted with ethyl acetate (3×50 mL) and the combined organic layers were washed with water (20 mL) and brine (20 mL). The organic layer was dried over magnesium sulfate, filtered and concentrated in rotavap to provide the crude product 19C as a slightly yellow solid which was used without further purification.

Step C—Synthesis of Compound 19D

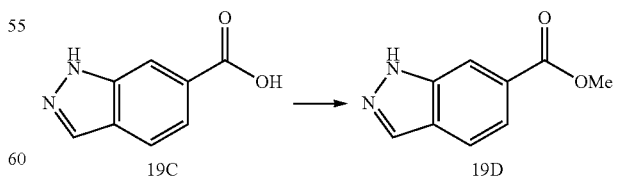

A solution of 1H-indazole-6-carboxylic acid 19C (1.73 g; 10.70 mmol) in toluene (80 mL) and methanol (30 mL) was treated with a solution of TMS-diazomethane (2 M soln in ether) until evolution of gas stopped. The reaction mixture was concentrated in vacuo and the resulting residue was adsorbed on silica gel. The product was purified on a Biotage 40-M silica gel column (gradient: 0 to 20% acetone in hexanes) to provide the product 19D (950 mg; 50% for two steps) as a slightly yellow solid. $^1$H-NMR (CDCl$_3$; 400 MHz): δ 8.28 (1H, s), 8.16 (1H, s), 7.86 (1H, d, J=8.54 Hz), 7.81 (1H, d, J=8.54 Hz), 3.98 (3H, s). LR-MS (ESI): calcd for C$_9$H$_9$N$_2$O$_2$ [M+H]$^+$ 177.07; found 177.20.

Step D—Synthesis of Compound 19E

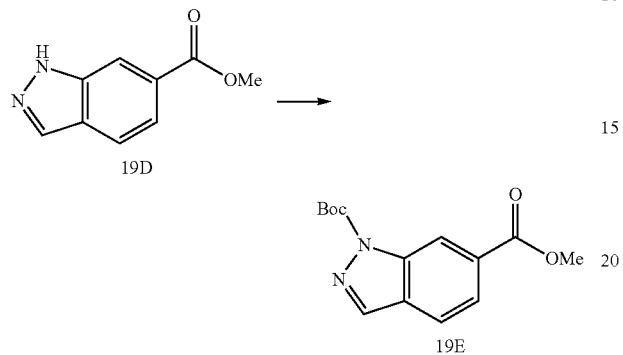

A solution of 1H-indazole-6-carboxylic acid methyl ester 19D (840 mg; 4.76 mmol) in 25 mL of acetonitrile was treated with Boc-anhydride (1.05 eq, 1.09 g) and a catalytic amount of DMAP (tip of spatula). The mixture was allowed to stir at 60° C. for 3 hours. The mixture was concentrated to half its volume in rotavap and then diluted with ethyl acetate (100 mL) and washed with aqueous saturated sodium bicarbonate (20 mL) and brine (20 mL). The organic layer was dried over magnesium sulfate, filtered and concentrated in rotavap. The resulting residue was purified on a Biotage 40-M silica gel column (gradient: 0 to 20% ethyl acetate in hexanes) to provide the product 19E (1.2 g; 93%) as a colorless oil. $^1$H-NMR (CDCl$_3$; 400 MHz): δ 8.91 (1H, s), 8.22 (1H, s), 7.99 (1H, dd, J=1.22, 8.54 Hz), 7.78 (1H, d, J=8.54 Hz), 3.97 (3H, s), 1.74 (9H, s).

Step E—Synthesis of Compound 19F

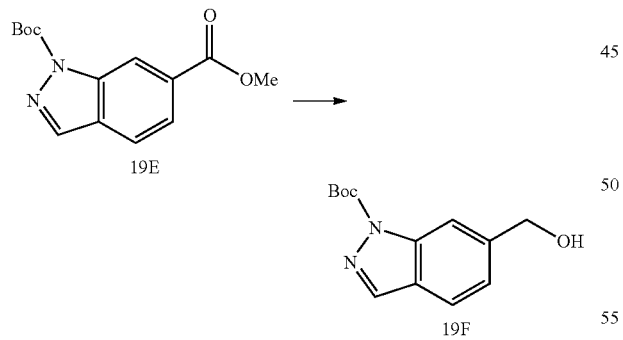

A solution of indazole 19E (460 mg; 1.66 mmol) in 16 mL of dry THE was cooled to −78° C. and treated with lithium triethylborohydride (2.5 eq, 4.15 mL of a 1 M soln in THF). The reaction mixture was allowed to stir at −78° C. and followed by TLC (25% ethyl acetate in hexanes). The reaction was completed in about 1 h and quenched by addition of aqueous saturated sodium hydrogen sulfate (3 mL). The mixture was extracted with ethyl acetate (100 mL) and washed with water (20 mL) and brine (20 mL). The organic layer was dried over magnesium sulfate, filtered and concentrated in rotavap to provide the crude product as a colorless oil. The resulting residue was chromatographed on a Biotage 40-S silica gel column (0 to 40% ethyl acetate in hexanes) to provide the following: des-Boc starting material (70 mg); alcohol product 19F (160 mg; 40%). $^1$H-NMR (CDCl$_3$; 400 MHz): δ 8.19 (1H, s), 8.13 (1H, s), 7.67 (1H, d, J=7.93 Hz), 7.30 (1H, d, J=7.93 Hz), 5.13 (2H, s), 1.71 (9H, s).

Step F—Synthesis of Compound 19G

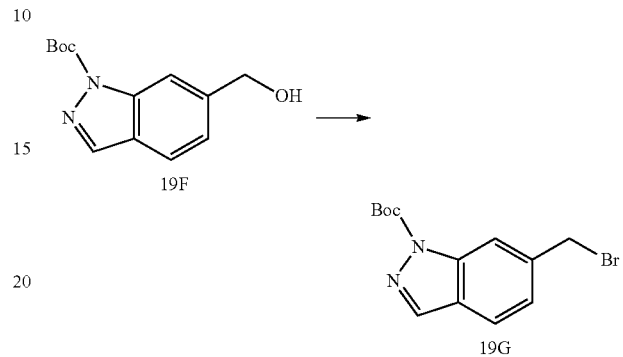

A solution of alcohol 19F (160 mg; 0.644 mmol) in dry chloroform (12 mL) was placed in an ice-water bath and treated with pyridine (4.0 eq, 0.208 mL, d 0.978) and a solution of thionyl bromide (1.2 eq, 0.060 mL, d 2.683) in 1 mL of chloroform. The ice-water bath was removed and the reaction mixture was allowed to stir at room temp for 30 minutes. TLC (30% ethyl acetate in hexanes) showed about 40% conversion and more thionyl bromide was added (0.2 eq). The mixture was heated to 70° C. for 10 minutes. Upon cooling the mixture was diluted with ethyl acetate (30 mL) and washed with aqueous saturated sodium bicarbonate (5 mL), aqueous sodium hydrogen sulfate (5 mL) and brine (5 mL). The organic layer was dried over magnesium sulfate, filtered and concentrated in rotavap. The resulting residue was purified on a Biotage 25-S silica gel column (gradient: 0 to 40% ethyl acetate in hexanes) to provide the product 19G (76 mg; 38%) as a colorless oil along with unreacted starting material (25 mg; 24%). $^1$H-NMR (CDCl$_3$; 400 MHz): δ 8.23 (1H, s), 8.14 (1H, s), 7.72 (1H, d, J=8.54 Hz), 7.32 (1H, dd, J=1.22, 8.54 Hz), 5.21 (1H, d, J=12.20 Hz), 5.09 (1H, d, J=12.20 Hz), 1.71 (9H, s).

Example 20

Preparation of Intermediate Compound 20C

Step A—Synthesis of Compound 20B

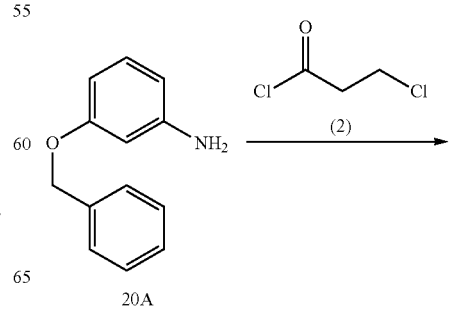

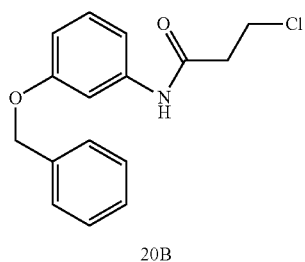

20B

Compound 20A (commercially available) (10.0 g, 50.25 mmol) was dissolved in water at room temperature and to resulting suspension K$_2$CO$_3$ (3.8 g, 27.64 mmol) was added. 3-Chloro propionylchloride (7.0 g, 55.28 mmol) was added dropwise for 30 minutes and stirred for 2 hours at room temperature. The precipitate was filtered and washed with water, 1 N HCl, dried at 50° C. under vacuum overnight to provide 7.2 g of the product 20B.

Step B—Synthesis of Compound 20C

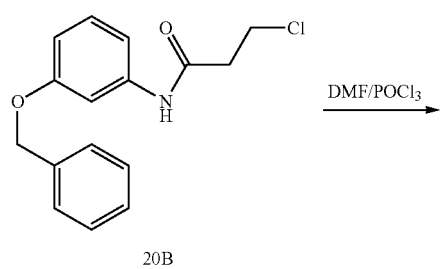

20B

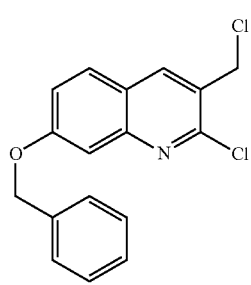

20C

To N,N-Dimethylformamide (3.6 g, 49.66 mmol) at 0° C. was added drop wise POCl$_3$ (26.6 g, 173.8 mmol) and stirred for 60 minutes, white precipitate was formed. The 7.2 g of the compound 20B was added by portion in reaction mixture and stirred for 24 hours at room temperature. Reaction mixture was diluted with ethyl acetate and slowly added to a beaker with ice, after ice was melted, organic layer was separated and washed with 0.5 N NaOH and water, brine, dried over sodium sulfate, and concentrated in vacuum, purified using flash chromatography, to provide compound 20C (5.5 g, 34% after two steps). M.S. found: 318.04 (M+H)$^+$.

Example 21

Preparation of Intermediate Compound 21E

Step A—Synthesis of Compound 21B

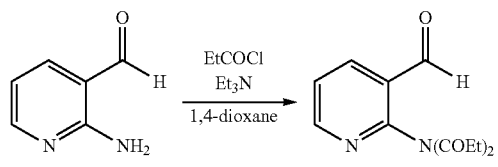

To a solution of 21A (7.2 g, 58.8 mmol) in 1,4-dioxane (39 mL) at 0° C. was added propionyl chloride (37.8 mL, 176.5 mmol) and Et$_3$N (24.6 mL, 176.5 mmol) with stirring. The reaction mixture was allowed to stir at room temperature for overnight. The solvent was removed under reduced pressure, and the resulting residue was taken up in EtOAc. The organic phase was washed with water, dried over MgSO$_4$, filtered, and concentrated in vacuo to provide a crude residue of 21B.

Step B—Synthesis of Compound 21C

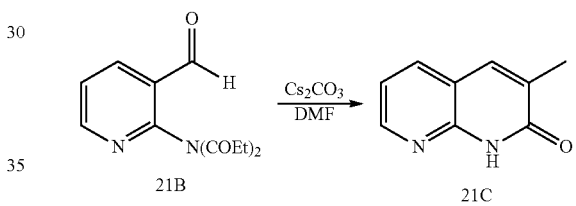

To a suspension of 21B (crude residue from above) in DMF (60 mL) was added cesium carbonate (38 g, 117.6 mmol), and the resulting mixture was heated at 65° C. for overnight. Reaction was cooled to room temperature, and the bulk of DMF was removed under reduced pressure. Water was then added to the crude residue and the mixture was filtered. The filter-cake was washed with water and EtOAc. 5.2 g of 21C was collected as a pale yellow solid.

Step C—Synthesis of Compound 21D

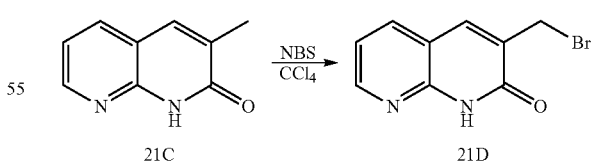

To a suspension of 21C (0.8 g, 5 mmol) in CCl$_4$ (25 mL) was added NBS (38 g, 117.6 mmol), and benzoyl peroxide (61 mg, 0.25 mmol), and the resulting mixture was then heated at 90° C. for 4 hours. Cooled the reaction to room temperature, and 300 mL of CH$_2$Cl$_2$ was added. The mixture was filtered, and filtrate was dried over MgSO$_4$, filtered, and concentrated in vacuo to provide 2 g of crude residue of 21D.

Step D—Synthesis of Compound 21E

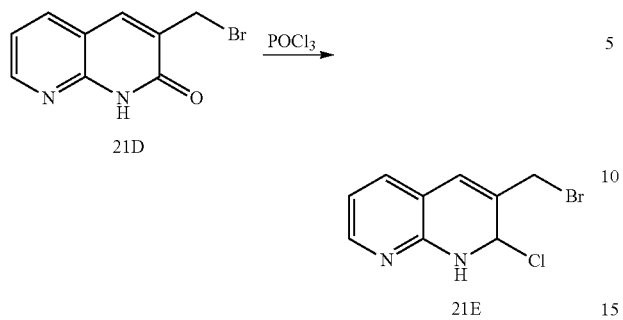

POCl₃ was added to a 100 mL round bottom flask containing crude 21D. The resulting suspension was then heated at 88° C. for 4 hours. Cooled the reaction to room temperature, and then poured into a 1 liter beaker containing ice. The resulting solution was neutralized to ph 8 using 6 N NaOH solution. Solid that precipitated from the solution was collected to provide 0.82 g of crude residue which was purified using column chromatography on silica gel (ISCO Combi-Flash Rf; gradient: 5 to 50% ethyl acetate in hexanes) to provide 330 mg of compound 21E.

Example 22

Preparation of Intermediate Compound 22D

Step A—Synthesis of Compound 22B

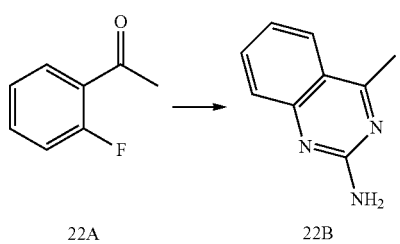

A mixture of ortho-fluoroacetophenone (22A, 3.45 g; 25 mmol) and guanidine carbonate (2 eq; 9.0 g) was prepared in 250 mL of N,N-dimethyl acetamide, set to stir, and heated at 135° C. under nitrogen purge overnight. The solvent was removed under reduced pressure and diluted with ethyl acetate (600 mL). The solution was washed with water (2×100 mL) and brine (40 mL). The organic layer was separated, dried over magnesium sulfate, filtered, and concentrated in vacuo. The solid was dissolved in methylene dichloride, loaded on silica gel and dried under reduced pressure. The material was purified on ISCO (80 g column; 0-70% THF in Hexanes). Fractions containing product were collected and concentrated in vacuo to afford product 22B as a creme colored solid (880 mg; 22%)

Step B—Synthesis of Compound 22C

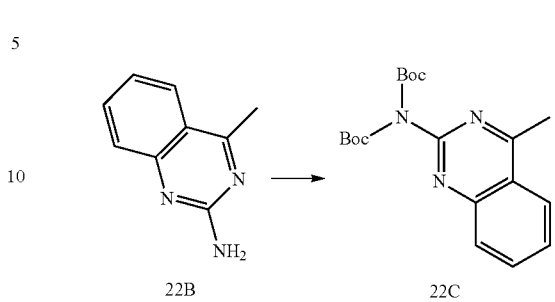

A solution of 4-Methyl-quinazolin-2-ylamine 22B (640 mg; 4.02 mmol) in 10 mL of dry acetonitrile was treated with a solution of Boc-anhydride (2.5 eq; 2.19 g) in 10.0 mL of dry acetonitrile. The resulting solution was treated with DMAP (0.2 eq; 98.2 mg). The mixture was set to stir overnight. TLC (50% THF in hexanes) showed a complete reaction. The mixture was diluted with ethyl acetate (500 mL) and washed with water (3×30 mL), and Brine (40 mL). The organic layer was dried over magnesium sulfate, filtered and concentrated in rotavap. The resulting residue was adsorbed on silica gel and purified on an ISCO column (120 g) (0% to 60% THF in hexanes). The fractions with product were collected and concentrated in vacuo to afford product 22C as a light yellow-white solid (1.3 g; 90%).

Step C—Synthesis of Compound 22D

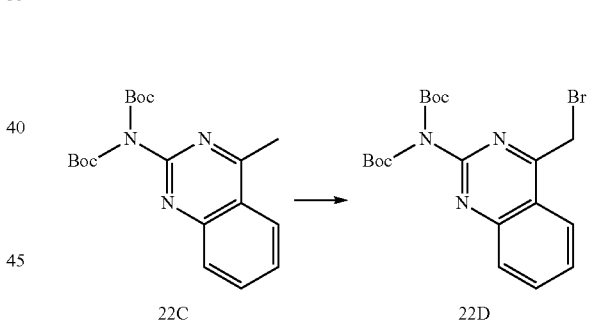

Intermediate 22C (1.11 g; 3.09 mmol), N-Bromosuccinimide (1.05 eq; 577 mg), and benzoyl peroxide (0.1 eq; 75 mg) were combined in round bottom and diluted with dry carbon tetrachloride (31 mL) The reaction was allowed to stir at room temperature for 10 minutes and then heated at reflux overnight. TLC (30% ethyl acetate in hexanes) revealed the reaction has partially progressed. The reaction mixture was concentrated in vacuo, diluted with ethyl acetate (300 mL), and washed with sat. aqueous sodium bicarbonate (40 mL) and brine (40 mL), dried over magnesium sulfate, filtered, concentrated in vacuo, diluted with methylene dichloride, adsorbed onto silica gel, and purified on ISCO (25-M Column; 0-40% ethyl acetate in hexanes). The fractions containing product were concentrated in vacuo and afforded product as a clear oil in a 2:1 mixture of pure product 22D and starting material (Total: 440 mg; 33%).

Example 23

Preparation of Intermediate Compound 23C

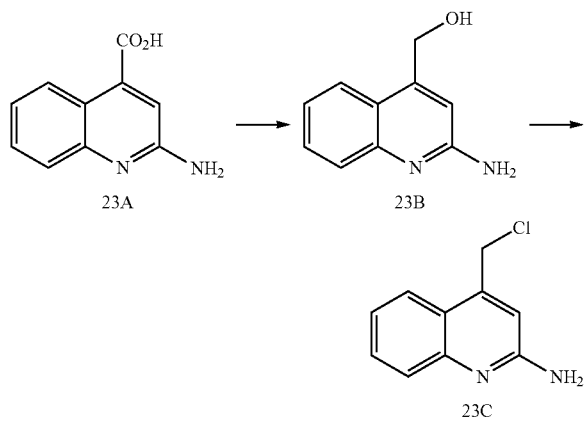

The starting materials 23A (2.0 g, 10.6 mmol), lithium aluminum hydride (2.0 g, 52.7 mmol), and THF (100 mL) were added to a 250 ml round-bottomed flask. The resulting suspension was allowed to stir at room temperature for 18 hours. The reaction was quenched with 10 ml of saturated ammonium chloride solution followed by 200 ml of ethyl acetate. After filtration, the organic layer was washed with brine (2×100 mL), dried over sodium sulfate, and concentrated in vacuo to provide 23B as a yellowish solid (1.05 g, 59%).

A 250 ml round-bottomed flask was charged with 23B (1.05 g, 6.03 mmol) and thionyl chloride (10 mL). The resulting mixture was allowed to stir at 60° C. for 4 hours before cooled to room temperature. After removal of excess of thionyl chloride, the resulting residue was dried under vacuum to afford 23C as an orange solid (1.45 g). This crude material was used without further purification.

Example 24

Preparation of Intermediate Compound 24G

Step A—Synthesis of Compound 24B

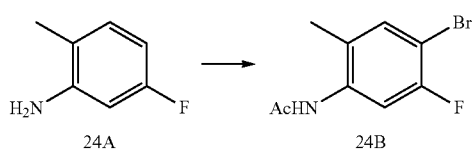

A solution of 5-fluoro-2-methylaniline (24A, 25 g, 200 mmol) in toluene (250 mL) was treated with acetic anhydride (25 mL 226 mmol) heated at reflux for 1 hour. The reaction mixture was cooled when a colorless solid precipitated out which was filtered and washed with a mixture of ether and hexanes. The colorless solid was taken in acetic acid (150 mL) and treated dropwise with a solution of bromine (9.6 mL, 186 mmol) in acetic acid (20 mL) and stirred at rt. for 12 hours. The solution was diluted with water and the solid separating out was filtered and washed to yield N-(4-bromo-5-fluoro-2-methylphenyl)acetamide (24B, 40 g) as a colorless solid.

Step B—Synthesis of Compound 24C

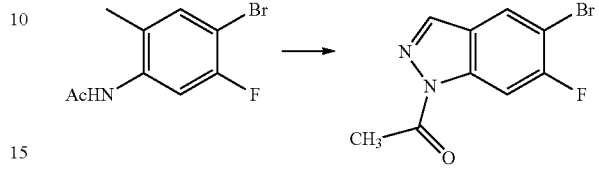

A solution of N-(4-bromo-5-fluoro-2-methylphenyl)acetamide (24B, 10.00 g, 40.64 mmol) in chloroform (100 mL) was treated with acetic anhydride (11.5 mL, 122.0 mmol), potassium acetate (8.00 g, 81.5 mmol), and 18-Crown-6 (540.00 mg, 2.0430 mmol) and then with isoamyl nitrite (12.3 mL, 871 mmol) and heated at 65° C. for 12 hours. The reaction mixture was cooled to room temperature and treated with EtOAc (500 mL), washed with water, dried (MgSO$_4$), filtered, and then concentrated in vacuo. A pale yellow solid of 1-(5-bromo-6-fluoro-1H-indazol-1-yl)ethanone (24C) precipitated out. The initial filtrate was concentrated and the resulting residue was purified using chromatography (SiO$_2$, EtOAc/Hexanes) to yield more of product 24C.

Step C—Synthesis of Compound 24D

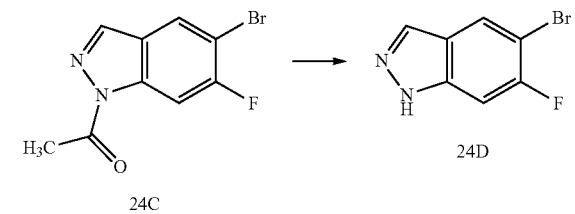

A solution of 1-(5-bromo-6-fluoro-1H-indazol-1-yl)ethanone (24C, 5.0 g, 19.5 mmol) was treated with aq HCl (3M soln., 100 mL) and methanol (20 mL) and heated at 90° C. for 3 h, when the reaction turns homogenous. The reaction mixture was cooled to room temperature and basified with aq. NaOH. A colorless solid precipitated out which was filtered and dried to yield 5-bromo-6-fluoro-1H-indazole (24D)

Step D—Synthesis of Compound 24E

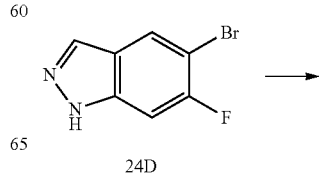

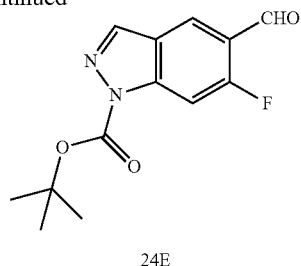

24E

A solution of 5-bromo-6-fluoro-1H-indazole (24D, 3.50 g, 16.28 mmol) in tetrahydrofuran (200.00 mL) was treated with sodium hydride (60% in mineral oil, 1.172 g) at 0° C. and stirred at rt. for 20 minutes. The reaction mixture was cooled to −78° C. (dry ice and acetone) and treated with 2.5 M of n-butyl lithium in hexane (8.2 mL, 20.3 mmol) dropwise. The reaction mixture was allowed to stir at that temperature for 20 minutes and treated with DMF (5.06 mL, 65.11 mmol). The reaction mixture was slowly warmed to room temperature when the viscous solution turn fluidic and stirring was efficient. Analysis of TLC (40% EtOAc/Hexanes) indicated complete conversion of starting material to product. The reaction mixture was acidified with aq. HCl taken up in EtOAc (500 mL) washed with aq. HCl (100 mL), brine (100 mL), dried ($MgSO_4$), filtered, concentrated in vacuo and used as it is in next step. A solution of product 6-fluoro-1H-indazole-5-carbaldehyde (2.3 g) in THF (100 mL) was treated with di-tert-butyldicarbonate (3.56 g, 16.28 mmol) and DMAP (300 mg) and stirred at room temperature for 3 hours. The reaction mixture was concentrated in vacuo and the resulting residue was purified using chromatography ($SiO_2$, EtOAc/Hexanes gradient 0-40%) to yield [2e]tert-butyl 6-fluoro-5-formyl-1H-indazole-1-carboxylate (24E, 3.5 g; Yield=81%) as a colorless solid.

Step E—Synthesis of Compound 24F

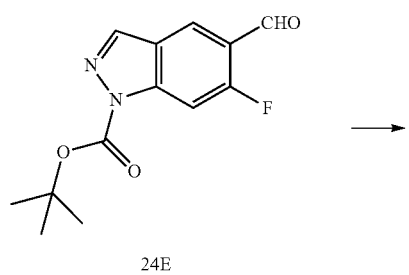

A solution of tert-butyl 6-fluoro-5-formyl-1H-indazole-1-carboxylate (29E, 3.55 g, 13.4 mmol) in methanol (50.00 mL) was treated with $NaBH_4$ (1.02 g, 26.9 mmol) at 0° C. and stirred for 1 h. The reaction mixture was diluted with water and EtOAc (500 mL). The organic layer was separated and washed with aq. HCl (1M, 200 mL), aq. NaOH (1M, 200 mL) brine (200 mL) dried ($MgSO_4$), filtered, concentrated in vacuo and resulting residue was purified using chromatography ($SiO_2$, EtOAc/hexanes) to yield tert-butyl 5-(hydroxymethyl)-6-fluoro-1H-indazole-1-carboxylate (29F, 3.00 g; Yield=83.9%) as a colorless solid.

Step F—Synthesis of Compound 24G

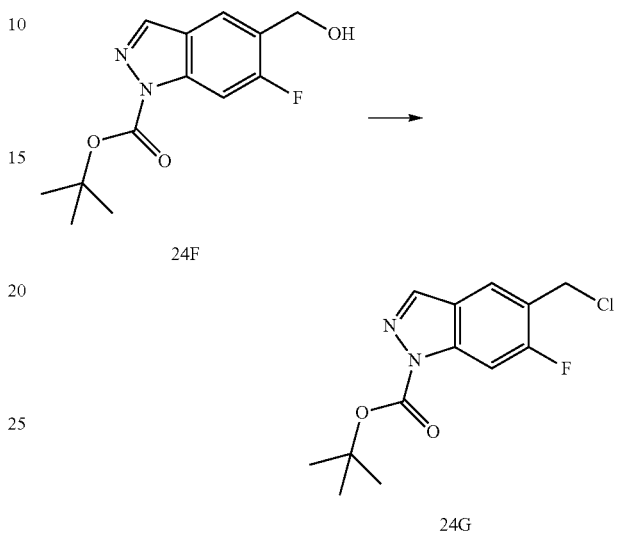

A solution of tert-butyl 5-(hydroxymethyl)-6-fluoro-1H-indazole-1-carboxylate (29F, 3.0 g, 11.27 mmol) in methylene chloride (50.00 mL, 780.0 mmol) at rt. was treated with pyridine (4.56 mL, 56.33 mmol) and methanesulfonyl chloride (1.31 mL) and stirred at rt. for 16 hours. The reaction mixture was concentrated in vacuo and the resulting residue was dissolved in EtOAc (300 mL) washed with aq HCl (100 mL), brine (100 mL), dried ($MgSO_4$), filtered, concentrated in vacuo, and purified using chromatography ($SiO_2$, EtOAc/Hexanes) to yield tert-butyl 5-(chloromethyl)-6-fluoro-1H-indazole-1-carboxylate (24G, 1.9 g; Yield=59%)

Example 25

Preparation of Intermediate Compound 25B

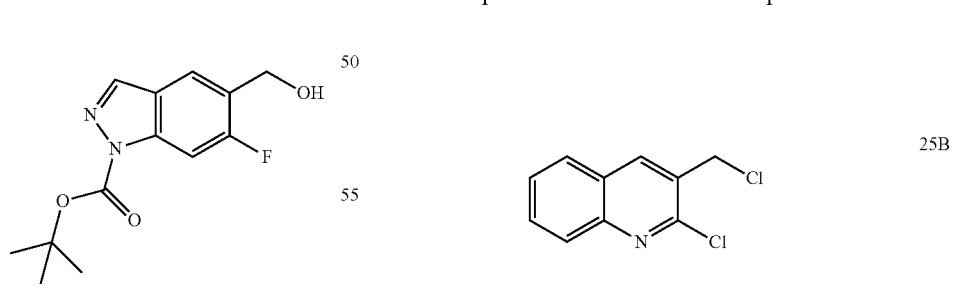

Step A—Synthesis of Compound 25A

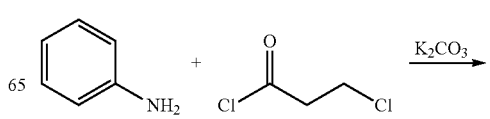

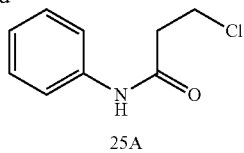

25A

A mixture of aniline (65.04 mL, 713.8 mmol), potassium carbonate (54.4 g, 394 mmol) and water (300 mL) were added to a 2000 mL flask. The resulting reaction was kept at room temperature using a room temperature water bath and stirred with a mechanic stirrer. 3-Chloro-propionyl chloride (75.18 mL, 787.6 mmol) was added dropwise via additional funnel and the resulting suspension was allowed to stir at room temperature for 3 hours. The reaction mixture was filtered and the collected solid was washed sequentially with water (300 mL), aq. HCl (1M, 2×300 mL), and water (300 mL), then dried to provide compound 25A, which was used without purification (114.5 g, 87%).

Step B—Synthesis of Compound 25B

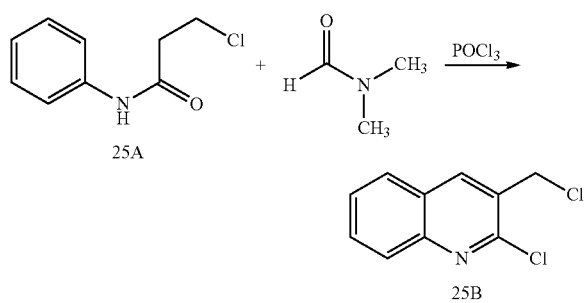

25A

25B

N,N-Dimethylformamide (53.7 mL, 694 mmol) was charged into a three necked flask and cooled to 0° C. and treated with phosphoryl chloride (177.7 mL, 1906 mmol) dropwise. The reaction was allowed to stir at that temperature for 10 minutes and treated with 3-Chloro-N-phenylpropanamide 25A (50.00 g, 272.3 mmol) and stirred at room temperature. for 30 minutes. The reaction mixture was heated at 80° C. for 3 h and slowly poured into ice. The solid separating out was filtered and washed extensively with water (2×1000 mL), aq. saturated sodium bicarbonate (500 mL), and taken in EtOAc (1 L), The solution was dried (MgSO$_4$) filtered concentrated in vacuo and the residue obtained was recrystallized from boiling hexanes to provide compound 25B (20 g).

Example 26

Preparation of Intermediate Compounds 26E and 26F

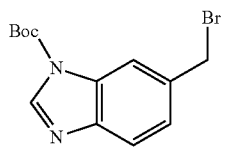

26F

Step A—Synthesis of Compound 26B

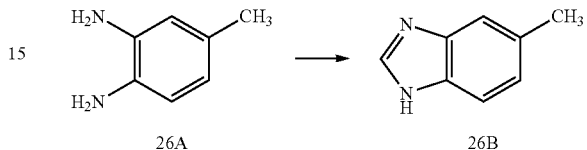

26A

26B

A solution of compound 26A (3 g, 24.5 mmol) in trimethyl orthoformate (15 mL) was treated with 2 drops conc. HCl and heated to 80° C. for 2 hours. The reaction mixture was cooled to room temperature and concentrated in vacuo to provide compound 26B (3.65 g), which was used without further purification. M.S. found for $C_8H_8N_2$: 133.2 $(M+H)^+$.

Step B—Synthesis of Compounds 26C and 26D

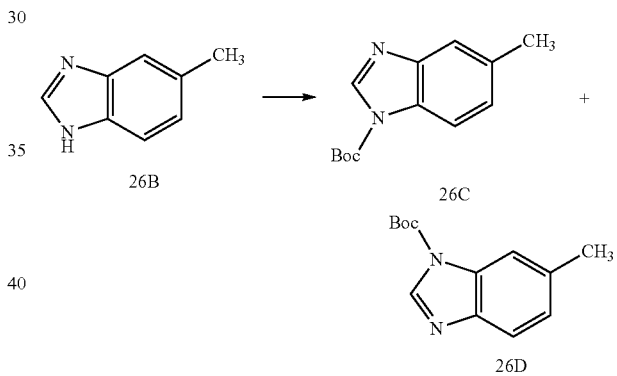

26B

26C

26D

To a solution of compound 26B (24.5 mmol) in CH$_3$CN (65 mL) was added di-tertbutyl dicarbonate (5.89 g, 27.0 mmol), triethylamine (3.76 mL, 27.0 mmol) and 4-dimethylamino pyridine (300 mg, 2.45 mmol) and the resulting reaction was heated to 80° C. and allowed to stir at this temperature for 1.5 hours. The reaction mixture was cooled to room temperature, concentrated in vacuo, and the residue obtained was purified using flash column chromatography (silica gel, EtOAc/Hexanes 5-20%) to provide a mixture of isomeric compounds 26C and 26D (5.38 g, 94.3% yield over steps A and B).

Step C—Synthesis of Compounds 26E and 26F

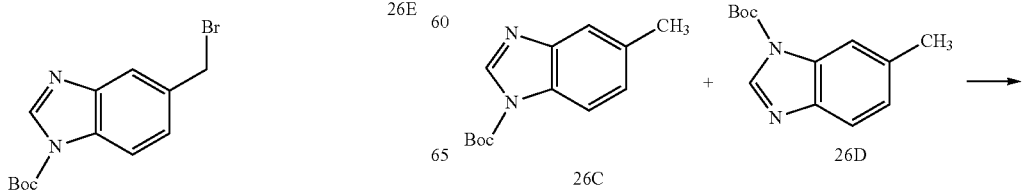

26C

26D

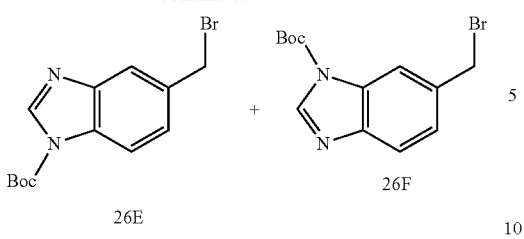

To a solution of compounds 26C and 26D (2 g, 8.61 mmol) in carbon tetrachloride (40 mL) was added N-bromosuccinimide (1.6 g, 9.04 mmol) and dibenzoyl peroxide (41.7 mg, 0.1722 mmol) and the resulting reaction was heated to 90° C. and allowed to stir at this temperature for 12 hours. The reaction was cooled to room temperature, solids were filtered off and the filtrate was washed with water, dried over sodium sulfate and concentrated in vacuo to provide compounds 26E and 26F (2.58 g) which was used without further purification. M.S. found for $C_{13}H_{15}BrN_2O_2$: 334.7 $(M+Na)^+$.

Example 27

Preparation of Intermediate Compound 27B

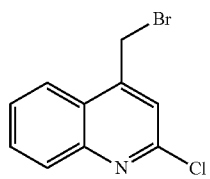

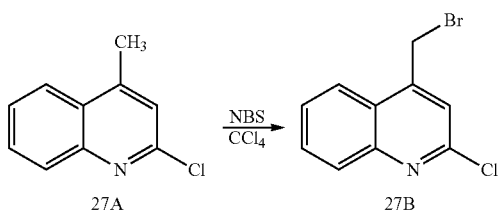

A mixture of compound 27A (1.5 g, 8.44 mmol), NBS (1.8 g, 10.11 mmol) in carbon tetrachloride (50 mL) was heated to reflux, then benzoyl peroxide (0.21 g, 0.866 mmol) was added. The resulting suspension was allowed to stir at reflux for 19 hours, then cooled to room temperature and filtered. The filtrate was washed with saturated sodium carbonate, dried over sodium sulfate and concentrated in vacuo to provide a mixture (1.7 g) which contains about 50% of compound 27B, and was used without further purification.

Example 28

Preparation of Intermediate Compound 28G

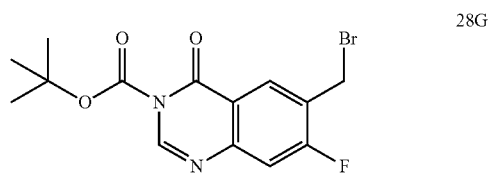 [SMILES: CC(C)(C)OC(=O)n1cnc2cc(F)c(CBr)cc2c1=O]

Step A—Synthesis of Compound 28B

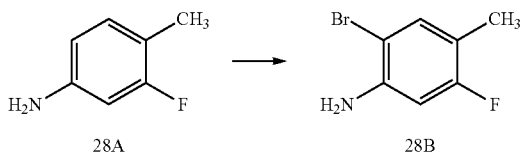

A mixture of compound 28A (6.00 g, 47.9 mmol) and anhydrous potassium carbonate (6.70 g, 48.5 mmol) in anhydrous dichloromethane (130 mL) was cooled to −15° C. in a salt-ice bath and then added dropwise to a solution of bromine (7.70 g, 48.2 mmol) in anhydrous dichloromethane (80 mL). After addition was complete, the reaction was allowed to stir at −15° C. for 1 hour. Ice water (100 mL) was added to the reaction mixture and the aqueous layer was extracted with dichloromethane (2×100 mL). The combined organic layers were dried over $MgSO_4$ and concentrated in vacuo to provide compound 28B (11.0 g, quant.), which was used without further purification.

Step B—Synthesis of Compound 28C

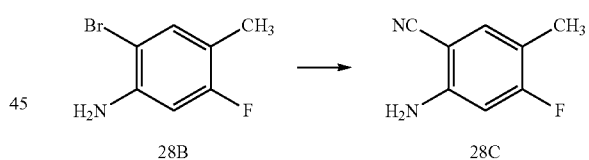

Compound 28B was dissolved in DMF (150 mL) and to this solution was added copper (I) cyanide (11.0 g, 123 mmol). The mixture was heated to 160° C. and allowed to stir at this temperature for 20 hours. After being cooled to room temperature, with water (200 mL), iron (III) chloride (42.0 g, 155 mmol) and concentrated hydrochloric acid (20 mL) were added to the reaction mixture and the resulting reaction was allowed to stir for 45 minutes. The reaction mixture was then basified to pH>10 using commercial ammonium hydroxide solution. The basic solution was then extracted with ethyl acetate (4×400 mL). The combined organic extracts were washed with water, dried over magnesium sulfate, filtered and concentrated in vacuo. The residue obtained was purified using flash chromatography to provide compound 28C (5.82 g, 81%). $^1$H NMR (400 MHz, $d_6$-DMSO): δ 7.34 (d, J=8.4 Hz, 1H), 6.52 (d, J=12.4 Hz, 1H), 6.10 (s, 2H), 2.08 (s, 3H).

Step C—Synthesis of Compound 28D

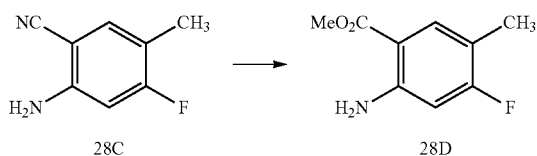

To a solution of 28C (2.0 g, 13.3 mmol) in anhydrous methanol (15 mL) at room temperature was added concentrated sulfuric acid (4.0 mL). The reaction mixture was heated to 70° C. and stirred for four days. After cooled to room temperature, it was poured into with ice water. The mixture was then diluted with ethyl acetate (200 mL) and was made basic (pH>10) with commercial ammonium hydroxide solution. The layers were separated. The aqueous layer was extracted with ethyl acetate (2×100 mL). The combined organic solution was dried over MgSO$_4$ and concentrated in vacuo to provide the crude product which was purified using flash chromatography to provide compound 28D (1.0 g, 41%) and some recovered 28C. $^1$H NMR (400 MHz, d$_6$-DMSO): δ 7.61 (d, J=8.8 Hz, 1H), 6.69 (s, 2H), 6.51 (d, J=12.0 Hz, 1H), 3.77 (s, 3H), 2.06 (s, 3H).

Step D—Synthesis of Compound 28E

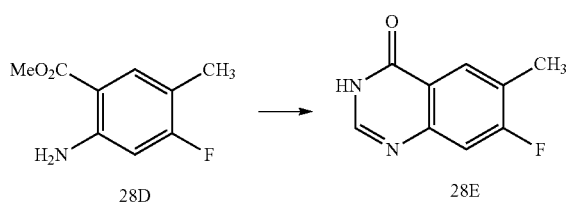

The solution of compound 28D (500 mg, 2.73 mmol) in formamide (6.0 mL) was heated to 150° C. in an oil bath and stirred for 18 hours. After cooled to room temperature, ethyl acetate (100 mL) and water (100 mL) were added and the layers were separated. The organic solution was washed with water (2×60 mL), dried over MgSO$_4$ and concentrated in vacuo to provide the crude product 28E (0.50 g, quant.) which was used without further purification. MS found for C$_9$H$_7$FN$_2$O: 179.0 (M+H)$^+$.

Step E—Synthesis of Compound 28F

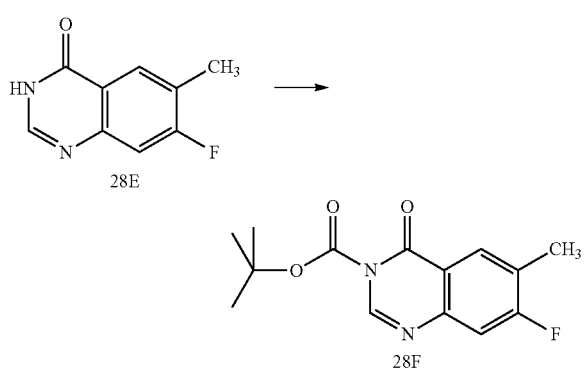

To a solution of 28E (from Step 4) in anhydrous THF (20 mL) at room temperature was added di-tert-butyl dicarbonate (1.84 g, 8.43 mmol), 4-dimethylaminopyridine (350 mg, 2.86 mmol) and triethyl amine (0.40 mL, 2.87 mmol). The reaction mixture was allowed to stir for 18 hours. Ethyl acetate (100 mL) and water (100 mL) were added and the layers were separated. The aqueous layer was extracted with ethyl acetate (2×50 mL). The combined organic solution was dried over MgSO$_4$ and concentrated in vacuo to provide the crude product which was purified using flash chromatography to provide compound 28F (285 mg, 36%). MS found for C$_{14}$H$_{15}$FN$_2$O$_3$: 179.0 (M+H−100)$^+$.

Step F—Synthesis of Compound 28G

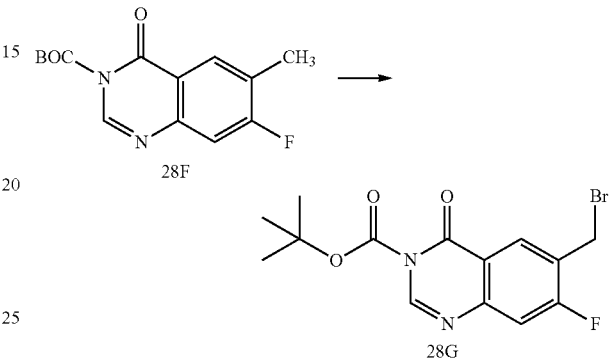

The mixture of 28F (282 mg, 1.01 mmol), NBS (253 mg, 1.42 mmol) and AIBN (58 mg, 0.353 mmol) in anhydrous carbon tetrachloride (60 mL) was heated to 90° C. in an oil bath and stirred for 4 hours. After cooled to room temperature and concentrated in vacuo, the resulting residue was dissolved in ethyl acetate (100 mL) and water (100 mL). The layers were separated. The organic solution was washed with water (100 mL), dried over MgSO$_4$ and concentrated in vacuo to provide the crude product 28G (453 mg, quant.) which was used without further purification.

Alternate Step E—Synthesis of Compound 28H

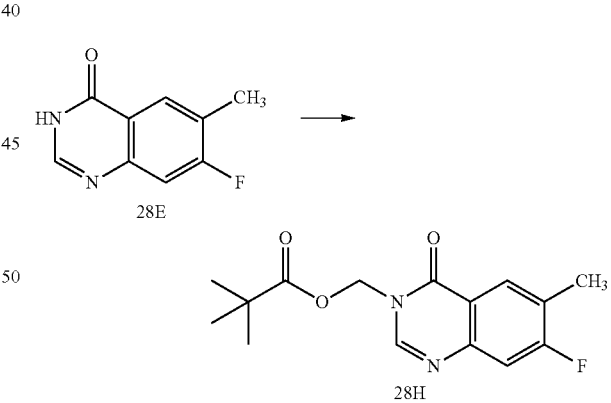

To a solution of 28E (0.8 g, 4.49 mmol) in anhydrous DMF (50 mL) at room temperature was added choromethylpivolate (0.085 mL, 5.9 mmol), and cesium carbonate (2.9 g, 8.91 mmol). The reaction mixture was allowed to stir for 18 hours. Ethyl acetate (100 mL) and water (100 mL) were added and the layers were separated. The aqueous layer was extracted with ethyl acetate (2×50 mL). The combined organic layer was back-washed twice with water, and then dried over MgSO$_4$ and concentrated in vacuo to provide the crude product. Purification via flash chromatography afforded compound 28H (0.8 g, 61%).

Alternate Synthesis of Compound 28G from Compound 28H

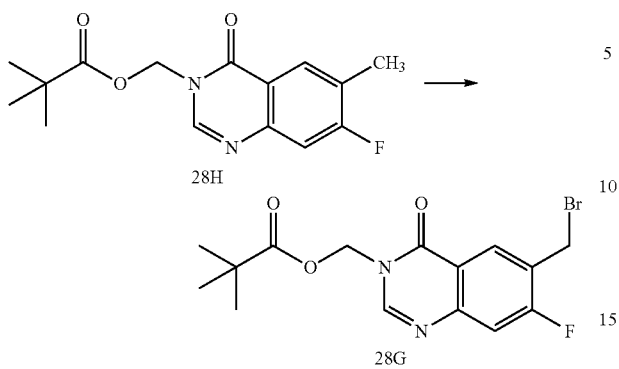

The mixture of 28H (0.8 g, 2.74 mmol), NBS (0.685 g, 3.85 mmol) and benzoylperoxide (0.28 g, 0.826 mmol) in anhydrous carbon tetrachloride (100 mL) was heated to 90° C. in an oil bath. After 6 hours the reaction was cold to room temperature and concentrated in vacuo, the resulting residue was dissolved in ethyl acetate (100 mL) and water (100 mL). The layers were separated. The organic solution was washed with water (100 mL), dried over MgSO₄ and concentrated in vacuo to provide the crude product 28I (1.0 g, quant.) which was used without further purification.

Example 29

Preparation of Intermediate Compound 29E

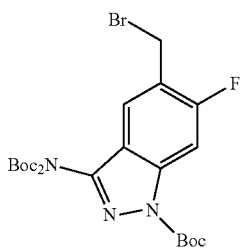

Step A—Synthesis of Compound 29A

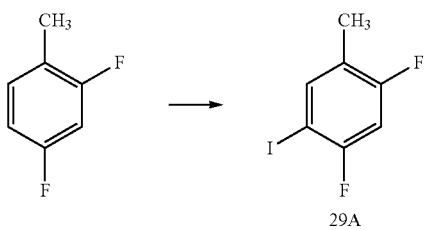

A solution of 2,4-difluorotoluene (4.72 g, 36.8 mmol) in trifluoroacetic acid (12.29 mL, 159.5 mmol) was cooled to 0° C., then N-Iodosuccinimide (9.59 g, 42.6 mmol) was added and the resulting reaction was allowed to stir at room temperature for about 15 hours. The reaction mixture was then concentrated in vacuo and the residue obtained was dissolved in hexanes (100 mL), washed with aqueous sodium thiosulfate (100 mL), brine (100 mL), then dried (MgSO₄), filtered and concentrated in vacuo. The resulting residue was purified using bulb-to-bulb distillation to provide compound 29A (7.2 g, 77%) as a colorless oil.

Step B—Synthesis of Compound 29B

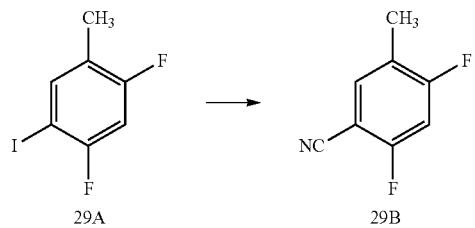

A solution of compound 29A (7.11 g, 28.0 mmol), zinc cyanide (1.97 g, 16.8 mmol) and tetrakis(triphenylphosphine) palladium(0) (3.23 g, 2.80 mmol) in DMF (30 mL) was heated to 90° C. and allowed to stir at this temperature for 1.5 hours. The reaction mixture was concentrated in vacuo and the residue obtained was taken up in water (400 mL) and extracted with ether (400 mL). The organic extract was washed with aqueous ammonium hydroxide solution (1N). The organic layer was dried (MgSO₄) filtered, concentrated in vacuo to provide a residue that was purified using flash column chromatography (SiO₂, EtOAc/Hexanes) to provide a mixture that contained product and triphenylphosphine. This mixture was further purified using sublimation at 1 mm/Hg at 45° C. to provide compound 29B (1.8 g; Yield=42%).

Step C—Synthesis of Compound 29C

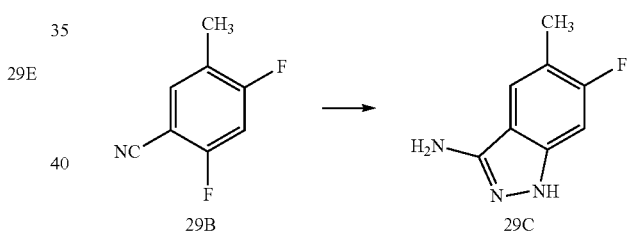

A solution of compound 29B (1.400 g, 9.154 mmol) and hydrazine (0.700 mL, 22.3 mmol) in isopropyl alcohol (50 mL, 653.1 mmol), was heated to reflux and allowed to stir at this temperature for 24 hours. The reaction mixture was cooled to room temperature, concentrated in vacuo and the residue obtained was purified using flash column chromatography (SiO₂, Acetone/Hexanes 0→50%) to provide compound 29C (330 mg, 22%).

Step D—Synthesis of Compound 29D

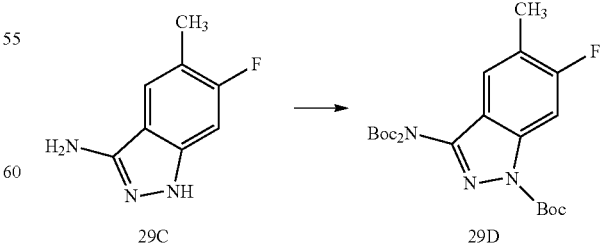

A solution of compound 29C (330.00 mg, 1.998 mmol), di-tert-butyldicarbonate (2.6163 g, 11.98 mmol) and 4-dimethylaminopyridine (48.817 mg, 0.39959 mmol) in acetonitrile (15 mL, 287.2 mmol) was heated to reflux and allowed to stir at this temperature for 2 hours. The reaction mixture was cooled to room temperature, concentrated in vacuo, and the resulting residue was purified using flash column chromatography (SiO$_2$, EtOAc/Hexanes 0-20%) to provide compound 29D (640.00 mg, 68%) as a colorless oil.

Step E—Synthesis of Compound 29E

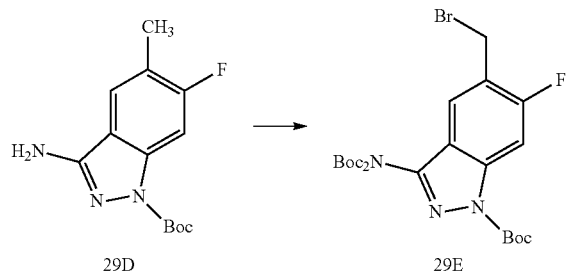

A solution of compound 29D (630.00 mg, 1.3533 mmol), N-bromosuccinimide (337.22 mg, 1.8947 mmol) and benzoyl peroxide (65.563 mg, 0.27067 mmol) in carbon tetrachloride (20 mL) was heated to reflux and allowed to stir at this temperature for 3 hours. The reaction mixture was cooled to room temperature, concentrated in vacuo and the residue obtained was dissolved in EtOAc (300 mL). The resulting solution was washed with aqueous sodium thiosulfate (100 mL), brine (100 mL), dried (MgSO$_4$), filtered, and concentrated in vacuo. The residue obtained was purified using flash column chromatography (SiO$_2$, EtOAc/Hexanes) to provide compound 29E as a colorless oil.

Example 30

Preparation of Intermediate Compounds 30E and 30F

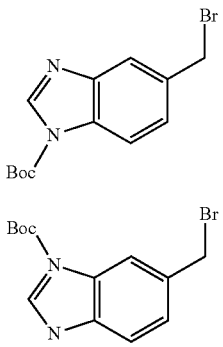

Step A—Synthesis of Compound 30B

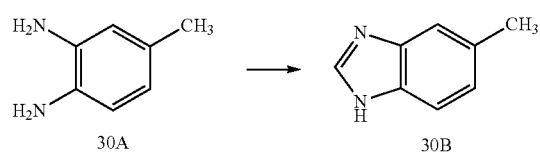

A solution of compound 30A (3 g, 24.5 mmol) in trimethyl orthoformate (15 mL) was treated with 2 drops conc. HCl and heated to 80° C. for 2 hours. The reaction mixture was cooled to room temperature and concentrated in vacuo to provide compound 30B (3.65 g), which was used without further purification. M.S. found for C$_8$H$_8$N$_2$: 133.2 (M+H)$^+$.

Step B—Synthesis of Compounds 30C and 30D

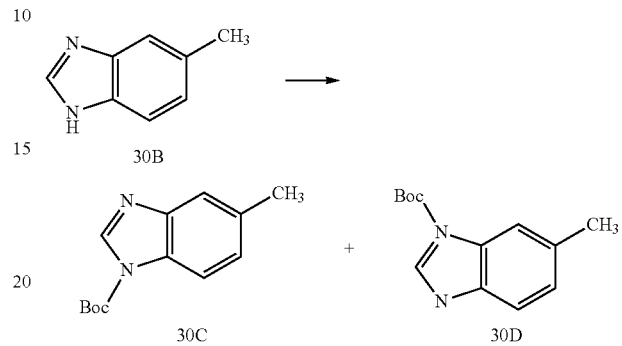

To a solution of compound 30B (24.5 mmol) in CH$_3$CN (65 mL) was added di-tertbutyl dicarbonate (5.89 g, 27.0 mmol), triethylamine (3.76 mL, 27.0 mmol) and 4-dimethylamino pyridine (300 mg, 2.45 mmol) and the resulting reaction was heated to 80° C. and allowed to stir at this temperature for 1.5 hours. The reaction mixture was cooled to room temperature, concentrated in vacuo, and the residue obtained was purified using flash column chromatography (silica gel, EtOAc/Hexanes 5-20%) to provide a mixture of isomeric compounds 30C and 30D (5.38 g, 94.3% yield over steps A and B).

Step C—Synthesis of Compounds 30E and 30F

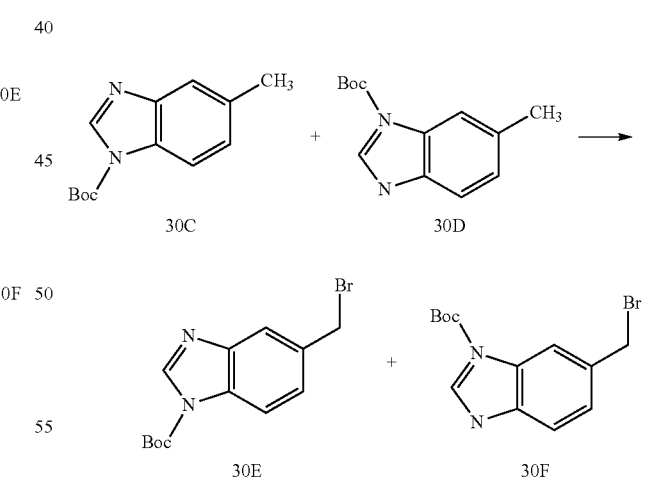

To a solution of compounds 30C and 30D (2 g, 8.61 mmol) in carbon tetrachloride (40 mL) was added N-bromosuccinimide (1.6 g, 9.04 mmol) and dibenzoyl peroxide (41.7 mg, 0.1722 mmol) and the resulting reaction was heated to 90° C. and allowed to stir at this temperature for 12 hours. The reaction was cooled to room temperature, solids were filtered off and the filtrate was washed with water, dried over sodium sulfate and concentrated in vacuo to provide compounds 30E and 30F (2.58 g) which was used without further purification. M.S. found for $C_{13}H_{15}BrN_2O_2$: 334.7 $(M+Na)^+$.

Example 31

Preparation of Intermediate Compound 31B

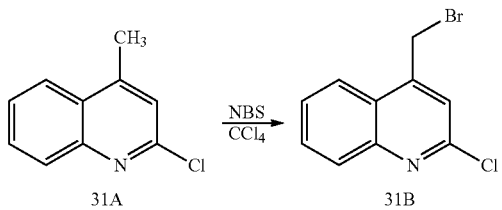

A mixture of compound 31A (1.5 g, 8.44 mmol), NBS (1.8 g, 10.11 mmol) in carbon tetrachloride (50 mL) was heated to reflux, then benzoyl peroxide (0.21 g, 0.866 mmol) was added. The resulting suspension was allowed to stir at reflux for 19 hours, then cooled to room temperature and filtered. The filtrate was washed with saturated sodium carbonate, dried over sodium sulfate and concentrated in vacuo to provide a mixture (1.7 g) which contains about 50% of compound 31B, and was used without further purification.

Example 32

Preparation of Intermediate Compound 32D

Step A—Synthesis of Compound 32B

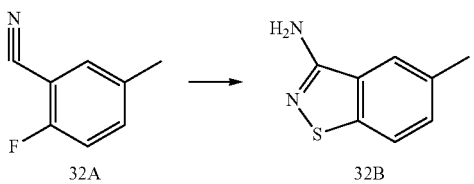

A mixture of 2-fluoro-5-methylbenzonitrile (32A, 2.0 g; 14.799 mmol) and sodium sulfide (1.0 eq, 1.15 g) was dissolved in 150 mL of DMSO and heated at 70° C. overnight. The mixture was placed in an ice-water bath and treated with concentrated aqueous ammonium hydroxide (20 mL) and aqueous sodium hypochlorite (20 mL). The reaction mixture was allowed to warm to room temperature and stirred for 5 hours. The mixture was diluted with ethyl acetate (300 mL) and washed with water (2×60 mL) and brine (50 mL). The organic layer was dried over magnesium sulfate, filtered and concentrated in vacuo. The resulting residue was adsorbed on silica gel and purified on a Biotage 40-M silica gel column (gradient: 0 to 30% acetone in hexanes) to provide the product 32B (860 mg; 36%) as a white solid. $^1$H-NMR (CDCl$_3$; 400 MHz): δ 7.68 (1H, d, J=8.54 Hz), 7.48 (1H, s), 7.33 (1H, d, J=8.54 Hz), 4.89 (2H, broad s), 2.50 (3H, s).

Step B—Synthesis of Compound 32C

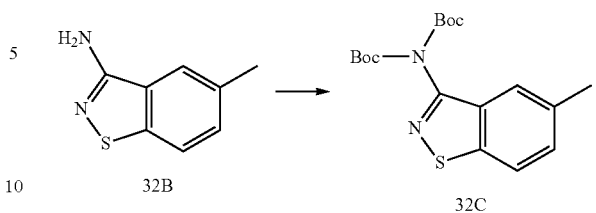

A solution of 5-methylbenzo[d]isothiazol-3-ylamine (32B, 850 mg; 5.176 mmol) in dry acetonitrile (50 mL) was treated with Boc-anhydride (2.1 eq, 2.37 g) and heated to 50° C. All starting material had been consumed after 2 h and the mixture was concentrated in vacuo to one third of its volume. The resulting residue was dissolved in ethyl acetate (100 mL) and washed with aqueous sodium hydrogen sulfate (20 mL), and brine (20 mL). The organic layer was dried over magnesium sulfate, filtered and concentrated in vacuo. The resulting residue was adsorbed on silica gel and purified on a Biotage 40-M silica gel column (gradient: 0 to 10% ethyl acetate in hexanes) to provide the product 32C (1.7 g; 91%) as a white powder. $^1$H-NMR (CDCl$_3$; 400 MHz): δ 7.77 (1H, d, J=8.54 Hz), 7.55 (1H, s), 7.38 (1H, dd, J=1.83, 8.54 Hz), 2.51 (3H, s), 1.36 (18H, s). LR-MS (ESI): caldc for $C_{18}H_{25}N_2O_4S$ $[M+H]^+$ 365.15. found 365.23.

Step C—Synthesis of Compound 32D

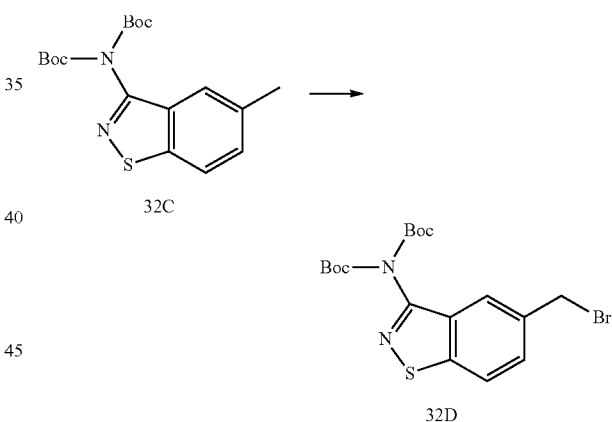

A solution of N,N-bis-Boc-5-methyl-benzo[d]isothiazol-3-ylamine (32D, 500 mg; 1.371 mmol) in 15 mL of carbon tetrachloride was treated N-bromosuccinimide (1.05 eq, 256 mg) and benzoyl peroxide (10 mol %; 33 mg). The solution was degassed (vacuum/argon flush) and then heated to 75° C. for 5 hours. The reaction mixture was concentrated to one third of its volume in vacuo and the resulting residue was dissolved in ethyl acetate (50 mL). The solution was washed with aqueous saturated sodium bicarbonate soln (2×10 mL) and brine (10 mL). The organic layer was dried over magnesium sulfate, filtered and concentrated in vacuo. The resulting residue was adsorbed on silica gel and purified on a Biotage 40-S silica gel column (gradient: hexanes then 0 to 10% ethyl acetate in hexanes) to provide the product 32D (396 mg; 69%) as a white solid. $^1$H-NMR (CDCl$_3$; 400 MHz): δ 7.87 (1H, d, J=8.54 Hz), 7.78 (1H, s), 7.58 (1H, dd, J=1.83, 8.54 Hz), 4.63 (2H, s), 1.37 (18H, s). LR-MS (ESI): caldc for $C_{18}H_{24}BrN_2O_4S$ $[M+H]^+$ 445.06; found 445.24.

Example 33

Preparation of Intermediate Compound 33D

Step A—Synthesis of Compound 33B

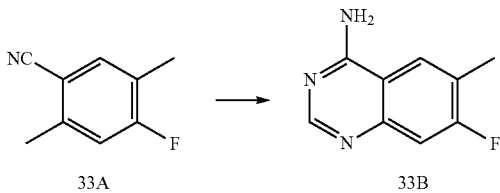

A solution of 33A (0.20 g, 1.33 mmol) in formamide (15 mL) was heated to 150° C. and stirred for 18 hours. After cooled to room temperature, ethyl acetate (60 mL) and water (30 mL) were added and the layers were separated. The organic solution was washed with water (3×20 mL), dried (MgSO$_4$), filtered, and concentrated in vacuo to provide the crude product 33B (0.22 g, 93%). MS found for $C_9H_8FN_3$: 178.2 (M+H)$^+$.

Step B—Synthesis of Compound 33C

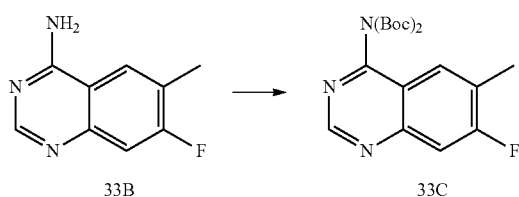

Compound 33B was treated with 3.0 equivalent of (Boc)$_2$O to provide compound 33C. MS found for $C_{19}H_{24}FN_3O_4$: 378.4 (M+H)$^+$.

Step C—Synthesis of Compound 33D

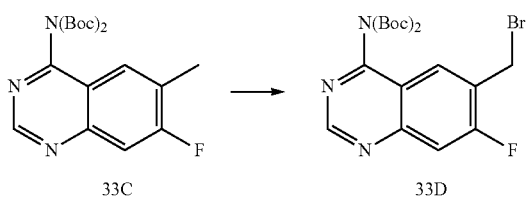

Bromination of compound 33C using standard conditions with N-bromo succinimide provided compound 33D. MS found for $C_{19}H_{23}BrFN_3O_4$: 458.3 (M+H)$^+$.

Example 34

Preparation of Intermediate Compound 34F

Step A—Synthesis of Compound 34B

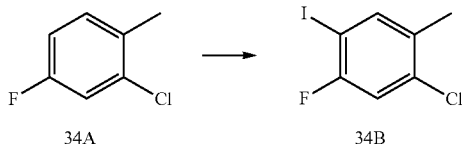

N-iodosuccinimide (1.1 eq; 17.1 g) was added to a solution of 2,4-difluoro toluene (34A, 10.0 g; 69.17 mmol; Alfa Aesar) in trifluoroacetic acid (46 mL). The reaction was set to stir for 12 hours. The volatiles were removed under reduced pressure; the remaining slurry was diluted with ether (400 mL) and washed with 5% aq sodium thiosulfate (5×40 mL), water (2×30 mL), and brine (40 mL). The organic layer was collected, dried over magnesium sulfate, filtered, and concentrated in vacuo. The reaction was purified via bulb to bulb distillation to afford product 34B as a colorless liquid (17 g; 91%)

Step B—Synthesis of Compound 34C

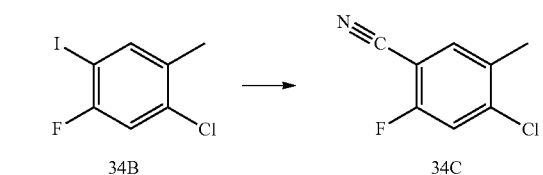

A solution of intermediate 34B (13.0 g; 48.06 mmol) and zinc cyanide (1 eq; 5.644 g) in N,N-dimethlyformamide (50 mL) was treated with tetrakis (triphenylphosphine) palladium (0) (0.1 eq; 5.55 g) and heated at 90° C. for 12 hours. The reaction mixture was diluted with ether (600 mL) and ammonium hydroxide (1:1 concentrated ammonium hydroxide: water 200 mL). The organic layer was separated and washed with water (100 mL) and brine (100 mL), dried over magnesium sulfate, filtered, concentrated in vacuo, and purified over silica gel first eluting with hexanes, then with 20% ethyl acetate/hexanes. Product 34C (4.48 g; 33%) was afforded as a clear oil.

Step C—Synthesis of Compound 34D

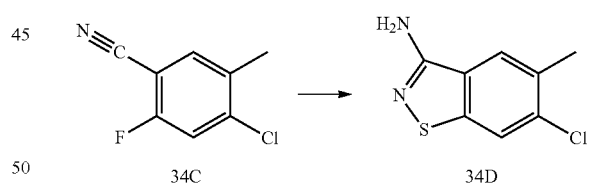

A solution of 34C (2.25 g; 13.27 mmol) and sodium sulfide (1 eq; 1.035 g) was prepared in DMSO (130 mL) and heated at 70° C. overnight. The mixture was placed in an ice water bath and treated with concentrated aqueous ammonium hydroxide (30 mL) and aqueous sodium hypochlorite (30 mL). The reaction mixture was allowed to stir for 5 h (temp from 0 to 25° C.). The mixture was diluted with ethyl acetate (400 mL) and washed with water (2×40 mL) and brine (50 mL). The organic layer was dried over magnesium sulfate, filtered and concentrated in vacuo. The resulting residue was adsorbed on silica gel and purified on an ISCO 330G column (gradient: 0-30% acetone in hexanes), affording product 34D (800 mg; 30.3%) as a white solid.

Step D—Synthesis of Compound 34E

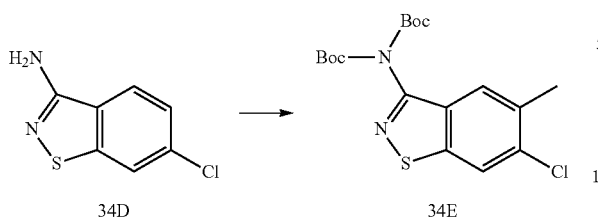

A solution of intermediate 34D (780 mg; 3.93 mmol) in dry acetonitrile (39 mL) was treated with Boc-anhydride (2.2 eq; 1.885 g) and heated to 50° C. All starting material had been consumed after 2 h and the mixture was concentrated in vacuo to one third of its volume. The resulting residue was dissolved in ethyl acetate (100 mL) and washed with aqueous sodium hydrogen sulfate (20 mL) and brine (20 mL). The organic layer was dried over magnesium sulfate, filtered and concentrated in vacuo. The resulting residue was adsorbed on silica gel and purified on a ISCO 80 gram column (gradient: 0 to 10% ethyl acetate in hexanes) to provide the product 34E (1.03 g; 66% yield) as a white solid.

Step E—Synthesis of Compound 34F

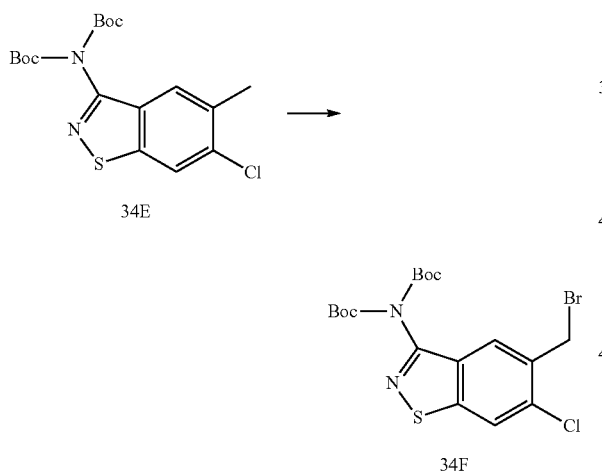

A solution of intermediate 34E (400 mg; 1.003 mmol), N-Bromosuccinimide (1.05 eq; 187.4 mg), and benzoyl peroxide (0.1 eq; 24.3 mg) in dry carbon tetrachloride (10 mL) was prepared and heated at reflux for 12 hours. TLC (30% ethyl acetate in hexanes) revealed the reaction had partially progressed. The reaction mixture was concentrated in vacuo, diluted with ethyl acetate (100 mL), washed with saturated aqueous sodium bicarbonate (25 mL) and brine (25 mL), dried over magnesium sulfate, filtered, and concentrated in vacuo. The resulting residue was then diluted with dichloromethane, adsorbed onto silica gel, and purified on ISCO (25-M Column; 0-40% ethyl acetate in hexanes). The fractions containing product were concentrated in vacuo affording intermediate 34F (278 mg; 58%) as a clear yellow oil.

Example 35

NMR Data for Selected Compounds of the Invention

| Cmpd No. | NMR data |
|---|---|
| 161 | 1H NMR δ (DMSO) 7.98 (d, 1H, J = 8.20 Hz), 7.81-7.76 (m, 2H), 7.66-7.64 (m, 1H), 7.59-7.55 (m, 2H), 7.48 (d, 1H, J = 7.57 Hz), 7.42 (d, 1H, J = 5.36 Hz), 7.20 (s, 1H), 6.36 (t, 1H, J = 6.62 Hz), 5.90 (s, 2H), 3.50 (s, 3H), 2.31 (s, 3H). |
| 162 | 1H NMR δ (DMSO) δ 7.99 (d, 1H, J = 8.2 Hz), 7.80-7.76 (m, 2H), 7.64 (dd, 1H, J = 6.6, 2.2 Hz), 7.58-7.54 (m, 2H), 7.44 (d, 1H, J = 4.7 Hz), 7.38 (d, 1H, J = 7.25 Hz), 7.18 (s, 1H), 6.37 (t, 1H, J = 6.6 Hz), 5.94 (s, 2H), 2.31 (s, 3H); 13C NMR δ (DMSO) δ 162.4, 161.3, 160.7 (d), 148.0, 145.9, 140.4, 136.6 (d), 134.4, 130.6, 130.3, 127.5, 127.3, 127.2, 126.7, 125.1, 122.6, 122.4, 122.3, 118.7 (d), 118.0, 105.1, 96.7 (d), 45.7, 14.4. |
| 163 | 1H NMR δ (CD3Cl) 8.00 (s, 1H), 7.84-7.79 (m, 2H), 7.68 (t, 1H, J = 7.25 Hz), 7.57 (d, 1H, J = 8.20 Hz), 7.45 (t, 1H, J = 7.57 Hz), 7.37 (s, 1H), 7.29 (d, 1H, J = 6.94 Hz), 6.87 (d, 1H, J = 9.77 Hz), 6.66-6.64 (m, 1H), 6.04 (s, 2H), 5.85 (s, 2H), 2.31 (s, 3H), 1.21 (s, 9H). |
| 164 | 1H NMR δ (CD3Cl) 8.02 (d, 1H, J = 8.20 Hz), 7.68 (t, 1H, J = 7.25 Hz), 7.61-7.58 (m, 2H), 7.54 (dd, 1H, J = 6.94, 1.6 Hz), 7.46 (t, 1H, J = 7.25 Hz), 7.38 (d, 1H, J = 7.57 Hz), 7.28 (s, 1H), 6.89 (d, 1H, J = 10.09 Hz), 6.34 (t, 1H, J = 6.62 Hz), 5.99 (s, 2H), 5.89 (s, 2H), 5.72 (s, 2H), 2.32 (s, 3H), 1.24 (s, 9H), 1.03 (s, 9H). |
| 180 | $^1$H NMR (400 MHz, D$_6$-DMSO), δ, 13.06 (b, 2 H), 11.79 (s, 1 H), 7.96 (s, 1 H), 7.55 (dd, 1 H, J = 1.8 & 6.7 Hz), 7.46 (d, 1 H, J = 11.0 Hz), 7.40 (dd, 1 H, J = 1.8 & 6.1 Hz), 7.34 (d, 1 H, J = 10.4 Hz), 7.31 (d, 1 H, J = 7.3 Hz), 7.04 (d, 1 H, J = 6.7 Hz), 6.32 (t, 1 H, J = 6.7 Hz), 5.87 (s, 2 H), 2.26 (s, 3 H). $^{13}$C NMR (125 MHz, D$_6$-DMSO, F-coupled), δ 163.7, 162.2, 161.5, 161.0, 159.6, 159.0, 141.1, 137.3, 137.2, 135.1, 134.5, 128.4, 126.2, 123.3, 123.0, 123.0, 120.6, 120.4, 120.2, 120.1, 120.2, 119.4, 119.2, 118.0, 106.1, 106.1, 97.9, 97.7, 96.8, 96.6, 43.3, 43.3, 15.5, 15.5, 67.8, 25.9. |
| 182 | 1H NMR δ (DMSO) δ 8.26 (d, 1H, J = 8.20 Hz), 7.87 (t, 1H, J = 8.20 Hz), 7.76 (d, 1H, J = 8.2 Hz), 7.63 (m, 2H), 7.51 (d, 1H, J = 11.0 Hz), 7.46 (d, 1H, J = 6.9 Hz), 7.41 (d, 1H, J = 7.25 Hz), 6.34 (t, 1H, J = 5.7 Hz), 6.21 (s, 2H), 5.60 (s, 1H), 2.31 (s, 3H). |
| 183 | 1H NMR δ (CD3OD) δ 7.93 (d, 1H, J = 8.20 Hz), 7.64 (d, 1H, J = 9.14 Hz), 7.50 (t, 1H, J = 7.25 Hz), 7.29-7.26 (m, 3H), 7.20 (d, 1H, J = 7.25 Hz), 6.85 (d, 1H, J = 10.72 Hz), 6.35 (t, 1H, J = 6.30 Hz), 6.10 (s, 2H), 5.53 (s, 1H), 2.19 (s, 3H). |
| 189 | 1H-NMR (400 MHz, in dmso-d6): δ 12.92 (1H, broad s), 11.77 (1H, s), 7.93 (1H, s), 7.79 (1H, d, J = 8.30 Hz), 7.53 (1H, dd, J = 1.95, 6.84 Hz), 7.46 (1H, d, J = 11.23 Hz), 7.39 (1H, d, J = 6.35 Hz), 7.29 (1H, d, J = 7.32 Hz), 7.05 (1H, dd, J = 0.98, 8.30 Hz), 6.75 (2H, broad s), 6.31 (1H, dd, J = 6.35, 6.84 Hz), 5.85 (2H, s), 2.26 (3H, s). |
| 200 | 1H NMR (500 MHz, CDCl3) δ 12.83 (s, 1H), 11.82 (s, 1H), 7.98 (d, J = 8.2 Hz, 1H), 7.78 (m, 2H), 7.63 (d, J = 6.9 Hz, 1H), 7.56 (t, J = 7.9 Hz, 1H), 7.44 (d, J = 5.7 Hz, 1H), 7.40 (s, 1H), 7.28 (s, 1H), 7.14 (s, 1H), 6.38 (d, J = 6.0 Hz, 1H), 5.93 (s, 2H), 2.29 (s, 6H). |
| 202 | 1H NMR (500 MHz, CDCl3) δ 7.26 (s, 1H), 6.96 (dd, J = 6.9, 1.9 Hz, 1H), 6.77 (d, J = 8.2 Hz, 1H), 6.70 (dd, J = 6.6, 1.9 Hz, 1H), 6.63 (d, J = 10.7 Hz, |

| Cmpd No. | NMR data |
|---|---|
| | 1H), 6.46 (s, 2H), 5.79 (t, J = 6.9 Hz, 1H), 5.20 (s, 2H), 1.57 (s, 3H), 1.53 (s, 3H). |
| 204 | 1H NMR (500 MHz, CDCl3) δ 11.48 (s, 1H), 8.29 (d, J = 8.2 Hz, 1H), 8.02 (d, J = 8.2 Hz, 1H), 7.91 (s, 1H), 7.82 (m, 2H), 7.59 (m, 1H), 7.31 (m, 1H), 7.19 (d, J = 7.6 Hz, 1H), 7.11 (m, 1H), 6.21 (m, 1H), 6.10 (s, 2H), 2.23 (s, 3H). |
| 205 | $^1$H NMR (500 MHz, d$_6$-DMSO): δ 12.9 (bs, 1 H), 12.3 (bs, 1 H), 11.8 (bs, 1 H), 8.39 (d, J = 3.07 H$_z$, 1 H), 7.55 (q, J = 2.04 H$_z$, 1 H), 7.51 (d, J = 11.1 H$_z$, 2 H), 7.43 (d, J = 8.32 H$_z$, 1 H), 7.34 (d, J = 7.20 H$_z$, 1 H), 5.91 (s, 2 H), 2.29 (s, 3 H), MS found for C$_{24}$H$_{16}$N$_4$O$_4$F$_2$: 463.3 (M + H)$^+$. |
| 212 | 1H NMR (500 MHz, CD3OD): δ 7.77 (d, J = 8.5 Hz, 1H), 7.71 (dd, J = 2.2 Hz, J = 6.9 Hz, 1H), 7.52 (dd, J = 1.8 Hz, J = 8.8 Hz, 1H), 7.47 (s, 1H), 7.38 (dd, J = 1.9 Hz, J = 6.6 Hz, 1H), 7.33 (s, 1H), 7.31 (d, J = 7.6 Hz, 1H), 6.92 (d, J = 10.7 Hz, 1H), 6.44 (t, J = 6.9 Hz, 1H), 5.97 (s, 2H), 2.40 (s, 3H), 2.27 (s, 3H). |
| 213 | 1H NMR (500 MHz, DMSO): δ 13.01 (bs, 1H), 11.79 (s, 1H), 7.75 (s, 1H), 7.67 (d, J = 8.5 Hz), 7.62 (d, 1H, J = 6.6 Hz), 7.54 (d, 1H, J = 11 Hz), 7.40 (m, 3H), 7.10 (s, 1H), 6.35 (t, 1H, J = 6.2, 6.3 Hz), 5.9 (s, 2H), 2.28 (s, 3H). M.S. found: 476.3 (M + H)$^+$. |
| 216 | 1H NMR (500 MHz, CD3OD): δ 7.76 (dd, J = 2.2 Hz, J = 6.9 Hz, 1H), 7.44-7.40 (m, 2H), 7.34 (d, J = 7.6 Hz, 1H), 7.29 (s, 1H), 7.02 (d, J = 1.9 Hz, 1H), 6.98 (dd, J = 2.2 Hz, J = 8.8 Hz, 1H), 6.94 (d, J = 10.4 Hz, 1H), 6.48 (t, J = 6.6 Hz, 1H), 5.93 (s, 2H), 2.31 (s, 3H). |
| 217 | 1H-NMR (400 MHz, in dmso-d6): δ 11.78 (1H, broad s), 7.95 (1H, d, J = 8.24 Hz), 7.85 (1H, s), 7.76 (2H, m), 7.62 (1H, dd, J = 1.65, 6.59 Hz), 7.54 (1H, dd, J = 7.14, 7.69 Hz), 7.46 (1H, s), 7.42 (1H, dd, J = 1.65, 6.59 Hz), 7.14 (1H, s), 6.35 (1H, t, J = 6.59), 5.94 (2H, s), 2.38 (3H, s); LC-MS (ESI): calcd. for C$_{25}$H$_{18}$ClN$_3$O$_3^+$ [M + H]$^+$ 478.07, found 477.96. |
| 218 | $^1$H NMR (500 MHz, d$_6$-DMSO): δ 12.9 (bs, 1 H), 11.7 (bs, 1 H), 11.3 (s, 1 H), 11.2 (s, 1 H), 7.54-7.47 (m, 2 H), 7.42 (d, J = 5.6 H$_z$, 1 H), 7.35-7.31 (m, 2 H), 6.92 (d, J = 10.6 H$_z$, 1 H), 6.33 (t, J = 6.3 H$_z$), 5.79 (s, 2 H), 2.28 (s, 3 H), MS found for C$_{24}$H$_{16}$N$_4$O$_5$F$_2$: 479.3 (M + H)$^{+\cdot}$ |
| 220 | 1H NMR (500 MHz, d$_6$-DMSO): δ 13.1 (bs, 1 H), 11.8 (bs, 1 H), 8.31 (d, J = 9.39 H$_z$, 1 H), 7.55-7.51 (m, 3 H), 7.43-7.253 (m, 1 H), 7.248 (s, 1 H), 7.20-6.38 (m, 1 H), 6.37-6.34 (m, 1 H), 5.95 (s, 2 H), 3.29 (s, 3 H), 2.37 (s, 3 H), MS found for C$_{24}$H$_{18}$N$_3$O$_5$F$_2$S: 480.3 (M + H)$^+$. |
| 221 | $^1$H NMR (500 MHz, DMSO): δ 12.88 (bs, 1H), 11.82 (s, 1H), 8.05 (dd, 1H, J = 5.6, 5.3 Hz), 7.70 (m, 2H), 7.62 (d, 1H, J = 6.6 Hz), 7.55 (d, 1H, J = 11 Hz), 7.45 (d, 1H, J = 6 Hz), 7.39 (d, 1H, J = 7.5 Hz), 7.21 (s, 1H), 6.35 (t, 1H, J = 6.2, 6.3 Hz) 5.92 (s, 2H), 2.30 (s, 3H). M.S. found: 480.3 (M + H)$^+$. |
| 222 | 1H NMR (500 MHz, CD3OD): δ 7.83 (dd, J = 6.0 Hz, J = 9.1 Hz, 1H), 7.75 (d, J = 2.2 Hz, J = 6.9 Hz, 1H), 7.58 (dd, J = 2.5 Hz, J = 9.8 Hz, 1H), 7.50 (s, 1H), 7.43 (dd, J = 1.9 Hz, J = 6.3 Hz, 1H), 7.38-7.32 (m, 2H), 6.98 (d, J = 10.7 Hz, 1H), 6.49 (t, J = 6.6 Hz, 1H), 6.03 (s, 2H), 2.31 (s, 3H). |
| 226 | 1H NMR (500 MHz, DMSO): δ 7.69 (d, J = 9.1 Hz, 1H), 7.61 (dd, J = 2.2 Hz, J = 6.9 Hz, 1H), 7.52 (J = 10.7 Hz, 1H), 7.44 (s, 1H), 7.39-7.36 (m, 2H), 7.18 (dd, J = 2.8 Hz, J = 8.8 Hz, 1H), 7.11 (s, 1H), 6.35 (t, J = 6.3 Hz, 1H), 5.89 (s, 2H), 3.89 (s, 3H), 2.30 (s, 3H). |
| 230 | $^1$H NMR (500 MHz, d$_6$-DMSO): δ 13.0 (bs, 1 H), 11.8 (bs, 1H), 7.53-7.48 (m, 3 H), 7.42 (m, 1 H), 7.39 (d, J = 7.62 H$_z$, 1 H), 6.34 (t, J = 6.60 Hz, 1 H), 5.93 (s, 2H), 3.29 (s, 3 H), 2.90 (s, 3 H), MS found for C$_{24}$H$_{17}$N$_3$O$_5$F$_2$S: 498.3 (M + H)$^+$. |
| 231 | $^1$H NMR (500 MHz, DMSO): δ 12.88 (bs, 1H), 11.82 (s, 1H), 8.05 (m, 2H), 7.61 (d, 1H, J = 6.62 Hz), 7.55 (d, 1H, J = 11 Hz), 7.45 (d, 1H, J = 5.6 Hz), 7.39 (d, 1H, J = 7.5 Hz), 7.26 (s, 1H), 6.37 (t, 1H, J = 6.2 Hz) 5.92 (s, 2H), 2.30 (s, 3H). M.S. found: 498.3 (M + H)$^+$. |
| 238 | 1H NMR (500 MHz, DMSO): δ 7.70-7.67 (m, 2H), 7.61 (dd, J = 1.9 Hz, J = 6.9 Hz, 1H), 7.53 (J = 11.0 Hz, 1H), 7.43 (m, 1H), 7.41 (dd, J = 2.2 Hz, J = 8.8 Hz, 1H), 7.37 (d, J = 7.9 Hz, 1H), 7.11 (s, 1H), 6.35 (t, J = 6.3 Hz, 1H), 5.90 (s, 2H), 2.60 (s, 3H), 2.30 (s, 3H). |
| 246 | $^1$H NMR (400 MHz, D$_6$-DMSO, TFA salt), δ 12.11 (s, 1 H), 9.55 (s, 1 H), 7.99 (d, 1 H, J = 8.2 Hz), 7.83-7.78 (m, 3 H), 7.63 (d, 1H, J = 11.0 Hz), 7.59-7.56 (m, 2 H), 7.52 (d, 1 H, J = 7.3 Hz), 7.28 (s, 1 H), 6.51 (t, 1 H, J = 6.6 Hz), 5.92 (s, 2 H), 4.38 (bt, 2 H, J = 4.7 Hz), 3.25 (b, 2 H), 2.71 (s, 6 H), 2.33 (s, 3 H). $^{13}$C NMR (125 MHz, D$_6$-DMSO, F-coupled), δ 162.3, 162.1, 161.8, 160.2, 149.1, 146.9, 141.6, 137.9, 137.8, 135.5, 135.4, 131.5, 131.2, 128.6, 128.3, 127.7, 126.5, 123.3, 123.2, 123.1, 120.5, 120.3, 118.8, 106.8, 98.1, 97.9, 59.4, 56.0, 47.0, 43.4, 15.6, 15.5. |
| 254 | 1H NMR δ (CD3Cl) 8.05 (d, 1H, 8.20 Hz), 7.70 (t, 1H, J = 6.94 Hz), 7.61-7.59 (m, 3H), 7.48 (t, 1H, J = 7.57 Hz), 7.39 (d, 1H, J = 7.25 Hz), 7.32 (s, 1H), 6.89 (d, 1H, J = 10.09 Hz), 6.37 (t, 1H, J = 6.94 Hz), 5.98 (s, 2H), 5.87 (s, 2H), 3.67 (s, 3H), 2.33 (s, 3H), 1.24 (s, 9H). |
| 255 | 1H NMR (500 MHz, DMSO): δ 7.66-7.63 (m, 1H), 7.61 (d, 1H, J = 8.8 Hz), 7.57 (J = 10.7 Hz, 1H), 7.46 (d, 1H, J = 7.6 Hz), 7.42 (m, 1H), 7.15 (s, 1H), 7.08 (m, 1H), 7.04 (s, 1H), 6.34 (t, J = 6.3 Hz, 1H), 5.85 (s, 2H), 5.61 (s, 2H), 2.31 (s, 3H), 0.89 (s, 9H). |
| 256 | $^1$H NMR (500 MHz, CDCl3): δ 11.52 (s, 1H), 7.64 (dd, 1H, J = 6.9, 2.2 Hz), 7.49 (d, 1H, J = 9.1 Hz), 7.4 (m, 2H), 7.37 (d, 1H, J = 2.5 Hz), 7.22 (s, 1H), 7.13 (dd, 1H, J = 8.8, 2.5 Hz), 6.93 (d, 1H, J = 10 Hz) 6.42 (t, 1H, J = 6.62 Hz), 5.90 (s, 2H), 5.76 (s, 2H), 3.94 (s, 3H), 2.35 (s, 3H), 1.05 (s, 9H). M.S. found: Decomposes to lactone under LCMS condns |
| 257 | $^1$H NMR (500 MHz, CDCl3): δ 8.01 (d, 1H, J = 8.19 Hz), 7.67 (t, 1H, J = 8.19 Hz), 7.59 (m, 2H), 7.53 (dd, 1H, J = 6.9, 2.2 Hz), 7.45 (t, 1H, J = 7.8, 7.2 Hz), 7.37 (d, 1H, J = 7.2 Hz), 7.27 (m, 1H) 6.87 (d, 1H, J = 10 Hz), 6.32 (t, 1H, J = 6.9, 6.6 Hz), 5.99 (s, 2H), 5.88 (s, 2H), 5.71 (s, 2H), 2.32 (s, 3H), 1.24 (s, 9H), 1.03 (s, 9H). M.S. found: 690.4 |
| 258 | 1H-NMR (400 MHz, in dmso-d6): δ 12.87 (1H, broad s), 11.79 (1H, broad s), 7.95 (1H, d, J = 8.24 Hz), 7.77 (1H, dd, J = 7.14, 8.24 Hz), 7.62 (1H, d, J = 6.59 Hz), 7.54 (2H, m), 7.42 (1H, d, J = 6.59 Hz), 7.35 (1H, d, J = 7.14 Hz), 7.20 (1H, s), 6.35 (1H, t, J = 6.59 Hz), 5.92 (2H, s), 2.67 (2H, ABq, J = 7.14, 7.69 Hz), 1.16 (3H, t, J = 7.14 Hz); LC-MS (ESI): calcd. for C$_{26}$H$_{20}$ClFN$_3$O$_3^+$ [M + H]$^+$ 476.12, found 476.13. |

Example 36

HCV NS5B Polymerase Inhibition Assay

An in vitro transcribed heteropolymeric RNA known as D-RNA or DCoH has been shown to be an efficient template for HCV NS5B polymerase (S.-E. Behrens et al., EMBO J. 15: 12-22 (1996); WO 96/37619). A chemically synthesized 75-mer version, designated DCoH75, whose sequence matches the 3'-end of D-RNA, and DCoH75ddC, where the 3'-terminal cytidine of DCoH75 is replaced by dideoxycytidine, were used for assaying the NS5B enzyme activity as described in Ferrari et al., 12$^{th}$ *International Symposium on HCV and Related Viruses*, P-306 (2005). A soluble C-terminal 21-amino acid truncated NS5B enzyme form (NS5BDeltaCT21) was produced and purified from *Escherichia coli* as C-terminal polyhistidine-tagged fusion protein as described in Ferrari et al., *J. Virol.* 73:1649-1654 (1999). A typical assay contained 20 mM Hepes pH 7.3, 10 mM $MgCl_2$, 60 mM NaCl, 100 µg/ml BSA, 20 units/ml RNasin, 7.5 mM DTT, 0.1 µM ATP/GTP/UTP, 0.026 µM CTP, 0.25 mM GAU, 0.03 µM RNA template, 20 µCi/ml [$^{33}$P]-CTP, 2% DMSO, and 30 or 150 nM NS5B enzyme. Reactions were incubated at 22° C. for 2 hours, then stopped by adding 150 mM EDTA, washed in DE81 filter plate in 0.5M di-basic sodium phosphate buffer, pH 7.0, and counted using Packard TopCount after the addition of scintillation cocktail. Polynucleotide synthesis was monitored by the incorporation of radiolabeled CTP. The effect of the 2-Carboxy Substituted Indole Derivatives on the polymerase activity was evaluated by adding various concentrations of a 2-Carboxy Substituted Indole Derivative, typically in 10 serial 2-fold dilutions, to the assay mixture. The starting concentrations of the indole derivatives ranged from 200 µM to 1 µM. An $IC_{50}$ value for the inhibitor, defined as the compound concentration that provides 50% inhibition of polymerase activity, was determined by fitting the cpm data to the Hill equation $Y=100/(1+10^{((LogIC50-X)*HillSlope)})$, where X is the logarithm of compound concentration, and Y is the % inhibition. Ferrari et al., 12$^{th}$ *International Symposium on HCV and Related Viruses,* P-306 (2005) described in detail this assay procedure. It should be noted that such an assay as described is exemplary and not intended to limit the scope of the invention. The skilled practitioner can appreciate that modifications including but not limited to RNA template, primer, nucleotides, NS5B polymerase form, buffer composition, can be made to develop similar assays that yield the same result for the efficacy of the compounds and compositions described in the invention.

NS5B polymerase inhibition data for selected 2-Carboxy Substituted Indole Derivatives of the present invention was obtained using the above method and calculated $IC_{50}$ values ranged from about 0.001 µM to about 14000 µM.

Example 37

Cell-Based HCV Replicon Assay

To measure cell-based anti-HCV activity of the 2-Carboxy Substituted Indole Derivatives of the present invention, replicon cells were seeded at 5000 cells/well in 96-well collagen 1-coated Nunc plates in the presence of the 2-Carboxy Substituted Indole Derivative. Various concentrations of a 2-Carboxy Substituted Indole Derivative, typically in 10 serial 2-fold dilutions, were added to the assay mixture, the starting concentration of the compound ranging from 250 µM to 1 µM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F. ATGGACAGGCGCCCTGA 3' (SEQ ID NO: 1): 5B.2R. TTGATGGGCAGCTTG-GTTTC3' (SEQ ID NO: 2): the probe sequence was FAM-labeled CACGCCATGCGCTGCGG 3' (SEQ ID NO: 3). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 min, 95° C. for 10 min, 40 cycles of 95° C. for 15 sec, 60° C. for 1 minute. The $\Delta$CT values ($CT_{5B}$-$CT_{GADPH}$) were plotted against the concentration of test compound and fitted to the sigmoid dose-response model using XLfit4 (MDL). $EC_{50}$ was defined as the concentration of inhibitor necessary to achieve $\Delta CT=1$ over the projected baseline; $EC_{90}$ the concentration necessary to achieve $\Delta CT=3.2$ over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV Replicon assay data for selected 2-Carboxy Substituted Indole Derivatives of the present invention was obtained using the above method and calculated $EC_{50}$ values ranged from about 0.001 µM to about 14000 µM.

Uses of the 2-Carboxy Substituted Indole Derivatives

The 2-Carboxy Substituted Indole Derivatives are useful in human and veterinary medicine for treating or preventing a viral infection or a virus-related disorder in a patient. In accordance with the invention, the 2-Carboxy Substituted Indole Derivatives can be administered to a patient in need of treatment or prevention of a viral infection or a virus-related disorder.

Accordingly, in one embodiment, the invention provides methods for treating a viral infection in a patient comprising administering to the patient an effective amount of at least one 2-Carboxy Substituted Indole Derivative or a pharmaceutically acceptable salt, solvate, ester or prodrug thereof. In another embodiment, the invention provides methods for treating a virus-related disorder in a patient comprising administering to the patient an effective amount of at least one 2-Carboxy Substituted Indole Derivative or a pharmaceutically acceptable salt, solvate, ester or prodrug thereof.

Treatment or Prevention of a Viral Infection

The 2-Carboxy Substituted Indole Derivatives can be used to treat or prevent a viral infection. In one embodiment, the 2-Carboxy Substituted Indole Derivatives can be inhibitors of viral replication. In a specific embodiment, the 2-Carboxy Substituted Indole Derivatives can be inhibitors of HCV replication. Accordingly, the 2-Carboxy Substituted Indole Derivatives are useful for treating viral diseases and disorders related to the activity of a virus, such as HCV polymerase.

Examples of viral infections that can be treated or prevented using the present methods, include but are not limited to, hepatitis A infection, hepatitis B infection and hepatitis C infection.

In one embodiment, the viral infection is hepatitis C infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology,* 30(2):192-195 (1998). The nomenclature set forth in Simmonds et al., *J Gen Virol,* 74(Pt11):2391-2399 (1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al, *J Gen Virol,* 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol,* 75(Pt 5):1053-1061 (1994)).

Treatment or Prevention of a Virus-Related Disorder

The 2-Carboxy Substituted Indole Derivatives can be used to treat or prevent a virus-related disorder. Accordingly, the 2-Carboxy Substituted Indole Derivatives are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The 2-Carboxy Substituted Indole Derivatives are useful for treating or preventing a RNA dependent polymerase (RdRp) related disorder in a patient. Such disorders include viral infections wherein the infective virus contain a RdRp enzyme.

Accordingly, in one embodiment, the present invention provides a method for treating a RNA dependent polymerase-related disorder in a patient, comprising administering to the patient an effective amount of at least one 2-Carboxy Substituted Indole Derivative or a pharmaceutically acceptable salt, solvate, ester or prodrug thereof.

Treatment or Prevention of a Disorder Related to HCV Infection

The 2-Carboxy Substituted Indole Derivatives can also be useful for treating or preventing a disorder related to an HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating an HCV-related disorder in a patient, wherein the method comprises administering to the patient a therapeutically effective amount of at least one 2-Carboxy Substituted Indole Derivative, or a pharmaceutically acceptable salt, solvate, ester or prodrug thereof Combination Therapy In another embodiment, the present methods for treating or preventing a viral infection can further comprise the administration of one or more additional therapeutic agents which are not 2-Carboxy Substituted Indole Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one 2-Carboxy Substituted Indole Derivative, or a pharmaceutically acceptable salt, solvate, ester or prodrug thereof, and (ii) at least one other antiviral agent that is other than a 2-Carboxy Substituted Indole Derivative, wherein the amounts administered are together effective to treat or prevent a viral infection.

When administering a combination therapy of the invention to a patient, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a 2-Carboxy Substituted Indole Derivative and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In one embodiment, the at least one 2-Carboxy Substituted Indole Derivative is administered during at time when the additional antiviral agent(s) exert their prophylactic or therapeutic effect, or vice versa.

In another embodiment, the at least one 2-Carboxy Substituted Indole Derivative and the additional antiviral agent(s) are administered in doses commonly employed when such agents are used as monotherapy for treating a viral infection.

In another embodiment, the at least one 2-Carboxy Substituted Indole Derivative and the additional antiviral agent(s) are administered in doses lower than the doses commonly employed when such agents are used as monotherapy for treating a viral infection.

In still another embodiment, the at least one 2-Carboxy Substituted Indole Derivative and the additional antiviral agent(s) act synergistically and are administered in doses lower than the doses commonly employed when such agents are used as monotherapy for treating a viral infection.

In one embodiment, the at least one 2-Carboxy Substituted Indole Derivative and the additional antiviral agent(s) are present in the same composition. In one embodiment, this composition is suitable for oral administration. In another embodiment, this composition is suitable for intravenous administration.

Viral infections and virus-related disorders that can be treated or prevented using the combination therapy methods of the present invention include, but are not limited to, those listed above.

In one embodiment, the viral infection is HCV infection.

The at least one 2-Carboxy Substituted Indole Derivative and the additional antiviral agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of at least one 2-Carboxy Substituted Indole Derivative and the additional antiviral agent(s) may inhibit the resistance of a viral infection to these agents.

Non-limiting examples of other therapeutic agents useful in the present compositions and methods include an HCV polymerase inhibitor, an interferon, a nucleoside, a viral replication inhibitor, an antisense agent, a therapeutic vaccine, a viral protease inhibitor, a virion production inhibitor, an antibody therapy (monoclonal or polyclonal), and any agent useful for treating an RNA-dependent polymerase-related disorder.

In one embodiment, the other antiviral agent is a viral protease inhibitor.

In another embodiment, the other antiviral agent is an HCV protease inhibitor.

In another embodiment, the other antiviral agent is an interferon.

In still another embodiment, the other antiviral agent is a viral replication inhibitor.

In one embodiment, the other antiviral agent is a viral replication inhibitor, which is an HCV replicase inhibitor.

In another embodiment, the other antiviral agent is an antisense agent.

In another embodiment, the other antiviral agent is a therapeutic vaccine.

In a further embodiment, the other antiviral agent is an virion production inhibitor.

In another embodiment, the other antiviral agent is antibody therapy.

In another embodiment, the other antiviral agents comprise a protease inhibitor and a polymerase inhibitor.

In still another embodiment, the other antiviral agents comprise a protease inhibitor and an immunosuppressive agent.

In yet another embodiment, the other antiviral agents comprise a polymerase inhibitor and an immunosuppressive agent.

In a further embodiment, the other antiviral agents comprise a protease inhibitor, a polymerase inhibitor and an immunosuppressive agent.

In another embodiment the other agent is ribavirin.

HCV polymerase inhibitors useful in the present methods and compositions include, but are not limited to VP-19744 (Wyeth/ViroPharma), HCV-796 (WyethNiroPharma), NM-283 (Idenix/Novartis), R-1626 (Roche), MK-0608 (Merck), A848837 (Abbott), GSK-71185 (Glaxo SmithKline), XTL-2125 (XTL Biopharmaceuticals), and those disclosed in Ni et al., *Current Opinion in Drug Discovery and Development*, 7(4446 (2004); Tan et al., *Nature Reviews*, 1:867 (2002); and Beaulieu et al., *Current Opinion in Investigational Drugs*, 5:838 (2004).

Interferons useful in the present methods and compositions include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, Boehringer Ingelheim, Ingelheim, Germany), interferon alpha fusion polypeptides, or consensus interferon as defined by determination of a consensus sequence of naturally occurring interferon alphas (Infergen™, Amgen, Thousand Oaks, Calif.).

Antibody therapy agents useful in the present methods and compositions include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like). Viral protease inhibitors useful in the present methods and compositions include, but are not limited to, NS3 serine protease inhibitors (including, but are not limited to, those disclosed in U.S. Pat. Nos. 7,012,066, 6,914,122, 6,911,428, 6,846,802, 6,838,475, 6,800,434, 5,017,380, 4,933,443, 4,812,561 and 4,634,697; and U.S. Patent Publication Nos. US20020160962, US20050176648 and US20050249702), HCV protease inhibitors (e.g., SCH503034 (Schering-Plough), VX-950 (Vertex), GS-9132 (Gilead/Achillion), ITMN-191 (InterMune/Roche)), amprenavir, atazanavir, fosemprenavir, indinavir, lopinavir, ritonavir, nelfinavir, saquinavir, tipranavir and TMC114.

Viral replication inhibitors useful in the present methods and compositions include, but are not limited to, HCV replicase inhibitors, NS3 helicase inhibitors, NS5A inhibitors, ribavirin, viramidine, A-831 (Arrow Therapeutics); an antisense agent or a therapeutic vaccine.

In one embodiment, viral replication inhibitors useful in the present methods and compositions include, but are not limited to, NS3 helicase inhibitors or NS5A inhibitors.

Examples of protease inhibitors useful in the present methods include, but are not limited to, an HCV protease inhibitor and a NS-3 serine protease inhibitor.

Examples of HCV protease inhibitors useful in the present methods include, but are not limited to, those disclosed in Landro et al., *Biochemistry*, 36(31):9340-9348 (1997); Ingallinella et al., *Biochemistry*, 37(25):8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10):7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181; WO 98/17679, WO 98/17679, WO 98/22496 and WO 99/07734 and WO 05/087731.

Further examples of HCV protease inhibitors useful in the present methods include, but are not limited to, the following compounds:

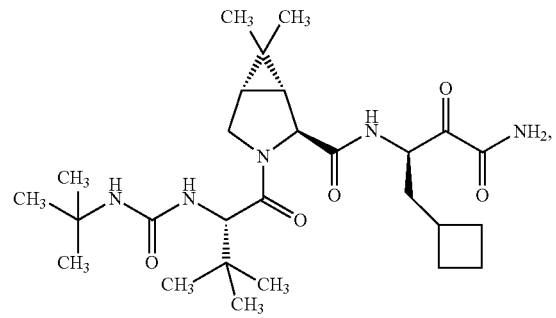

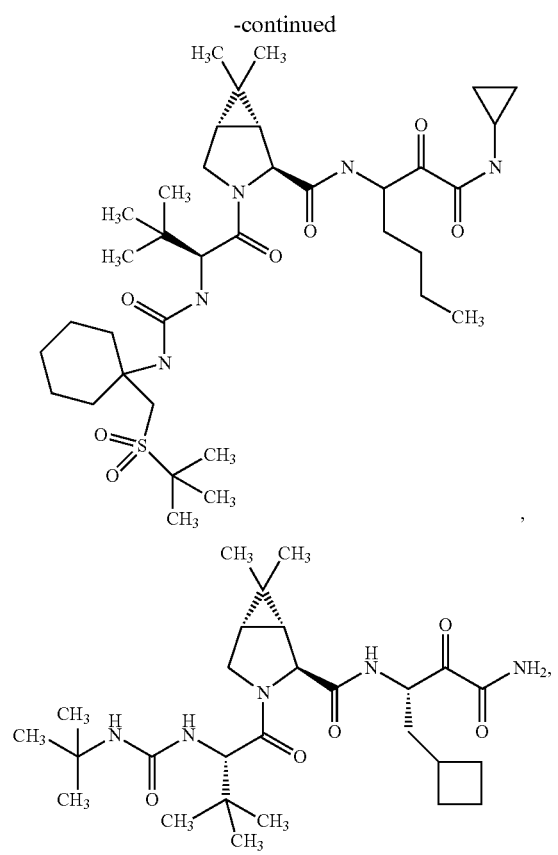
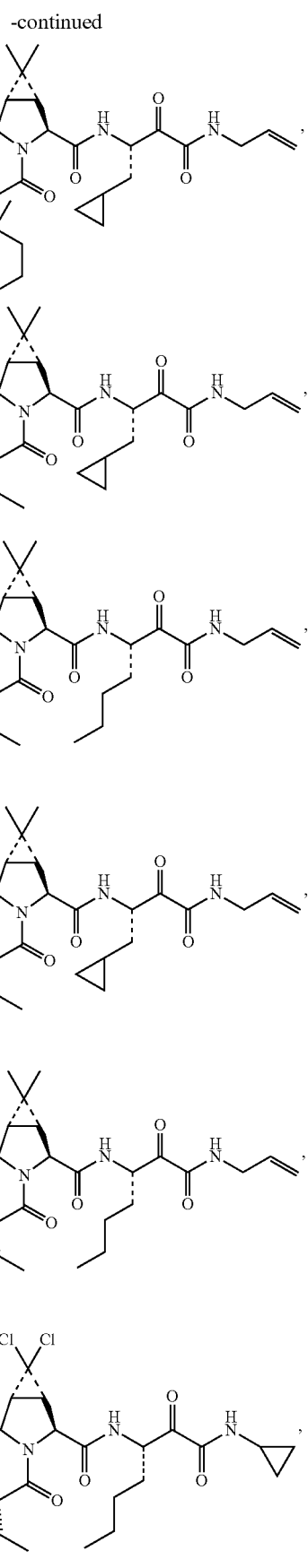

-continued

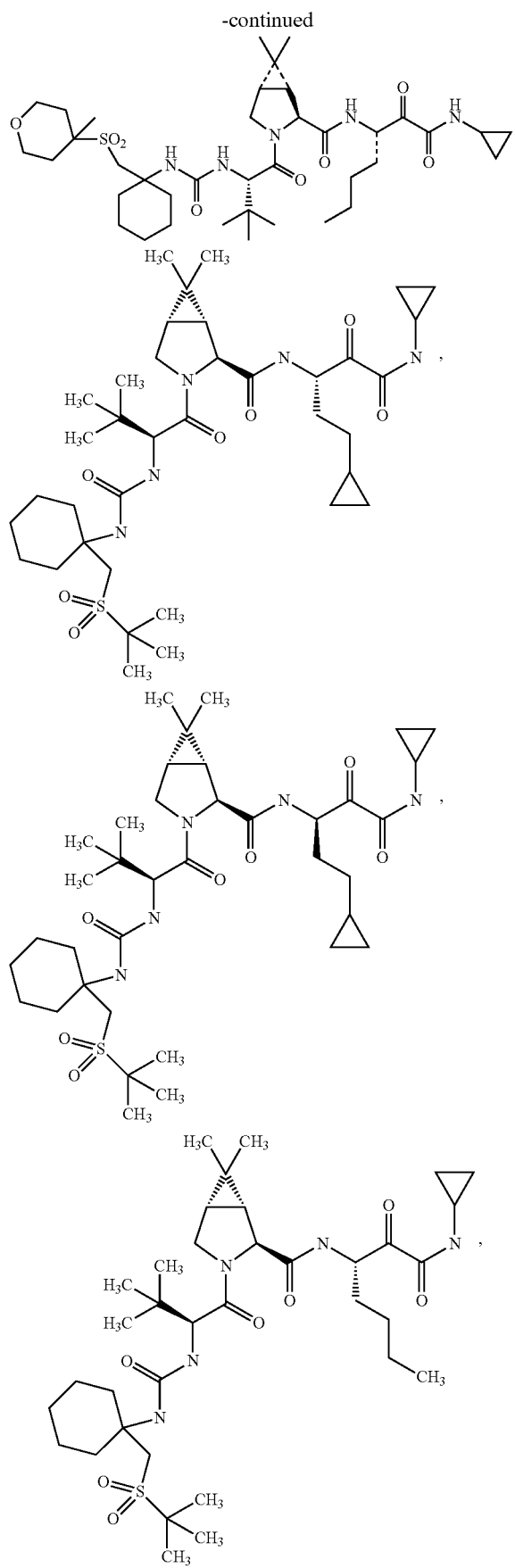

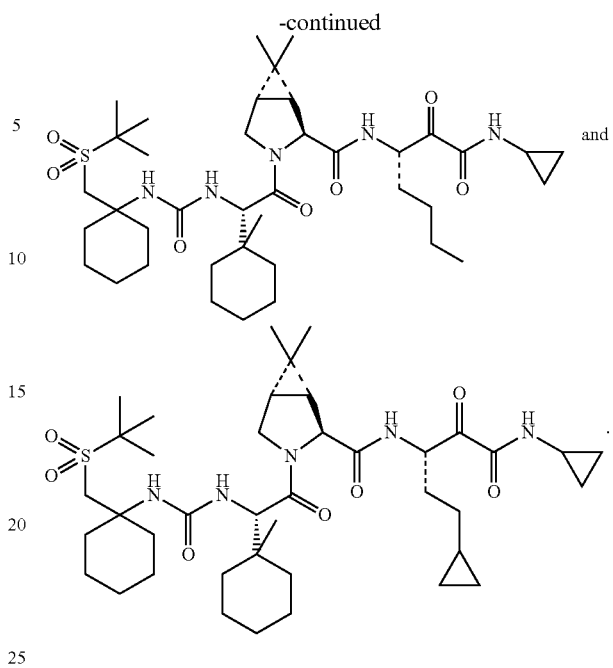

Additional examples of other therapeutic agents useful in the present methods include, but are not limited to, Levovirin™ (ICN Pharmaceuticals, Costa Mesa, Calif.), VP 50406™ (Viropharma, Incorporated, Exton, Pa.), ISIS 14803™ (ISIS Pharmaceuticals, Carlsbad, Calif.), Heptazyme™ (Ribozyme Pharmaceuticals, Boulder, Colo.), VX-950™ (Vertex Pharmaceuticals, Cambridge, Mass.), Thymosin™ (SciClone Pharmaceuticals, San Mateo, Calif.), Maxamine™ (Maxim Pharmaceuticals, San Diego, Calif.), NKB-122 (JenKen Bioscience Inc., North Carolina), mycophenolate mofetil (Hoffman-LaRoche, Nutley, N.J.).

The doses and dosage regimen of the other agents used in the combination therapies of the present invention for the treatment or prevention of a viral infection can be determined by the attending clinician, taking into consideration the the approved doses and dosage regimen in the package insert; the age, sex and general health of the patient; and the type and severity of the viral infection or related disease or disorder. When administered in combination, the 2-Carboxy Substituted Indole Derivative(s) and the other agent(s) for treating diseases or conditions listed above can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the at least one 2-Carboxy Substituted Indole Derivative and the additional antiviral agent(s), when administered as combination therapy, can range from about 0.1 to about 2000 mg per day, although variations will necessarily occur depending on the target of the therapy, the patient and the route of administration. In one embodiment, the dosage is from about 10 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the other therapeutic agent is INTRON-A interferon alpha 2b (commercially available from Schering-Plough Corp.), this agent is administered by subcutaneous injection at 3MIU(12 mcg)/0.5 mL/TIW is for 24 weeks or 48 weeks for first time treatment.

In another embodiment, when the other therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the other therapeutic agent is ROFERON A inteferon alpha 2a (commercially available from Hoffmann-La Roche), this agent is administered by subcutaneous or intramuscular injection at 3MIU(11.1 mcg/mL)/TIW for at least 48 to 52 weeks, or alternatively 6MIU/TIW for 12 weeks followed by 3MIU/TIW for 36 weeks.

In still another embodiment, when the other therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the other therapeutic agent is INFERGEN interferon alphacon-1 (commercially available from Amgen), this agent is administered by subcutaneous injection at 9 mcg/TTW is 24 weeks for first time treatment and up to 15 mcg/TIW for 24 weeks for non-responsive or relapse treatment.

In a further embodiment, when the other therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from an HCV protease inhibitor, an HCV replicase inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an HCV replicase inhibitor, a nucleoside, an interferon, a pegylated interferon and ribavirin.

In another embodiment, one or more compounds of the present invention are administered with two additional therapeutic agents selected from an HCV protease inhibitor, an HCV replicase inhibitor, a nucleoside, an interferon, a pegylated interferon and ribavirin.

In still another embodiment, one or more compounds of the present invention are administered with two additional therapeutic agents selected from an HCV protease inhibitor, an HCV replicase inhibitor, a nucleoside, an interferon, a pegylated interferon and ribavirin. In a specific embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replicase inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and ribavirin. In one embodiment, one compound of the present invention is administered with one additional therapeutic agents selected from an HCV polymerase inhibitor, a viral protease inhibitor, an interferon, and a viral replication inhibitor. In another embodiment, one compound of the present invention is administered with two additional therapeutic agents selected from an HCV polymerase inhibitor, a viral protease inhibitor, an interferon, and a viral replication inhibitor. In another embodiment, one compound of the present invention is administered with ribavirin. In still another embodiment, one compound of the present invention is administered with ribavirin and another therapeutic agent. In still another embodiment, one compound of the present invention is administered with ribavirin and another therapeutic agent, wherein the other therapeutic agent is selected from an HCV polymerase inhibitor, a viral protease inhibitor, an interferon, and a viral replication inhibitor.

Compositions and Administration

Due to their activity, the 2-Carboxy Substituted Indole Derivatives are useful in veterinary and human medicine. As described above, the 2-Carboxy Substituted Indole Derivatives are useful for treating or preventing a viral infection or a virus-related disorder in a patient in need thereof.

When administered to a patient, the 2-Carboxy Substituted Indole Derivatives can be administered as a component of a composition that comprises a pharmaceutically acceptable carrier or vehicle. The present invention provides pharmaceutical compositions comprising an effective amount of at least one 2-Carboxy Substituted Indole Derivative and a pharmaceutically acceptable carrier. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The 2-Carboxy Substituted Indole Derivatives of the present invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more 2-Carboxy Substituted Indole Derivatives are administered orally.

In another embodiment, the one or more 2-Carboxy Substituted Indole Derivatives are administered intravenously.

In another embodiment, the one or more 2-Carboxy Substituted Indole Derivatives are administered topically.

In still another embodiment, the one or more 2-Carboxy Substituted Indole Derivatives are administered sublingually.

In one embodiment, a pharmaceutical preparation comprising at least one 2-Carboxy Substituted Indole Derivative is in unit dosage form. In such form, the preparation is subdivided into unit doses containing appropriate quantities of the active component, e.g., an effective amount to achieve the desired purpose.

Compositions can be prepared according to conventional mixing, granulating or coating methods, respectively, and the present compositions can contain, in one embodiment, from about 0.1% to about 99% of the 2-Carboxy Substituted Indole Derivative(s) by weight or volume. In various embodiments, the the present compositions can contain, in one embodiment, from about 1% to about 70% or from about 5% to about 60% of the 2-Carboxy Substituted Indole Derivative(s) by weight or volume.

The quantity of 2-Carboxy Substituted Indole Derivative in a unit dose of preparation may be varied or adjusted from about 0.1 mg to about 2000 mg. In various embodiment, the quantity is from about 1 mg to about 2000 mg, 100 mg to about 200 mg, 500 mg to about 2000 mg, 100 mg to about 1000 mg, and 1 mg to about 500 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the 2-Carboxy Substituted Indole Derivatives will be regulated according to the judgment of the attending clinician considering such factors as age, condition and size of the patient as well as severity of the symptoms being treated. Generally, a total daily dosage of the 2-Carboxy Substituted Indole Derivatives range from about 0.1 to about 2000 mg per day, although variations will necessarily occur depending on the target of the therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one 2-Carboxy Substituted Indole Derivative or a pharmaceutically acceptable salt, solvate, ester or prodrug thereof; (ii) one or more additional therapeutic agents that are not a 2-Carboxy Substituted Indole Derivative; and (iii) a pharmaceutically acceptable carrier, wherein the amounts in the composition are together effective to treat a viral infection or a virus-related disorder.

Kits

In one aspect, the present invention provides a kit comprising a therapeutically effective amount of at least one 2-Carboxy Substituted Indole Derivative, or a pharmaceutically acceptable salt, solvate, ester or prodrug of said compound and a pharmaceutically acceptable carrier, vehicle or diluent.

In another aspect the present invention provides a kit comprising an amount of at least one 2-Carboxy Substituted Indole Derivative, or a pharmaceutically acceptable salt, solvate, ester or prodrug of said compound and an amount of at least one additional therapeutic agent listed above, wherein the amounts of the two or more ingredients result in a desired therapeutic effect.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula:

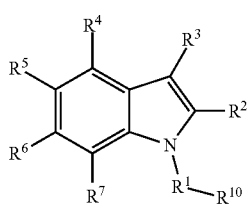

(Ia)

or a pharmaceutically acceptable salt thereof, wherein:

$R^1$ is —$CH_2$—;
$R^2$ is —C(O)OH or —C(O)Oalkyl;
$R^3$ is:

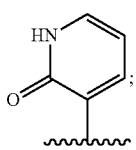 [SMILES: *c1ccc[nH]c1=O]

$R^4$, $R^5$, $R^6$ and $R^7$ are each, independently, H, alkyl, —[C($R^{12}$)$_2$]$_q$-cycloalkyl, —[C($R^{12}$)$_2$]$_q$-heterocycloalkyl, haloalkyl, halo, —OH, —$OR^9$ or —N($R^9$)$_2$;

each occurrence of $R^9$ is independently H, alkyl, cycloalkyl, heterocycloalkyl, haloalkyl or hydroxyalkyl;

$R^{10}$ is:

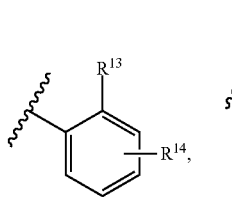 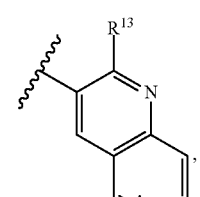

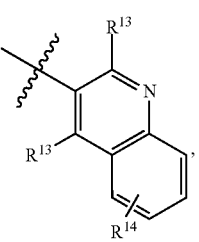 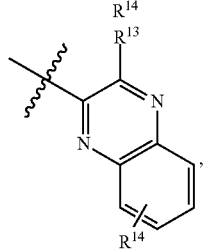

-continued

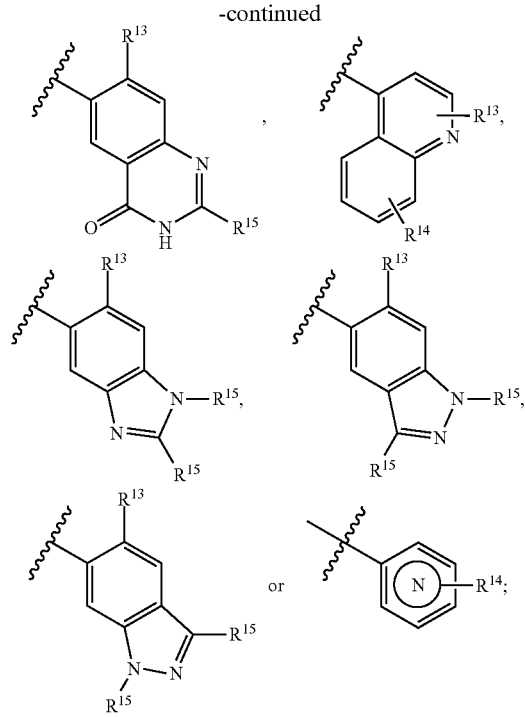

each occurrence of $R^{12}$ is independently H, halo, —N(alkyl)$_2$, —OH, —O-alkyl, alkyl, cycloalkyl or heterocycloalkyl, or two $R^{12}$ groups, together with the carbon atoms to which they are attached, join to form a cycloalkyl, heterocycloalkyl or C=O group;

$R^{13}$ is H, F, Br or Cl;

$R^{14}$ represents up to 4 optional and additional substituents, each independently selected from alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl;

each occurrence of $R^{15}$ is independently alkyl, cycloalkyl, CF$_3$, —CN, halo, —O-alkyl, —O-haloalkyl, —NHSO$_2$-alkyl, —NO$_2$, —C(O)NH$_2$, —C(O)NH-alkyl, —C(O)OH, —OH, —NH$_2$, —SO$_2$-alkyl, —SO$_2$NH-alkyl, —S-alkyl, —CH$_2$NH$_2$, —CH$_2$OH, —SO$_2$NH$_2$, —NHC(O)-alkyl, —C(O)O-alkyl, —C(O)-heterocycloalkyl or heteroaryl;

each occurrence of q is independently an integer ranging from 0 to 4;

and

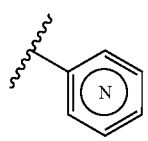

represents a pyridyl group, wherein the ring nitrogen atom can be at any of the five unsubstituted ring atom positions.

2. The compound of claim 1, wherein $R^{10}$ is:

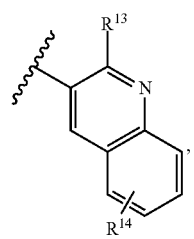

wherein $R^{13}$ is Cl and $R^{14}$ represents up to 4 optional and additional substituents, each independently selected from alkyl, cycloalkyl or halo.

3. The compound of claim 2, wherein $R^4$ and $R^7$ are each H and $R^5$ and $R^6$ are each independently H, alkyl, halo or haloalkyl.

4. A compound having the structure:

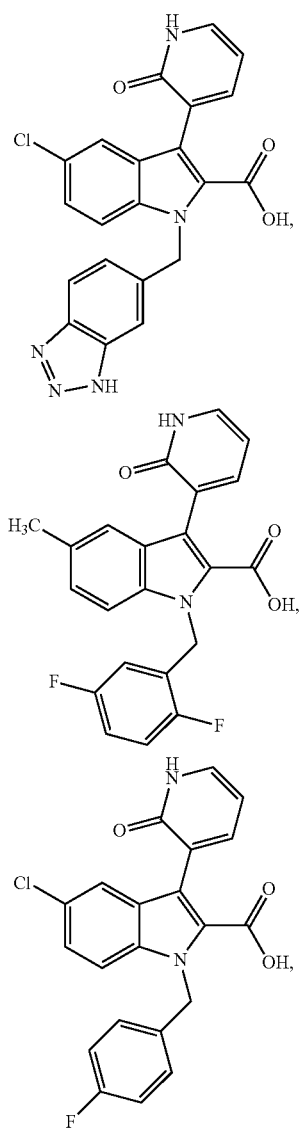

-continued
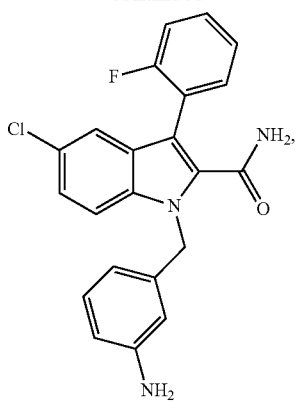
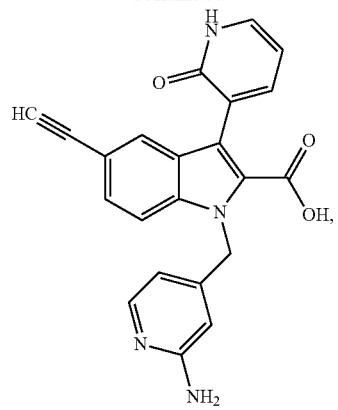
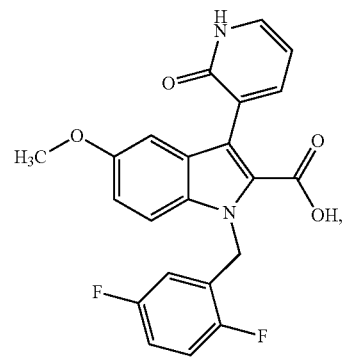
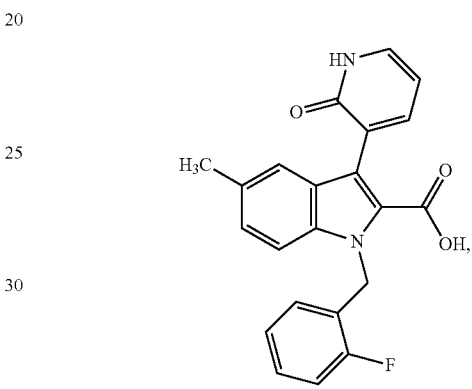
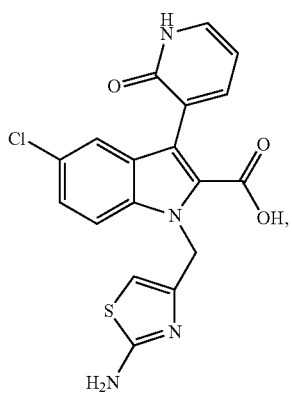
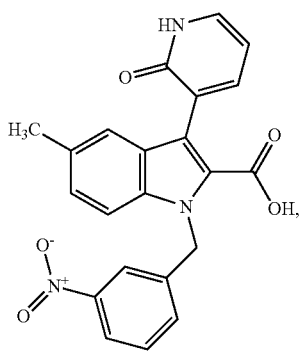
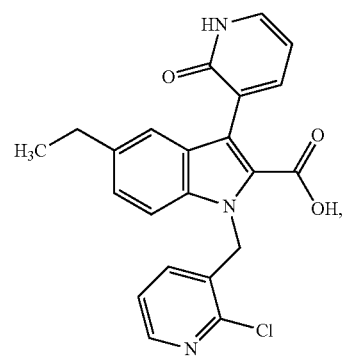
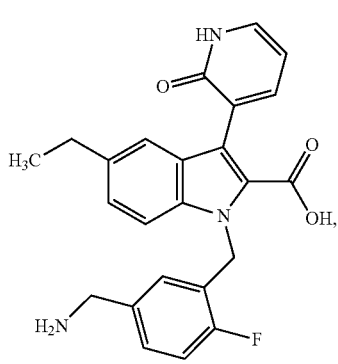

277
-continued
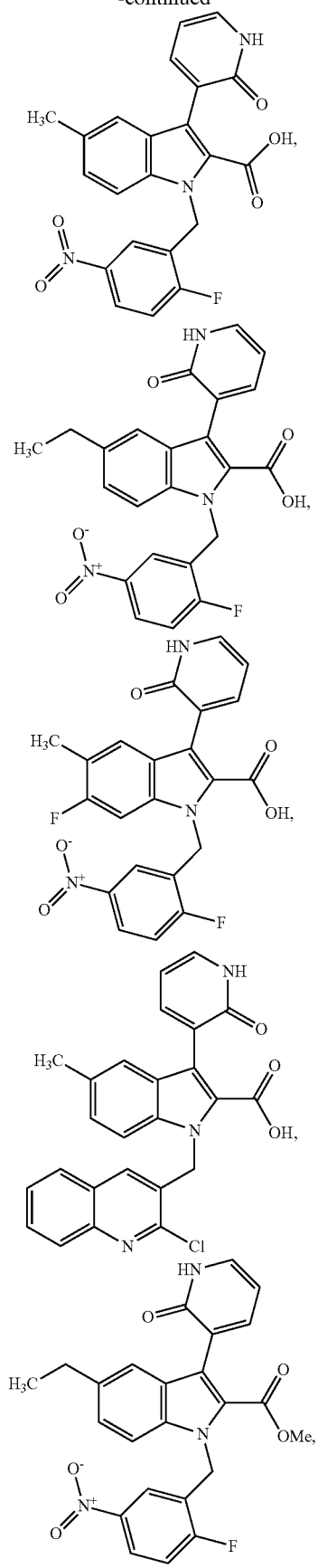
278
-continued
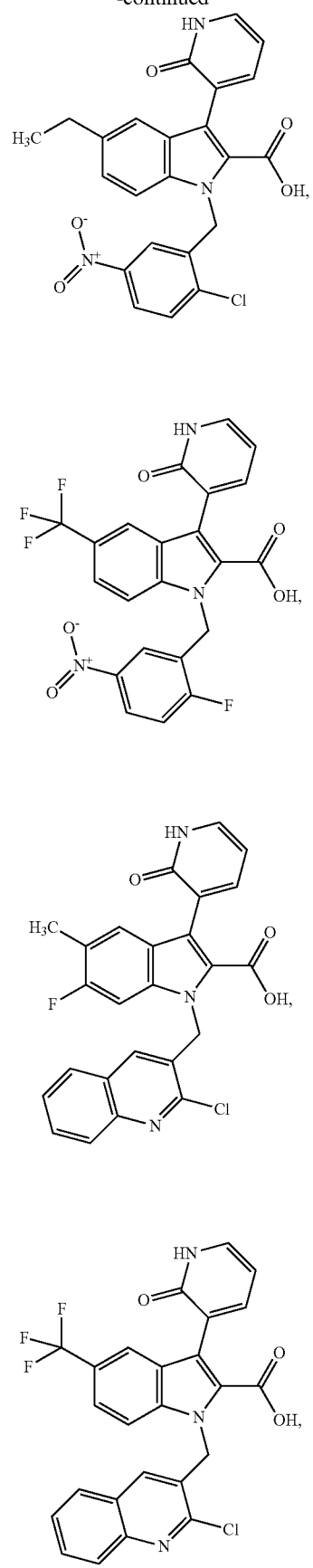

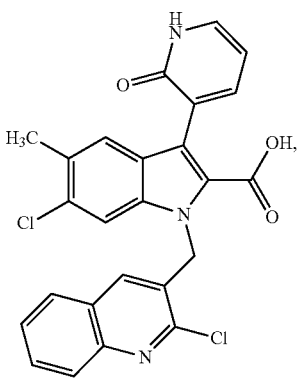
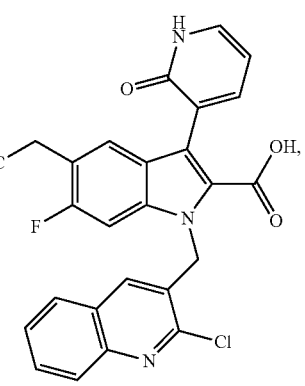
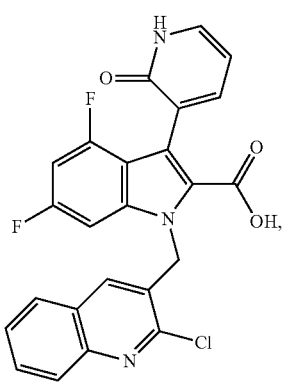
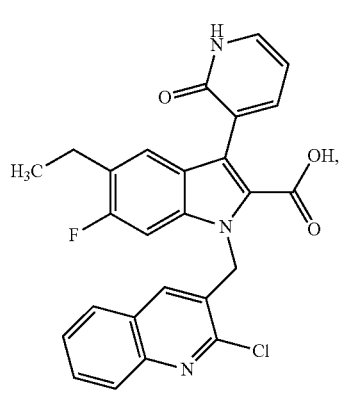
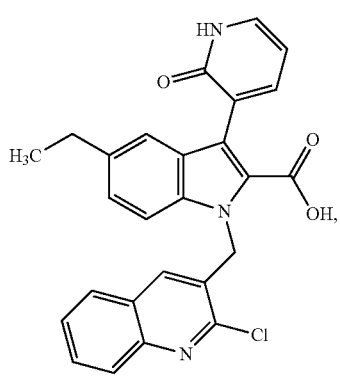
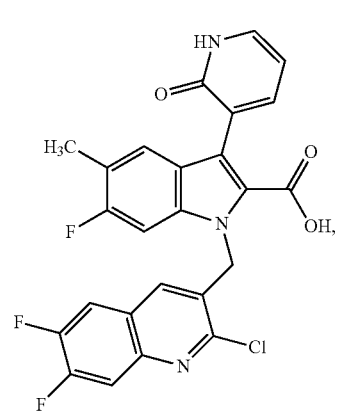
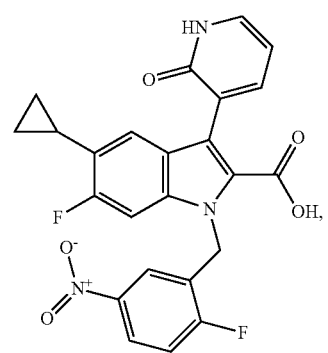
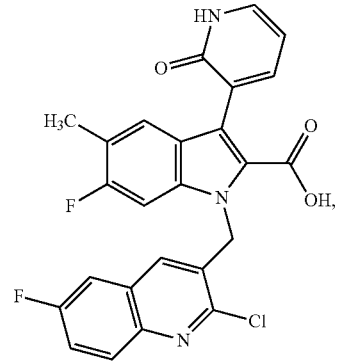

281
-continued
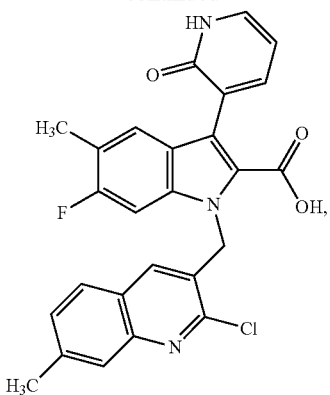
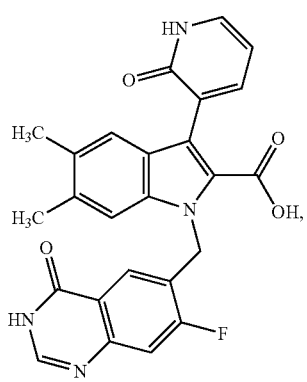
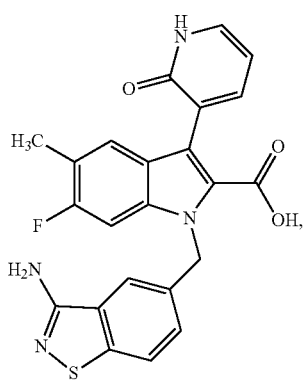
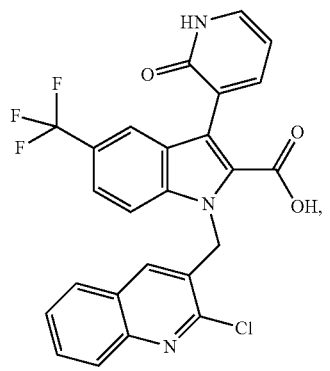
282
-continued
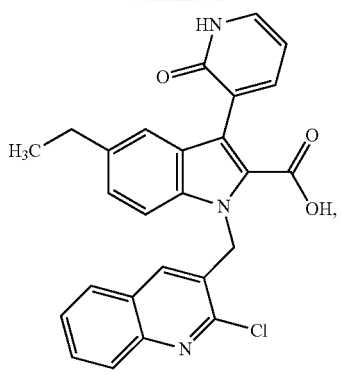
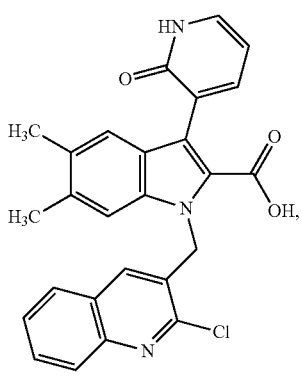 [SMILES: Cc1cc2c(-c3ccc[nH]c3=O)c(C(=O)O)n(Cc3cc4ccccc4nc3Cl)c2cc1F]
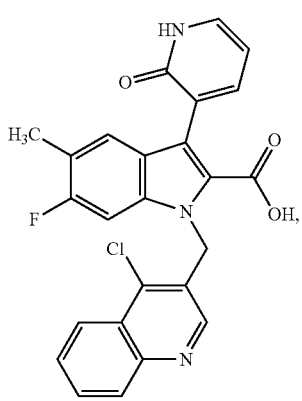
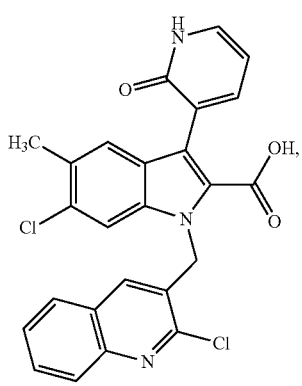

283
-continued
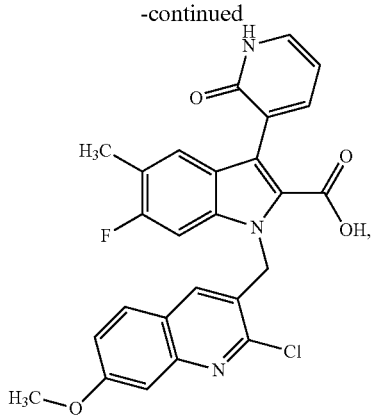
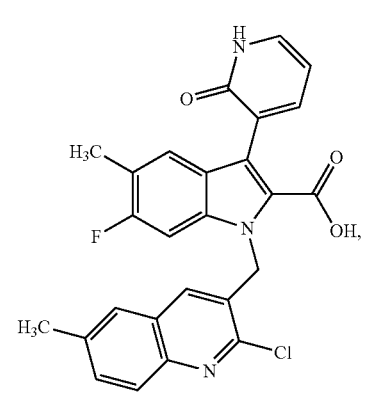
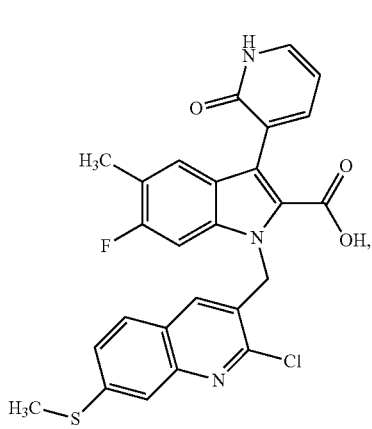
284
-continued
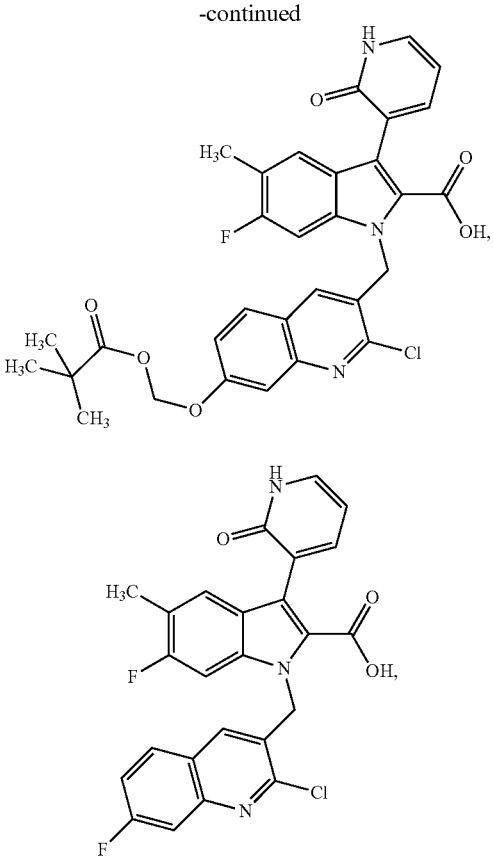
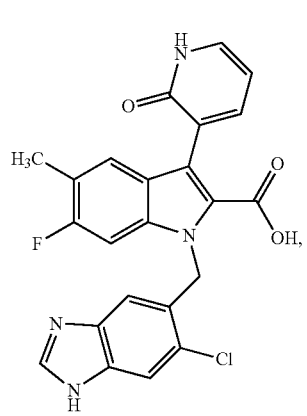
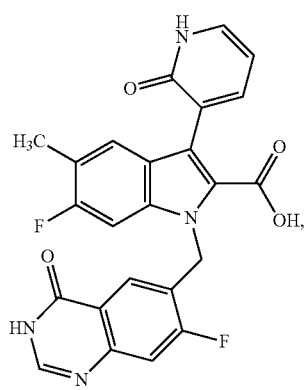

285
-continued

286
-continued

287
-continued
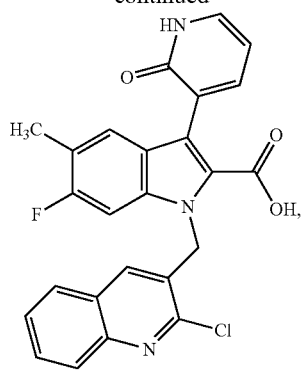
288
-continued
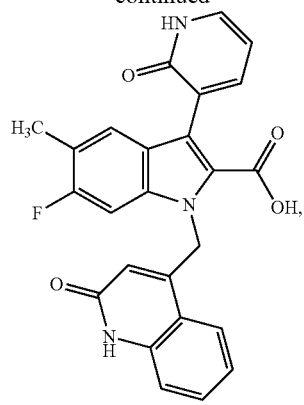
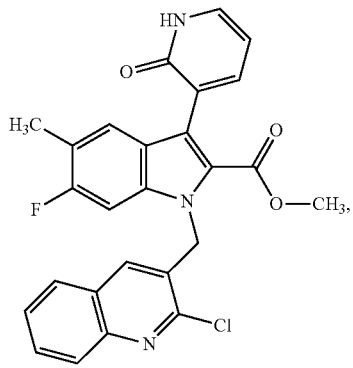
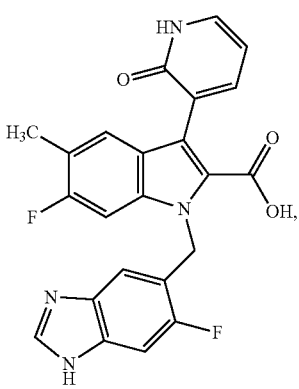
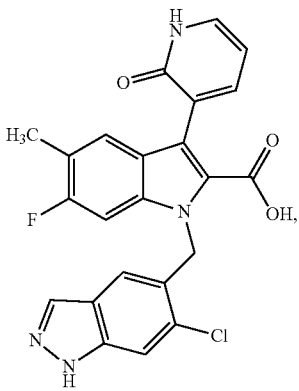

-continued

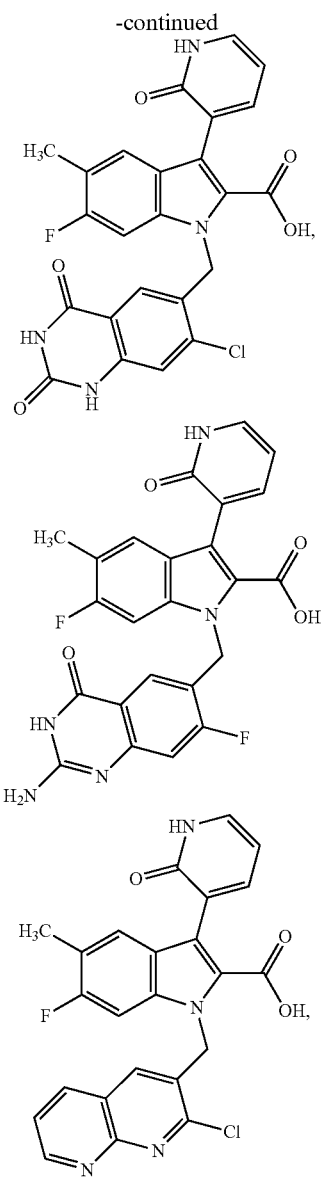

or a pharmaceutically acceptable salt thereof.

5. The compound of claim 4, wherein the pharmaceutically acceptable salt is choline.

6. A composition comprising at least one compound of claim 1, or a pharmaceutically acceptable salt thereof, and at least one pharmaceutically acceptable carrier.

7. A method for treating hepatitis C virus (HCV) infection in a patient, the method comprising administering to the patient an effective amount of at least one compound of claim 1, or a pharmaceutically acceptable salt thereof.

8. The method of claim 7, further comprising administering to the patient at least one antiviral agent, wherein the antiviral agent is selected from an HCV polymerase inhibitor, an interferon, a nucleoside, a viral replication inhibitor, an antisense agent, a therapeutic vaccine, a viral protease inhibitor, a virion production inhibitor, and an antibody therapy (monoclonal or polyclonal).

9. A compound having the structure:

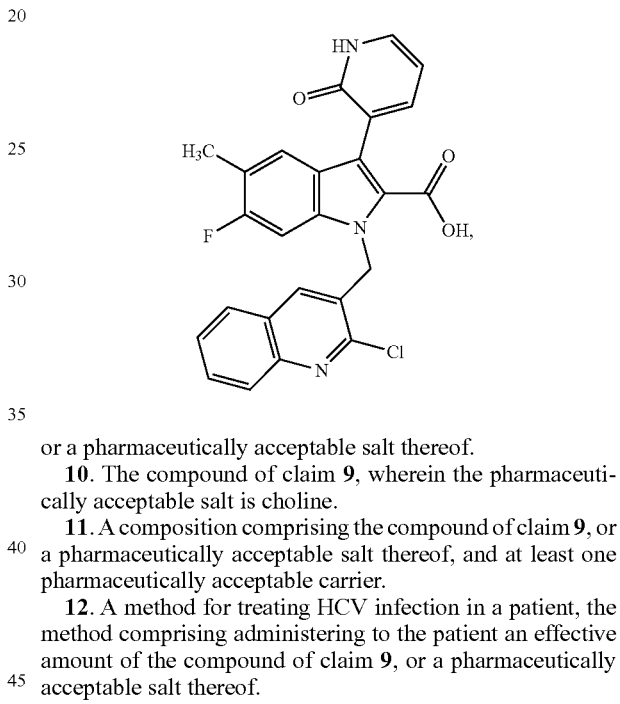

or a pharmaceutically acceptable salt thereof.

10. The compound of claim 9, wherein the pharmaceutically acceptable salt is choline.

11. A composition comprising the compound of claim 9, or a pharmaceutically acceptable salt thereof, and at least one pharmaceutically acceptable carrier.

12. A method for treating HCV infection in a patient, the method comprising administering to the patient an effective amount of the compound of claim 9, or a pharmaceutically acceptable salt thereof.

* * * * *

UNITED STATES PATENT AND TRADEMARK OFFICE
CERTIFICATE OF CORRECTION

PATENT NO. : 8,614,229 B2  Page 1 of 1
APPLICATION NO. : 12/675891
DATED : December 24, 2013
INVENTOR(S) : Anilkumar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 627 days.

Signed and Sealed this
Twenty-second Day of September, 2015

Michelle K. Lee
*Director of the United States Patent and Trademark Office*

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: 5B.2F Primer

<400> SEQUENCE: 1
atggacaggc gccctga                                                      17

<210> SEQ ID NO 2
<211> LENGTH: 20
<212> TYPE: DNA
<213> ORGANISM: Artificial Sequence
<220> FEATURE:
<223> OTHER INFORMATION: 5B.2R Primer

<400> SEQUENCE: 2
ttgatgggca gcttggtttc                                                   20

<210> SEQ ID NO 3
<211> LENGTH: 17
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: FAM labeled

<400> SEQUENCE: 3
cacgccatgc gctgcgg                                                      17
```